US006953793B2

(12) United States Patent
Butler et al.

(10) Patent No.: US 6,953,793 B2
(45) Date of Patent: Oct. 11, 2005

(54) SUBSTITUTED PYRAZOLES

(75) Inventors: Christopher R. Butler, San Diego, CA (US); Hui Cai, San Diego, CA (US); James P. Edwards, San Diego, CA (US); Cheryl A. Grice, Carlsbad, CA (US); Darin J. Gustin, San Diego, CA (US); Haripada Khatuya, San Diego, CA (US); Steven P. Meduna, San Diego, CA (US); Barbara A. Pio, San Diego, CA (US); Clark A. Sehon, San Diego, CA (US); Kevin L. Tays, Cardiff, CA (US); Jianmei Wei, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/927,324

(22) Filed: Aug. 10, 2001

(65) Prior Publication Data

US 2003/0078419 A1 Apr. 24, 2003

Related U.S. Application Data

(60) Provisional application No. 60/225,178, filed on Aug. 14, 2000.

(51) Int. Cl.$^7$ ..................... A61K 31/454; C07D 403/06
(52) U.S. Cl. ............................. 514/217.09; 514/230.5; 514/266.21; 514/303; 514/326; 514/422; 540/603; 544/105; 544/284; 546/119; 546/211; 548/264.1
(58) Field of Search ................................. 544/109, 284; 540/603; 546/119, 211; 548/264.1; 514/217.09, 230.5, 266.21, 303, 326, 422

(56) References Cited

U.S. PATENT DOCUMENTS

| | | | |
|---|---|---|---|
| 4,500,525 A | 2/1985 | Winters et al. | 514/210 |
| 5,264,576 A | 11/1993 | Shutske et al. | 546/119 |
| 5,776,718 A | 7/1998 | Palmer et al. | 435/23 |
| 5,856,514 A | * 1/1999 | Peignier et al. | 548/357.5 |
| 5,976,858 A | 11/1999 | Palmer et al. | 435/219 |
| 6,030,946 A | 2/2000 | Klaus et al. | 514/12 |
| 6,287,840 B1 | 9/2001 | Palmer et al. | 435/219 |

FOREIGN PATENT DOCUMENTS

| | | |
|---|---|---|
| EP | 0254241 A1 | 1/1988 |
| EP | 382637 B1 | 7/1993 |
| EP | 502786 B1 | 4/1996 |
| EP | 655248 B1 | 9/1999 |
| GB | 1 489 280 | 10/1977 |
| JP | S49-24148 | 3/1974 |
| JP | S50-90172 | 7/1975 |
| WO | WO 94/29276 A1 | 12/1994 |
| WO | WO 95/23222 A1 | 8/1995 |
| WO | WO 96/30353 A1 | 10/1996 |
| WO | WO 97/21439 A1 | 6/1997 |
| WO | WO 97/40066 A1 | 10/1997 |
| WO | WO 98/56785 | 12/1998 |
| WO | WO 99/24460 A2 | 5/1999 |
| WO | WO 99/48911 A | 9/1999 |
| WO | WO 99/58153 A | 11/1999 |
| WO | WO 00/49008 A | 8/2000 |
| WO | WO 00/51998 A | 9/2000 |
| WO | WO 00/55144 A | 9/2000 |
| WO | WO 01/09110 A | 2/2001 |
| WO | WO 01/19796 A | 3/2001 |
| WO | WO 01/40204 A | 6/2001 |

OTHER PUBLICATIONS

Andronati, et al., "Synthesis of 3–aryl–1–[(4–phenyl–1–piperazinyl)butyl]indazole derivatives and their affinity to 5–HT$_{1A}$ serotonin and dopamine D$_1$ receptors", Pharmazie 54 (1999), pp 99–101.
English Abstract—Japanese Patent—WO 98/56785 (1998).
PCT Search Report for PCT/US 01/25290 dated Apr. 5, 2002.
Palmer, J. T. et al.; "Vinyl Sulfones as Mechanism–Based Cysteine Protease Inhibitors"; J. Med. Chem. (1995) 38(17):3193–3196.
Bromme, D. et al.; "Peptidyl vinyl sulphones: a new class of potent and selective cysteine protease inhibitors"; Biochem. J. (1996) 315:85–89.
McGrath, M.E. et al.: "Crystal structure of human cathepsin S"; Protein Science (1998) 7:1294–1302.
Nerenberg, J. B. et al.; "Design and Synthesis of N–Alkylated Saccharins as Selective a–1A Adrenergic Receptor Antagonists"; Bioorg. Med. Chem. Lett. (1998) 8:2467–2472.
Honey, K. et al.; "Role of Lysosomal Cysteine Proteinases in Antigen Presentation to CD4 T Cells"; Inflammation Research (2001) Sup.3, vol. 50, pS159 abstr. Oct. 2001.
Li, W. et al.; "Tissue Specific Expression of Cathepsins and Antigen Presentation"; Inflammation Research (2001) Sup 3. vol. 50 p S159 abstr. Oct. 2002.
Magill, C. et al.; "Cysteine Proteases in Antigen Presentation and Models of Inflammation"; Inflammation Research (2001) Sup 3, vol. 50, p S159, abstr. Oct. 2003.
Allen, E.M. et al.; "Reversible Cathepsin S (CATS) Inhibitors Block Invariant Chain Degradation Both In Vitro and In Vivo"; Inflammation Research (2001) Sup 3, vol. 50, p S159, abstr. Oct. 2004.
Podolin, P. L. et al.; "Inhibition of Cathepsin S Blocks Invariant Chain Processing and Antigen–Induced Proliferation in Vitro, and Reduces the Severity of Collagen–Induced Arthritis in Vivo"; Inflammation Research (2001) Sup. 3, vol. 50, p S159, abstr. Oct. 2005.
Spero, D. et al.; "Design and Synthesis of Novel Cathepsin S Inhibitors"; Inflammation Research (2001) Sup. 3, vol. 50, p S206, abstr. 079.

(Continued)

*Primary Examiner*—Richard L. Raymond

(57) ABSTRACT

Substituted pyrazoles, methods of manufacturing them, compositions containing them, and methods of using them to treat, for example, autoimmune diseases mediated by cathepsin S are described.

79 Claims, No Drawings

OTHER PUBLICATIONS

Andronati, S.A. et al.: "Synthesis of 1-[4-(4-phenyl-1-piperazinyl)butyl]1,2-dihydro-3H-1,4-benzodiazepin-2-ones and 1H-indazoles and their effinity for benzodiazepine receptors"; Chemical Abstracts Number (CAN) 122:314528; (1994) 8:126–131.

Bromme, D. et al.; "High level expression and crystallization of recombinant human cathepsin S"; Protein Science (1996) 5:789–791.

Kirschke, H. et al.; "Cathepsin S"; Handbook of Proteolytic Enzymes: Barrett, A.J.: Rawlings, N.D.; Woessner, J.F., Editors, Academic Press (1998) 621–624.

Nakagawa T.Y. et al.; "Impaired Invariant Chain Degradation and Antigen Presentation and Diminished Collagen-Induced Arthritis in Cathepsin S Null Mice"; Immunity (1999) 10:207–217.

Riese, R.J. et al.; "Cathepsin S Activity Regulates Antigen Presentation and Immunity"; J. Clin. Invest. (1998) 101(11):2351–2363.

Shi, G.P., et al.; "Cathepsin S Required for Normal MHC Class II Peptide Loading and Germinal Center Development"; Immunity (1999) 10:197–206.

Singh, P., et al.; "Quantitative Structure–Activity Relationship Studies on a New Class of Antihypertensive Agents: Derivatives of 3-Aryl-4,5,6,7-tetrahydro-1H-pyrazolo[4,3-c]pyridine"; Quant. Struct.-Act. Relat. (1990) 9:29–32.

Winters, G. et al.; "Synthesis in Vitro [3H]Prazosin Displacement and in Vivo Activity of 3-Aryl-4,5,6,7-tetrahydropyrazolo[4,3-c]pyridines, a New Class of Antihypertensive"; J. Med. Chem. (1985) 28(7):934–940.

Nakatsuka, Masashi et al, "Preparation of pyrazole derivatives as immunosuppressants" retrieved from STN Database accession No. 130:52417, XP002193692 abstract; Chemical Abstracts Service, Columbus, Ohio, US.

Saegusa, Kaoru et al, "Cathepsin S Inhibitor Prevents Autoantigen Presentation and Autoimmunity" The Journal of Clinical Investigation. vol. 110, No. 3, Aug. 2000, pp. 361–369.

* cited by examiner

SUBSTITUTED PYRAZOLES

This application claims benefit of U.S. Provisional Application No. 60/225,178 filed Aug. 14, 2000.

FIELD OF THE INVENTION

This invention relates to a series of substituted pyrazoles, pharmaceutical compositions containing these compounds, and intermediates used in their manufacture, and methods of using them.

BACKGROUND OF THE INVENTION

Cathepsin S (EC 3.4.22.27) is a cysteine protease of the papain family found primarily in lysosomes (Bromme, D.; McGrath, M. E. High Level Expression and Crystallization of Recombinant Human Cathepsin S. *Protein Science* 1996, 5, 789–791).

The role of cathepsin S in the immune response is anticipated by its tissue distribution: cathepsin S is found primarily in lymphatic tissues, lymph nodes, the spleen, B lymphocytes, and macrophages (Kirschke, H. Chapter 211. Cathepsin S. In Handbook of Proteolytic Enzymes. Barrett, A. J.; Rawlings, N. D.; Woessner, J. F., Eds. San Diego: Academic Press, 1998. pp. 621–624.). Cathepsin S inhibitors have been shown in animal models to modulate antigen presentation and are effective in an animal model of asthma (Riese, R. J.; Mitchell, R. N.; Villadangos, J. A.; Shi, G.-P.; Palmer, J. T.; Karp, E. R.; De Sanctis, G. T.; Ploegh, H. L.; Chapman, H. A. Cathepsin S Activity Regulates Antigen Presentation and Immunity. *J. Clin. Invest.* 1998, 101, 2351–2363 and Shi, G.-P.; Villadangos, J. A.; Dranoff, G.; Small, C.; Gu, L.; Haley, K. J.; Riese, R.; Ploegh, H. L.; Chapman, H. A. Cathepsin S Required for Normal MHC Class II Peptide Loading and Germinal Center Development. *Immunity* 1999, 10, 197–206.).

Mice in which the gene encoding cathepsin S has been knocked out are less susceptible to collagen-induced arthritis and their immune systems have an impaired ability to respond to antigens (Nakagawa, T. Y.; Brissette, W. H.; Lira, P. D.; Griffiths, R. J.; Petrushova, N.; Stock, J.; McNeish, J. D.; Eastman, S. E.; Howard, E. D.; Clarke, S. R. M.; Rosloniec, E. F.; Elliott, E. A.; Rudensky, A. Y. Impaired Invariant Chain Degradation and Antigen Presentation and Diminished Collagen-Induced Arthritis in Cathepsin S Null Mice. *Immunity* 1999, 10, 207–217).

These data demonstrate that compounds that inhibit the proteolytic activity of human cathepsin S should find utility in the treatment of chronic autoimmune diseases including, but not limited to, lupus, rheumatoid arthritis, and asthma; and have potential utility in modulating the immune response to tissue transplantation.

There are a number of cathepsin S inhibitors reported in the literature. The most important patents are listed below.

Certain dipeptidyl nitriles are claimed by Novartis as cathepsin S inhibitors in: Altmann, et. al. WO-99/24460.

Dipeptidyl vinyl sulfones are claimed by Arris (now Axys) as cysteine protease (including cathepsin S) inhibitors in: Palmer, et. al. U.S. Pat. No. 5,976,858.

Certain peptidyl sulfonamides are claimed by Arris/Axys as cysteine protease (including cathepsin S) inhibitors in: Palmer, et. al. U.S. Pat. No. 5,776,718 (assigned to Arris, now Axys) & Klaus, et. al. U.S. Pat. No. 6,030,946 (assigned to Axys).

Compounds somewhat similar to those of the present invention are described in the following references.

Winters, et. al. (Winters, G.; Sala, A.; Barone, D.; Baldoli, E. *J. Med. Chem.* 1985, 28, 934–940; Singh, P.; Sharma, R. C. *Quant. Struct.-Act. Relat.* 1990, 9, 29–32; Winters, G.; Sala, A.; Barone, D. in U.S. Pat. No. 4,500,525 (1985)) have described bicyclic pyrazoles of the type shown below. R never contains a heterocyclic ring and no protease inhibitor activity is ascribed to these molecules; they are described as α1-adrenergic receptor modulators.

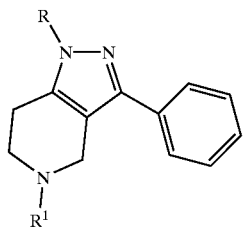

Shutske, et. al. claim the bicylic pyrazoles below. The pyridine ring is aromatic in their system (Shutske, G. M.; Kapples, K. J.; Tomer, J. D. U.S. Pat. No. 5,264,576 (1993)). Although reference is made to R being a linker to a heterocycle, the claims specify only R=hydrogen. The compounds are referred to as serotonin reuptake inhibitors.

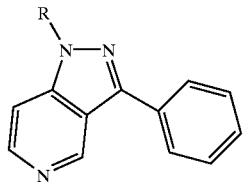

The compound 2-[4-[4-(3-methyl-5-phenyl-1H-pyrazol-1-yl)butyl]-1-piperazinyl]-pyrimidine is known from EP-382637, which describes pyrimidines having anxiolytic properties. This compound and analogs are further described in EP-502786 as cardiovascular and central nervous system agents. Pharmaceutical formulations with such compounds are disclosed in EP-655248 for use in the treatment of gastric secreation and as anti-ulcer agents. WO-9721439 describes medicaments with such compounds for treating obsessive-compulsive disorders, sleep apnea, sexual dysfunctions, emesis and motion sickness.

The compounds 5-methyl-3-phenyl-1-[4-(4-phenyl-1-piperazinyl)butyl]-1H-indazole and 5-bromo-3-(2-chlorophenyl)-1-[4-(4-phenyl-1-piperazinyl)butyl]-1H-indazole, in particular the hydrochloride salts thereof, are known from WO-9852940 and CA 122:314528, where these and similar compounds are described as kinase inhibitors in the former reference and possessing affinity for benzodiazepine receptors in the latter reference.

SUMMARY OF THE INVENTION

The present invention concerns compounds which can be represented by formula (I):

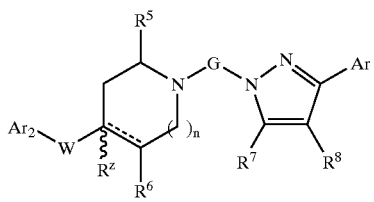

(I)

wherein:

$Ar_2$ is a monocyclic or bicyclic ring system, unsaturated, saturated or aromatic, optionally fused, optionally including between 1 and 5 heteroatom ring moieties independently selected from O, S, N, $SO_2$, and C=O; said $Ar_2$ ring system being optionally substituted with between 1 and 4 substituents;

$R^5$ and $R^6$ are independently selected from hydrogen and $C_{1-5}$ alkyl;

$R^7$ and $R^8$ are independently hydrogen, $C_{1-5}$ alkyl, $C_{2-5}$ alkenyl, $C_{1-5}$ alkoxy, $C_{1-5}$ alkylthio, halogen, or a 4–7 membered carbocyclyl or heterocyclyl;

alternatively, $R^7$ and $R^8$ can be taken together to form an optionally substituted 5- to 7-membered carbocyclic or heterocyclic ring, which ring may be unsaturated or aromatic, and may be optionally substituted with between one and three substituents independently selected from halo, cyano, amino, hydroxy, nitro, $R^4$, $R^4O—$, $R^4S—$, $R^4O(C_{1-5}$ alkylene)—, $R^4O(C=O)—$, $R^4(C=O)—$, $R^4(C=S)—$, $R^4(C=O)O—$, $R^4O(C=O)(C=O)—$, $R^4SO_2$, $NHR^{44}(C=NH)—$, $NHR^{44}SO_2—$, and $NHR^{44}(C=O)—$;

$R^4$ is H, $C_{1-5}$ alkyl, $C_{2-5}$ alkenyl, $C_{1-5}$ heterocyclyl, $(C_{1-5}$ heterocyclyl)$C_{1-6}$ alkylene, phenyl, benzyl, phenethyl, $NH_2$, mono- or di($C_{1-6}$ alkyl)$N—$, $(C_{1-6}$ alkoxy)carbonyl- or $R^{42}OR^{43}—$, wherein $R^{42}$ is H, $C_{1-5}$ alkyl, $C_{2-5}$ alkenyl, phenyl, benzyl, phenethyl, $C_{1-5}$ heterocyclyl, or $(C_{1-5}$ heterocyclyl)$C_{1-6}$ alkylene and $R^{43}$ is $C_{1-5}$ alkylene, phenylene, or divalent $C_{1-5}$ heterocyclyl;

$R^{44}$ is any one of the values for $R^4$;

n is 0, 1, or 2;

G is $C_{3-6}$ alkenediyl or $C_{3-6}$ alkanediyl, optionally substituted with hydroxy, halogen, $C_{1-5}$ alkoxy, $C_{1-5}$ alkyl, oxo, hydroximino, $CO_2R^k$, $R^kR^lN$, $R^kR^lNCO_2$, (L)-$C_{1-4}$ alkylene-, (L)-$C_{1-5}$ alkoxy, $N_3$ or [(L)-$C_{1-5}$ alkylene] amino;

each of $R^k$ and $R^l$ is independently hydrogen, $C_{1-5}$ alkyl, $C_{3-5}$ alkenyl, phenyl, benzyl, phenethyl, or $C_{1-5}$ heterocyclyl; alternatively $R^k$ and $R^l$, can be taken together to form an optionally substituted 4- to 7-membered heterocyclic ring, which ring may be saturated, unsaturated or aromatic;

L is amino, mono- or di-$C_{1-5}$ alkylamino, pyrrolidinyl, morpholinyl, piperidinyl homopiperidinyl, or piperazinyl, wherein available ring nitrogens may be optionally substituted with $C_{1-5}$ alkyl, benzyl, $C_{2-5}$ acyl, $C_{1-5}$ alkylsulfonyl, or $C_{1-5}$ alkoxycarbonyl;

Ar represents a monocyclic or bicyclic aryl or heteroaryl ring, optionally substituted with between 1 and 3 substituents independently selected from halogen, $C_{1-5}$ alkoxy, $C_{1-5}$ alkyl, $C_{2-5}$ alkenyl, cyano, azido, nitro, $R^{22}R^{23}N$, $R^{24}SO_2$, $R^{24}S$, $R^{24}SO$, $R^{24}OC=O$, $R^{22}R^{23}NC=O$, $C_{1-5}$ haloalkyl, $C_{1-5}$ haloalkoxy, $C_{1-5}$ haloalkylthio, and $C_{1-5}$ alkylthio;

$R^{22}$ is hydrogen, $C_{1-5}$ alkyl, $C_{3-5}$ alkenyl, phenyl, phenethyl, benzyl, or $C_{1-5}$ heterocyclyl, $C_{2-8}$ acyl, aroyl, $R^{38}OC=O$, $R^{25}R^{26}NC=O$, $R^{38}SO$, $R^{38}SO_2$, $R^{38}S$, or $R^{25}R^{26}NSO_2$;

$R^{38}$ is H, $C_{1-5}$ alkyl, $C_{3-5}$ alkenyl, phenyl, benzyl, phenethyl, or $C_{1-5}$ heterocyclyl;

$R^{23}$ is hydrogen, $C_{1-5}$ alkyl, $C_{3-5}$ alkenyl, phenyl, benzyl or $C_{1-5}$ heterocyclyl; alternatively, $R^{22}$ and $R^{23}$ can be taken together to form an optionally substituted 4- to 7-membered heterocyclic ring, which ring may be saturated, unsaturated or aromatic;

$R^{24}$ is $C_{1-5}$ alkyl, $C_{3-5}$ alkenyl, phenyl, benzyl, or $C_{1-5}$ heterocyclyl;

$R^{25}$ and $R^{26}$ independently are hydrogen, $C_{1-5}$ alkyl, $C_{3-5}$ alkenyl, phenyl, benzyl, or $C_{1-5}$ heterocyclyl; or, alternatively, $R^{25}$ and $R^{26}$ can be taken together to form an optionally substituted 4- to 7-membered heterocyclic ring, which ring may be saturated, unsaturated or aromatic;

W represents O, S, $NR^{27}$, C=O, (C=O)NH, NH(C=O), $CHR^{28}$, or a covalent bond;

$R^z$ is H or OH and the dashed line is absent; or $R^z$ is absent where the dashed line is an $sp^2$ bond;

$R^{27}$ is hydrogen, $C_{1-5}$ alkyl, $C_{3-5}$ alkenyl, phenyl, naphthyl, benzyl, phenethyl, $C_{1-5}$ heterocyclyl, $C_{2-8}$ acyl, aroyl, $R^{29}OC=O$, $R^{30}R^{31}NC=O$, $R^{29}SO$, $R^{29}S$, $R^{29}SO_2$, or $R^{30}R^{31}NSO_2$; or, alternatively, $R^{27}$ and part of $Ar_2$ can be taken together to form an optionally substituted 5- or 6-membered heterocyclic ring with optionally 1 to 3 additional heteroatom moieties in the ring selected from O, $NR^9$, $NR^{10}$, N, $SO_2$, C=O, and S; which ring may be saturated, unsaturated or aromatic; $R^9$ and $R^{10}$ are independently selected from H, $C_{1-3}$ alkyl, and $—CH_2CO_2$ ($C_{1-4}$ alkyl);

$R^{28}$ is hydrogen, $C_{1-5}$ alkyl, $C_{3-5}$ alkenyl, hydroxy, phenyl, benzyl, $C_{1-5}$ heterocyclyl, $R^{29}O$, $R^{30}R^{31}NC=O$, $R^{29}S$, $R^{29}SO$, $R^{29}SO_2$, or $R^{30}R^{31}NSO_2$;

$R^{29}$ is $C_{1-5}$ alkyl, $C_{3-5}$ alkenyl, phenyl, benzyl, or $C_{1-5}$ heterocyclyl;

$R^{30}$ and $R^{31}$ are independently selected from hydrogen, $C_{1-5}$ alkyl, $C_{3-5}$ alkenyl, phenyl, benzyl, phenethyl, naphthyl, and $C_{1-5}$ heteroaryl; alternatively, $R^{30}$ and $R^{31}$ can be taken together to form an optionally substituted 4- to 7-membered ring carbocyclic or heterocyclic ring, which ring may be saturated, unsaturated or aromatic;

wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino]$C_{2-5}$ alkyl-NH—CO—, and $C_{1-5}$ haloalkoxy;

or a pharmaceutically acceptable salt, amide, or ester thereof; or a stereoisomeric form thereof.

One embodiment of the invention is a compound of formula(I), wherein $Ar_2$ is selected from 5–7 membered monocyclic rings, and [5,6], [6,6], [6,5], and [5,5] fused bicyclic ring systems, said ring or ring system being carbocyclic or heterocyclic, saturated, unsaturated, or aromatic, optionally substituted with halo, $C_{1-4}$ alkyl, $C_{1-4}$ haloalkyl, $C_{1-4}$ hydroxyalkyl, nitro, hydroxy, amino, mono- or di-($C_{1-6}$ alkyl)amino, $C_{1-4}$ alkoxy, $C_{2-4}$ alkoxycarbonyl, $C_{2-6}$ acyl, $C_{2-6}$ acyloxy, $C_{1-5}$ alkylsulfonyl, $C_{1-5}$ alkoxycarbonyl$C_{1-4}$ alkoxy, cyano, and mono- or di-($C_{1-6}$ alkyl)carbamoyl.

Another embodiment of the invention is a compound of formula (I), wherein $Ar_2$ is selected from 2,5-di($C_{1-6}$ alkyl) aminopyrrolyl and the following 6 formulae:

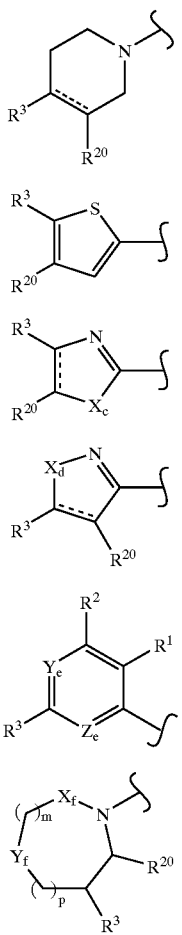

(a)
(b)
(c)
(d)
(e)
(f)

wherein
each dashed line may be an $sp^2$ bond or absent;
$X_c$ is O, S, or N; and $X_d$ is O or S;
$R^1$ is hydrogen, halogen, $C_{1-5}$ alkoxy, hydroxy, $C_{1-5}$ alkyl, $C_{2-5}$ alkenyl, cyano, nitro, $R^aR^bN$, $C_{2-8}$ acyl, $C_{1-5}$ heterocyclyl, $(C_{1-5}$ heterocyclyl$)C_{1-5}$ alkylene, $R^{11}S$, $R^{11}SO$, $R^{11}SO_2$, $R^cOC=O$, $R^cR^dNC=O$, or $R^cR^dNSO_2$; or $R^1$ can be taken together with $R^{27}$ as provided below;
$R^2$ is hydrogen, halogen, $C_{1-5}$ alkoxy, hydroxy, $C_{1-5}$ alkyl, $C_{2-5}$ alkenyl, cyano, nitro, $R^eR^fN$, $C_{1-5}$ heterocyclyl, or $C_{2-8}$ acyl;
$R^3$ is hydrogen, halogen, $C_{1-5}$ alkoxy, hydroxy, $C_{1-5}$ alkyl, $C_{2-5}$ alkenyl, cyano, nitro, $R^gR^hN$, $C_{2-8}$ acyl, $C_{1-5}$ heterocyclyl, $R^hOC=O$, $R^gR^hNC=O$, or $R^gR^hNSO_2$;
$R^a$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^jOC=O$, $R^iR^jNC=O$, $R^{12}SO$, $R^{12}SO_2$, $R^{12}S$, and $R^iR^jNSO_2$;
$R^e$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{32}OC=O$, $R^{32}R^{33}NC=O$, $R^{13}SO$, $R^{13}SO_2$, $R^{13}S$, and $R^{32}R^{33}NSO_2$;
$R^m$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{34}OC=O$, $R^{34}R^{35}NC=O$, $R^{15}SO$, $R^{15}SO_2$, $R^{15}S$, and $R^{34}R^{35}NSO_2$;
$R^o$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{36}OC=O$, $R^{36}R^{37}NC=O$, $R^{19}SO$, $R^{19}SO_2$, $R^{19}S$, and $R^{36}R^{37}NSO_2$;

each of $R^b$, $R^f$, $R^n$, $R^p$, $R^{32}$, $R^{33}$, $R^{34}$, $R^{35}$, $R^{36}$, $R^{37}$, $R^{39}$, and $R^{40}$ is independently selected from hydrogen, $C_{1-5}$ alkyl, $C_{3-5}$ alkenyl, phenyl, benzyl, phenethyl, and $C_{1-5}$ heteroaryl;
alternatively, $R^a$ and $R^b$, $R^e$ and $R^f$, $R^m$ and $R^n$, and $R^o$ and $R^p$, independently, can be taken together to form an optionally substituted 4- to 7-membered heterocyclic ring, which ring may be saturated, unsaturated or aromatic;
each of $R^{11}$, $R^{12}$, $R^{13}$, $R^{14}$, $R^{15}$, $R^{16}$, $R^{19}$, $R^{38}$, and $R^{41}$ is independently $C_{1-5}$ alkyl, $C_{3-5}$ alkenyl, phenyl, benzyl, phenethyl, or $C_{1-5}$ heterocyclyl;
each of $R^c$ and $R^d$, and $R^i$ and $R^j$ are independently are hydrogen, $C_{1-5}$ alkyl, $C_{3-5}$ alkenyl, phenyl, benzyl, phenethyl, or $C_{1-5}$ heteroaryl; alternatively, $R^c$ and $R^d$, and $R^i$ and $R^j$, independently, can be taken together to form an optionally substituted 4- to 7-membered heterocyclic ring, which ring may be saturated, unsaturated or aromatic;
$R^g$ is hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{17}OC=O$, $R^{17}R^{18}NC=O$, $R^{16}S$, $R^{16}SO$, $R^{16}SO_2$, or $R^{17}R^{18}NSO_2$;
$R^h$ is hydrogen, $C_{1-5}$ alkyl, $C_{3-5}$ alkenyl, phenyl, benzyl, phenethyl or $C_{1-5}$ heterocyclyl; alternatively, $R^g$ and $R^h$ can be taken together to form an optionally substituted 4- to 7-membered heterocyclic ring, which ring may be saturated, unsaturated or aromatic;
$R^{17}$ and $R^{18}$ independently are hydrogen, $C_{1-5}$ alkyl, $C_{3-5}$ alkenyl, phenyl, benzyl, or $C_{1-5}$ heterocyclyl;
alternatively, $R^{17}$ and $R^{18}$ can be taken together to form an optionally substituted 4- to 7-membered heterocyclic ring, which ring may be saturated, unsaturated or aromatic;
$Y_e$ is nitrogen or $R^{20}C$;
$Z_e$ is nitrogen or $R^{21}C$;
$R^{20}$ is hydrogen, halogen, $C_{1-5}$ alkoxy, $C_{1-5}$ alkyl, $C_{2-5}$ alkenyl, cyano, nitro, $R^mR^nN$, $C_{2-8}$ acyl, $R^mOC=O$, $R^{14}S$, $R^{14}SO$ or $R^{14}SO_2$;
$R^{21}$ is hydrogen, halogen, $C_{1-5}$ alkoxy, $C_{1-5}$ alkyl, $C_{2-5}$ alkenyl, cyano, nitro, $R^oR^pN$, $C_{2-8}$ acyl, $R^{16}OC=O$, $R^{11}S$, $R^{11}SO$ or $R^{11}SO_2$;
alternatively, $R^3$ and $R^{20}$ or $R^3$ and $R^{21}$ can be taken together to form an optionally substituted 5- or 6-membered carbocyclic or heterocyclic ring, which ring may be saturated, unsaturated or aromatic; wherein said ring may be optionally substituted with halo, di($C_{1-5}$ alkyl)amino, $C_{2-5}$ acyl, and $C_{1-5}$ alkoxy;
$R^{27}$ is hydrogen, $C_{1-5}$ alkyl, $C_{3-5}$ alkenyl, phenyl, naphthyl, benzyl, phenethyl, $C_{1-5}$ heterocyclyl, $C_{2-8}$ acyl, aroyl, $R^{29}OC=O$, $R^{30}R^{31}NC=O$, $R^{29}SO$, $R^{29}S$, $R^{29}SO_2$, or $R^{30}R^{31}NSO_2$;
or, alternatively, $R^{27}$ and $R^1$ can be taken together to form an optionally substituted 5- or 6-membered heterocyclic ring with optionally 1 to 3 additional heteroatom moieties in the ring selected from O, $NR^9$, $NR^{10}$, N, $SO_2$, C=O, and S; which ring may be saturated, unsaturated or aromatic; $R^9$ and $R^{10}$ are independently selected from H, $C_{1-3}$ alkyl, and —$CH_2CO_2(C_{1-4}$ alkyl);
$X_f$ is $CHR^{1f}$, =N—, NH, C=O, $SO_2$, $CHSR^{1f}$ wherein, in formula (f), $R^{1f}$ is hydrogen, halogen, $C_{1-5}$ alkoxy, hydroxy, $C_{1-5}$ alkyl, $C_{3-5}$ alkenyl, cyano, nitro, $R^{39}R^{40}N$, $C_{2-8}$ acyl, $C_{1-5}$ heterocyclyl, $(C_{1-5}$ heterocyclyl$)C_{1-5}$ alkylene, $R^{41}S$, $R^{41}SO$, $R^{41}SO_2$, $R^{39}OC=O$, $R^{39}R^{40}NC=O$, $R^{39}R^{40}NSO_2$, $R^{41}SO_3$— or $R^{39}$ (C=O) O—;
$Y_f$ is $CH_2$, $CHR^{2f}$, =$CR^{2f}$, O, or $NR^{2f}$, wherein $R^{2f}$ is H, $C_{1-7}$ alkyl, $C_{3-5}$ alkenyl, $C_{2-8}$ acyl, $C_{1-5}$ heterocyclyl, ($C_{1-5}$ heterocyclyl)-$C_{1-5}$ alkylene, phenyl, (phenyl)-$C_{1-5}$ alkylene, ($C_{3-7}$ cycloalkyl)-$C_{1-5}$ alkylene, ($H_2NCO$)—$C_{1-5}$ alkylene, $C_{1-5}$ haloalkyl, $C_{1-5}$ cyanoalkyl, ($C_{1-5}$ alkoxycarbonyl)$C_{1-5}$ alkylene, and (phenylcarbonyl)NH—;

m is 0 or 1;

p is 0 or 1;

wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino]$C_{2-5}$ alkylene, [di($C_{1-4}$ alkyl)amino]$C_{2-5}$ alkyl-NH—CO—, and $C_{1-5}$ haloalkoxy.

The disclosed compounds are high-affinity inhibitors of the proteolytic activity of human cathepsin S. For use in medicine, the preparation of pharmaceutically acceptable salts of compounds of formula (I) may be desirable.

Certain compounds of the present invention may have one stereogenic atom and may exist as two enantiomers. Certain compounds of the present invention may have two or more stereogenic atoms and may further exist as diastereomers. It is to be understood by those skilled in the art that all such stereoisomers and mixtures thereof in any proportion are encompassed within the scope of the present invention.

Another aspect of the invention provides pharmaceutical compositions comprising a compound of formula (I) and a pharmaceutically acceptable carrier. A further embodiment of the invention is a process for making a pharmaceutical composition comprising mixing a disclosed compound as described above, with a suitable pharmaceutically acceptable carrier.

The invention also contemplates pharmaceutical compositions comprising more than one compound of formula (I) and compositions comprising a compound of formula (I) and another pharmaceutically active agent.

The invention features a method of treating disorders or conditions mediated by the cathepsin S enzyme, in a subject in need thereof, comprising administering to the subject a therapeutically effective amount of any of the compounds or pharmaceutical compositions described above. If more than one active agent is administered, the therapeutically effective amount may be a jointly effective amount. The compounds described herein inhibit the protease activity of human cathepsin S, an enzyme involved in the immune response. In preferred embodiments, cathepsin S inhibition is selective. As such, the disclosed compounds and compositions are useful in the prevention, inhibition, or treatment of autoimmune diseases such as lupus, rheumatoid arthritis, and asthma, and for the prevention, inhibition, or treatment of tissue transplant rejection.

Additional features and advantages of the invention will become apparent from the detailed description below, including examples, and the appended claims.

DETAILED DESCRIPTION OF THE INVENTION

The invention features pyrazole compounds of formula (I), methods of making them, compositions containing them, and methods of using them to treat diseases and conditions, including those mediated by Cathepsin S.

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino,and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro or bromo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66:1–19 which is incorporated herein by reference. Representative pharmaceutically acceptable amides of the invention include those derived from ammonia, primary $C_{1-6}$ alkyl amines and secondary di($C_{1-6}$alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product which results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is G in formula (I) which links two rings.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on.

Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional sp² bond, if it is absent, the appropriate hydrogen atom(s) is(are) included.

Preferred substitutions for Ar or $Ar_1$ include methyl, methoxy, fluoromethyl, difluoromethyl, perfluoromethyl (trifluoromethyl), 1-fluoroethyl, 2-fluoroethyl, ethoxy, fluoro, chloro, and bromo, and particularly methyl, bromo, chloro, perfluoromethyl, perfluoromethoxy, methoxy, and fluoro. Preferred substitution patterns for Ar or $Ar_1$ are 4-substituted or 3,4-disubstituted phenyl.

Compounds of the invention are further described in the next section.

B. Compounds

The invention features compounds of formula (I) as described in the Summary section.

Preferred compounds include those wherein:
(a) $Ar_2$ is selected from formulae (e);
(b) $Ar_2$ is selected from formulae (f);
(c) $Ar_2$ is selected from formula (a)–(d);
(d) $R^1$ is halogen, $C_{1-5}$ alkoxy, hydroxy, $C_{1-5}$ alkyl, cyano, nitro, $R^a R^b N$ or is taken together with $R^{27}$;
(e) $R^1$ is taken together with $R^{27}$;
(f) $R^1$ and $R^{27}$ taken together are selected from:
   (1) —$CH_2NR^9$—(C=O)—
   (2) $OCH_2$(C=O)—
   (3) —$CH_2CH_2$(C=O)—
   (4) —$CH_2$—O(C=O)—
   (5) —$CH_2$S(C=O)—
   (6) —O(C=O)—
   (7) —$CH_2$(C=O)—
   (8) —$NR^9$(C=O)—
   (9) —$NR^9$($SO_2$)—
   (10) —$CH_2NR^9SO_2$—
   (11) —$NR^9CH_2$(C=O)— and —$SCH2$(C=O)—
(g) $R^1$ and $R^{27}$ taken together are selected from:
   a) —$CH_2$—(C=O)—
   b) —O(C=O)—
   c) —$CH_2CH_2$—
   d) —S(C=O)—
   e) —N=N—
   f) —$NR^9SO_2$—
   g) —N=$CR^9$—
   h) —$NR^9$(C=O)— and
   i) —CH=CH—;
(h) $R^2$ is hydrogen, halogen, $C_{1-5}$ alkoxy, $C_{1-5}$ alkyl, cyano, or $R^e R^f N$, where $R^e$ and $R^f$ are H or $C_{1-5}$ alkyl, or are taken together to form a 5–7 membered heterocyclic ring;
(i) $R^3$ is hydrogen, halogen, $C_{1-5}$ alkoxy, $C_{1-5}$ alkyl, cyano, nitro, or $R^g R^h N$, where $R^e$ and $R^f$ are H or $C_{1-5}$ alkyl, or are taken together to form a 5–7 membered heterocyclic ring;
(j) $R^5$ and $R^6$ are independently selected from hydrogen and $C_{1-3}$ alkyl;
(k) one of $R^5$ and $R^6$ is H;
(l) $R^5$ and $R^6$ are each H;
(m) one of $R^7$ and $R^8$ is H and the other is 5–7 membered carbocyclyl or heterocyclyl;
(n) $R^7$ and $R^8$ are taken together to form an optionally substituted 5- to 7-membered carbocyclic or heterocyclic ring;
(o) $R^7$ and $R^8$ taken together form a six-membered heterocyclyl;
(p) $R^7$ and $R^8$ taken together form pyridinyl, pyrimidinyl, or piperazinyl, optionally N-substituted with —(C=O)$R^4$, —$SO_2R^4$, or —(C=O)$NHR^{44}$;
(q) each of $R^a$, $R^e$, $R^m$, and $R^o$ is independently selected from hydrogen, $C_{1-5}$ alkyl, $C_{2-8}$ acyl, and the respective ROC=O, RRNC=O, RSO, $RSO_2$, and $RRNSO_2$ groups;
(r) each of $R^a$, $R^e$, $R^m$, $R^o$, $R^b$, $R^f$, $R^n$, and $R^p$ is independently selected from hydrogen and $C_{1-5}$ alkyl; or, independently, $R^a$ and $R^b$, $R^e$ and $R^f$, $R^m$ and $R^n$, and $R^o$ and $R^p$, taken together, form an optionally substituted 4- to 7-membered carbocyclic or heterocyclic ring;
(s) (1)$R^a$ and $R^b$ taken together are independently morpholinyl, piperidinyl, or pyrrolidinyl; (2) $R^e$ and $R^f$ taken together are morpholinyl, piperidinyl, or pyrrolidinyl; or (3) both (1) and (2) apply;
(t) each of $R^c$ and $R^d$, $R^i$ and $R^j$, $R^k$ and $R^l$ is independently hydrogen or $C_{1-5}$ alkyl, alternatively, $R^c$ and $R^d$, $R^i$ and $R^j$, and $R^k$ and $R^l$, independently, can be taken together to form an optionally substituted 4- to 7-membered heterocyclic ring, which ring may be saturated, unsaturated or aromatic;
(u) $R^c$ and $R^d$, $R^i$ and $R^j$, and $R^k$ and $R^l$, independently, are taken together to form an optionally substituted 4- to 7-membered heterocyclic ring, which ring may be saturated, unsaturated or aromatic;
(v) each of $R^b$, $R^f$, $R^n$, $R^p$, $R^{32}$, $R^{33}$, $R^{34}$, $R^{35}$, $R^{36}$, $R^{37}$, $R^{39}$, and $R^{40}$ is independently H or $C_{1-5}$ alkyl;
(w) each of $R^{11}$, $R^{12}$, $R^{13}$, $R^{14}$, $R^{15}$, $R^{16}$, $R^{19}$, $R^{38}$, and $R^{41}$ is independently H or $C_{1-5}$ alkyl;
(x) $R^g$ is $C_{1-5}$ alkyl, $C_{2-8}$ acyl, $R^{17}$OC=O, $R^{17}R^{18}$NC=O, $R^{16}$S, $R^{16}$SO, $R^{16}SO_2$, or $R^{17}R^{18}NSO_2$; and $R^h$ hydrogen or $C_{1-5}$ alkyl; alternatively, $R^g$ and $R^h$ can be taken together to form an optionally substituted 4- to 7-membered heterocyclic ring;
(y) $R^{17}$ and $R^{18}$ independently are hydrogen or $C_{1-5}$ alkyl;
(z) n is 1;
(aa) n is 0;
(bb) G is $C_{3-4}$ alkanediyl, optionally substituted with hydroxy, halogen, (L)-$C_{1-5}$ alkyloxy, or [(L)-$C_{1-5}$ alkylene]amino;
(cc) G is $C_3$ alkanediyl, optionally substituted with hydroxy, (L)-$C_{1-5}$ alkyloxy, or [(L)-$C_{1-5}$ alkylene]amino;
(dd) each of $R^{20}$ and $R^{21}$ is independently selected from hydrogen, halogen, $C_{1-5}$ alkoxy, $C_{1-5}$ alkyl, cyano, nitro, and $R^m R^n N$ or $R^o R^p N$, respectively;
(ee) each of $R^{20}$ and $R^{21}$ is independently selected from hydrogen, halogen, $C_{1-3}$ alkyl, and $R^m R^n N$ or $R^o R^p N$, respectively;
(ff) Ar represents a monocyclic ring, optionally substituted with 1 to 2 substituents selected from halogen, $C_{1-5}$ alkyl, cyano, azido, nitro, $R^{22} R^{23} N$, halomethyl, and halomethoxy;
(gg) Ar is a six membered ring substituted with between 1 and 2 substituents independently selected from methyl, halogen, $CF_3$, and $OCF_3$, said substituent or substituents being at the 4-position, or at the 3- and 4-positions, respectively;
(hh) each of $R^{22}$, $R^{23}$, and $R^{24}$ is hydrogen or $C_{1-5}$ alkyl;
(ii) $R^{25}$ and $R^{26}$ independently are hydrogen or $C_{1-5}$ alkyl; or, alternatively, $R^{25}$ and $R^{26}$ can be taken together to form an optionally substituted 4- to 7-membered heterocyclic ring;

(jj) each of $R^{25}$ and $R^{26}$ is independently hydrogen or $C_{1-5}$ alkyl;

(kk) W is $NR^{27}$;

(ll) W is $CHR^{28}$, and $R^{28}$ is hydrogen or $C_{1-5}$ alkyl;

(mm) $R^{29}$ is $C_{1-5}$ alkyl; or $R^{30}$ and $R^{31}$ are independently selected from hydrogen and $C_{1-5}$ alkyl, or $R^{30}$ and $R^{31}$ are taken together to form a 5–6 membered heterocyclyl;

(nn) $Ar_2$ is formula (e) and $R^1$ is halogen, $C_{1-5}$alkoxy, hydroxy, $C_{1-5}$ alkyl, cyano, nitro, and $R^aR^bN$, or $R^1$ can be taken together with $R^{27}$ as provided below; $R^2$ is hydrogen, halogen, $C_{1-5}$ alkoxy, $C_{1-5}$ alkyl, or $R^eR^fN$; $R^3$ is hydrogen, halogen, $C_{1-5}$ alkoxy, hydroxy, $C_{1-5}$ alkyl, cyano, $R^gR^hN$; $R^5$ and $R^6$ are independently selected from hydrogen and $C_{1-3}$ alkyl;

(oo) $R^7$ and $R^8$ independently are taken together to form an optionally substituted 5- to 7-membered carbocyclic or heterocyclic ring, which ring may be saturated, unsaturated or aromatic;

(pp) each of $R^a$ $R^e$, $R^m$, and $R^o$ is independently selected from hydrogen, $C_{1-5}$ alkyl, $C_{2-8}$ acyl, and the respective ROC=O, RRNC=O, RS, RSO, $RSO_2$, and $RRNSO_2$ groups;

(qq) each of $R^b$, $R^f$, $R^n$, and $R^p$, is independently selected from hydrogen and $C_{1-5}$ alkyl; each of $R^{11}$, $R^{12}$, $R^{13}$, $R^{14}$, $R^{15}$, $R^{16}$, $R^{19}$, and $R^{38}$ is independently $C_{1-5}$ alkyl; each of $R^c$ and $R^d$, $R^i$ and $R^j$, $R^k$ and $R^l$, $R^{32}$ and $R^{33}$, $R^{34}$ and $R^{35}$, $R^{36}$ and $R^{37}$ are independently are hydrogen or $C_{1-5}$ alkyl, or are taken together to form an optionally substituted 4- to 7-membered heterocyclic ring;

(rr) $R^g$ is hydrogen, $C_{1-5}$ alkyl, $C_{2-8}$ acyl, $R^{17}OC=O$, $R^{17}R^{18}NC=O$, $R^{16}S$, $R^{16}SO$, $R^{16}SO_2$, or $R^{17}R^{18}NSO_2$; $R^h$ is hydrogen or $C_{1-5}$ alkyl; alternatively, $R^g$ and $R^h$ can be taken together to form an optionally substituted 4- to 7-membered heterocyclic ring; $R^{17}$ and $R^{18}$ independently are hydrogen or $C_{1-5}$ alkyl; n is 0 or 1;

(ss) G is $C_{3-4}$ alkenediyl or $C_{3-4}$ alkanediyl, optionally substituted with hydroxy, halogen, $C_{1-5}$ alkyloxy, (L)-$C_{1-5}$ alkoxy, or [(L)-$C_{1-5}$ alkylene]amino; L is amino, mono- or di-$C_{1-5}$ alkylamino, pyrrolidinyl, morpholinyl, piperidinyl homopiperidinyl, or piperazinyl, wherein available ring nitrogens may be optionally substituted with $C_{1-5}$ alkyl, benzyl, $C_{1-5}$ alkylcarbonyl, or $C_{1-5}$ alkyloxycarbonyl;

(tt) $Y_e$ is nitrogen or $R^{20}C$; $Z_e$ is nitrogen or $R^{21}C$;

(uu) $R^{20}$ and $R^{21}$ are independently selected from hydrogen, halogen, $C_{1-5}$ alkoxy, $C_{1-5}$ alkyl, cyano, nitro, and $R^mR^nN$ or $R^oR^pN$, respectively; alternatively, $R^3$ and $R^{20}$ or $R^3$ and $R^{21}$ can be taken together to form an optionally substituted 5- or 6-membered carbocyclic or heterocyclic ring;

(vv) Ar represents a monocyclic or bicyclic aryl or heteroaryl ring, optionally substituted with between 1 and 3 substituents independently selected from halogen, $C_{1-5}$ alkoxy, $C_{1-5}$ alkyl, cyano, azido, nitro, $R^{22}R^{23}N$, $R^{24}SO_2$, $R^{24}OC=O$, $R^{25}R^{26}NC=O$, $CF_3$, $OCF_3$, $CF_3S$, and $C_{1-5}$ alkylthio; $R^{22}$ is hydrogen, $C_{1-5}$ alkyl, phenyl, benzyl, phenethyl, $C_{1-5}$ heterocyclyl, $C_{2-8}$ acyl, aroyl, $R^{24}OC=O$, $R^{25}R^{26}NC=O$, $R^{24}SO$, $R^{24}SO_2$, or $R^{25}R^{26}NSO_2$; $R^{23}$ is hydrogen or $C_{1-5}$alkyl;

(ww) alternatively, $R^{22}$ and $R^{23}$ can be taken together to form an optionally substituted 4- to 7-membered heterocyclic ring; $R^{24}$ is hydrogen or $C_{1-5}$ alkyl; $R^{25}$ and $R^{26}$ are independently hydrogen or $C_{1-5}$ alkyl; or, alternatively, $R^{25}$ and $R^{26}$ can be taken together to form an optionally substituted 4- to 7-membered heterocyclic; W is $NR^{27}$ or $CHR^{28}$; $R^{27}$ is hydrogen, $C_{1-5}$ alkyl, $R^{29}OC=O$, $R^{30}R^{31}NC=O$, $R^{29}SO$, $R^{29}SO_2$, or $R^{30}R^{31}NSO_2$; or, alternatively, $R^{27}$ and $R^1$ can be taken together to form an optionally substituted 5- or 6-membered heterocyclic ring, which ring may be saturated, unsaturated or aromatic; $R^{28}$ is hydrogen, hydroxy, $C_{1-5}$ heterocyclyl, phenyl, or $C_{1-5}$ alkyl; $R^{29}$ is $C_{1-5}$ alkyl; $R^{30}$ and $R^{31}$ are independently selected from hydrogen, $C_{1-5}$ alkyl; alternatively, $R^{30}$ and $R^{31}$ can be taken together to form an optionally substituted 4- to 7-membered heterocyclic;

(xx) one of $R^5$ and $R^6$ is H; $R^7$ and $R^8$ are taken together to form an optionally substituted 6-membered carbocyclic or heterocyclic ring; and Ar represents a monocyclic ring, optionally substituted with 1 to 2 substituents selected from halogen, $C_{1-5}$ alkyl, cyano, azido, nitro, $R^{22}R^{23}N$, $CF_3$ and $OCF_3$;

(yy) both $R^5$ and $R^6$ are each H, and Ar is a six membered ring substituted with between 1 and 2 substituents independently selected from halogen, methyl, $CF_3$, and $OCF_3$, said substituent or substituents being at the 4-position, or at the 3- and 4-positions;

(zz) a $R^7$ and $R^8$ taken together form tetrahydropyridinyl, optionally N-substituted with —(C=O)$R^4$, —$SO_2R^4$, or —(C=O)$NHR^{44}$;

(aaa) $X_f$ is C=O, $SO_2$, or $CHR^{1f}$, and $Y_f$ is O or $NR^{2f}$, where $R^{2f}$ is H, $C_{1-5}$ alkyl, $C_{2-5}$ heterocyclyl, $C_{1-5}$ cyanoalkyl, or ($C_{1-5}$ alkoxycarbonyl)$C_{1-5}$ alkylene;

(bbb) $R^{2f}$ is H, $C_{1-3}$ alkyl, or a $C_{2-5}$ heterocyclyl;

(ccc) $X_f$ is C=O, and $Y_f$ is O, $CHR^{2f}$ or $NR^{2f}$, where $R^{2f}$ is H, $C_{1-5}$ alkyl, $C_{2-5}$ heterocyclyl, $C_{1-5}$ cyanoalkyl, or ($C_{1-5}$ alkoxycarbonyl)$C_{1-5}$ alkylene;

(ddd) $X_f$ is C=O and $Y_f$ is O;

(eee) m is 0 and p is 0; m is 0 and p is 1; or m is 1 and p is 0;

(fff) p is 0;

(ggg) $R^z$ is H;

(hhh) $R^z$ is OH;

(iii) $R^z$ is absent;

(jjj) $R^{20}$ and $R^3$ taken together are a six-membered carbocyclic or heterocyclic ring optionally substituted with between 1 and 3 substituents independently selected from halo, $C_{1-3}$ alkoxy, di($C_{1-3}$ alkyl)amino, and $C_{2-5}$ acyl;

(kkk) each of $R^{20}$ and $R^3$ is H; and (lll) combinations of the above.

Specific preferred compounds include those in the Examples provided, such as:

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one; 1-(1-{3-[3-(3,4-Dichloro-phenyl)-5-methanesulfonyl-4,5,6,7-tetrahydro-pyrazolo[4,3-c]pyridin-1-yl]-propyl}-piperidin-4-yl)-1,3-dihydro-benzoimidazol-2-one; 3-(3,4-Dichloro-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid amide; 6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one; 3-(3,4-Dichloro-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide; [3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile; [3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetic acid ethyl ester; 5-Chloro-3-

(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one; 1-{3-[4-(6-Chloro-3-methyl-2-oxo-2,3-dihydro-benzoimidazol-1-yl)-piperidin-1-yl]-propyl}-3-(3,4-dichloro-phenyl)-1,4,6,7-tetrahydro-pyrazolo[4,3-c]pyridine-5-carboxylic acid amide; 3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dimethyl-1,3-dihydro-benzoimidazol-2-one; 3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one; 3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-methoxy-1,3-dihydro-imidazo[4,5-b]pyridin-2-one; 3-(4-Bromo-phenyl)-1-{2-hydroxy-3-[4-(5-methoxy-2-oxo-1,2-dihydro-imidazo[4,5-b]pyridin-3-yl)-piperidin-1-yl]-propyl}-1,4,6,7-tetrahydro-pyrazolo[4,3-c]pyridine-5-carboxylic acid amide; 3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one; 5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one; 6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one; 1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one; 4-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one; 4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one; and 1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one.

Furthermore, preferred compounds include those wherein Ar or $Ar_1$ is selected from 4-trifluoromethylphenyl, 4-bromophenyl, 4-chlorophenyl, 4-chloro-3-methylphenyl and 3,4-dichlorophenyl.

More preferred compounds include Examples 37 and 50.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, 3$^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(/midazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protection Groups

Examples of special NH protective groups include N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di (4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N'N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

C. Synthesis

The compounds of the present invention may be prepared by conventional synthetic organic chemistry and by matrix or combinatorial methods according to Schemes 1 to 10 below, and Examples 1 to 31. Those of ordinary skill in the art will be able to modify and adapt the guidance provided herein to make the disclosed compounds.

Scheme 1

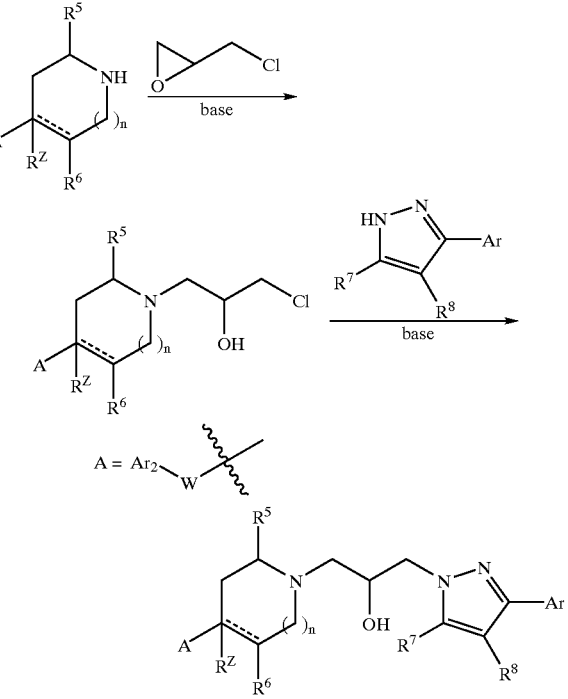

Scheme 2
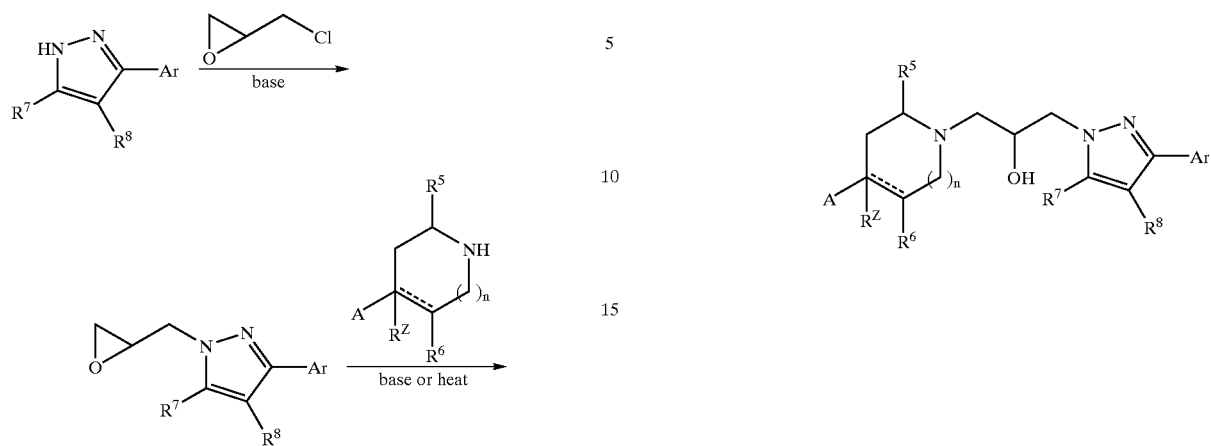
Scheme 3
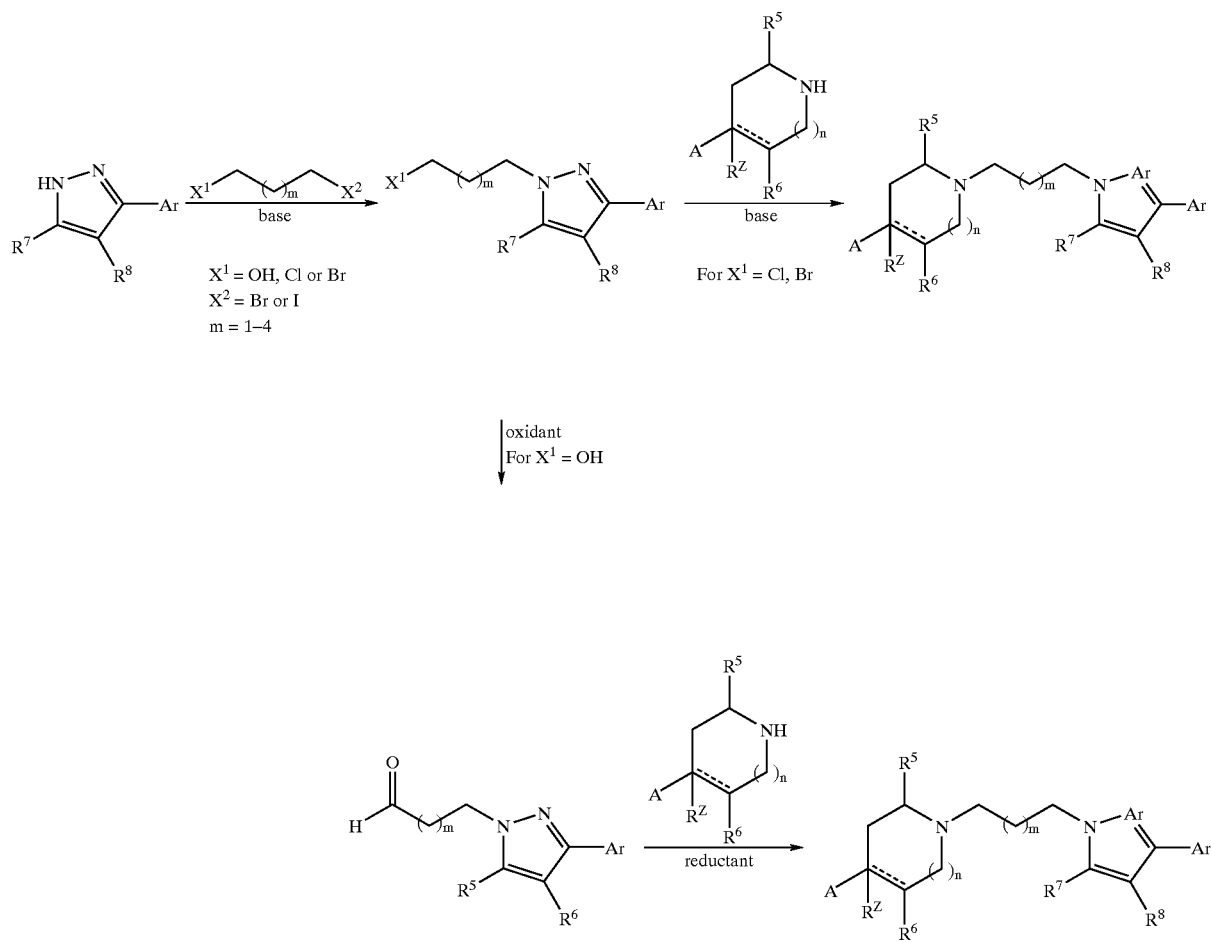

Scheme 4
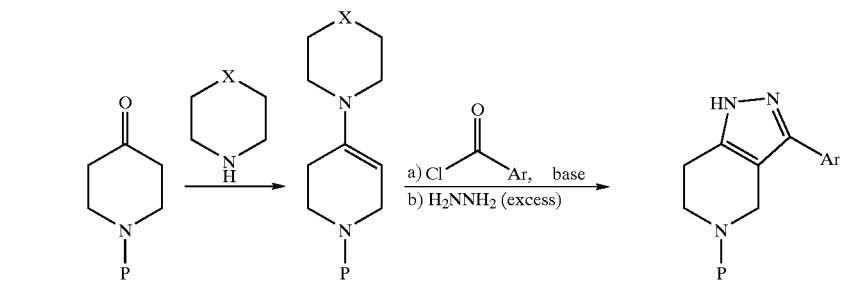
P = SO₂Me, BOC, EtOCO, Ac, etc.
X = O, CH₂, covalent bond
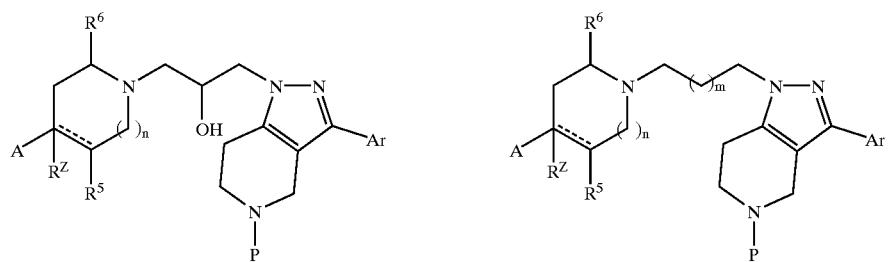
Scheme 5
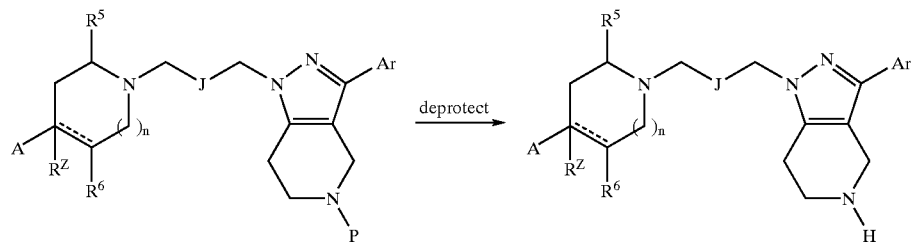
P = BOC, EtOCO, Ac, etc.
J = (CH₂)$_m$ or CHOH
m = 1–4
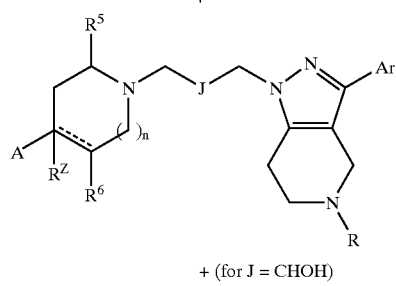
+ (for J = CHOH)
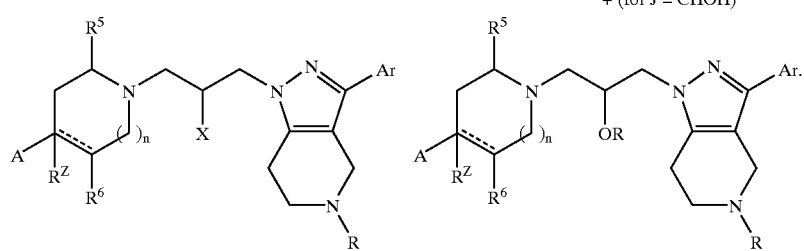

Scheme 6
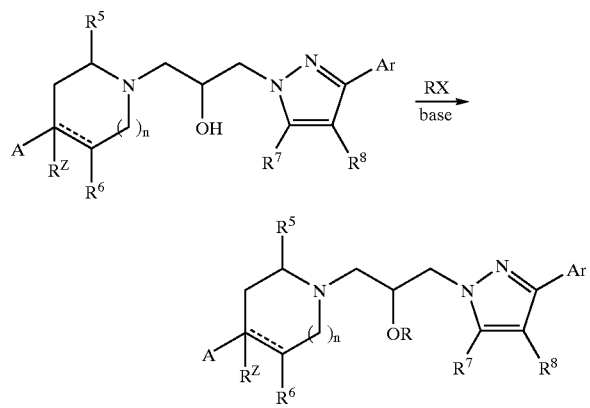
Scheme 7
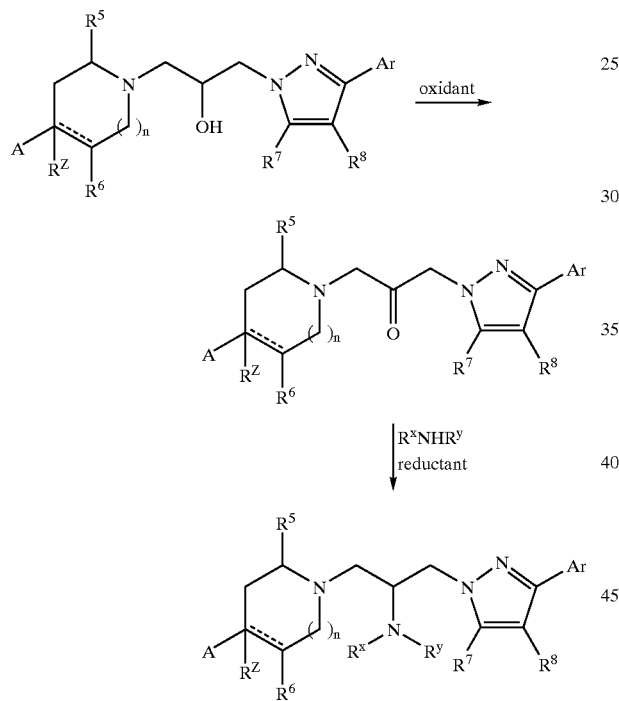
Scheme 8
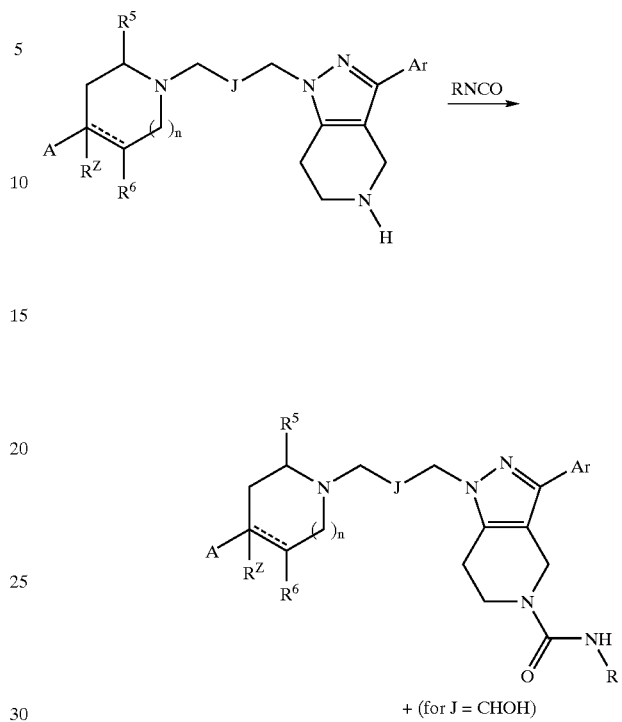
+ (for J = CHOH)
Scheme 9
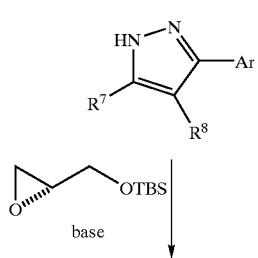

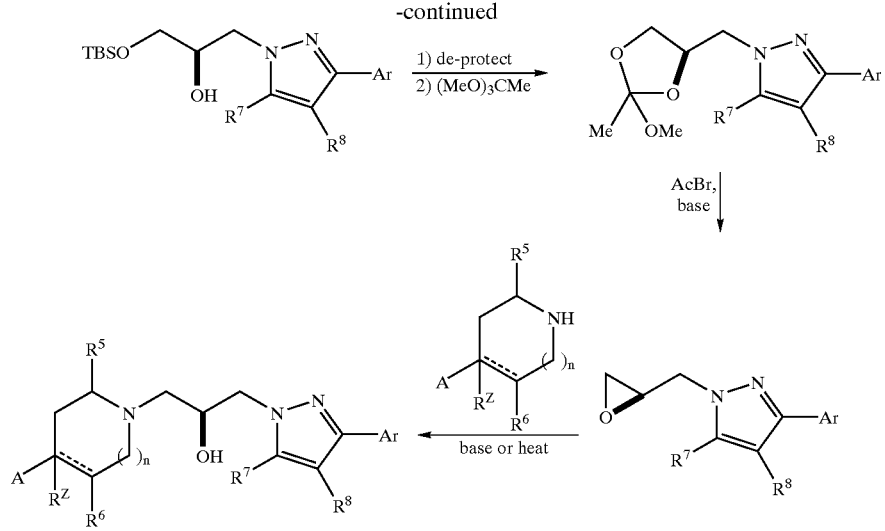

Scheme 10

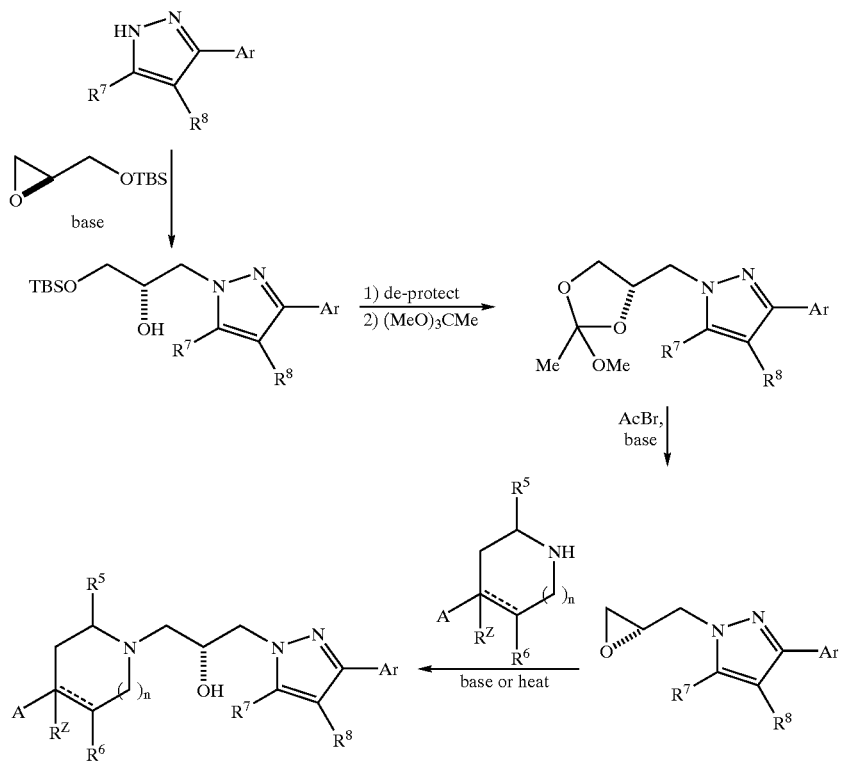

D. Formulation and Administration

The present compounds inhibit the proteolytic activity of human cathepsin S and therefore are useful as a medicine especially in methods for treating patients suffering from disorders or conditions which are modulated or regulated by the inhibition of cathepsin S activity.

The invention features a method for treating a subject with a condition mediated by cathepsin S, said method comprising administering to the subject a therapeutically effective amount of a pharmaceutical composition comprising a compound of the invention. The invention also provides a method for inhibiting cathepsin S activity in a subject, wherein the method comprises administering to the subject a therapeutically effective amount of a pharmaceutical composition comprising a compound of the invention. A third method is a method for treating an autoimmune disease, or inhibiting the progression of an autoimmune disease, in a subject, said method comprising administering to the subject a therapeutically effective amount of a pharmaceutical composition comprising a disclosed compound. The autoimmune disease can be, for example, lupus, rheumatoid arthritis, or preferably, asthma. The invention also provides a method for treating or inhibiting the progression of tissue transplant rejection in a subject, the method comprising administering to the subject a therapeutically effective amount of a pharmaceutical composition comprising a compound of the invention. The administration step can occur before, during, and/or after a tissue transplant procedure.

In view of their inhibitory effect on the proteolytic activity of human cathepsin S the compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula I, due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active non-toxic acid addition salt forms which the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates which the disclosed componds, as well as the salts thereof, are able to form. Such solvates are for example hydrates, alcoholates and the like. Conversely the salt form can be converted by treatment with alkali into the free base form.

Stereoisomeric form defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the cathepsin S enzyme could easily determine the effective daily amount from the test results presented hereinafter and other information. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the preparation, characterization, and use of the disclosed compounds.

E. EXAMPLES

Example 1

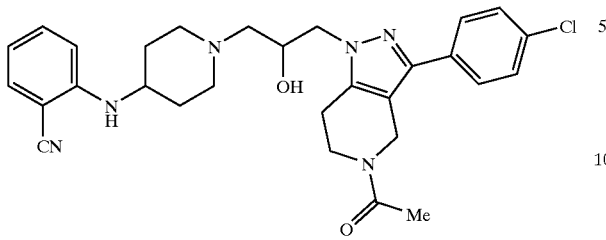

2-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-ylamino)-benzonitrile A. 1-[3-(4-Chloro-phenyl)-1,4,6,7-tetrahydro-pyrazolo[4,3-c]pyridin-5-yl]-ethanone.

To a stirred solution of 50 g (0.35 mol) of N-acetyl-4-piperidone and 31 g (0.35 mol) of morpholine in benzene (350 mL) was added a catalytic amount (~0.25 g) of p-toluenesulfonic acid. The mixture was heated to reflux for 10 h with a Dean-Stark trap. The solvent was removed under reduced pressure to give a brown oil. The crude product was diluted with $CH_2Cl_2$ (175 mL) and 50.0 mL (0.35 mol) of $Et_3N$ was added. The mixture was cooled to 0° C. and a solution of 45.0 mL (0.35 mol) of 4-chlorobenzoyl chloride in $CH_2Cl_2$ (50 mL) was added slowly by dropping funnel over 1 h. The mixture was allowed to warm to room temperature and stirred overnight. The reaction was then diluted with 1 N HCl (150 mL) and stirred vigorously for 3 h. The aqueous layer was extracted with $CH_2Cl_2$ (3×250 mL) and the combined extracts were dried over $Na_2SO_4$ and the solvent was removed under reduced pressure. The crude oil was diluted with EtOH (350 mL) and cooled to 0° C. To this stirred solution was slowly added 33.0 mL (1.06 mol) of hydrazine and the mixture was allowed to warm to room temperature and stir overnight during which time a white precipitate formed. The volume of the reaction was reduced to ~150 mL and EtOAc (750 mL) was added to the mixture. The suspension was stirred vigorously for 2 h and was filtered then washed with EtOAc (2×200 mL) and dried under vacuum to afford 41.4 g (42% over 3 steps) of a pale yellow solid. TLC (silica, 5% MeOH/$CH_2Cl_2$): $R_f$=0.3. MS (electrospray): m/z calculated for $C_{14}H_{14}ClN_3O$ $[M+H]^+$ 276.08, observed 276.0. $^1H$ NMR (400 MHz, $CDCl_3$, a mixture of amide rotamers): 7.65 (d, J=8.4 Hz, 2H), 7.64 (d, J=9.3 Hz, 2H), 7.58 (d, J=10.5 Hz, 2H), 7.55 (d, J=8.5 Hz, 2H), 4.94 (s, 2H), 4.78 (s, 2H), 4.08 (t, J=5.9 Hz, 2H), 3.90 (t, J=5.8 Hz, 2H), 3.02 (t, J=5.8 Hz, 2H), 2.96 (t, J=5.9 Hz, 2H), 2.36 (s, 3H), 2.31 (s, 3H).

B. 1-[3-(4-Chloro-phenyl)-1-oxiranylmethyl-1,4,6,7-tetrahydro-pyrazolo[4,3-c]pyridin-5-yl]-ethanone.

To a stirred solution of 1.00 g (3.63 mmol) of 1-[3-(4-chloro-phenyl)-1,4,6,7-tetrahydro-pyrazolo[4,3-c]pyridin-5-yl]-ethanone and 2.85 mL (36.3 mmol) of epichlorohydrin was added 1.30 g (3.99 mmol) of solid $Cs_2CO_3$. The reaction was stirred for 48 h and the solvent was removed under reduced pressure. The residue was then diluted with $H_2O$ (50 mL) and EtOAc (50 mL). The layers were separated, and the organic layer was washed with $H_2O$ (25 mL) and brine (25 mL), dried over $Na_2SO_4$ and the solvent was removed under reduced pressure. Purification by flash chromatography (silica, 0–15% acetone/$CH_2Cl_2$) afforded 0.72 g (60%) of a white solid. TLC (silica, 5% MeOH/$CH_2Cl_2$): $R_f$=0.5. MS (electrospray): m/z calculated for $C_{17}H_{18}ClN_3O_2$ $[M+H]^+$, 332.11, observed 332.0. $^1H$ NMR (400 MHz, $CDCl_3$, a mixture of amide rotamers): 7.60 (d, J=8.6 Hz, 2H), 7.54 (d, J=8.4 Hz, 2H), 7.40 (d, J=8.6 Hz, 2H), 7.36 (d, J=8.4 Hz, 2H), 4.80 and 4.73 (A and B of AB quartet, $J_{ab}$=15.8 Hz, 2H), 4.60 (s, 2H), 4.47 (dd, J=15.3, 2.5 Hz, 1H), 4.42 (dd, J=15.0, 2.7 Hz, 1H), 4.11 (dd, J=5.3, 2.5 Hz, 1H), 4.08 (dd, J=5.1, 3.3 Hz, 1H), 3.99–3.85 (m, 2H), 3.73 (dt, J=5.9, 1.8 Hz, 2H), 3.37 (m, 2H), 2.87–2.80 (m, 3H), 2.80–2.69 (m, 3H), 2.53 (dd, J=4.7, 2.5 Hz, 1H), 2.48 (dd, J=4.6, 2.6, 1H), 2.19 (s, 3H), 2.15 (s, 3H).

C. 1-{3-(4-Chloro-phenyl)-1-[3-(1,4-dioxa-8-aza-spiro[4.5]dec-8-yl)-2-hydroxy-propyl]-1,4,6,7-tetrahydro-pyrazolo[4,3-c]pyridin-5-yl}-ethanone.

To a stirred solution of 3.20 g (9.64 mmol) of 1-[3-(4-chloro-phenyl)-1-oxiranylmethyl-1,4,6,7-tetrahydro-pyrazolo[4,3-c]pyridin-5-yl]-ethanone and 2.07 g (14.5 mmol) of 1,4-dioxa-8-azaspiro[4.5]decane in $CH_2Cl_2$ (65 mL) was added 1.79 g (2.89 mmol) of $Yb(OTf)_3 \cdot H_2O$. The reaction was stirred overnight and was then directly purified by flash chromatography (silica, 0–5% MeOH/$CH_2Cl_2$) to afford 3.70 g (81%) of the title compound. TLC (silica, 5% MeOH/$CH_2Cl_2$): $R_f$=0.35. MS (electrospray), m/z calculated for $C_{24}H_{31}ClN_4O_4$ $[M^++H]$, 475.20, observed 475.1.

D. 1-{3-[5-Acetyl-3-(4-chloro-phenyl)-4,5,6,7-tetrahydro-pyrazolo[4,3-c]pyridin-1-yl]-2-hydroxy-propyl}-piperidin-4-one.

A suspension of 0.50 g (0.96 mmol) of 1-{3-(4-chloro-phenyl)-1-[3-(1,4-dioxa-8-aza-spiro[4.5]dec-8-yl)-2-hydroxy-propyl]-1,4,6,7-tetrahydro-pyrazolo[4,3-c]pyridin-5-yl}-ethanone in 1 N HCl (2.0 mL) was heated to 65° C. for 48 h in a sealed vessel. The reaction was allowed to cool to room temperature and was diluted with $CHCl_3$ (20 mL) and saturated $NaHCO_3$ (20 mL). The aqueous phase was extracted with $CHCl_3$ (2×10 mL) and the combined organic extracts were dried over $Na_2SO_4$ and the solvent was removed under reduced pressure. The crude material was then diluted with $Ac_2O$ (3.0 mL) and was stirred for 48 h. The solvent was removed under reduced pressure and the crude material was pumped down overnight. The resulting solid was dissolved in MeOH (5.0 mL) and a catalytic amount (0.05 g) of $K_2CO_3$ was added to the mixture and stirring was continued overnight. The reaction was then diluted with $H_2O$ (20 mL) and $CH_2Cl_2$ (20 mL) and the layers were separated. The aqueous phase was extracted with $CH_2Cl_2$ (2×10 mL) and the combined organic extracts were dried over $Na_2SO_4$ and the solvent was removed under reduced pressure. Purification by flash chromatography (silica, 0–10% MeOH/$CH_2Cl_2$) afforded 0.29 g (65% over 3 steps) of a white solid. TLC (silica, 5% MeOH/$CH_2Cl_2$): $R_f$=0.35. MS (electrospray); m/z calculated for $C_{22}H_{27}ClN_4O_3$, $[M+H]^+$, 431.18, observed 431.1. $^1H$ NMR (400 MHz, $CDCl_3$, a mixture of amide rotamers): 7.59 (d, J=8.3 Hz, 1H), 7.53 (d, J=8.6 Hz, 1H), 7.41 (d, J=8.5 Hz, 1H), 7.37 (d, J=8.5 Hz, 1H), 4.85 and 4.73 (A and B of AB quartet, $J_{ab}$=15.8 Hz, 1H), 4.62 (s, 1H), 4.26–4.12 (m, 2H), 4.09–3.68 (m, 4H), 3.49 (s, 1.5H), 3.28 (s, 1.5H).

E. 2-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-ylamino)-benzonitrile.

To a stirred solution of 50.0 mg (116.0 µmol) of 5-1-{3-[5-acetyl-3-(4-chloro-phenyl)-4,5,6,7-tetrahydro-pyrazolo[4,3-c]pyridin-1-yl]-2-hydroxy-propyl}-piperidin-4-one and 9.6 mg (82.5 µmol) of 2-aminobenzonitrile in AcOH (0.5 mL) was added 130.0 mg (917.0 µmol) $Na_2SO_4$ and the reaction was allowed to stir for 1 h. To this mixture was added 58.0 mg (275.0 µmol) $NaBH(OAc)_3$ and the reaction was stirred for 48 h. The mixture was diluted with $CH_2Cl_2$ (20 mL) and saturated NaHCO$_3$ (20 mL). The aqueous phase was extracted with CH$_2$Cl$_2$ (2×10 mL) and the combined organic extracts were dried over Na$_2$SO$_4$ and the solvent was removed under reduced pressure. Purification by flash chromatography (silica, 0–5% MeOH/CH$_2$Cl$_2$) afforded 9.0 mg (20%) of a white solid. TLC (silica, 5% MeOH/CH$_2$Cl$_2$): R$_f$=0.2. MS (electrospray): m/z calculated for C$_{29}$H$_{33}$ClN$_6$O$_2$, [M+H]$^+$, 533.24, observed 533.3. $^1$H NMR (400 MHz, CDCl$_3$, a mixture of amide rotamers): 7.58 (d, J=8.6 Hz, 1H), 7.52 (d, J=8.4 Hz, 1H), 7.43–7.34 (m, 4H), 6.69 (dt, J=7.6, 4.0 Hz, 1H), 6.64 (d, J=8.6 Hz, 1H), 4.83 and 4.73 (A and B of AB quartet, J$_{ab}$=15.7 Hz, 1H), 4.61 (s, 1H), 4.44 (d, J=7.3 Hz, 1H), 4.33–4.14 (m, 2H), 4.11–3.84 (m, 2H), 3.83–3.67 (m, 1H), 3.55–3.43 (m, 1H), 3.17–2.94 (m, 1H), 2.93–2.75 (m, 2H), 2.74–2.54 (m, 2H), 2.21 (s, 1.5H), 2.16 (s, 1.5H), 2.23–1.53 (m, 9H).

Example 2

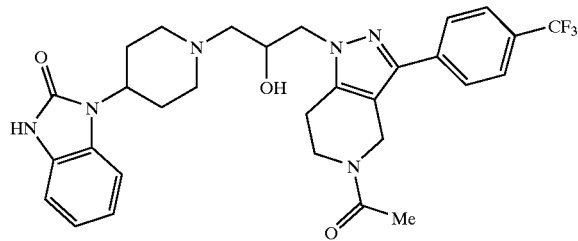

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one A. 1-[3-(4-Trifluoromethyl-phenyl)-1,4,6,7-tetrahydro-pyrazolo[4,3-c]pyridin-5-yl]-ethanone.

A solution of N-acetyl-4-piperidone (2.82 g, 20 mmol), morpholine (1.93 mL, 22 mmol) and p-toluenesulfonic acid (5 mg) in benzene (8.5 mL) was refluxed for 8 h in a Dean-Stark apparatus. The solvent was removed and the residue dissolved in CH$_2$Cl$_2$ (20 mL). Triethylamine (3.1 mL) was added and p-trifluoromethylbenzoyl chloride (3.27 mL, 22 mmol) in CH$_2$Cl$_2$ (4 mL) was added dropwise into the solution at 0° C. The reaction mixture was stirred at 25° C. for 24 h and diluted with aqueous HCl (5%, 25 mL). After stirring for another 30 min, the organic layer was separated, washed with H$_2$O (20 mL), dried (Na$_2$SO$_4$), and concentrated. The residue was dissolved in EtOH (95%, 18 mL) and treated at 0° C. with hydrazine (2.9 mL, 60 mmol). The mixture was stirred at 25° C. for 3 h and H$_2$O (4 mL) was added. Most of the volatiles were removed and the residue extracted with CH$_2$Cl$_2$ (50 mL). The organic layer was separated, washed with H$_2$O (20 mL), dried over Na$_2$SO$_4$, and concentrated. Column chromatography (silica, 5% MeOH/CH$_2$Cl$_2$) provided 5.1 g (83%) of a white powder. TLC (silica, 10% MeOH/CH$_2$Cl$_2$): R$_f$=0.30. MS (electrospray): m/z 332.0 ([M+Na]$^+$, C$_{15}$H$_{14}$F$_3$N$_3$O requires 309.1). $^1$H NMR (CDCl$_3$, 400 MHz, a mixture of two rotamers): 7.73–7.67 (m, 4H), 4.85 (s, 1.2H), 4.68 (s, 0.8H), 3.96 (t, J=4.5 Hz, 0.8H), 3.78 (t, J=4.5 Hz, 1.2H), 2.89 (t, J=4.5 Hz, 1.2H), 2.83 (t, J=4.5 Hz, 0.8H), 2.23 (s, 1.8H), 2.18 (s, 1.2H).

B. 1-[1-Oxiranylmethyl-3-(4-trifluoromethyl-phenyl)-1,4,6,7-tetrahydro-pyrazolo[4,3-c]pyridin-5-yl]-ethanone.

A solution of 1-[3-(4-trifluoromethyl-phenyl)-1,4,6,7-tetrahydro-pyrazolo[4,3-c]pyridin-5-yl]-ethanone(2.4 g, 7.77 mmol) in DMF (15 mL) was treated with cesium carbonate (5.05 g, 15.5 mmol) and epichlorohydrin (6.1 mL, 77.7 mmol) at 25° C. and stirred for 24 h before it was diluted with EtOAc (100 mL) and H$_2$O (50 mL). The organic layer was separated, washed with H$_2$O (2×50 mL), brine (50 mL), dried over Na$_2$SO$_4$, and concentrated. Column chromatography (silica, 10% acetone/CH$_2$Cl$_2$) provided 2.30 g (81%) of a white powder. TLC (silica, 10% MeOH/CH$_2$Cl$_2$): R$_f$=0.35. MS (electrospray): m/z 388.0 ([M+Na]$^+$, C$_{18}$H$_{18}$F$_3$N$_3$O$_2$ requires 365.1). $^1$H NMR (CDCl$_3$, 400 MHz, a mixture of two rotamers): 7.77 and 7.63 (AB pattern, J$_{ab}$=8.2 Hz, 2H), 7.71 and 7.67 (AB pattern, J$_{ab}$=8.4 Hz, 2H), 4.82 and 4.76 (AB pattern, J$_{ab}$=15.5 Hz, 1.2H), 4.58 (s, 0.8H), 4.45–4.35 (m, 1H), 4.08–4.02 (m, 1H), 3.92–3.80 (m, 1H), 3.70–3.63 (m, 1H), 3.30 (m, 1H), 2.80–2.67 (m, 3H), 2.48–2.42 (m, 1H), 2.13 (s, 1.3H), 2.08 (s, 1.7H).

C. 1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one.

A solution of 1-[1-oxiranylmethyl-3-(4-trifluoromethyl-phenyl)-1,4,6,7-tetrahydro-pyrazolo[4,3-c]pyridin-5-yl]-ethanone (1.17 g, 3.2 mmol) in DMF (10 mL) was treated with ytterbium(III) triflate (0.4 g, 0.64 mmol) and 4-(2-keto-1-benzimidazolinyl)piperidine (1.04 g, 4.8 mmol) at 25° C. and stirred for 48 h before it was diluted with CH$_2$Cl$_2$ (100 mL) and H$_2$O (50 mL). The organic layer was separated, washed with H$_2$O (2×50 mL), dried over Na$_2$SO$_4$, and concentrated. Flash column chromatography (silica, 5% MeOH/CH$_2$Cl$_2$) afforded 1.71 g (92%) of a white powder. TLC (silica, 10% MeOH/CH$_2$Cl$_2$): R$_f$=0.25. MS (electrospray): m/z 583.5 ([M+H]$^+$, C$_{30}$H$_{33}$F$_3$N$_6$O$_3$ requires 582.3). $^1$H NMR (CDCl$_3$, 400 MHz, a mixture of two rotamers): 9.30 (br s, 0.5H), 9.25 (br s, 0.5H), 7.82 and 7.68 (AB pattern, J$_{ab}$=8.2 Hz, 2H), 7.76 and 7.72 (AB pattern, J$_{ab}$=8.4 Hz, 2H), 7.25–7.05 (m, 4H), 4.92 and 4.80 (AB pattern, J$_{ab}$=15.6 Hz, 1.1H), 4.70 (s, 0.9H), 4.40–3.70 (m, 7H), 3.20–2.82 (m, 4H), 2.60–2.45 (m, 4H), 2.35–2.25 (m, 1H), 2.25 (s, 1.5H), 2.20 (s, 1.5H), 1.90–1.87 (m, 2H).

Example 3

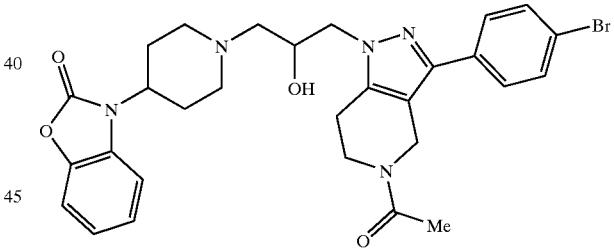

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3H-benzooxazol-2-one A. 1-[3-(4-Bromo-phenyl)-1,4,6,7-tetrahydro-pyrazolo[4,3-c]pyridin-5-yl]-ethanone.

A flask equipped with a Dean-Stark trap, was charged with N-acetyl-4-piperidone (100.1 g, 709 mmol), piperidine (68 mL, 779 mmol), pTsOH (3.7 g) and benzene (500 mL). The mixture was heated to 125° C. After 17 h the mixture was allowed to cool and divided into two portions. A solution of p-bromobenzoyl chloride (70.0 g, 319 mmol) in CH$_2$Cl$_2$ (400 mL) was added dropwise to a 0° C. solution of the enamine (ca. 355 mmol) in CH$_2$Cl$_2$ (320 mL) over 15 h. The mixture was then allowed to warm to 23° C. and stirred for an additional 5 h. The solution was treated with 1 N HCl (500 mL) and stirred vigorously for 1.5 h. The layers were separated and the aqueous layer was extracted with CH$_2$Cl$_2$ (2×300 mL). The combined extracts were washed with sat. aqueous NaHCO$_3$ (300 mL), H$_2$O (300 mL), brine (300 mL), dried over Na$_2$SO$_4$ and concentrated. The residue was dissolved in MeOH (300 mL) and treated with NH$_2$NH$_2$ (50.0 mL, 1.59 mol). The mixture was stirred for 17 h before the precipitate formed was collected by filtration and air dried to give 52 g (50%) of the title compound which was suitable for use without further purification. TLC (silica, 5% MeOH/CH$_2$Cl$_2$): R$_f$=0.3. MS (electrospray): m/z calculated for C$_{14}$H$_{15}$$^{79}$BrN$_3$O [M+H]$^+$, 320.04. found 320. $^1$H NMR (CD$_3$OD/CDCl$_3$, 400 MHz, a mixture of amide rotamers): 7.53 and 7.35 (A and B of AA'BB', J=8.5 Hz, 2H), 7.51 and 7.39 (A and B of AA'BB', J=8.6 Hz, 2H), 4.72 (s, 2H), 4.58 (s, 2H), 3.85 (t, J=5.9 Hz, 2H), 3.71 (t, J=5.8 Hz, 2H), 2.81, (t, J=5.8 Hz, 2H), 2.74, (t, J=5.8 Hz, 2H), 2.16 (s, 3H), 2.11 (s, 3H).

B. 1-[3-(4-Bromo-phenyl)-1-oxiranylmethyl-1,4,6,7-tetrahydro-pyrazolo[4,3-c]pyridin-5-yl]-ethanone.

Cs$_2$CO$_3$ (11.58 g, 35.5 mmol) was added to a solution of 1-[3-(4-bromo-phenyl)-1,4,6,7-tetrahydro-pyrazolo[4,3-c]pyridin-5-yl]-ethanone (7.59 g, 23.7 mmol) and epichlorohydrin (20 mL, 234 mmol) in DMF (100 mL). The mixture was stirred for 18 h then diluted with EtOAc (800 mL) and washed with saturated aqueous NaHCO$_3$ (2×100 mL), H$_2$O (2×100 mL), and brine (100 mL). The NaHCO$_3$ layer was extracted with EtOAc (2×150 mL). The combined washes were extracted with EtOAc (2×100 mL). The combined extracts were dried over Na$_2$SO$_4$ and concentrated. Column chromatography (silica, 10–20% acetone/CH$_2$Cl$_2$) afforded 4.98 g (56%) of the title compound. HPLC, t$_R$=4.90 min. (Reverse phase conditions: HP 1100 LCMS, Phenomenex luna 2.1×150 mm column, 60% MeOH/H$_2$O (0.5% AcOH) to 90% MeOH/H$_2$O (0.5% AcOH), held at initial conditions for 2 min then ramped to final conditions over 5 min.) MS (electrospray): m/z calculated for C$_{17}$H$_{19}$$^{79}$BrN$_3$O$_2$, [M+H]$^+$, 376.07. found 376.0. $^1$H NMR (CDCl$_3$, 400 MHz, a mixture of amide rotamers): 7.47 (d with fine splittings, J=8.5, Hz, 2H), 7.44 (m, 4H), 7.38 (d with fine splittings, J=8.5, Hz, 2H), 4.71 and 4.64 (A and B of AB quartet, J$_{ab}$=15.7 Hz, 2H), 4.51 (s, 2H), 4.39 (dd, J=15.1, 2.5 Hz, 1H), 4.34 (dd, J=15.0, 2.9 Hz, 1H), 4.02 (dd, J=5.2, 3.9 Hz, 1H), 3.98 (dd, J=5.3, 3.7 Hz, 1H), 3.83 (m, 2H), 3.64 (m, 2H), 3.25 (br m, 2H), 2.80–2.60 (m, 6H), 2.46 (dd, J=4.6, 2.6 Hz, 1H), 2.38 (dd, J=4.6, 2.6 Hz, 1H), 2.10 (s, 3H), 2.06 (s, 3H).

C. 4-(2-Oxo-benzooxazol-3-yl)-piperidine-1-carboxylic acid tert-butyl ester.

To a stirred solution of 1.00 g (5.01 mmol) of tert-butyl 4-oxo-1-piperidinecarboxylate and 0.55 g (5.01 mmol) of 2-aminophenol in CH$_2$Cl$_2$ (15 mL) under nitrogen at rt was added 1.62 g (7.52 mmol) of NaBH(OAc)$_3$ in one portion and the mixture was stirred for 14 h. The mixture was diluted with CH$_2$Cl$_2$ (50 mL) and saturated NaHCO$_3$ (75 mL) and the layers were separated. The aqueous layer was extracted with CH$_2$Cl$_2$ (2×25 mL) and the combined organic layers were washed with brine, dried over Na$_2$SO$_4$, and the solvent was removed under reduced pressure. The crude solid was diluted with CH$_2$Cl$_2$ (15 mL) and 0.89 g (5.51 mmol) of carbonyidiimidazole was added in one portion and mixture was stirred for 16 h. The mixture was diluted with CH$_2$Cl$_2$ (50 mL) and 1 N HCl (50 mL) and the layers were separated. The aqueous layer was extracted with CH$_2$Cl$_2$ (2×25 mL) and the combined organic layers were washed with brine, dried over Na$_2$SO$_4$, and the solvent was removed under reduced pressure. Flash chromatography (silica, 0–5% acetone/CH$_2$Cl$_2$) afforded 1.59 g (99%) of a white solid. TLC (silica, 5% acetone/CH$_2$Cl$_2$): R$_f$=0.6. MS (electrospray): m/z calculated for C$_{17}$H$_{22}$N$_2$O$_4$, [M+Na]$^+$, 341.1, observed 341.1.

D. 3-Piperidin-4-yl-3H-benzooxazol-2-one.

To a stirred solution of 1.00 g (2.87 mmol) of 4-(2-oxo-benzooxazol-3-yl)-piperidine-1-carboxylic acid tert-butyl ester in CH$_2$Cl$_2$ (6.0 mL) was added TFA (6.0 mL) and the mixture was stirred for 12 h. The solvents were removed under reduced pressure and the crude solid was diluted in MeOH (10 mL) and saturated NaHCO$_3$ (15 mL) was added to the mixture and stirring was continued for 10 min. The solution was diluted with CH$_2$Cl$_2$ (30 mL) and the layers were separated. The aqueous phase was extracted with CH$_2$Cl$_2$ (2×20 mL) and the organic layers were combined, dried over Na$_2$SO$_4$ and the solvent was removed under reduced pressure to afford 1.02 g (88%) of a pale yellow solid. TLC (silica, 10% MeOH/CH$_2$Cl$_2$): R$_f$=0.1. MS (electrospray): m/z calculated for C$_{12}$H$_{14}$N$_2$O$_2$, [M+H]$^+$, 219.11, observed 219.1.

E. 3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3H-benzooxazol-2-one.

To a stirred mixture of 0.025 g (0.066 mmol) of 3-piperidin-4-yl-3H-benzooxazol-2-one and 0.015 g (0.066 mmol) of 1-[3-(4-bromo-phenyl)-1-oxiranylmethyl-1,4,6,7-tetrahydro-pyrazolo[4,3-c]pyridin-5-yl]-ethanone in EtOH (0.5 mL) was added 0.01 mL (0.066 mmol) of Et$_3$N. The mixture was heated to 80° C. in a sealed vessel for 16 h. The reaction was cooled and the solvent was removed under reduced pressure. Flash chromatography (silica, 0–5% MeOH/CH$_2$Cl$_2$) afforded 0.030 g (79%) of a white foam. TLC (silica, 5% MeOH/CH$_2$Cl$_2$): R$_f$=0.4. MS (electrospray): m/z calculated for C$_{29}$H$_{32}$BrN$_5$O$_4$, [M+H]$^+$, 594.16, observed 594.2. $^1$H NMR (400 MHz, CDCl$_3$, a mixture of amide rotamers): 7.60–7.43 (m, 4H), 7.23–7.06 (m, 4H), 4.83 and 4.73 (A and B of AB quartet, J$_{ab}$=15.4 Hz, 1H), 4.61 (s, 1H), 4.38–3.66 (m, 7H), 3.37–3.02 (m, 2H), 2.99–2.28 (m, 6H), 2.21 (s, 1.5H), 2.16 (s, 1.5H), 1.99–1.83 (m, 3H).

Example 4

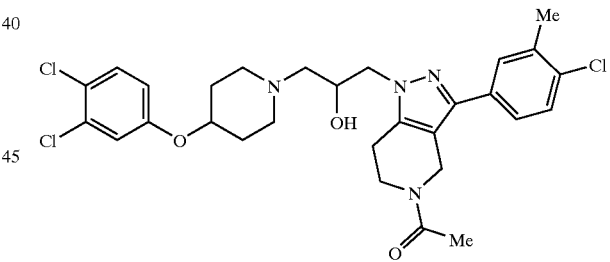

1-(3-(4-Chloro-3-methyl-phenyl)-1-{3-[4-(3,4-dichloro-phenoxy)-piperidin-1-yl]-propyl}-1,4,6,7-tetrahydro-pyrazolo[4,3-c]pyridin-5-yl)-ethanone A. 1-[3-(4-Chloro-3-methyl-phenyl)-1,4,6,7-tetrahydro-pyrazolo[4,3-c]pyridin-5-yl]-ethanone.

To a stirred solution of 1-acetyl-4-piperidone (3 g, 0.021 mol) and morpholine (1.86 g, 0.21 mol) in benzene (21 mL) was added a catalytic amount (~0.015 g) of p-toluenesulfonic acid. The mixture was heated to reflux for 10 h under a Dean-Stark trap. The solvent was removed under reduced pressure to give a brown oil. The crude product was diluted with CH$_2$Cl$_2$ (10.5 mL), and Et$_3$N (3.0 mL, 0.021 mol) was added. The mixture was cooled to 0° C., and a solution of 3-methyl-4-chlorobenzoyl chloride (2.7 mL, 0.021 mol) in CH$_2$Cl$_2$ (3.0 mL) was added slowly by dropping funnel over 1 h. The mixture was allowed to warm to room temperature and stir overnight. The reaction mixture was then diluted with 1 N HCl (9.0 mL) and stirred vigorously for 3 h. The aqueous layer was extracted with $CH_2Cl_2$ (3×15 mL). The combined extracts were dried over $Na_2SO_4$, and the solvent was removed under reduced pressure. The crude oil was diluted with EtOH (21 mL) and cooled to 0° C. To this stirred solution was slowly added hydrazine (2.0 mL, 0.064 mol), and the mixture was allowed to warm to room temperature and stir overnight, during which time a white precipitate formed. The volume of the reaction mixture was reduced to ~9 mL, and EtOAc (45 mL) was added. The suspension was stirred vigorously for 2 h and was filtered then washed with EtOAc (2×12 mL) and dried under vacuum to afford 4.93 g (81% over 3 steps) of a pale yellow solid. TLC (silica, 10% acetone/$CH_2Cl_2$): $R_f$=0.2. MS (electrospray): exact mass calculated for $C_{15}H_{16}ClN_3O$, 289.10. m/z found, 290.1 [M$^+$+H].

B. 1-[3-(4-Chloro-3-methyl-phenyl)-1-oxiranylmethyl-1,4,6,7-tetrahydro-pyrazolo[4,3-c]pyridin-5-yl]-ethanone.

$Cs_2CO_3$ (11 g, 33.8 mmol) was added to a solution of 1-[3-(4-chloro-3-methyl-phenyl)-1,4,6,7-tetrahydro-pyrazolo[4,3-c]pyridin-5-yl]-ethanone (4.9 g, 16.9 mmol) in DMF (49 mL), which was then stirred for 15 min. Epichlorohydrin (13.2 mL, 169 mmol) was added, and the mixture was stirred under $N_2$ at room temperature for 16 h. EtOAc (250 mL) was added to the reaction mixture, which was then stirred for 5 min. The resulting solution was washed with water (2×50 mL) and brine (1×50 mL). The organic extracts were dried over $Na_2SO_4$ and concentrated. The residue was purified by column chromatography (silica, 10–20% acetone/$CH_2Cl_2$) to obtain 3.8 g (65%) of a white solid. TLC (silica, 10% acetone/$CH_2Cl_2$): $R_f$=0.3. MS (electrospray): exact mass calculated for $C_{18}H_{20}ClN_3O_2$, 345.12. m/z found, 346.1 [M$^+$+H], 368.0 [M$^+$+Na], C. 4-(3,4-Dichlorophenoxy)-piperidinium trifluoroacetate.

A suspension of 0.69 g (20.0 mmol) of triphenylphosphine (polymer supported, 3 mmol P/g) in $CH_2Cl_2$ (4.0 mL) was stirred for 15 min to swell the resin. To this suspension was added 0.20 g (1.00 mmol) of 1-tert-butoxycarbonyl-4-piperidinol, 0.16 g (1.00 mmol) of 3,4-dichlorophenol, and 0.35 g (1.50 mmol) of di-tert-butyl azodicarboxylate. The reaction was stirred for 4 h and was filtered and the resin was washed with 5% MeOH/$CH_2Cl_2$ (2×20 mL) and $Et_2O$ (20 mL). The organic layers were combined and the solvent was removed. The crude oil was diluted with $CH_2Cl_2$ (2.0 mL) and TFA (2.0 mL) and the mixture was stirred overnight. The solvent was removed under reduced pressure to afford the crude TFA salt which was used without further purification. TLC (silica, 10% MeOH/$CH_2Cl_2$): $R_f$=0.1. MS (electrospray): m/z calculated for $C_{11}H_{13}Cl_2NO$, [M+H]$^+$, 246.04, observed 246.1.

D. 1-(3-(4-Chloro-3-methyl-phenyl)-1-{3-[4-(3,4-dichlorophenoxy)-piperidin-1-yl]-propyl}-1,4,6,7-tetrahydro-pyrazolo[4,3-c]pyridin-5-yl)-ethanone.

To a stirred solution of 25.0 mg (0.066 mmol) of 1-[3-(4-chloro-3-methyl-phenyl)-1-oxiranylmethyl-1,4,6,7-tetrahydro-pyrazolo[4,3-c]pyridin-5-yl]-ethanone and 25.0 mg (0.10 mmol) of 4-(3,4-dichlorophenoxy)-piperidinium trifluoroacetate in EtOH (0.5 mL) was added 0.019 mL (0.014 mmol) of $Et_3N$. The mixture was heated to 80° C. in a sealed vessel for 16 h. The reaction was cooled and the solvent was removed under reduced pressure. Flash chromatography (0–5% MeOH/$CH_2Cl_2$) afforded 28 mg (74%) of a pale yellow foam. TLC (silica, 5% MeOH/$CH_2Cl_2$): $R_f$=0.5. MS (electrospray): m/z calculated for $C_{29}H_{33}Cl_3N_4O_3$, [M+H]$^+$, 591.16, observed 591.2. $^1$H NMR (400 MHz, $CDCl_3$, a mixture of amide rotamers): 7.51 (d, J=6.9 Hz, 1H), 7.41–7.29 (m, 3H), 6.99 (d, J=2.9 Hz, 1H), 6.74 (dd, J=9.0, 3.1 Hz, 1H), 4.82 and 4.73 (A and B of AB quartet, $J_{ab}$=15.7 Hz, 1H), 4.60 (s, 1H), 4.46–3.93 (m, 4H), 3.92–3.83 (m, 1H), 3.82–3.68 (m, 1H), 3.08–2.51 (m, 6H), 2.43 (s, 1.5H), 2.41 (s, 1.5H), 2.21 (s, 1.5H), 2.15 (s, 1.5H) 2.00–1.83 (m, 3H), 1.75–1.39 (m, 4H).

Example 5

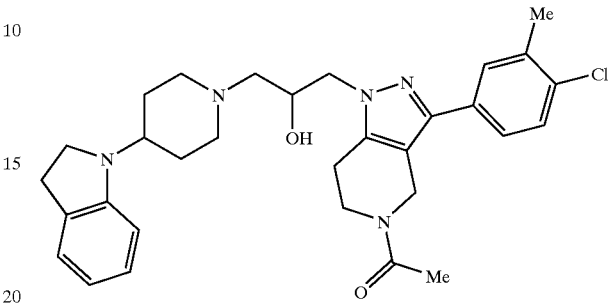

1-(3-(4-Chloro-3-methyl-phenyl)-1-{3-[4-(2,3-dihydro-indol-1-yl)-piperidin-1-yl]-2-hydroxy-propyl}-1,4,6,7-tetrahydro-pyrazolo[4,3-c]pyridin-5-yl)-ethanone A. 1-Piperidin-4-yl-2,3-dihydro-1H-indole.

Indoline (11.0 g, 92 mmol) and N-BOC-4-piperidone (18.4 g, 92 mmol) were set stirring in 300 mL of $CH_2Cl_2$ under an atmosphere of nitrogen at rt. Acetic acid (5.5 mL, 96 mmol) was then added. After 1.5 h sodium triacetoxyborohydride (27.4 g, 129 mmol) was added and the mixture was left stirring for 4 days. The mixture was quenched by the slow addition of saturated $NaHCO_3$. The organics were separated, dried ($MgSO_4$) and the solvent was evaporated under reduced pressure to give 28 g (100%) of a clear dark green liquid. The crude material was brought up in 1:1 TFA/$CH_2Cl_2$ (100 mL) and stirred at room temperature. After 45 min the solvent was evaporated under reduced pressure, the oil brought up in EtOAc, and cooled on ice to form a beige precipitate. The solid was filtered, washed with $Et_2O$ and air dried to give 22.5 g (57%) of a white solid as a TFA salt. MS (electrospray): exact mass calculated for $C_{13}H_{18}N_2$, 202.15. m/z found, 203.2. $^1$H NMR (400 MHz, DMSO-d$_6$): 8.74 (br s, 1H), 8.46 (br s, 1H), 7.07 (m, 2H), 6.63 (m, 2H), 3.81 (br s, 1H), 3.46 (m, 2H), 3.37 (m, 2H), 3.12 (m, 2H), 2.95 (m, 2H), 1.86 (m, 4H).

B. 1-(3-(4-Chloro-3-methyl-phenyl)-1-{3-[4-(2,3-dihydro-indol-1-yl)-piperidin-1-yl]-2-hydroxy-propyl}-1,4,6,7-tetrahydro-pyrazolo[4,3-c]pyridin-5-yl)-ethanone.

1-Piperidin-4-yl-2,3-dihydro-1H-indole (TFA salt) (506 mg, 1.18 mmol) and 1-[3-(4-chloro-3-methyl-phenyl)-1-oxiranylmethyl-1,4,6,7-tetrahydro-pyrazolo[4,3-c]pyridin-5-yl]-ethanone (261 mg, 0.75 mmol) were set stirring in 20 mL of EtOH and heated to 80° C. After 20 h the mixture was cooled, evaporated, brought up in EtOAc and washed with saturated $NaHCO_3$. The organics were dried ($MgSO_4$) and evaporated to give a clear golden oil. Flash chromatography (silica, 100% acetone) gave 260 mg (63%) of a white solid. TLC (silica, 100% acetone): $R_f$=0.10. MS (electrospray): exact mass calculated for $C_{31}H_{28}ClN_5O_2$, 547.27. m/z found, 548.3. $^1$H NMR 400 MHz,$CDCl_3$): 7.64 (m, 1H), 7.43 (m, 2H), 7.16 (m, 2H), 6.72 (s, 1H), 6.50 (m, 1H), 4.88 (m, 1H), 4.73 (s, 1H), 4.28 (m, 2H), 4.13 (m, 2H), 3.92 (m, 2H), 3.47 (m, 3H), 30.9 (m, 6H), 2.55 (m, 6H), 2.27 (m, 3H), 1.84 (m, 4H).

Example 6

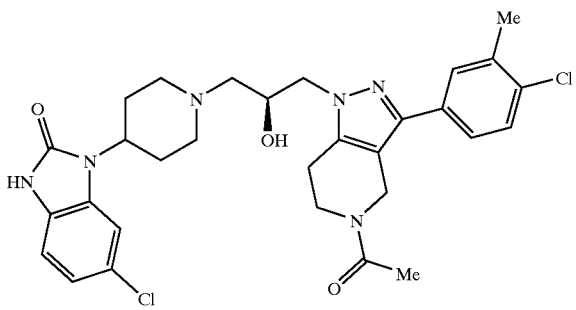

(S)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one A. (R)-1-[3-(4-Chloro-3-methyl-phenyl)-1-(2,3-dihydroxy-propyl)-1,4,6,7-tetrahydro-pyrazolo[4,3-c]pyridin-5-yl]-ethanone.

A solution of KHMDS (0.5 M, 8.4 mL, 4.1 mmol) was added to a solution of 1-[3-(4-chloro-3-methyl-phenyl)-1,4,6,7-tetrahydro-pyrazolo[4,3-c]pyridin-5-yl]-ethanone (1.01 g, 3.49 mmol) in DMF (8.5 mL). The mixture was stirred for 1 h then (2R)-1-tert-butyldimethylsilylglycidol (1.97 g, 10.5 mmol) was added. The mixture was stirred for 17 h then partitioned between EtOAc (500 mL) and saturated aqueous NaHCO$_3$ (100 mL). The EtOAc layer was washed with H$_2$O (3×100 mL), and brine (100 mL). The combined washes were extracted with EtOAc (2×100 mL). The combined extracts were dried over Na$_2$SO$_4$ and concentrated. The residue was dissolved in MeOH (50 mL) and treated with CSA (171 mg). The resulting mixture was stirred for 24 h then concentrated to near dryness. The residue was diluted with EtOAc (300 mL), washed with NaHCO$_3$ (100 mL), dried over Na$_2$SO$_4$ and concentrated. Flash chromatography (silica, 5–10% MeOH/CH$_2$Cl$_2$) provided 652 mg (50%) of the non-racemic diol. TLC (silica, 10% MeOH/CH$_2$Cl$_2$): R$_f$=0.2. MS (electrospray): m/z calculated for C$_{18}$H$_{23}$$^{35}$ClN$_3$O$_3$ ([M+H]$^+$, 364.14. found 364.1.

B. (R)-1-[3-(4-Chloro-3-methyl-phenyl)-1-oxiranylmethyl-1,4,6,7-tetrahydro-pyrazolo[4,3-c]pyridin-5-yl]-ethanone.

(R)-1-[3-(4-Chloro-3-methyl-phenyl)-1-(2,3-dihydroxy-propyl)-1,4,6,7-tetrahydro-pyrazolo[4,3-c]pyridin-5-yl]-ethanone (452 mg, 1.24 mmol) and pyridinium p-toluenesulfonate (85 mg) were combined in MeC(OMe)$_3$ (50 mL) and briefly sonicated. The mixture was stirred for 17 h, concentrated, and the residue dissolved in CH$_2$Cl$_2$ (8 mL). The solution was cooled to 0° C. and treated with AcBr (0.15 mL, 2.0 mmol). After 5 h the mixture was partitioned between EtOAc (300 mL) and saturated aqueous NaHCO$_3$ (75 mL). The EtOAc layer was washed with H$_2$O (75 mL) and brine (75 mL), dried over Na$_2$SO$_4$ and concentrated. The residue was combined with K$_2$CO$_3$ (243 mg, 1.84 mmol) in MeOH (50 mL) and stirred for 3 h then worked up as described above. Purification by column chromatography (silica, 10–40% acetone/CH$_2$Cl$_2$) gave 159 mg (37%) of the title compound. Chiral HPLC (Daicel OD, 0.5% Et$_2$NH/MeOH) analysis indicated >95% optical purity. HPLC (reverse phase conditions), t$_R$=4.97 min. MS (electrospray): exact mass calculated for C$_{18}$H$_{20}$ClN$_3$O$_2$ [M$^+$+Na], 368.11. m/z found 368.05. $^1$H NMR (CDCl$_3$, 400 MHz, a mixture of amide rotamers): 7.54 (br d, J=6.3 Hz, 2H), 7.41–7.35 (m, 3H), 7.29 (dd, J=8.2, 1.9 Hz, 1H), 4.81 and 4.74 (A and B of AB quartet, J$_{ab}$=15.7 Hz, 2H), 4.60 (s, 2H), 4.48 (dd, J=15.2, 2.4 Hz, 1H), 4.42 (dd, J=15.4, 2.8 Hz, 1H), 4.13 (t, J=4.7 Hz, 1H), 4.09 (dd, J=4.6 Hz, 1H), 3.93 (m, 2H), 3.74 (t, J=5.8 Hz, 1H), 3.73 (t, J=5.8 Hz, 1H), 3.34 (m, 2H), 2.85–2.75 (m, 6H), 2.53 (dd, J=4.6, 2.5 Hz, 1H), 2.48 (dd, J=4.6, 2.6 Hz, 1H), 2.43 (s, 3H), 2.41 (s, 3H), 2.20 (s, 3H), 2.15 (s, 3H).

C. 4-(5-Chloro-2-nitro-phenylamino)-piperidine-1-carboxylic acid ethyl ester.

To a solution of 2.03 g (11.6 mmol) of 4-chloro-2-fluoro-nitrobenzene in DMF (12.0 mL) at rt was added 2.00 g (11.6 mmol) of ethyl 4-amino-1-piperidinecarboxylate. A yellow precipitate formed within 30 min and the reaction was further diluted with DMF (12.0 mL) and CH$_2$Cl$_2$ (5.0 mL) and was shaken at 300 RPM overnight. The solvent was removed under reduced pressure and the resulting solid was dried under vacuum. The crude product was purified by flash chromatography (silica, 0–5% MeOH/CH$_2$Cl$_2$) to afford 2.83 g (81%) of the title compound. TLC (silica, 5% MeOH/CH$_2$Cl$_2$): R$_f$=0.4. MS (electrospray): m/z calculated for C$_{14}$H$_{18}$ClN$_3$O$_4$ [M$^+$+Na] 350.09, observed 350.0. $^1$H NMR (400 MHz, CDCl$_3$): 8.13 (apparent d, J=9.1 Hz, 2H), 6.84 (d, J=2.0 Hz, 1H), 6.62 (dd, J=9.4, 2.3 Hz, 1H), 4.15 (q, J=14.9, 7.3 Hz, 2H), 4.08 (br d, J=12.4 Hz, 2H), 3.70–3.58 (m, 1H), 3.17–3.05 (m, 2H), 2.07 (br dd, J=13.1, 3.1 Hz, 2H), 1.63–1.50 (m, 2H), 1.28 (t, J=7.0 Hz, 3H).

D. 4-(6-Chloro-2-oxo-2,3-dihydro-benzoimidazol-1-yl)-piperidine-1-carboxylic acid ethyl ester.

To a stirred solution of 0.50 g (1.52 mmol) of 4-(5-chloro-2-nitro-phenylamino)-piperidine-1-carboxylic acid ethyl ester in EtOH (15.0 mL) was added concentrated HCl (3.0 mL) followed by 0.99 g (15.2 mmol) of zinc powder. After 1 h, additional concentrated HCl (1.5 mL) followed by 0.99 g (15.2 mmol) of zinc powder was added and the reaction was stirred for 1.5 h. The mixture was filtered through a pad of celite and was washed with 5% MeOH/CH$_2$Cl$_2$. The mixture was diluted with saturated NaHCO$_3$ and a precipitate formed. The layers were separated and the aqueous phase was extracted (3×5% MeOH/CH$_2$Cl$_2$). The combined organic layers were dried over Na$_2$SO$_4$ and the solvent was removed under reduced pressure to afford a brown oil. The crude oil was diluted with CH$_2$Cl$_2$ (15.0 mL) and 0.64 mL (4.56 mmol) of Et$_3$N was added followed by 0.45 g (1.52 mmol) of triphosgene. The reaction was allowed to stir overnight and was then diluted with 1 N NaOH (20 mL) and stirred for an additional 1 h. The layers were separated and the aqueous phase was extracted with CH$_2$Cl$_2$ (3×20 mL). The combined organic extracts were dried over Na$_2$SO$_4$ and the solvent was removed under reduced pressure. Purification by flash chromatography (silica, 0–5% MeOH/CH$_2$Cl$_2$) afforded 0.33 g (67% over 2 steps) of the title compound. TLC (silica, 5% MeOH/CH$_2$Cl$_2$): R$_f$=0.5. MS (electrospray): m/z calculated for C$_{15}$H$_{18}$ClN$_3$O$_3$ [M$^+$+Na] 346.10, observed 346.0. $^1$H NMR (400 MHz, CDCl$_3$): 9.41 (s, 1H), 7.11 (d, J=2.0 Hz, 1H), 7.04 (d, J=1.8 Hz, 1H), 7.02 (s, 1H), 4.48–4.33 (m, 3H), 4.20 (q, J=7.1 Hz, 2H), 2.92 (t, J=12.5 Hz, 2H), 2.30 (dq, J=12.9, 4.6 Hz, 2H), 2.10 (d, J=12.6 Hz, 2H), 1.31 (t, J=7.1 Hz, 3H).

E. 6-Chloro-1-piperidin-4-yl-1,3-dihydro-benzoimidazol-2-one.

A suspension of 0.20 g (0.62 mmol) of 4-(6-chloro-2-oxo-2,3-dihydro-benzoimidazol-1-yl)-piperidine-1-carboxylic acid ethyl ester in 10% NaOH (0.62 mL) was heated to 105° C. for 6 h and then cooled. The solution was adjusted to pH 1 (conc. HCl) and then back to pH 10 (NaOH). Then, the mixture was diluted with 5% MeOH/CH$_2$Cl$_2$ (~30 mL) until both layers were clear. The layers were separated and the aqueous phase was extracted with 5% MeOH/CH$_2$Cl$_2$ (2×30 mL). The combined organic layers were dried over Na₂SO₄ and the solvent was removed under reduced pressure to afford 0.12 g (76%) of a light brown solid. TLC (silica, 10% MeOH/CH₂Cl₂): R_f=0.1. MS (electrospray): m/z calculated for C₁₂H₁₄ClN₃O [M⁺+H] 252.08, observed 252.1. ¹H NMR (400 MHz, CDCl₃): 7.27 (d, J=1.6 Hz, 2H), 7.02 (d, J=1.6 Hz, 1H), 7.01 (s, 1H), 4.38 (m, 1H), 3.30 (br d, J=11.9 Hz, 2H), 2.82 (dt, J=12.3, 2.0 Hz, 2H ), 2.35 (dq, J=12.3, 3.5 Hz, 2H), 1.85 (br dd, J=12.1, 2.1 Hz, 2H).

F. (S)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one.

(R)-1-[3-(4-Chloro-3-methyl-phenyl)-1-oxiranylmethyl-1,4,6,7-tetrahydro-pyrazolo[4,3-c]pyridin-5-yl]-ethanone (31 mg, 0.10 mmol) and 6-chloro-1-piperidin-4-yl-1,3-dihydro-benzoimidazol-2-one (36 mg, 0.17 mmol) were combined in EtOH (0.3 mL) and heated to 70° C. After 18 h the mixture was allowed to cool, diluted with CH₂Cl₂ and purified by preparative TLC (silica, 8% MeOH/CH₂Cl₂) to give 7 mg (12%) of the title compound. HPLC (reverse phase conditions), t_R=3.49 min. MS (electrospray): m/z calculated for C₃₀H₃₅³⁵Cl₂N₆O₃ [M⁺+H] 597.22. found 597.20. ¹H NMR (CDCl₃, 400 MHz, a mixture of amide rotamers): 9.16 (br d, J=10.1 Hz, 1H), 7.55 (br m, 1H), 7.40–7.28 (m, 2H), 7.18 (br s, 1H), 7.03 and 6.98 (A and B of ABX (with fine splittings), J_ab=8.4 Hz, 2H), 4.85 and 4.74 (A and B of ABX (with fine splittings), J_ab=15.7 Hz, 1H), 4.62 (s, 1H), 4.29–4.18 (m, 4H), 4.09–4.00 (m, 2H), 3.91–3.71 (m, 2H), 3.16–2.78 (m, 4H), 2.55–2.50 (m, 4H), 2.43 (s, 1.5H), 2.41 (s, 1.5H), 2.23 (m, 1H), 2.21 (s, 1.5H), 2.16 (s, 1.5H), 1.84 (br s, 2H).

Example 7

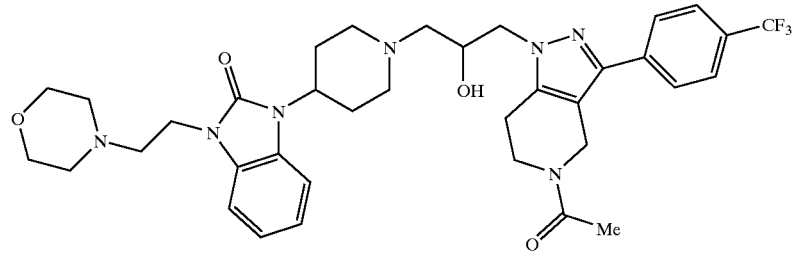

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-(2-morpholin-4-yl-ethyl)-1,3-dihydro-benzoimidazol-2-one A solution of 1-(1-{3-[5-acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one (130 mg, 0.22 mmol) in DMF (1 mL) was treated with cesium carbonate (146 mg, 0.45 mmol) and 4-(2-chloroethyl)morpholine hydrochloride (329 mg, 2.2 mmol) at 25° C. and stirred for 24 h before it was diluted with EtOAc (10 mL) and H₂O (5 mL). The organic layer was separated, washed with H₂O (2×5 mL), dried over Na₂SO₄, and concentrated. Column chromatography (silica, 5% MeOH/CH₂Cl₂) afforded 124 mg (81%) of a white powder. TLC (10% MeOH/CH₂Cl₂): R_f=0.31. MS (electrospray): m/z 696.3 ([M+H]⁺, C₃₆H₄₄F₃N₇O₄ requires 695.3). ¹H NMR (CDCl₃, 400 MHz, a mixture of two rotamers): 7.82 and 7.65 (AB pattern, J_ab=8.2 Hz, 2H), 7.74 and 7.68 (AB pattern, J_ab=8.4 Hz, 2H), 7.23–7.05 (m, 4H), 4.92 and 4.80 (AB pattern, J_ab=15.6 Hz, 1.2H), 4.69 (s, 0.8H), 4.38–4.00 (m, 5H), 4.02 (t, J=7.0 Hz, 2H), 3.92–3.70 (m, 2H), 3.70 (t, J=4.5 Hz, 4H), 3.15–2.80 (m, 4H), 2.70 (t, J=7.1 Hz, 2H), 2.60–2.20 (m, 9H), 2.24 (s, 1.6H), 2.18 (s, 1.4H), 1.85–1.75 (m, 2H).

Example 8

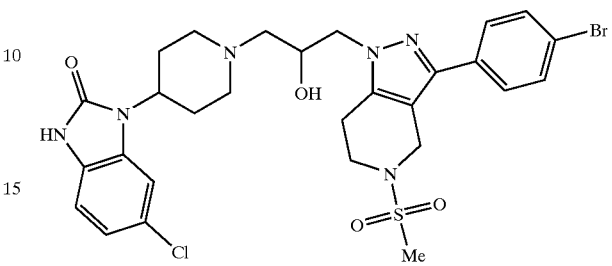

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one A. 3-(4-Bromo-phenyl)-1,4,6,7-tetrahydro-pyrazolo[4,3-c]pyridine-5-carboxylic acid tert-butyl ester.

To a stirred solution of 500.0 g (2.51 mol) of 1-tert-butoxycarbonyl-4-piperidone and 87.1 g (2.76 mol) of morpholine in benzene (1.25 L) was added a catalytic amount (~0.25 g) of p-TsOH. The mixture was heated to reflux for 36 h with a Dean-Stark trap. The solvent was removed under reduced pressure to give a brown oil, which solidified on standing. The crude product was divided and 335.0 g (1.25 mol) of the enamine was diluted with CH₂Cl₂ (1.25 L) and 175.0 mL (1.25 mol) of Et₃N was added. The mixture was cooled to 0° C. and a solution of 275.0 g (1.25 mol) of 4-bromobenzoyl chloride in CH₂Cl₂ (150 mL) was added slowly by dropping funnel over 1 h. The mixture was allowed to warm to rt and stir overnight. The reaction was then diluted with 1 N HCl (450 mL) and stirred vigorously for 3 h. The aqueous layer was extracted with CH₂Cl₂ (3×500 mL) and the combined extracts were dried over Na₂SO₄ and the solvent was removed under reduced pressure. The crude oil was diluted with EtOH (850 mL) and cooled to 0° C. To this stirred solution was slowly added 120.0 g (3.75 mol) of hydrazine and the mixture was allowed to warm to rt and stir overnight during which time a white precipitate formed. The volume of the reaction was reduced to ~350 mL and EtOAc (1.50 L) was added to the mixture. The suspension was stirred vigorously for 2 h and was filtered then washed with EtOAc (2×500 mL) and dried under vacuum to afford 309.0 g (62% over 3 steps) of a white solid. TLC (silica, 5% MeOH/CH₂Cl₂): R_f=0.3. MS (electrospray): m/z calculated for C₁₇H₂₀BrN₃O₂ [M⁺+H] 378.07, observed 378.0. ¹H NMR (400 MHz, CDCl₃):

7.65–7.26 (m, 4H), 4.64 (br s, 2H), 3.84–3.68 (br m, 2H), 2.87–2.74 (br m, 2H), 1.48 (br s, 9H).

B. 3-(4-Bromophenyl)-4,5,6,7-tetrahydro-1H-pyrazolo[4,3-c]pyridinium trifluoroacetate.

To a stirred solution of 10.0 g (26.4 mmol) of the 3-(4-bromo-phenyl)-1,4,6,7-tetrahydro-pyrazolo[4,3-c]pyridine-5-carboxylic acid tert-butyl ester in $CH_2Cl_2$ (26.0 mL) was added 26.0 mL of TFA. The resulting mixture was allowed to stir overnight. The solvent was removed under reduced pressure and the solid was dried in vacuo. The dried solid was suspended in $Et_2O$ and stirred vigorously for 2 h and then filtered and dried in vacuo to give 10.1 g of a white solid, which was used without further purification. TLC (silica, 10% $MeOH/CH_2Cl_2$): $R_f$=0.05. MS (electrospray): m/z calculated for $C_{12}H_{12}BrN_3$ [M$^+$+H] 278.02, observed 278.0.

C. 3-(4-Bromo-phenyl)-5-methanesulfonyl-4,5,6,7-tetrahydro-1H-pyrazolo[4,3-c]pyridine.

To a stirred solution of 3.11 g (11.1 mmol) of 3-(4-bromophenyl)-4,5,6,7-tetrahydro-1H-pyrazolo[4,3-c]pyridinium trifluoroacetate and 4.71 mL (33.5 mmol) of $Et_3N$ in DMF (55 mL) was slowly added 1.21 mL (15.6 mmol) of methanesulfonyl chloride. After 2.5 h, the solvent was removed under reduced pressure and the residue was diluted with $CH_2Cl_2$ (100 mL) and saturated $NaHCO_3$ (100 mL). The layers were separated and the aqueous phase was extracted with $CH_2Cl_2$ (2×30 mL). The combined organic layers were dried over $Na_2SO_4$ and the solvent was removed under reduced pressure. Purification by column chromatography (silica, 0–5% $MeOH/CH_2Cl_2$) afforded 2.01 g (50%) of the title compound. TLC (silica, 5% $MeOH/CH_2Cl_2$): $R_f$=0.3. MS (electrospray): m/z calculated for $C_{13}H_{14}BrN_3O_2S$ [M$^+$+H] 356.00, observed 356.0.

D. 3-(4-Bromo-phenyl)-5-methanesulfonyl-1-oxiranylmethyl-4,5,6,7-tetrahydro-1H-pyrazolo[4,3-c]pyridine.

To a stirred solution of 2.50 g (7.00 mmol) of 3-(4-bromo-phenyl)-5-methanesulfonyl-4,5,6,7-tetrahydro-1H-pyrazolo[4,3-c]pyridine and 5.52 mL (70.0 mmol) of epichlorohydrin was added 2.50 g (7.72 mmol) of solid $Cs_2CO_3$. The reaction was allowed to stir for 48 h and the solvent was removed under reduced pressure. The residue was then diluted with $H_2O$ (150 mL) and EtOAc (150 mL). The layers were separated, and the organic layer was washed with $H_2O$ (50 mL) and brine (50 mL), dried over $Na_2SO_4$ and the solvent was removed under reduce pressure. Purification by flash chromatography (silica, 0–20% acetone/$CH_2Cl_2$) afforded 1.52 g (53%) of a white solid. TLC (silica, 5% MeOH/$CH_2Cl_2$): $R_f$=0.5. MS (electrospray): m/z calculated for $C_{16}H_{18}BrN_3O_3S$ [M$^+$+H] 412.03, observed 412.0. $^1$H NMR (400 MHz, $CDCl_3$): 7.54 and 7.47 (A and B of AA'BB', J=8.6 Hz, 4H), 4.56–4.45 (m, 3H), 4.10 (dd, J=15.1, 5.4 Hz, 1H), 3.73–3.58 (m, 2H), 3.38–3.32 (m, 1H), 2.96–2.87 (m, 2H), 2.86 (s, 3H), 2.83 (dd, J=4.4, 4.2 Hz, 1H), 2.48 (dd, J=4.6, 2.6 Hz, 1H).

E. 1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one.

A stirred solution of 25.0 mg (0.061 mmol) of 3-(4-bromo-phenyl)-5-methanesulfonyl-1-oxiranylmethyl-4,5,6,7-tetrahydro-1H-pyrazolo[4,3-c]pyridine and 19.0 mg (0.073 mmol) of 6-chloro-1-piperidin-4-yl-1,3-dihydro-benzoimidazol-2-one in EtOH (0.5 mL) was heated to 80° C. in a sealed vessel for 16 h. The reaction was cooled and the solvent was removed under reduced pressure. The crude product was purified by column chromatography (silica, 0–5% $MeOH/CH_2Cl_2$) to afford 0.025 g (63%) of the title compound. TLC (silica, 5% $MeOH/CH_2Cl_2$): $R_f$=0.4. MS (electrospray): m/z calculated for $C_{28}H_{32}BrClN_6O_4S$ [M$^+$+H] 663.11, observed 663.0. $^1$H NMR (400 MHz, $CDCl_3$): 10.2 (s, 1H), 7.52 and 7.46 (A and B of AA'BB', J=8.6 Hz, 4H), 7.15 (br d, J=1.5 Hz, 1H), 7.04–6.95 (m, 2H), 4.52 and 4.49 (A and B of AB quartet, $J_{ab}$=14.5 Hz, 2H), 4.33–4.14 (m, 3H), 4.07–3.97 (m, 1H), 3.74–3.58 (m, 2H), 3.17–2.89 (m, 4H), 2.86 (s, 3H), 2.57–2.30 (m, 5H), 2.20 (t, J=11.1 Hz, 1H), 1.87–1.73 (m, 2H).

Example 9

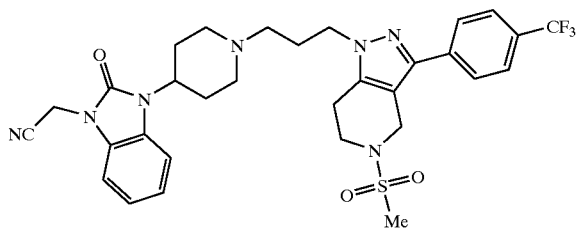

[3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile A. 3-(4-Trifluoromethyl-phenyl)-1,4,6,7-tetrahydro-pyrazolo[4,3-c]pyridine-5-carboxylic acid tert-butyl ester.

To a stirred solution of 500 g (2.51 mol) of 1-tert-butoxycarbonyl-4-piperidone and 87.1 g (2.76 mol) of morpholine in benzene (1.25 L) was added a catalytic amount (~0.25 g) of p-TsOH. The mixture was heated to reflux for 36 h with a Dean-Stark trap. One half of the solvent was removed under reduced pressure and the resulting solution was cooled and filtered. The filtrate was then concentrated to yield 630 g (94%) of an orange red oil. The eneamine was divided and 320 g (1.19 mol) was diluted with $CH_2Cl_2$ (1.0 L) and 165.0 mL (1.19 mol) of $Et_3N$ was added. The mixture was cooled to 0° C. and a solution of 225 g (1.08 mol) of 4-trifluoromethylbenzoyl chloride in $CH_2Cl_2$ (0.5 L) was added slowly by dropping funnel over 1 h. The mixture was allowed to warm to rt and stir overnight. The reaction was then diluted with 1 N HCl (450 mL) and stirred vigorously for 3 h. The aqueous layer was extracted with $CH_2Cl_2$ (3×500 mL) and the combined extracts were dried over $Na_2SO_4$ and the solvent was removed under reduced pressure. The crude oil was diluted with EtOH (1 L) and cooled to 0° C. To this stirred solution was slowly added 115 g (3.57 mol) of hydrazine and the mixture was allowed to warm to rt and stir overnight during which time a white precipitate formed. The volume of the reaction was reduced to ~500 mL and cooled. The precipitate was collected to afford 285 g (72% from eneamine) of a white solid. $^1$H NMR (400 MHz, $CDCl_3$): 7.63–7.55 (m, 4H), 4.58 (br s, 2H), 3.69–3.62 (br m, 2H), 2.74–2.68 (br m, 2H), 1.47 (s, 9H).

B. 1-(2-Methoxycarbonyl-ethyl)-3-(4-trifluoromethyl-phenyl)-1,4,6,7-tetrahydro-pyrazolo[4,3-c]pyridine-5-carboxylic acid tert-butyl ester.

3-(4-Trifluoromethyl-phenyl)-1,4,6,7-tetrahydro-pyrazolo[4,3-c]pyridine-5-carboxylic acid tert-butyl ester (1.85 g, 5.04 mmol) and methyl acrylate (0.50 mL, 5.6 mmol) were combined in toluene (30 mL) and heated to 75° C. The resulting mixture was treated with t-BuONa (100 mg), and heating continued for 48 h. The mixture was allowed to cool and partitioned between EtOAc (300 mL) and $NaHCO_3$ (75 mL). The aqueous layer was extracted with EtOAc (3×75 mL). The combined extracts were dried over Na$_2$SO$_4$ and concentrated. Column chromatography (silica, 30–60% EtOAc/hexanes) afforded 343 mg (15%) of the title compound. TLC (silica, 50% EtOAc/hexanes): R$_f$=0.4. MS (electrospray): m/z calculated for C$_{22}$H$_{27}$F$_3$N$_3$O$_4$ [M$^+$+H] 454.20. found 454.1. $^1$H NMR (CDCl$_3$, 400 MHz): 7.75 (br d, J=8.1 Hz, 2H), 7.64 (br s, 2H), 4.63 (br s, 2H), 4.30 (t, J=6.6 Hz, 2H), 3.75 (br s, 2H), 3.68 (s, 3H), 2.98 (t, J=6.6 Hz, 2H), 2.79 (br t, J=5.6 Hz, 2H), 1.48 (s, 9H).

C. 1-(3-Hydroxy-propyl)-3-(4-trifluoromethyl-phenyl)-1,4,6,7-tetrahydro-pyrazolo[4,3-c]pyridine-5-carboxylic acid tert-butyl ester.

A solution of LiBH$_4$ (26 mg, 1.2 mmol) in THF (0.5 mL) was added to a 0° C. solution of 1-(2-methoxycarbonyl-ethyl)-3-(4-trifluoromethyl-phenyl)-1,4,6,7-tetrahydro-pyrazolo[4,3-c]pyridine-5-carboxylic acid tert-butyl ester (317 mg, 0.70 mmol) in THF (4.0 mL). The mixture was stirred for 5 min then additional LiBH$_4$ (15 mg) was added and stirring continued for 17 h. The mixture was partitioned between EtOAc (80 mL) and saturated aqueous NaHCO$_3$ (20 mL). The aqueous layer was extracted with EtOAc (2×20 mL). The combined extracts were dried over Na$_2$SO$_4$ and concentrated. Column chromatography (silica, 0–8% MeOH/CH$_2$Cl$_2$) afforded 268 mg (95%) of the title compound. HPLC (reverse phase conditions), t$_R$=6.82 min. MS (electrospray): m/z calculated for C$_{21}$H$_{26}$F$_3$N$_3$O$_3$ [M$^+$+Na] 448.18. found 448.10. $^1$H NMR (CDCl$_3$, 400 MHz): 7.73 (br d, J=8.2 Hz, 2H), 7.65 (br s, 2H), 4.64 (br s, 2H), 4.21 (t, J=6.4 Hz, 2H), 3.76 (br s, 2H), 3.66 (t, J=5.7 Hz, 2H), 2.73 (br t, J=5.4 Hz 2H), 2.04 (q, J=6.1, 2H), 1.48 (s, 9H).

D. 4-(2-Oxo-2,3-dihydro-benzoimidazol-1-yl)-piperidine-1-carboxylic acid tert-butyl ester.

1-Piperidin-4-yl-1,3-dihydro-benzoimidazol-2-one (7.24 g, 34.1 mmol) and di-tert-butyl dicarbonate (9.12 g, 41.0 mmol) were combined in DMF (80 mL) and the mixture heated to 40° C. under N$_2$ for 17 h. The mixture was allowed to cool, diluted with EtOAc (800 mL) and washed with saturated aq. NaHCO$_3$ (150 mL), H$_2$O (3×150 mL) and brine (150 mL). The combined aqueous washes were extracted with EtOAc (2×150 mL). The combined extracts were dried over Na$_2$SO$_4$ and concentrated to afford 12.4 g of the title compound. TLC (silica, 50% EtOAc/hexanes): R$_f$=0.3. MS (electrospray): m/z calculated for C$_{17}$H$_{23}$N$_3$O$_3$ [M$^+$+Na] 340.16. found 340.1. $^1$H NMR (CDCl$_3$, 400 MHz): 10.59 (s, 1H), 7.15–7.11 (m, 2H), 7.08–7.02 (m, 2H), 4.49 (tt, J=8.4, 4.0 Hz, 1H), 4.32 (br s, 2H), 2.89 (br t, J=11.6, 2H), 2.34 (dq, J=12.6, 4.4 Hz, 2H), 1.83 (br d, J=10.5 Hz, 2H) 1.36 (s, 9H).

E. (2-Oxo-3-piperidin-4-yl-2,3-dihydro-benzoimidazol-1-yl)-acetonitrile.

A solution of 4-(2-oxo-2,3-dihydro-benzoimidazol-1-yl)-piperidine-1-carboxylic acid tert-butyl ester (2.91 g, 9.16 mmol) in THF (10 mL) was added dropwise to a solution of KHMDS (2.19 g, 11.0 mmol) in THF (20 mL). The mixture was stirred for 10 min then bromoacetonitrile (3.2 mL, 46 mmol) was added. The resulting mixture was stirred for 4 h then partitioned between EtOAc (750 mL) and saturated aqueous NaHCO$_3$ (200 mL). The EtOAc layer was washed with H$_2$O (3×200 mL) and brine (200 mL). The combined washes were extracted with EtOAc (2×150 mL). The combined extracts were dried over Na$_2$SO$_4$ and concentrated. Column chromatography (silica, 20–60% EtOAc/hexanes) afforded 2.20 g (67%) of 4-(3-cyanomethyl-2-oxo-2,3-dihydro-benzoimidazol-1-yl)-piperidine-1-carboxylic acid tert-butyl ester. The purified material was dissolved in CH$_2$Cl$_2$ (40 mL) and diluted with TFA (25 mL). The resulting mixture was stirred for 1 h then diluted with CH$_2$Cl$_2$ (250 mL) and washed with 1 N NaOH (100 mL). The aqueous layer was extracted with CH$_2$Cl$_2$ (2×100 mL). The combined extracts were dried over Na$_2$SO$_4$ and concentrated to 1.59 g (95%) of the title compound which was suitable for further use without purification. TLC (silica, 5% MeOH/CH$_2$Cl$_2$): R$_f$=0.1. MS (electrospray): m/z calculated for C$_{14}$H$_{17}$N$_4$O [M$^+$+H] 257.14. found 257.1. $^1$H NMR (CDCl$_3$, 400 Hz): 733–7.29 (m, 1H), 7.17–7.02 (m, 3H), 4.75 (s, 2H), 4.41 (tt, J=12.2, 4.4 Hz, 1H), 3.28 (br d, J=9.8 Hz, 2H), 3.11 (br s, 1H), 2.80 (t, J=10.0 Hz, 2H), 2.37 (dq, J=12.5, 4.2 Hz, 2H), 1.83 (br d, J=11.8 Hz, 2H).

F. [3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile.

1-(3-Hydroxy-propyl)-3-(4-trifluoromethyl-phenyl)-1,4,6,7-tetrahydro-pyrazolo[4,3-c]pyridine-5-carboxylic acid tert-butyl ester (268 mg, 0.63 mmol) was dissolved in CH$_2$Cl$_2$ (10 mL) and TFA (10 mL). The mixture was stirred for 1 h then concentrated to dryness. The residue was dissolved in CH$_2$Cl$_2$ (4.0 mL), cooled to 0° C. and treated with i-Pr$_2$NEt (0.36 mL, 2.1 mmol), followed by methanesulfonyl chloride (0.16 mL, 2.1 mmol). The reaction mixture was stirred for 4 h, then diluted with EtOAc (200 mL) and washed with saturated aqueous NaHCO$_3$ (2×25 mL). The washes were extracted with EtOAc (2×25 mL). The combined extracts were dried over Na$_2$SO$_4$ and concentrated. A portion of the crude mesylate (197 mg, ca. 0.41 mmol) was combined with (2-oxo-3-piperidin-4-yl-2,3-dihydro-benzoimidazol-1-yl)-acetonitrile (321 mg, 1.25 mmol) in CH$_2$Cl$_2$ (2.0 mL) and DMF (0.5 mL). The resulting mixture was treated with i-Pr$_2$NEt (0.22 mL, 1.3 mmol) and stirred for 60 h. The reaction mixture was partitioned between EtOAc (150 mL) and saturated aqueous NaHCO$_3$ (75 mL). The EtOAc layer was washed with H$_2$O (2×75 mL), and brine (75 mL). The combined washes were extracted with EtOAc (3×50 mL). The combined extracts were dried over Na$_2$SO$_4$ and concentrated. Purification of the residue by preparative TLC (silica, 1% MeOH/CH$_2$Cl$_2$ then 25% acetone/CH$_2$Cl$_2$) gave 37 mg (14%) of the title compound. HPLC (reverse phase conditions), t$_R$=2.94 min. MS (electrospray): m/z calculated for C$_{31}$H$_{35}$F$_3$N$_7$O$_3$S [M$^+$+H] 642.25, found 642.25. $^1$H NMR (CDCl$_3$, 400 MHz): 7.73 and 7.76 (A and B of AA'BB' J$_{ab}$=8.2 Hz, 4H), 7.26–7.05 (m, 4H), 4.81 (s, 2H), 4.56 (s, 2H), 4.26 (m, 1H), 4.15 (t, J=6.8 Hz, 2H), 3.70 (t, J=5.8 Hz, 2H), 3.03 (br d, J=11.1 Hz, 2H), 2.95 (t, J=5.7 Hz, 2H), 2.91 (s, 3H), 2.43 (m, 4H), 2.12 (m, 4H), 1.82 (br d, J=9.9 Hz, 2H).

Example 10

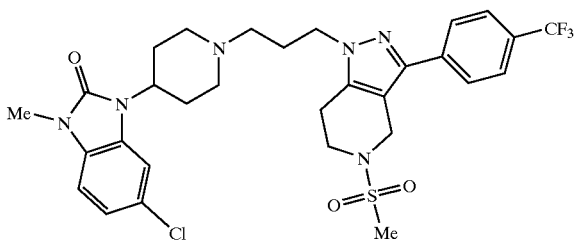

5-Chloro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one A. 1-Methanesulfonyl-piperidin-4-one.

Potassium carbonate (324 g, 2340 mmol) was added to a solution of 4-piperidone monohydrate hydrochloride (90 g, 586 mmol) in chloroform (300 mL) and water (300 mL). The slurry was cooled to 0° C. and treated with methylsulfonyl chloride (136 mL, 1760 mmol) by dropwise addition over a 1 h period. The reaction mixture was allowed to shake for 72 h and was partitioned between $CH_2Cl_2$ (500 mL) and saturated aqueous $NaHCO_3$ (500 mL). The aqueous layer was extracted with $CH_2Cl_2$ (3×200 mL). The organic layer was washed with 1% $KHSO_4$ (250 mL), dried ($Na_2SO_4$), and concentrated to afford 90.5 g (87%) of a white solid. HPLC (reverse phase conditions), $t_R$=2.19 min. MS (electrospray): exact mass calculated for $C_6H_{11}NO_3S$, 177.1. m/z found, 178.1 [M+H]$^+$. $^1$H NMR (400 MHz, $CDCl_3$): 3.60 (t, J=6.5 Hz, 4H), 2.89 (s, 3H), 2.59 (t, J=6.3 Hz, 4H).

B. 5-Methanesulfonyl-3-(4-trifluoromethyl-phenyl)-4,5,6,7-tetrahydro-1H-pyrazolo[4,3-c]pyridine.

p-Toluenesulfonic acid (1.34 g, 7.0 mmol) and morpholine (25.83 mL, 296 mmol) were added to a solution of 1-methanesulfonyl-piperidin-4-one (50.0 g. 282 mmol) in benzene (282 mL). The reaction mixture was heated in a flask equipped with a condenser and a Dean-Stark trap at reflux for 15 h. The reaction mixture was cooled and concentrated in vacuo to give the enamine which was used without further purification. The enamine was dissolved in $CH_2Cl_2$ (200 mL) and cooled to 0° C. To this was added triethylamine (47.2 mL, 339 mmol) followed by dropwise addition of 4-trifluoromethylbenzoyl chloride (42.3 mL, 285 mmol) dissolved in $CH_2Cl_2$ (82 mL). The reaction mixture was allowed to warm to room temperature and stirred for 20 h. The reaction mixture was washed with 1 N HCl (250 mL) and the $CH_2Cl_2$ layer was separated, dried ($Na_2SO_4$), and concentrated. The resulting oil was taken up in ethanol (300 mL) and treated with hydrazine (44.3 mL, 1.41 mol) at 0° C. The reaction mixture was allowed to warm to room temperature and stirred for 24 h. The mixture was concentrated and the resulting solid was filtered with ethanol wash and dried in vacuo to afford 70 g (72%) of 5-methanesulfonyl-3-(4-trifluoromethyl-phenyl)-4,5,6,7-tetrahydro-1H-pyrazolo[4,3-c]pyridine as a white solid. HPLC (reverse phase conditions), $t_R$=6.33 min. MS (electrospray): exact mass calculated for $C_{14}H_{14}F_3N_3O_2S$, 345.0. m/z found, 346.0 [M+H]$^+$. $^1$H NMR (400 MHz, $CDCl_3$): 7.72 (s, 4H), 4.58 (s, 2H), 3.69 (t, J=5.7 Hz, 2H), 2.99 (t, J=5.7 Hz, 2H), 2.92 (s, 3H).

C. 3-[5-Methanesulfonyl-3-(4-trifluoromethyl-phenyl)-4,5,6,7-tetrahydro-pyrazolo[4,3-c]pyridin-1-yl]-propan-1-ol.

$Cs_2CO_3$ (33.74 g, 103.5 mmol) was added to a solution of 5-methanesulfonyl-3-(4-trifluoromethyl-phenyl)-4,5,6,7-tetrahydro-1H-pyrazolo[4,3-c]pyridine (29.8 g, 86.3 mmol) in anhydrous DMF (70 mL) and stirred for 25 min. 3-Bromo-1-propanol (8.6 mL, 13.2 g, 94.9 mmol) was added and stirred under $N_2$ at room temperature for 18 h. Water (500 mL) was added to the reaction and stirred for 5 min. The precipitated material was filtered out and washed with water (4×100 mL) and dried in a Freeze Drying System. The crude material (31.0 g) was taken up in anhydrous DMF (65 mL) and $Cs_2CO_3$ (33.74 g, 103.5 mmol) was added, and stirred for 10 min. 3-Bromo-1-propanol (8.6 mL, 13.2 g, 94.9 mmol) and MeOH (6.0 mL, 4.75 g, 148 mmol) were added and stirring continued under $N_2$ at rt for 15 h. Water (500 mL) was added to the reaction and stirred for 10 min. The precipitated material was filtered and washed with water (3×100 mL). The filter cake was dissolved in $CH_2Cl_2$ (200 mL) and washed with brine (50 mL), dried ($Na_2SO_4$), and concentrated. The solid was triturated with $Et_2O$ (200 mL), filtered, then washed with $Et_2O$, and dried to furnish 16.0 g of the desired compound. The mother liquor was chromatographed (silica, 0–10% acetone/EtOAc) to obtain an additional 3.0 g of the title compound. The combined yield was 54.6%. MS (electrospray): exact mass calculated for $C_{17}H_{20}F_3N_3O_3S$, 403.12. m/z found, 404.0 [M+H]$^+$, 426.0 [M+Na]$^+$. $^1$H NMR (400 MHz, $CDCl_3$): 7.71 (d, J=8.2 Hz, 2H), 7.66 (d, J=8.5 Hz, 2H), 4.55 (s, 2H), 4.23 (t, J=6.5 Hz, 2H), 3.70–3.63 (m, 4H), 2.90 (s, 3H), 2.90 (t, J=5.1 Hz, 2H), 2.62 (t, J=5.9 Hz, 1H), 2.06 (q, J=6.1 Hz, 2H).

D. 5-Chloro-1-methyl-3-piperidin-4-yl-1,3-dihydro-benzoimidazol-2-one.

To a stirred suspension of 0.97 g (2.99 mmol) of 4-(6-chloro-2-oxo-2,3-dihydro-benzoimidazol-1-yl)-piperidine-1-carboxylic acid ethyl ester in THF (30 mL) was added 0.5 M KHMDS in toluene. This mixture was stirred for 1 h and 0.25 mL (3.89 mmol) of MeI was added in one portion. After 1.5 h the reaction was diluted with 1 N HCl (75 mL) and EtOAc (75 mL). The layers were separated, and the organic layer was washed with $H_2O$ (50 mL) and brine (50 mL), dried over $Na_2SO_4$ and the solvent was removed under reduced pressure. Purification by flash chromatography (silica, 0–5% MeOH/$CH_2Cl_2$) afforded 0.92 g (91%) of a white solid. A suspension of 0.92 g (2.72 mmol) of the ethyl carbamate in 1:1 EtOH (7.0 mL) and 10% NaOH (7.0 mL) was heated to 110° C. for 36 h and then cooled. The mixture was diluted with EtOAc (30 mL) and $H_2O$. The layers were separated and the aqueous phase was extracted with EtOAc (2×30 mL). The combined organic layers were dried over $Na_2SO_4$ and the solvent was removed under reduced pressure to afford 0.56 g (78%) of a pale yellow solid. TLC (silica, 10% MeOH/$CH_2Cl_2$): $R_f$=0.1. MS (electrospray): m/z calculated for $C_{13}H_{16}ClN_3O$ [M$^+$+H] 266.10, observed 266.0. $^1$H NMR (400 MHz, $CDCl_3$): 7.28 (d, J=1.8 Hz, 2H), 7.05 (dd, J=8.3, 2.0 Hz, 1H), 6.87 (d, J=8.3 Hz, 1H), 4.41 (tt, J=12.5, 4.3 Hz, 1H), 3.39 (s, 3H), 3.30 (br d, J=11.9 Hz, 2H), 2.82 (dt, J=12.4, 2.0 Hz, 2H), 2.30 (dq, J=12.3, 4.3 Hz, 2H), 1.81 (br dd, J=12.1, 2.3 Hz, 2H).

E. 5-Chloro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one.

To a stirred solution of 0.33 mL (3.72 mmol) of oxalyl chloride in $CH_2Cl_2$ (10 mL) under $N_2$ at −78° C. was added 0.36 mL (4.96 mmol) of DMSO and the reaction was stirred for 15 min. To this solution was added a solution of 1.0 g (2.48 mmol) of 3-[5-methanesulfonyl-3-(4-trifluoromethyl-phenyl)-4,5,6,7-tetrahydro-pyrazolo[4,3-c]pyridin-1-yl]-propan-1-ol in 10 mL over 10 min and stirring was continued for 25 min. To this solution was added 1.40 mL (9.92 mmol) of $Et_3N$ and the reaction was stirred for 10 min at −78° C. and was then allowed to warm to rt and stir for 1 h. The mixture was diluted with EtOAc (75 mL) and saturated $NaHCO_3$ (75 mL) and the layers were separated. The combined organic layers were dried over $Na_2SO_4$ and the solvent was removed under reduced pressure. The resulting solid was dried in vacuo and was suspended in $Et_2O$ (20 mL) and stirred vigorously for 1 h. The solid was filtered and washed with $Et_2O$ (2×10 mL) to afford the crude aldehyde which was carried on without further purification. The crude aldehyde, 5-chloro-1-methyl-3-piperidin-4-yl-1,3-dihydro-benzoimidazol-2-one (0.60 g, 2.3 mmol), and 0.20 mL (3.72 mmol) of AcOH was dissolved in $CH_2Cl_2$ (15 mL) followed by 0.69 g (3.25 mmol) of NaBH(OAc)$_3$, and the reaction was allowed to stir overnight. The mixture was diluted with $CH_2Cl_2$ (75 mL) and saturated $NaHCO_3$ (75 mL) and the layers were separated. The combined organic layers were dried over $Na_2SO_4$ and the solvent was removed under reduced pressure. Purification by flash chromatography (silica, 0–4% MeOH/$CH_2Cl_2$) afforded 1.28 g (79% over 2 steps) of a white solid. TLC (silica, 5% MeOH/$CH_2Cl_2$):

$R_f$=0.5. MS (electrospray): m/z calculated for $C_{30}H_{34}ClF_3N_6O_3S$ [M++H] 651.21, observed 651.2. $^1$H NMR (400 MHz, $CDCl_3$): 7.71 and 7.63 (A and B of AA'BB", $J_{AB}$=8.17 Hz, 4H), 7.16 (d, J=1.8 Hz, 1H), 7.04 (d, J=8.3, 1.8 Hz, 1H), 6.86 (d, J=8.3 Hz, 1H), 4.55 (s, 2H), 4.23 (tt, J=12.4, 4.3 Hz, 1H), 4.13 (t, J=6.7 Hz, 2H), 3.69 (t, J=5.7 Hz, 2H), 3.36 (s, 3H), 3.0 (d, J=11.6 Hz 2H), 2.95 (t, J=5.7 Hz, 2H), 2.90 (s, 3H), 2.45–2.32 (m, 4H), 2.16–2.04 (m, 4H), 1.76 (dd, J=11.9, 2.0 Hz, 2H). $^{13}$C NMR (100 MHZ, $CDCl_3$): 171.0, 153.7, 144.7, 137.1, 136.8, 129.3, 129.0, 128.7, 126.4, 125.5 (q, J=3.8 Hz), 122.7, 120.7, 109.8, 109.2, 108.0, 60.3, 54.7, 53.0, 51.3, 46.8, 43.1, 42.4, 36.8, 29.0, 27.2, 27.0, 22.3, 21.0, 14.1.

Example 11

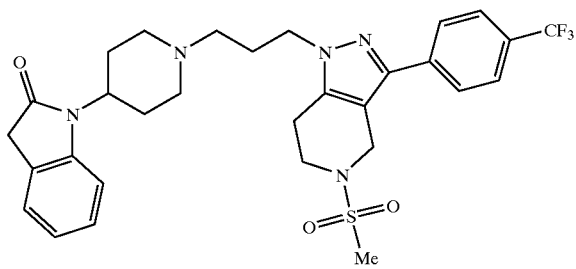

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one A. Methyl 2-nitrophenylacetate.

2-Nitrophenylacetic acid (60 g, 0.3 mol) was set stirring in 250 mL of methanol. Sulfuric acid (0.5 mL) was added and the mixture heated to reflux. After 20 h the mixture was cooled and evaporated under reduced pressure to give a clear yellow oil. The oil was brought up in EtOAc and washed with saturated $NaHCO_3$. The organics were dried ($MgSO_4$) and evaporated to give 63 g (98%) of the ester as a clear orange liquid. TLC (silica, 25% EtOAc/hexanes): $R_f$=0.36. $^1$H NMR (400 MHz, $CDCl_3$): 8.24 (m, 1H), 7.16 (m, 1H), 7.60 (m, 1H), 7.47 (m, 1H), 4.15 (s, 2H), 3.83 (s, 3H).

B. Methyl 2-aminophenylacetate.

Methyl 2-nitrophenylacetate (10.1 g, 51.2 mmol) in 125 mL of methanol containing 221 mg of 10% Pd/C was placed on the Parr hydrogenator at 40 psi. After 5 h the mixture was filtered through celite and evaporated under reduced pressure to give a clear red oil. The solvent was evaporated under reduced pressure to give 8.5 g (100%) of methyl 2-aminophenylacetate as a clear red oil. TLC (silica, EtOAc/hexanes): $R_f$=0.24. $^1$H NMR (400 MHz, $CDCl_3$): 7.21 (m, 2H), 6.86 (m, 2H), 3.81 (s, 3H), 3.70 (s, 2H).

C. 4-(2-Oxo-2,3-dihydro-indol-1-yl)-piperidine-1-carboxylic acid tert-butyl ester.

Methyl 2-aminophenylacetate (3.0 g, 18.2 mmol) and 1-tert-butoxycarbonyl-4-piperidone (4.5 g, 22.6 mmol) were set stirring in 50 mL of $CH_2Cl_2$ under an atmosphere of nitrogen. Sodium triacetoxyborohydride (5.4 g, 25.5 mmol) was added followed by 1 mL of acetic acid. After 20 h at rt the mixture was quenched by the slow addition of saturated $NaHCO_3$. After stirring for 30 min, the organics were separated, dried ($MgSO_4$), and evaporated to afford 7.5 g of a purple oil. Purification by column chromatography (silica, 10–50% EtOAc/hexanes) gave 3.9 g (62%) of the title compound. TLC (silica, 25% EtOAc/hexanes): $R_f$=0.15. $^1$H NMR (400 MHz, $CDCl_3$): 7.25 (m, 2H), 7.01 (m, 2H), 4.40 (m, 1H), 3.53 (s, 2H), 2.83 (m, 2H), 2.32 (m, 2H), 1.70 (m, 2H), 1.51 (s, 9H).

D. 1-Piperidin-4-yl-1,3-dihydro-indol-2-one.

4-(2-Oxo-2,3-dihydro-indol-1-yl)-piperidine-1-carboxylic acid tert-butyl ester (3.9 g, 12.3 mmol) was set stirring in 30 mL of 1:1 TFA/$CH_2Cl_2$. After 45 min the solvent was evaporated under reduced pressure to give a clear purple oil. The oil was brought up in diethyl ether and cooled on ice to give a precipitate. The solid was filtered, washed with ether and air dried to give 4.0 g (100%) of the title compound as a TFA salt. $^1$H NMR (400 MHz, DMSO-$d_6$): 8.6 (br s, 1H), 7.27 (m, 3H), 7.03 (m, 1H), 4.45 (m, 1H), 3.56 (s, 2H), 3.42 (m, 2H), 3.09 (m, 2H), 2.53 (m, 2H), 1.78 (m, 2H).

E. 1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one.

3-[5-Methanesulfonyl-3-(4-trifluoromethyl-phenyl)-4,5,6,7-tetrahydro-pyrazolo[4,3-c]pyridin-1-yl]-propan-1-ol (304 mg, 0.754 mmol) was set stirring in 5 mL of $CH_2Cl_2$ at rt under nitrogen. Dess-Martin reagent (394 mg, 0.929 mmol) was added in one portion and the reaction mixture was left stirring. After 1.5 h the mixture was added to a stirring solution of thiosulphate (10 equiv) in 20 mL of water and 5 mL of saturated $NaHCO_3$. After 2 h the organic layer was separated, dried ($MgSO_4$) and evaporated to give the aldehyde as a light yellow solid. The above aldehyde (303 mg, 0.754 mmol) and 1-piperidin-4-yl-1,3-dihydro-indol-2-one were set stirring in 15 mL of $CH_2Cl_2$ containing $Et_3N$ (0.15 mL, 1.1 mmol). A solution of Na(AcO)$_3$BH in 5 mL of $CH_2Cl_2$ was added dropwise via pipette over 10 min and the mixture was left to stir overnight. The mixture was quenched with saturated $NaHCO_3$ and the organic layer separated. The organics were dried ($MgSO_4$) and evaporated to a clear purple oil. Purification with column chromatography (silica, 50–100% acetone/$CH_2Cl_2$) gave 240 mg (53%) of a light pink solid. TLC (silica, 50% acetone/$CH_2Cl_2$): $R_f$=0.17. $^1$H NMR (400 MHz, DMSO-$d_6$): 7.82 (m, 4H), 7.24 (m, 2H), 7.11 (m, 1H), 6.98 (m, 1H), 4.49 (s, 2H), 4.12 (m, 3H), 3.54 (s, 2H) 3.32 (s, 4H), 2.95 (m, 7H), 2.32 (m, 4H), 1.99 (m, 4H), 1.55 (m, 2H).

Example 12

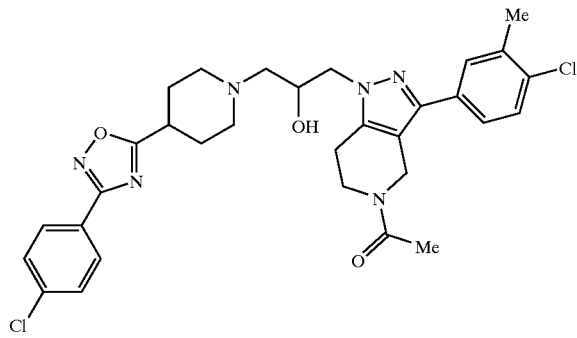

1-[3-(4-Chloro-3-methyl-phenyl)-1-(3-{4-[3-(4-chloro-phenyl)-[1,2,4]oxadiazol-5-yl]-piperidin-1-yl}-2-hydroxy-propyl)-1,4,6,7-tetrahydro-pyrazolo[4,3-c]pyridin-5-yl]-ethanone 1-[3-(4-Chloro-3-methyl-phenyl)-1-oxiranylmethyl-1,4,6,7-tetrahydro-pyrazolo[4,3-c]pyridin-5-yl]-ethanone (0.069 g. 0.20 mmol) was dissolved in $CH_2Cl_2$ (1 mL), and 4-[3-(4-chlorophenyl)-1,2,4-oxadiazol-5-yl]piperidine (0.105 g, 0.4 mmol) was added, followed by Yb(OTf)$_3$ (0.031 g, 0.22 mmol). The mixture was stirred at room temperature for 16 h. Preparative TLC (silica, 7.5% MeOH/$CH_2Cl_2$) afforded 84 mg (69%) of the title compound. MS (electrospray): exact mass calculated for $C_{31}H_{34}Cl_2N_6O_3$, 608.21. m/z found, 609.2 [M$^+$+H]. $^1$H NMR (400 MHz, CDCl$_3$, 1:1 mixture of rotamers): 8.00 (d, J=8.4 Hz, 2H), 7.56–7.53 (m, 1H), 7.48–7.42 (d, J=8.6 Hz, 2H), 7.41–7.30 (m, 2H), 4.84 and 4.73 (A and B of AB quartet J=15.6 Hz, 1H), 4.62 (br s, 1H), 4.25–4.13 (m, 2H), 4.10–3.98 (m, 2H), 3.90–3.70 (m, 2H), 3.04–2.71 (m, 5H), 2.51–2.40 (m, 6H), 2.30–2.15 (m, 6H), 2.10–1.90 (m, 2H).

Example 13

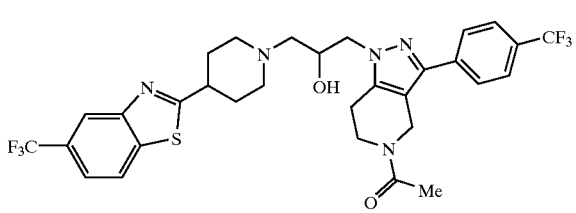

1-[1-{2-Hydroxy-3-[4-(5-trifluoromethyl-benzothiazol-2-yl)-piperidin-1-yl]-propyl}-3-(4-trifluoromethyl-phenyl)-1,4,6,7-tetrahydro-pyrazolo[4,3-c]pyridin-5-yl]-ethanone A. 2-Piperidin-4-yl-5-trifluoromethyl-benzothiazole.

To a stirred solution of 5 g (29.2 mmol) of 1-acetyl-piperidine-4-carboylic acid in toluene (100 mL) and a catalytic amount of DMF (1 mL) was added dropwise 2.4 mL of oxalyl chloride (33.3 mmol). The reaction mixture was allowed to stir at room temperature overnight. A 20 mL aliquot (6 mmol) of the acid chloride solution was then placed in a separate flask and treated with a solution of 1.4 g (6.10 mmol) of 2-amino-4-(trifluoromethyl)thiophene hydrochloride in triethyl amine (4 mL). The reaction was then heated to 80° C. for 30 min and then partitioned between ethyl acetate (50 mL) and water (20 mL) and separated. The aqueous layer was further extracted with EtOAc (2×30 mL). The combined organic layers were then washed with water (25 mL), brine, dried over Na$_2$SO$_4$, and the solvent was removed under reduced pressure. This was then heated to 60° C. in a 1 N HCl/MeOH solution overnight with stirring. The reaction mixture was cooled and concentrated to dryness. The solid was then taken back up in 35 mL MeOH and stirred over sodium bicarbonate (1 g) for 1 h then filtered and stripped to give 1.05 g (60%) of the desired product which was used without further purification. MS (electrospray): exact mass calculated for $C_{13}H_{13}F_3N_2S$, 286.08. m/z found, 287.1 [M+H]$^+$. $^1$H NMR (CDCl$_3$, 400 MHz): 8.25 (s, 1H), 7.98 (d, J=8.41 Hz, 1H), 7.65 (d, J=8.41 Hz, 1H), 3.38 (tt, J=11.35, 4.11 Hz, 1H), 3.28 (ddd, J=13.69, 11.74, 2.74 Hz, 1H), 3.16 (ddd, J=13.89, 11.15, 2.74 Hz, 1H), 2.85 (m, 1H), 2.25 (br m, 2H), 1.97 (br m, 2H).

B. 1-[1-{2-Hydroxy-3-[4-(5-trifluoromethyl-benzothiazol-2-yl)-piperidin-1-yl]-propyl}-3-(4-trifluoromethyl-phenyl)-1,4,6,7-tetrahydro-pyrazolo[4,3-c]pyridin-5-yl]-ethanone.

A solution of 63 mg (0.22 mmol) 2-piperidin-4-yl-5-trifluoromethyl-benzothiazole was dissolved in 4 mL EtOH and treated with 40 mg (0.11 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0–10% MeOH/EtOAc) to afford 57 mg (80%) of a white solid. MS (electrospray): exact mass calculated for $C_{31}H_{31}F_6N_5O_2S$, 651.21. m/z found, 652.2 [M+H]$^+$. $^1$H NMR (CDCl$_3$, 400 MHz, a mixture of rotamers): 8.24 (s, 1H), 7.97 (d, J=8.41 Hz, 1H), 7.78 (d, J=8.41 Hz, 1H), 7.70 (m, 2H), 7.65 (d, J=8.41 Hz, 1H), 7.60 (dd, J=8.41, 1.37 Hz, 1H), 4.88 and 4.76 (A and B of AB quartet, J=15.85 Hz, 1H), 4.66 (br s, 1H), 4.25–4.15 (m, 2H), 4.08–3.99 (m, 1.5H), 3.91–3.83 (m, 0.5H), 3.82–3.68 (m, 1H), 3.16 (tt, J=11.35, 3.52 Hz, 1H), 3.12–3.06 (m, 1H), 3.02–2.97 (m, 1H), 2.9–2.87 (m, 1.4H), 2.87–2.75 (m, 0.6H), 2.55–2.43 (m, 3H), 2.27–2.17 (m, 3H), 2.21 (s, 1.5H), 2.17 (s, 1.5H), 2.04–1.87 (m, 2H).

Example 14

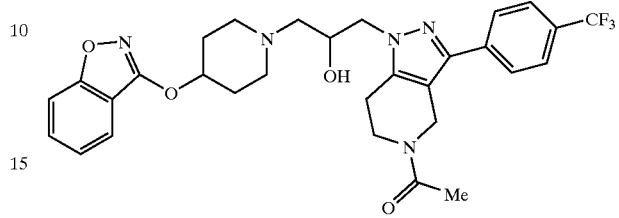

1-[1-{3-[4-(Benzo[d]isoxazol-3-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone A. 4-(Benzo[d]isoxazol-3-yloxy)-piperidine-1-carboxylic acid tert-butyl ester.

To a stirred solution of 263 mg of t-butyl-4-hydroxy-1-piperidinecarboxylate (1.3 mmol) in 5 mL of dry DMF was added 52 mg of 60% NaH in mineral oil (1.3 mmol). After stirring at room temperature for 10 min, 100 mg (0.65 mmol) of 3-chloro-1,2-benzisoxazole in DMF (1 mL) was added. The mixture was stirred at 40° C. overnight and then partitioned between EtOAc (50 mL) and water (20 mL) and separated. The aqueous layer was further extracted with EtOAc (2×30 mL). The combined organic layers were then washed with water (25 mL), brine, dried over Na$_2$SO$_4$, and the solvent was removed under reduced pressure to give crude product. Purification by chromatography (silica, gradient elution of 40% hexanes/CH$_2$Cl$_2$ to 100%CH$_2$Cl$_2$) gave 176 mg (85%) product as a light yellow solid. MS (electrospray): exact mass calculated for $C_{17}H_{22}N_2O_4$, 318.16. m/z found, 341.1 [M+Na]$^+$. $^1$H NMR (CDCl$_3$, 400 MHz): 7.64 (dt, J=8.02, 1.17 Hz, 1H), 7.53 (ddd, J=8.41, 7.04, 1.17 Hz, 1H), 7.43 (dt, J=8.41, 0.78 Hz, 1H), 7.27 (ddd, J=8.02, 7.04, 0.78 Hz, 1H), 5.07 (m, 1H), 3.87–3.77 (br m, 2H), 3.30 (m, 2H), 2.17–2.10 (br m, 2H), 1.93–1.84 (br m, 2H), 1.48 (s, 9H).

B. 1-[1-{3-[4-(Benzo[d]isoxazol-3-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone.

A solution of 176 mg (0.55 mmol) of 4-(benzo[d]isoxazol-3-yloxy)-piperidine-1-carboxylic acid tert-butyl ester in CH$_2$Cl$_2$(2 mL) was treated with trifluoroacetic acid (0.5 mL) at room temperature overnight. The solvent was then removed and the crude product dissolved in methanol and stirred over 100 mg of sodium bicarbonate for 1 h, the solid was then filtered off and the filtrate concentrated. The crude piperidine was then dissolved in 4 mL EtOH and treated with 202 mg (0.55 mmol) of 1-[1-oxiranylmethyl-3-(4-trifluoromethyl-phenyl)-1,4,6,7-tetrahydro-pyrazolo[4,3-c]pyridin-5-yl]-ethanone The solution was heated to 60° C. overnight. The solvent was then removed by rotary evaporation and the crude product was purified by column chromatography (silica, 0–10% MeOH/EtOAc) to afford 220 mg (68%) of a white solid. MS (electrospray): exact mass calculated for $C_{30}H_{32}F_3N_5O_4$, 583.24. m/z found, 584.2 [M+H]$^+$. $^1$H NMR (CDCl$_3$, 400 MHz, a mixture of amide rotamers): 7.77 (d, J=8.22 Hz, 1H), 7.69 (m, 2H), 7.66–7.61 (m, 2H), 7.54–7.49 (m, 1H), 7.41 (d, J=8.41 Hz, 1H), 7.28–7.23 (m, 1H), 4.93 (br m, 1H), 4.88 and 4.75 (A and B of AB quartet, J=15.65 Hz, 1H), 4.65 (br s, 1H), 4.24–4.18 (m, 0.75H), 4.18–4.09 (m, 1.25H), 4.07–3.98 (m, 1.5H), 3.91–3.79 (m, 0.5H), 3.79–3.67 (m, 1H), 3.02–2.85 (m, 2.4H), 2.85–2.70 (m, 1.6H), 2.61–2.52 (m, 1H), 2.51–2.40 (m, 2H), 2.39–2.30 (m, 1H), 2.24–2.12 (br m, 2H), 2.20 (s, 1.5H), 2.16 (s, 1.5H), 2.02–1.86 (m, 2H).

Example 15

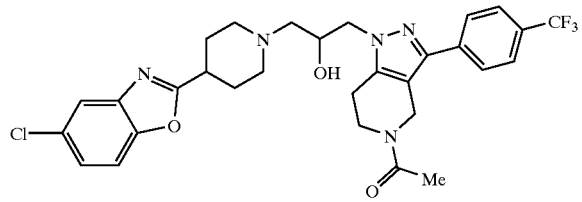

1-[1-{3-[4-(5-Chloro-benzooxazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone A. 5-Chloro-2-piperidin-4-yl-benzooxazole.

A flask was charged with 1.35 mL (10 mmol) of methyl isonipicotate, 1.43 g (10 mmol) of 2-amino-4-chlorophenol, and 5 g of polyphosphoric acid. The flask was then heated to 180° C. for 5 h. The reaction mixture was then poured into water while still warm and treated with 50% KOH solution until pH 12. This was then extracted with $CH_2Cl_2$ (3×50 mL), then washed with water (25 mL), brine, dried over $Na_2SO_4$, and the solvent was removed under reduced pressure to give 1.53 g (57%) of crude product which was used without further purification. MS (electrospray): exact mass calculated for $C_{12}H_{13}ClN_2O$, 236.07; m/z found, 237.1 [M+H]$^+$.

B. 1-[1-{3-[4-(5-Chloro-benzooxazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone.

A solution of 130 mg (0.55 mmol) of 5-chloro-2-piperidin-4-yl-benzooxazole was dissolved in 4 mL EtOH and treated with 100 mg (0.27 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0–10% MeOH/EtOAc) to afford 156 mg (95%) of a white solid. MS (electrospray): exact mass calculated for $C_{30}H_{31}ClF_3N_5O_3$, 601.21. m/z found, 602.2 [M+H]$^+$. $^1$H NMR (CDCl$_3$, 400 MHz, a mixture of amide rotamers):7.76 (d, J=8.41 Hz, 1H), 7.71 and 7.67 (A and B of AB quartet, J=8.41 Hz, 2H), 7.65–7.61 (m, 2H), 7.38 (d, J=8.61 Hz, 1H), 7.26 (dd, J=8.61, 1.96, 1H), 4.86 and 4.74 (A and B of AB quartet, J=15.65 Hz, 1H), 4.64 (br s, 1H), 4.24–4.10 (m, 2.3H), 4.07–3.97 (m, 1.7H), 3.89–3.67 (m, 2H), 3.06–3.00 (m, 1H), 3.00–2.90 (m, 2H), 2.90–2.74 (m, 2H), 2.51–2.38 (m, 3H), 2.25–2.10 (m, 2.3H), 2.20 (s, 1.5H), 2.15 (s, 1.5H), 2.06–1.83 (m, 2.7H).

Example 16

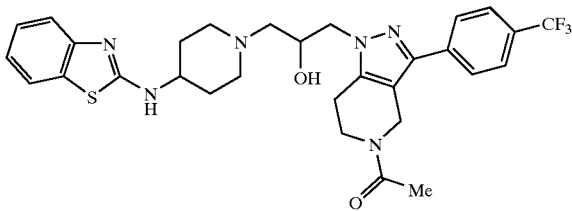

1-[1-{3-[4-(Benzothiazol-2-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone A. 4-(Benzothiazol-2-ylamino)-piperidine-1-carboxylic acid tert-butyl ester.

To a stirred solution of 300 mg (1.77 mmol) of 2-chlorobenzothiazole in dry DMF (3.5 mL) was added 2.9 g of cesium carbonate (8.8 mmol) and 535 mg of tert-butyl-4-hydroxy-1-piperidinecarboxylate (2.66 mmol). The mixture was stirred at room temperature for 4 h before it was partitioned between EtOAc (70 mL) and water (30 mL) and separated. The aqueous layer was further extracted with EtOAc (2×50 mL). The combined organic layers were washed with water (25 mL), brine, dried over $Na_2SO_4$, and the solvent was removed under reduced pressure. Purification by flash chromatography (silica, 0–15% EtOAc/hexanes) afforded 220 mg (37%) of the desired product as a white solid. MS (electrospray): exact mass calculated for $C_{17}H_{23}N_3O_2S$, 333.15. m/z found, 334.2 [M+H]$^+$. $^1$H NMR (CDCl$_3$, 400 MHz): 7.65 (t, J=7.63 2H), 7.36 (ddd, J=8.41, 7.43, 1.37 Hz, 1H), 7.22 (dt, J=7.63, 1.17 Hz, 1H), 5,36 (m, 1H), 3.79–3.70 (br m, 2H), 3.36 (m, 2H), 2.12–2.04 (br m, 2H), 1.92–1.82 (br m, 2H), 1.48 (s, 9H).

B. 1-[1-{3-[4-(Benzothiazol-2-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone.

A solution of 220 mg (0.66 mmol) of 4-(benzothiazol-2-ylamino)-piperidine-1-carboxylic acid tert-butyl ester in dichloromethane (2 mL) was treated with trifluoroacetic acid (0.5 mL) at room temperature overnight. The solvent was then removed and the crude product dissolved in MeOH and stirred over 100 mg of sodium bicarbonate for 1 h. The solid was filtered off and the filtrate concentrated. The crude piperidine was then dissolved in 4 mL EtOH and treated with 220 mg (0.60 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0–10% MeOH/EtOAc) to afford 240 mg (66%) of a white solid. MS (electrospray): exact mass calculated for $C_{30}H_{33}F_3N_6O_2S$: 598.23. m/z found, 599.3 [M+H]$^+$. $^1$H NMR (CDCl$_3$, 400 MHz, a mixture of amide rotamers): 7.78 (d, J=8.22 Hz, 1H), 7.72 and 7.68 (A and B of AB quartet, J=8.41 Hz, 2H), 7.64 (d, J=8.22 Hz, 1H), 7.56 (bd, J=8.02 Hz, 1H), 7.51 (bd, J=8.02 Hz, 1H), 7.29 (bd, J=7.63 Hz, 1H), 7.08 (bt, J=7.63 Hz, 1H), 5.29 (br s, 1H), 4.88 and 4.75 (A and B of AB quartet, J=15.65 Hz, 1H), 4.65 (br s, 1H), 4.23–4.16 (m, 1H), 4.16–4.08 (m, 1H), 4.06–3.98 (m, 2H), 3.92–3.65 (m, 3H), 3.03–2.70 (m, 4H), 2.52–2.41 (m, 3H), 2.26–2.18 (m, 1H), 2.21 (s, 1.5H), 2.16 (s, 1.5H), 2.16–2.08 (m, 2H), 1.66–1.44 (m, 2H).

Example 17

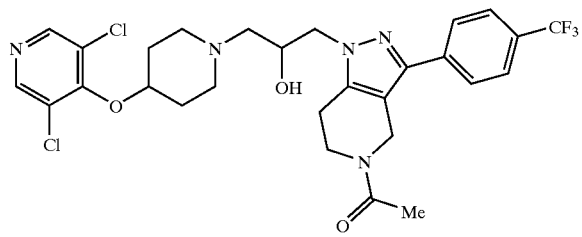

1-[1-{3-[4-(3,5-Dichloro-pyridin-4-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone A. 4-(3,5-Dichloro-pyridin-4-yloxy)-piperidine-1-carboxylic acid tert-butyl ester.

To a stirred solution of 828 mg (4.12 mmol) of tert-butyl-4-hydroxy-1-piperidinecarboxylate in 10 mL of dry DMF was added 165 mg of 60% NaH in mineral oil (4.12 mmol). After stirring at room temperature for 10 min, 500 mg (2.74 mmol) of 3,4,5-trichloropyridine was added. The mixture was stirred at 80° C. overnight and then partitioned between EtOAc (50 mL) and water (20 mL) and separated. The aqueous layer was further extracted with EtOAc (2×30 mL). The combined organic layers were washed with water (25 mL), brine, dried over $Na_2SO_4$, and the solvent was removed under reduced pressure. Column chromatography (silica, 60–100% $CH_2Cl2$/hexanes) gave 265 mg (28%) of desired product. MS (electrospray): exact mass calculated for $C_{15}H_{20}Cl_2N_2O_3$, 346.09. m/z found, 369.1 [M+Na]$^+$. $^1$H NMR (CDCl$_3$, 400 MHz): 8.45 (s, 2H), 4.66 (m, 1H), 3.90–3.80 (br m, 2H), 3.26 (m, 2H), 1.96–1.83 (br m, 4H), 1.47 (s, 9H).

B. 1-[1-{3-[4-(3,5-Dichloro-pyridin-4-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone.

A solution of 103 mg (0.30 mmol) of 4-(3,5-dichloro-pyridin-4-yloxy)-piperidine-1-carboxylic acid tert-butyl ester in $CH_2Cl_2$ (2 mL) was treated with trifluoroacetic acid (0.5 mL) at room temperature overnight. The solvent was then removed and the crude product dissolved in MeOH and stirred over 100 mg of sodium bicarbonate for 1 h. The solid was filtered off and the filtrate concentrated. The crude piperidine was then dissolved in 4 mL EtOH and treated with 100 mg (0.27 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0–10% MeOH/EtOAc) to afford 90 mg (54%) of a white solid. MS (electrospray): exact mass calculated for $C_{28}H_{30}Cl_2F_3N_5O_3$, 611.17. m/z found, 612.2 [M+H]$^+$. $^1$H NMR (CDCl$_3$, 400 MHz, a mixture of amide rotamers): 8.44 (s, 2H), 7.77 (d, J=8.41 Hz, 1H), 7.72 and 7.68 (A and B of AB quartet, J=8.41 Hz, 2H), 7.65 (d, J=8.41 Hz, 1H), 4.88 and 4.76 (A and B of AB quartet, J=15.65 Hz, 1H), 4.66 (br s, 1H), 4.55 (br s, 1H), 4.26–4.08 (m, 2H), 4.08–3.98 (m, 2H), 3.91–3.69 (m, 2H), 3.03–2.92 (m, 1.6H), 2.91–2.85 (m, 0.8H), 2.85–2.75 (m, 1.6H), 2.52–2.40 (m, 3H), 2.35–2.24 (br m, 1H), 2.22 (s, 1.5H), 2.17 (s, 1.5H), 2.03–1.90 (m, 4H).

Example 18

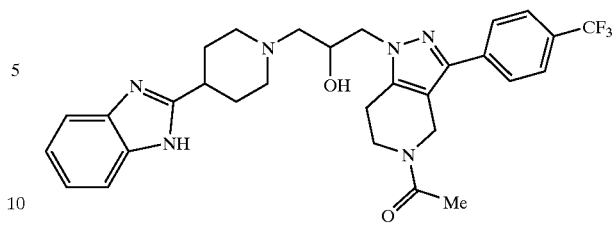

1-[1-{3-[4-(1H-Benzoimidazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone A. 2-Piperidin-4-yl-1H-benzoimidazole.

A flask was charged with 1.35 mL (10 mmol) of methyl isonipicotate, 1.0 g (10 mmol) of 1,2-phenylenediamine and 5 g of polyphosphoric acid. The flask was then heated to 180° C. for 5 h. The reaction mixture was then poured into water while still warm and treated with 50% KOH solution until pH 12. This was then extracted with $CH_2Cl_2$ (3×50 mL), washed with water (25 mL), brine, dried over $Na_2SO_4$, and the solvent was removed under reduced pressure to give 530 mg (27%) of crude product which was used without further purification. MS (electrospray): exact mass calculated for $C_{12}H_{15}N_3$, 201.13. m/z found, 202.1 [M+H]$^+$. $^1$H NMR (400 MHz, DMSO-d$_6$):12.1 (br s, 1H), 7.49 (br m, 1H), 7.38 (br m, 1H), 7.09 (br m, 2H), 3.00 (dt, J=12.13, 3.33 Hz, 2H), 2.88 (tt, J=11.54, 3.74 Hz, 1H), 2.57 (dt, J=12.13, 2.35 Hz, 2H), 1.90 (m, 2H), 1.66 (m, 2H).

B. 1-[1-{3-[4-(1H-Benzoimidazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone.

A solution of 83 mg (0.41 mmol) of 2-piperidin-4-yl-1H-benzoimidazole was dissolved in 4 mL EtOH and treated with 100 mg (0.27 mmol) of 1-[1-oxiranylmethyl-3-(4-trifluoromethyl-phenyl)-1,4,6,7-tetrahydro-pyrazolo[4,3-c]pyridin-5-yl]-ethanone. The solution was heated to 60° C. overnight. The solvent was then removed by rotary evaporation and the crude product was purified by column chromatography (silica, 0–10% MeOH/EtOAc) to afford 55 mg (36%) of a white solid. MS (electrospray): exact mass calculated for $C_{30}H_{33}F_3N_6O_2$, 566.26. m/z found, 567.3 [M+H]$^+$. $^1$H NMR (CDCl$_3$, 400 MHz, a mixture of amide rotamers):10.66 (br s, 0.5H), 10.57 (br s, 0.5H), 7.73 (bd, J=8.41 Hz, 1H), 7.72–7.63 (m, 3H), 7.60 (bd, J=8.41 Hz, 1H), 7.39–7.32 (m, 1H), 7.23–7.13 (m, 2H), 7.02 (br s, 1), 4.86 and 4.75 (A and B of AB quartet, J=15.85 Hz, 1.25H), 4.64 (br s, 1H), 4.21–4.06 (m, 2H), 4.06–3.81 (m, 2H), 3.80–3.63 (m, 1H), 3.80–3.69 (m, 1H), 3.00–2.68 (m, 5H), 2.44–2.36 (m, 2H), 2.39–2.23 (m, 2H), 2.19 (s, 1.6H), 2.15 (s, 1.4H), 2.13–2.00 (m, 4H), 2.00–1.80 (m, 2H).

Example 19

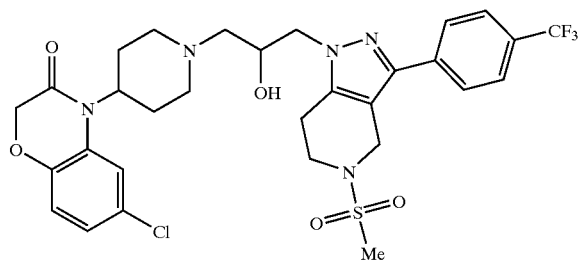

6-Chloro-4-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one A. 5-Methanesulfonyl-1-oxiranylmethyl-3-(4-trifluoromethyl-phenyl)-4,5,6,7-tetrahydro-1H-pyrazolo[4,3-c]pyridine.

5-Methanesulfonyl-3-(4-trifluoromethyl-phenyl)-4,5,6,7-tetrahydro-1H-pyrazolo[4,3-c]pyridine (10.0 g, 29.0 mmol) and epichlorohydrin (24 mL, 307 mmol) were set stirring in DMF (150 mL) containing $Cs_2CO_3$ (10.4 g, 31.9 mmol). After stirring at room temperature for 4 days the mixture was evaporated, brought up in EtOAc and washed with water. The organics were dried ($MgSO_4$) and evaporated to give a light yellow solid. Column chromatography (silica, 5% acetone/$CH_2Cl_2$) gave 4.1 g (35%) of a white solid. TLC (silica, 5% acetone/$CH_2Cl_2$): $R_f$=0.28. MS (electrospray): exact mass calculated for $C_{17}H_{18}F_3N_3O_3S$, 401.10. m/z found, 402.1 [M+H]$^+$. $^1$H NMR (400 MHz, CDCl$_3$); 7.84 (d, J=8.3 Hz, 2H), 7.79 (d, J=8.3 Hz, 2H), 4.70–4.62 (m, 3H), 4.25 (d, J=5.4 Hz, 1H), 3.90–3.70 (m, 2H), 3.47 (m, 1H), 3.10–2.9 (m, 6H), 2.65–2.60 (m, 1H).

B. 4-(5-Chloro-2-hydroxy-phenylamino)-piperidine-1-carboxylic acid tert-butyl ester.

2-Amino-4-chloro-phenol (30.0 g, 209 mmol) and 4-oxo-piperidine-1-carboxylic acid tert-butyl ester (46.0 g, 231 mmol) were set stirring in dichloromethane (600 mL). Sodium triacetoxyborohydride (58.0 g, 274 mmol) was added in portions over 10 min. Acetic acid (12 mL, 210 mmol) was then added and the mixture left to stir for 18 h. Saturated NaHCO$_3$ was added and the organics seperated. The organics were dried (MgSO$_4$) and evaporated to give 56 g (82%) of a light beige solid. TLC (silica, 50% EtOAc/hexanes): $R_f$=0.66. MS (electrospray): exact mass calculated for $C_{16}H_{23}ClN_2O_3$, 326.14. m/z found, 349.1 [M+Na]$^+$. $^1$H NMR (400 MHz, DMSO-d$_6$): 6.70 (d, J=8.3 Hz, 1H), 6.63 (s, 1H), 6.47 (d, J=8.2 Hz, 1H), 3.97 (d, J=12.2 Hz, 2H), 3.55–3.50 (m, 1H), 2.93 (br s, 2H), 1.93 (d, J=11.1 Hz, 2H), 1.48 (s, 9H), 1.35 (d, J=11.2 Hz, 2H).

C. 4-[(5-Chloro-2-hydroxy-phenyl)-ethoxycarbonylmethyl-amino]-piperidine-1-carboxylic acid tert-butyl ester.

4-(5-Chloro-2-hydroxy-phenylamino)-piperidine-1-carboxylic acid tert-butyl ester (15.6 g, 47.7 mmol) was set stirring in THF (200 mL) and cooled to 5° C. Sodium hydride (1.37 g, 54.2 mmol) was added in portions over 10 min and the mixture left to stir for 1 h. Ethyl bromoacetate (5.8 mL, 52.3 mmol) was added and the ice bath removed. After stirring for 20 h the mixture was evaporated, brought up in EtOc and washed with water. The organics were dried (MgSO$_4$) and evaporated to give 22.5 g of a deep red oil. The oil was purified (silica, 5% acetone/$CH_2Cl_2$) to give 12.9 g (65%) of a clear orange liquid. TLC (silica, 5% acetone/$CH_2Cl_2$): $R_f$=0.43. MS (electrospray): exact mass calculated for $C_{20}H_{29}ClN_2O_5$, 412.18. m/z found, 413.2 [M+H]$^+$. $^1$H NMR (400 MHz, CDCl$_3$): 6.75–6.62 (m, 3H), 4.71 (s, 1H), 4.37 (q, J=7.2 Hz, 2H), 4.14 (br s, 2H), 3.55–3.50 (m, 1H), 3.08 (br t, 2H), 2.14 (m, 2H), 1.65–1.45 (m, 12H), 1.41 (t, J=7.2 Hz, 3H).

D. 4-(6-Chloro-3-oxo-2,3-dihydro-benzo[1,4]oxazin-4-yl)-piperidine-1-carboxylic acid tert-butyl ester.

4-[(5-Chloro-2-hydroxy-phenyl)-ethoxycarbonylmethyl-amino]-piperidine-1carboxylic acid tert-butyl ester (12.9 g, 31.2 mmol) was set stirring in MeOH (100 mL). A solution of NaOH (2.5 g, 62.5 mmol) in water (100 mL) was added and the mixture stirred at room temperature for 3 h. The mixture was acidified to pH 2 and MeOH evaporated. The aqueous layer was extracted twice with EtOAc. The organics were combined, dried (MgSO$_4$) and evaporated to give 11 g of a clear orange oil. The oil was set stirring in $CH_2Cl_2$ (150 mL) and EDC (8.2 g, 42.8 mmol) was added. After 1 h the organics were washed with 1 N HCl (100 mL), water (100 mL) and dried (MgSO$_4$). The solvent was evaporated to give 7.2 g (63%) of a clear orange solid. TLC (silica, 5% acetone/$CH_2Cl_2$): $R_f$0.53. MS (electrospray): exact mass calculated for $C_{18}H_{23}ClN_2O_4$, 366.13; m/z found, 389.1 [M+Na]$^+$. $^1$H NMR (400 MHz, CDCl$_3$): 7.19 (s, 1H), 7.11–7.00 (m, 2H), 4.60 (s, 2H), 4.50–4.30 (m, 3H), 3.00–2.80 (m, 2H), 2.70–2.60 (m, 2H), 1.86 (d, J=11.4 Hz, 2H), 1.60 (s, 9H).

E. 6-Chloro-4-piperidin-4-yl-4H-benzo[1,4]oxazin-3-one.

4-(6-Chloro-3-oxo-2,3-dihydro-benzo[1,4]oxazin-4-yl)-piperidine-1-carboxylic acid tert-butyl ester (7.2 g, 19.6 mmol) was set stirring and a 1:1 TFA/$CH_2Cl_2$ solvent mixture was added. After 1 h the mixture was evaporated under reduced pressure and the resulting red oil brought up in Et$_2$O. A solid formed and was filtered and air dried to give 7.2 g (96%) of a light beige solid. MS (electrospray): exact mass calculated for $C_{13}H_{15}ClN_2O_2$, 266.08. m/z found, 267.1 [M+H]$^+$. $^1$H NMR (400 MHz, CD$_3$OD): 7.52 (s, 1H), 7.20–7.00 (m, 2H), 4.60 (s, 2H), 4.50–4.40 (m, 1H), 3.65–3.55 (m, 2H), 3.28 (t, J=13.1 Hz, 2H), 3.10–3.00 (m, 2H), 2.15 (d, J=13.9 Hz, 2H).

F. 6-Chloro-4-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one.

6-Chloro-4-piperidin-4-yl-4H-benzo[1,4]oxazin-3-one (252 mg, 0.66 mmol) and 5-methanesulfonyl-1-oxiranylmethyl-3-(4-trifluoromethyl-phenyl)-4,5,6,7-tetrahydro-1H-pyrazolo[4,3-c]pyridine (209 mg, 0.52 mmol) were set stirring in EtOH (10 mL) containing Et$_3$N (115 µL, 0.83 mmol) at 70° C. After 2 days the mixture was cooled, evaporated, brought up in EtOAc and washed with saturated NaHCO$_3$. The organics were dried (MgSO$_4$) and evaporated to give a clear golden oil. The oil was purified (silica, 50% acetone/$CH_2Cl_2$) to give 191 mg (55%) of a white solid. TLC (silica, 50% acetone/$CH_2Cl_2$): $R_f$=0.38. MS (electrospray): exact mass calculated for $C_{30}H_{33}ClF_3N_5O_5S$, 667.18. m/z found, 668.2 [M+H]$^+$. $^1$H NMR (400 MHz, CDCl$_3$): 7.83 (d, J=8.3 Hz, 2H), 7.77 (d, J=8.3 Hz, 2H), 7.21 (s, 1H), 7.10–7.00 (m, 2H), 4.68 (d, J=5.1 Hz, 2H), 4.58 (s, 2H), 4.40–4.10 (m, 4H), 3.90–3.70 (s, 2H), 3.30–3.0 (m, 4H), 3.00 (s, 3H), 2.90–2.70 (m, 2H), 2.65–2.50 (m, 3H), 2.35–2.20 (m, 2H), 1.88 (d, J=11.3 Hz, 2H).

Example 20

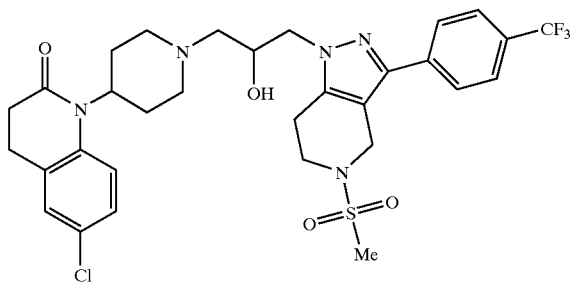

6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one A. 3-(2-Amino-5-chloro-phenyl)-acrylic acid ethyl ester.

2-Amino-5-chlorobenzaldehyde (7.58 g, 48.7 mmol) and 36 g (103 mmol) of (carbethoxymethylene) triphenylphosphorane were added in benzene (300 mL) and heated to reflux for 20 h. The reaction mixture was cooled and concentrated to give an orange oil. The oil was brought up in Et$_2$O and precipitated appeared. This was filtered and washed with Et$_2$O. The organics were evaporated to give a clear orange oil. The oil was purified by column chromatography (silica, 10–40% EtOAc/hexanes) to obtain 10.4 g (95%) of a yellow solid. MS (electrospray): exact mass calculated for $C_{11}H_{12}ClNO_2$, 225.06. m/z found, 226.1 [M$^+$+H]. $^1$H NMR (400 MHz, CDCl$_3$): 7.69 (d, J=15.85 Hz, 1H), 7.30 (d, J=2.54 Hz, 1H), 7.07 (dd, J=6.26 Hz, 2.35 Hz, 1H), 6.60 (d, J=8.61 Hz, 1H), 6.30 (d, J=15.85 Hz, 1H), 4.22 (dd, J=7.24 Hz, 7.24 Hz, 2H), 3.98 (br s, 2H), 1.30 (t, J=7.04 Hz, 3H).

B. 4-[4-Chloro-2-(2-ethoxycarbonyl-vinyl)-phenylamino]-piperidine-1-carboxylic acid tert-butyl ester.

3-(2-Amino-5-chloro-phenyl)-acrylic acid ethyl ester (10.4 g, 46 mmol) and 4-oxo-piperidine-1-carboxylic acid tert-butyl ester (13.8 g, 69 mmol) were set stirring in CH$_2$Cl$_2$ (230 mL). Sodium triacetoxyborohydride (14.6 g, 69 mmol) was added in portions over 10 min. Acetic acid (1.3 mL, 25 mmol) was then added and the mixture left to stir. After 18 h saturated NaHCO$_3$ was added and the organics separated. The organics were dried over Na$_2$SO$_4$ and concentrated. The residue was purified by column chromatography (silica, 20–50% EtOAc/hexanes) to obtain 12.4 g (66%) of a light beige solid. TLC (silica, 25% EtOAc/hexanes): R$_f$=0.5. MS (electrospray): exact mass calculated for $C_{21}H_{29}ClN2O_4$, 408.18. m/z found, 409.1 [M$^+$+H]. $^1$H NMR (400 MHz, CDCl$_3$): 7.64 (d, J=15.65 Hz, 1H), 7.29 (d, J=2.35 Hz, 1H), 7.14 (dd, J=6.26 Hz, 2.54 Hz, 1H), 6.59 (d, J=9.00 Hz, 1H), 6.28 (d, J=15.65 Hz, 1H), 4.23 (dd, J=7.04 Hz, 7.04 Hz, 2H), 4.11–3.98 (m, 2H), 3.81 (br s, 1H), 3.46–3.36 (m, 1H), 2.89 (t, J=11.74 Hz, 2H), 2.04–1.95 (m, 2H), 1.44 (s, 9H), 1.42–1.33 (m, 2H), 1.30 (t, J=7.24 Hz, 3H).

C. 4-[4-Chloro-2-(2-ethoxycarbonyl-ethyl)-phenylamino]-piperidine-1-carboxylic acid tert-butyl ester.

4-[4-Chloro-2-(2-ethoxycarbonyl-vinyl)-phenylamino]-piperidine-1-carboxylic acid tert-butyl ester (12.4 g, 30.4 mmol) in EtOAc (150 mL) containing PtO$_2$ (1 g) was placed on a Parr hydrogenator at 60 psi H$_2$. After 18 h the mixture was filtered through celite and evaporated to give a clear brown liquid. The liquid was purified by column chromatography (silica, 20–50% EtOAc/hexanes) to obtain 5.7 g (46%) of the title compound. TLC (silica, 25% EtOAc/hexanes): R$_f$=0.5. MS (electrospray): exact mass calculated for $C_{21}H_{31}ClN_2O_4$, 410.2. m/z found, 411.2 [M$^+$+H]. $^1$H NMR (400 MHz, CDCl$_3$): 7.05 (dd, J=6.06 Hz, 2.54 Hz, 1H), 6.99 (d, J=2.35 Hz, 1H), 6.55 (d, J=8.61 Hz, 1H), 4.13 (dd, J=7.04 Hz, 3.13 Hz, 2H), 4.11–3.98 (m, 2H), 3.81 (br s, 1H), 3.72 (t, J=6.26 Hz, 2H), 3.46–3.36 (m, 1H), 2.75 (t, J=7.43 Hz, 2H), 2.60 (t, J=7.04 Hz, 2H), 2.04–1.95 (m, 2H), 1.46 (s, 9H), 1.42–1.33 (m, 2H), 1.26 (t, J=7.24 Hz, 3H).

D. 4-[2-(2-Carboxy-ethyl)-4-chloro-phenylamino]-piperidine-1-carboxylic Acid tert-butyl ester.

4-[4-Chloro-2-(2-ethoxycarbonyl-ethyl)-phenylamino]-piperidine-1-carboxylic acid tert-butyl ester (5.7 g, 13.9 mmol) was set stirring in MeOH (40 mL). A solution of NaOH (1.4 g, 34.7 mmol) in water (10 mL) was added and the mixture stirred at room temperature. After 3 h the mixture was acidified to pH 7 and MeOH was evaporated. The aqueous layer was extracted with CH$_2$Cl$_2$ (3×100 mL). The organics were combined, dried over Na$_2$SO$_4$ and concentrated to afford 3.9 g (73%) of the desired product. TLC (silica, 50% EtOAc/hexanes): R$_f$=0.4. MS (electrospray): exact mass calculated for $C_{19}H_{27}ClN_2O_4$, 382.17; m/z found, 381.1 [M$^{31}$ −H].

E. 4-(6-Chloro-2-oxo-3,4-dihydro-2H-quinolin-1-yl)-piperidine-1-carboxylic Acid tert-butyl ester.

4-[2-(2-Carboxy-ethyl)-4-chloro-phenylamino]-piperidine-1-carboxylic acid tert-butyl ester (3.9 g, 10.1 mmol) and EDC (2.9 g, 15.3 mmol) were set stirring in CH$_2$Cl$_2$ (50 mL) for 2 h. The reaction mixture was dissolved in CH$_2$Cl$_2$ (150 mL), washed with water (2×50 mL) and brine (1×50 mL). The organic layer was dried over Na$_2$SO$_4$ and concentrated. The residue was purified by column chromatography (silica, 30–50% EtOAc/hexanes) to obtain 1.9 g (52%) of the desired product. TLC (silica, 50% EtOAc/hexanes): R$_f$=0.67. MS (electrospray): exact mass calculated for $C_{19}H_{25}ClN_2O_3$, 364.16. m/z found, 365.1 [M$^+$+H]. $^1$H NMR (400 MHz, CDCl$_3$): 7.14–7.08 (m, 2H), 6.98 (d, J=8.61 Hz, 1H), 4.33–3.98 (m, 3H), 2.75 (t, J=7.83 Hz, 4H), 2.55–2.36 (m, 4H), 1.70–1.65 (m, 2H), 1.44 (s, 9H).

F. 6-Chloro-1-piperidin-4-yl-3,4-dihydro-1H-quinolin-2-one.

4-(6-Chloro-2-oxo-3,4-dihydro-2H-quinolin-1-yl)-piperidine-1-carboxylic acid tert-butyl ester (1.2 g, 3.28 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 1.3 g (93%) of a white solid. MS (electrospray): exact mass calculated for $C_{13}H_{17}ClN_2O$, 264.10. m/z found, 265.1 [M$^+$+H].

G. 6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-guinolin-2-one.

6-Chloro-1-piperidin-4-yl-3,4-dihydro-1H-quinolin-2-one (270 mg, 0.62 mmol) and 5-methanesulfonyl-1-oxiranylmethyl-3-(4-trifluoromethyl-phenyl)-4,5,6,7-tetrahydro-1H-pyrazolo[4,3-c]pyridine (165 mg, 0.41 mmol) were set stirring in EtOH (10 mL) containing Et$_3$N (97 μL, 0.70 mmol) at 80° C. After 16 h the mixture was cooled, evaporated, brought up in dichloromethane and washed with water. The organics were dried over Na$_2$SO$_4$ and concentrated. The residue was purified by column chromatography (silica, 5–10% MeOH/CH$_2$Cl$_2$) to obtain 205 mg (75%) of a white solid. TLC (silica, 10% MeOH/CH$_2$Cl$_2$): R$_f$=0.75. MS (electrospray): exact mass calculated for $C_{31}H_{35}ClF_3N_5O_4S$, 665.21; m/z found, 666.2 [M$^+$+H]. $^1$H NMR (CDCl$_3$, 400 MHz): 7.69 (d, J=8.41 Hz, 2H), 7.62 (d, J=8.41 Hz, 2H), 7.16–7.08 (m, 2H), 7.00 (d, J=9.00 Hz, 1H), 4.52 (dd, J=14.28 Hz, 5.48 Hz, 2H), 4.18 (dd, J=10.56 Hz, 3.13 Hz, 1H), 4.14–4.04 (m, 2H), 4.03–3.96 (m, 1H), 3.72–3.56 (m, 2H), 3.10–2.96 (m, 2H), 2.95–2.86 (m, 2H), 2.85 (s, 3H), 2.75 (t, J=6.26 Hz, 2H), 2.69–2.54 (m, 2H), 2.53–2.47 (m, 2H), 2.44–2.31 (m, 3H), 2.15–2.05 (m, 1H), 1.71–1.62 (m, 2H).

Example 21

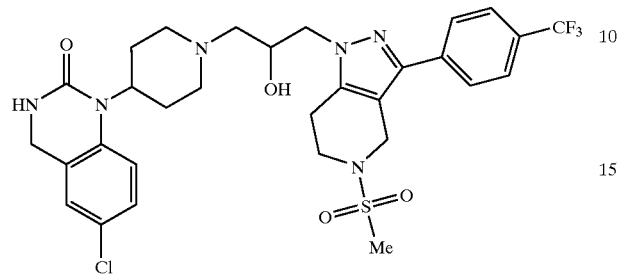

6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one A. Spiro[piperidine-4,2'(1'H)-6'-chloro-3', 4'-dihydro-4'-oxo-quinazoline]-1-carboxylic acid tert-butyl ester.

To a stirred solution of 2-amino-5-chlorobenzamide (5.67 g, 33.2 mmol) and 4-oxo-piperidine-1-carboxylic acid tert-butyl ester (6.62 g, 33.2 mmol) in benzene (70 mL) was added a catalytic amount (~0.3 g) of p-toluenesulfonic acid. The mixture was heated to reflux for 20 h under a Dean-Stark trap. The resulting suspension was concentrated. Saturated NaHCO$_3$ (68 mL) was added. The mixture was extracted with EtOAc and the precipitated crystal in the aqueous layer was collected by filtration. The solid was washed with water and dried to afford 11.22 g (96%) of the desired product. MS (electrospray): exact mass calculated for C$_{17}$H$_{22}$ClN$_3$O$_3$, 351.13. m/z found, 352.1 [M$^+$+H]. $^1$H NMR (CD$_3$OD, 400 MHz): 7.50 (d, J=2.54 Hz, 1H), 7.13 (dd, J=6.06 Hz, 2.54 Hz, 1H), 6.65 (d, J=8.61 Hz, 1H), 3.56–3.47 (m, 2H), 3.36–3.25 (m, 2H), 1.79–1.66 (m, 4H), 1.32 (s, 9H).

B. 4-(2-Aminomethyl-4-chloro-phenylamino)-piperidine-1-carboxylic acid tert-butyl ester.

Spiro[piperidine-4,2'(1'H)-6'-chloro-3',4'-dihydro-4'-oxo-quinazoline]-1-carboxylic acid tert-butyl ester (1 g, 2.8 mmol) and borane-tetrahydrofurane complex (1.0 M, 9.9 mL, 9.9 mmol) were added in THF (10 mL) and heated to reflux for 6 h. The reaction mixture was cooled and poured into ice water. The resulting suspension was extracted with CH$_2$Cl$_2$ (2×100 mL). The organics were dried and concentrated. The residue was purified by column chromatography (silica, 5–10% MeOH/CH$_2$Cl$_2$) to obtain 795 mg (79%) of the product. MS (electrospray): exact mass calculated for C$_{17}$H$_{26}$ClN$_3$O$_2$, 339.17; m/z found, 362.1 [M$^+$+Na]. $^1$H NMR (CDCl$_3$, 400 MHz): 7.07 (dd, J=6.06 Hz, 2.54 Hz, 1H), 6.97 (d, J=2.54 Hz, 1H), 6.54 (d, J=8.61 Hz, 1H), 3.94–3.70 (m, 4H), 3.48–3.38 (m, 1H), 3.05 (t, J=11.15 Hz, 2H), 2.68–2.55 (m, 1H), 2.02–1.90 (m, 4H), 1.46 (s, 9H).

C. 4-(6-Chloro-2-oxo-3,4-dihydro-2H-quinazolin-1-yl)-piperidine-1-carboxylic acid tert-butyl ester.

1,1'-Carbonyldiimidazole (0.51 g, 3.15 mmol) was added to a solution of 4-(2-aminomethyl-4-chloro-phenylamino)-piperidine-1-carboxylic acid tert-butyl ester (0.79 g, 2.25 mmol) in CH$_3$CN (10 mL) over 3 h with stirring at 50° C. The reaction mixture was then cooled to room temperature and stirred for additional 2 h. The reaction mixture was dissolved in CH$_2$Cl$_2$ (100 mL), washed with water (2×10 mL), brine (1×10 mL). The organic layer was dried over Na$_2$SO$_4$ and concentrated. The residue was purified by column chromatography (silica, 30–50% EtOAc/hexanes) to obtain 0.46 g (63%) of the desired product. TLC (silica, 50% EtOAc/hexanes): R$_f$=0.5. MS (electrospray): exact mass calculated for C$_{18}$H$_{24}$ClN$_3$O$_3$, 365.15. m/z found, 388.1 [M$^+$+Na]. $^1$H NMR (CDCl$_3$, 400 MHz): 7.18 (dd, J=6.26 Hz, 2.54 Hz, 1H), 7.05 (d, J=2.15 Hz, 1H), 6.94 (d, J=9.00 Hz, 1H), 6.29 (s, 1H), 4.32–4.18 (m, 4H), 4.13–4.02 (m, 1H), 2.88–2.71 (m, 2H), 2.64–2.50 (m, 2H), 1.82–1.73 (m, 2H), 1.49 (s, 9H).

D. 6-Chloro-1-piperidin-4-yl-3,4-dihydro-1H-guinazolin-2-one.

4-(6-Chloro-2-oxo-3,4-dihydro-2H-quinazolin-1-yl)-piperidine-1-carboxylic acid tert-butyl ester (0.52 g, 1.42 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 0.52 g (97%) of an off-white solid. MS (electrospray): exact mass calculated for C$_{13}$H$_{16}$ClN$_3$O, 265.10. m/z found, 266.1 [M$^+$+H].

E. 6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one.

6-Chloro-1-piperidin-4-yl-3,4-dihydro-1H-quinazolin-2-one (183 mg, 0.42 mmol) and 5-methanesulfonyl-1-oxiranylmethyl-3-(4-trifluoromethyl-phenyl)-4,5,6,7-tetrahydro-1H-pyrazolo[4,3-c]pyridine (112 mg, 0.28 mmol) were set stirring in EtOH (10 mL) containing Et$_3$N (66 μL, 0.47 mmol) at 80° C. After 16 h the mixture was cooled, evaporated, brought up in CH$_2$Cl$_2$ and washed with water. The organics were dried over Na$_2$SO$_4$ and concentrated. The residue was purified by column chromatography (silica, 5–10% MeOH/CH$_2$Cl$_2$) to obtain 141 mg (76%) of a white solid. TLC (silica, 10% MeOH/CH$_2$Cl$_2$): R$_f$=0.6. MS (electrospray): exact mass calculated for C$_{30}$H$_{34}$ClF$_3$N$_6$O$_4$S, 666.20. m/z found, 667.2 [M$^+$+H]. $^1$H NMR (CDCl$_3$, 400 MHz): 7.70 (d, J=7.83 Hz, 2H), 7.63 (d, J=8.02 Hz, 2H), 7.12 (dd, J=6.65 Hz, 2.35 Hz, 1H), 7.01 (br s, 1H), 6.92 (d, J=9.00 HZ, 1H), 5.44 (br s, 1H), 4.54 (dd, J=14.67 Hz, 6.46 Hz, 2H), 4.23–4.08 (m, 4H), 4.05–3.97 (m, 1H), 3.92–3.80 (m, 1H), 3.74–3.57 (m, 2H), 3.14–2.99 (m 2H), 2.97–2.87 (m, 2H), 2.86 (s, 3H), 2.78–2.57 (m, 2H), 2.48–2.32 (m, 3H), 2.10 (t, J=11.50 Hz 1H), 1.80–1.70 (m, 2H).

Example 22

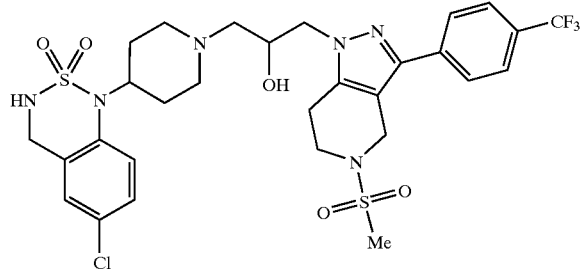

1-[4-(6-Chloro-2,2-dioxo-3,4-dihydro-2H-2λ$^6$-benzo[1,2,6]thiadiazin-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol A. 4-(6-Chloro-2,2-dioxo-3,4-dihydro-2H-2λ$^6$-benzo[1,2,6]thiadiazin-1-yl)-piperidine-1-carboxylic acid tert-butyl ester.

A solution of 4-(2-aminomethyl-4-chloro-phenylamino)-piperidine-1-carboxylic acid tert-butyl ester (678 mg, 2 mmol) and sulfamide (596 mg, 6.2 mmol) in pyridine (12 mL) was heated to reflux for 6 h. The reaction mixture was then cooled to room temperature and poured into ice water (50 mL). The solution was extracted with $CH_2Cl_2$ (4×100 mL). The organic extracts was dried over $Na_2SO_4$ and concentrated. The residue was purified by column chromatography (silica, 30–50% EtOAc/hexanes) to obtain 767 mg (96%) of the desired product. TLC (silica, 50% EtOAc/hexanes): $R_f$=0.75. MS (electrospray): exact mass calculated for $C_{17}H_{24}ClN_3O_4S$, 401.12. m/z found, 400.1 [M$^-$-H]. $^1$H NMR (CDCl$_3$, 400 MHz): 7.13 (dd, J=6.46 Hz, 2.15 Hz, 1H), 7.00 (d, J=1.96 Hz, 1H), 6.92 (d, J=8.60 Hz, 1H), 5.54 (br s, 1H), 4.35 (s, 2H), 4.11–3.81 (m, 3H), 2.62 (br s, 2H), 1.90–1.66 (m, 4H), 1.34 (s, 9H).

B. 6-Chloro-1-piperidin-4-yl-3,4-dihydro-1H-benzo[1,2,6]thiadiazine 2,2-dioxide.

4-(6-Chloro-2,2-dioxo-3,4-dihydro-2H-2l6-benzo[1,2,6]thiadiazin-1-yl)-piperidine-1-carboxylic acid tert-butyl ester (767 mg, 1.91 mmol) was set stirring in 1:1 TFA/$CH_2Cl_2$. After 45 min the mixture was evaporated and the golden oil brought up in $Et_2O$. A solid formed and was filtered, washed with $Et_2O$ and air dried to give 730 mg (91%) of an off-white solid. MS (electrospray): exact mass calculated for $C_{12}H_{16}ClN_3O_2S$, 301.07. m/z found, 302.0 [M$^+$+H].

C. 1-[4-(6-Chloro-2,2-dioxo-3,4-dihydro-2H-2$\lambda^6$-benzo[1,2,6]thiadiazin-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol.

6-Chloro-1-piperidin-4-yl-3,4-dihydro-1H-benzo[1,2,6]thiadiazine 2,2-dioxide (440 mg, 1.03 mmol) and 5-methanesulfonyl-1-oxiranylmethyl-3-(4-trifluoromethyl-phenyl)-4,5,6,7-tetrahydro-1H-pyrazolo[4,3-c]pyridine (415 mg, 1.03 mmol) were set stirring in EtOH (20 mL) containing Et$_3$N (215 µL, 1.54 mmol) at 80° C. After 16 h the mixture was cooled, evaporated, brought up in $CH_2Cl_2$ and washed with water. The organics were dried over $Na_2SO_4$ and concentrated. The residue was purified by column chromatography (silica, 0–5% MeOH/$CH_2Cl_2$) to obtain 229 mg (32%) of a white solid. TLC (silica, 5% MeOH/$CH_2Cl_2$): $R_f$=0.8. MS (electrospray): exact mass calculated for $C_{29}H_{34}ClF_3N_6O_5S_2$, 702.17. m/z found, 703.2 [M$^+$+H]. $^1$H NMR (CDCl$_3$, 400 MHz, a mixture of two rotamers): 7.66 (d, J=8.61 Hz, 2H), 7.60 (d, J=8.61 Hz, 2H), 7.16 (dd, J=6.85 Hz, 1.96 Hz, 1H), 6.98 (s, 1H), 6.95 (d, J=9.00 HZ, 1H), 4.47 (s, 2H), 4.33 (s, 2H), 4.16–3.99 (m, 2H), 3.98–3.90 (m, 1H), 3.89–3.78 (m, 1H), 3.62–3.52 (m, 2H), 3.05–2.95 (m, 1H), 2.93–2.84 (m, 2H), 2.82 (s, 3H), 2.81–2.76 (m, 1H), 2.33 (d, J=6.46 Hz, 2H), 2.25 (t, J=11.24 Hz, 1H), 2.09–1.90 (m, 3H), 1.90–1.78 (m, 2H).

Example 23

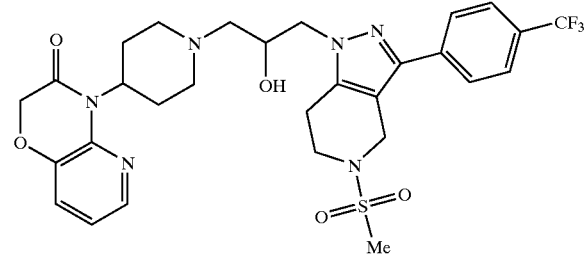

4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-pyrido[3,2-b][1,4]oxazin-3-one A. 4-(3-Hydroxy-pyridin-2-ylamino)-piperidine-1-carboxylic acid tert-butyl ester.

To a stirring solution of 4.7 g (0.042 mol) of 2-amino-3-hydroxypyridine and 12.75 g (0.064 mol) of 4-oxo-piperidine-1-carboxylic acid tert-butyl ester in $CH_2Cl_2$/AcOH (150 mL/60 mL) was added 10 g (0.070 mol) of $Na_2SO_4$. After 3.5 h, 9.9 g (0.047) of sodium triacetoxyborohydride was added in three portions, and the mixture was stirred at room temperature for 15 h. The reaction was then quenched with NaHCO$_3$ (150 mL), extracted with $CH_2Cl_2$ (500 mL), washed with NaHCO$_3$(2×100 mL), and the combined aqueous layers were extracted with EtOAc (150 mL). The combined organic layers were dried over $Na_2SO_4$, concentrated, and purified using flash chromatography (silica, 3–10% MeOH/$CH_2Cl_2$) to afford 5.9 g (48%) of a beige powder. MS (electrospray): exact mass calculated for $C_{15}H_{23}N_3O_3$, 293.17. m/z found, 294.2 [M+H]$^+$. $^1$H NMR (400 MHz, CDCl$_3$): 7.52 (dd, J=5.3 Hz, 1.3 Hz, 1H), 6.79 (dd, J=7.6 Hz, 1.3 Hz, 1H), 6.40 (dd, J=7.6 Hz, 5.3 Hz, 1H), 4.06–3.94 (m, 3H), 3.02–2.86 (m, 2H), 2.72 (br s, 1H), 2.06–1.97 (m, 2H), 1.42 (s, 9H), 1.46–1.28 (m, 2H).

B. 4-(3-Ethoxycarbonylmethoxy-pyridin-2-ylamino)-piperidine-1-carboxylic Acid tert-butyl ester.

A stirring solution of 1.4 g (0.0048 mol) of 4-(3-hydroxy-pyridin-2-ylamino)-piperidine-1-carboxylic acid tert-butyl ester was dissolved in THF (24 mL) was cooled to 0° C., and 0.13 g (0.0052 mol) of NaH was added. After 30 min, 0.8 g (0.0052 mol) of ethyl bromoacetate was added, and reaction was allowed to warm to room temperature and stirred overnight. Saturated NaHCO$_3$ (20 mL) was added and the reaction mixture was partitioned between EtOAc (200 mL) and saturated NaHCO$_3$ (75 mL). The organic layer was washed with water (50 mL) and NaCl (50 mL), dried over $Na_2SO_4$, and concentrated to afford 0.9 g (49%) of a white powder. MS (electrospray): exact mass calculated for $C_{19}H_{29}N_3O_5$, 379.21. m/z found, 380.2 [M+H]$^+$. $^1$H NMR (400 MHz, CDCl$_3$): 7.74 (d, J=5.3 Hz, 1H), 6.76 (d, J=7.8 Hz, 1H), 6.46 (dd, J=7.8 Hz, 5.3 Hz, 1H), 5.05 (d, J=7.33 Hz, 1H), 4.59 (s, 2H), 4.26 (q, J=7.3 Hz, 2H), 4.18–3.92 (m, 3H), 2.97 (t, J=11.6 Hz, 2H), 2.06 (d, J=12.1 Hz, 2H), 1.46 (s, 9H), 1.46–1.34 (m, 2H) 1.29 (t, J=7.3 Hz, 3H).

C. 4-(3-Oxo-2,3-dihydro-pyrido[3,2-b][1,4]oxazin-4-yl)-piperidine-1-carboxylic acid tert-butyl ester.

To a stirring solution of 0.9 g (0.0023 mol) of 4-(3-ethoxycarbonylmethoxy-pyridin-2-ylamino)-piperidine-1-carboxylic acid tert-butyl ester in H$_2$O/MeOH (1 mL/11 mL) was added 0.05 g (0.0023 mol) of LiOH. After 6 h, the solvent was removed under reduced pressure. The residue was dissolved in DMF (12 mL) and to the stirring solution was added 1.82 g (0.0048 mol) of HATU. After 3 h, the reaction was partitioned between EtOAc (250 mL) and saturated NaHCO$_3$ (100 mL), and washed with water (3×100 mL). The combined aqueous layers were extracted with EtOAc (100 mL). The combined organic layers were washed with brine (100 mL), dried over $Na_2SO_4$, and concentrated to afford 0.37 g (46%) of a white solid. MS (electrospray): exact mass calculated for $C_{17}H_{23}N_3O_4$, 333.17. m/z found, 356.1 [M+Na]$^+$. $^1$H NMR (400 MHz, CDCl$_3$): 7.97 (dd, J=4.8 Hz, 1.5 Hz, 1H), 7.25 (dd, J=8.1 Hz, 1.5 Hz, 1H), 6.96 (dd, J=8.1 Hz, 4.8 Hz, 1H), 5.03 (tt, J=11.9 Hz, 4.0 Hz, 1H), 4.55 (s, 2H), 4.13 (d, J=10.9 Hz, 2H), 2.82–2.69 (m, 2H), 2.68 (qd, J=12.4 Hz, 4.0 Hz, 2H), 1.65 (d, J=12.1 Hz, 2H), 1.46 (s, 9H).

D. 4-Piperidin-4-yl-4H-pyrido[3,2-b][1,4]oxazin-3-one.

To a stirring solution of 0.37 g (0.0011 mol) of 4-(3-oxo-2,3-dihydro-pyrido[3,2-b][1,4]oxazin-4-yl)-piperidine-1-carboxylic acid tert-butyl ester in $CH_2Cl_2$ (2.5 mL) was added 2.5 mL of TFA. After 2.5 h, the solvent was removed. The residue was partitioned between EtOAc (200 mL) and 1 N NaOH (150 mL). The aqueous layer was extracted with EtOAc (3×100 mL) and the combined organic layers were dried over $Na_2SO_4$, and concentrated to afford 0.24 g (94%) of a white/pink solid. $^1$H NMR (400 MHz, $CDCl_3$): 7.87 (dd, J=4.8 Hz, 1.5 Hz, 1H), 7.25 (dd, J=7.8 Hz, 1.8 Hz, 1H), 6.84 (dd, J=7.8 Hz, 4.8 Hz, 1H), 4.98–4.83 (m, 1H), 4.45 (s, 2H), 3.90 (s, 1H), 3.06 (d, J=8.3 Hz, 2H), 2.65–2.53 (m, 4H), 1.65–1.53 (m, 2H).

E. 4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-pyrido[3,2-b][1,4]oxazin-3-one.

To a stirring solution of 0.24 g (0.001 mol) of 4-piperidin-4-yl-4H-pyrido[3,2-b][1,4]oxazin-3-one in EtOH/Dichloroethane (2 mL/2 mL) was added 0.27 g (0.0007 mol) of 5-methanesulfonyl-1-oxiranylmethyl-3-(4-trifluoromethyl-phenyl)-4,5,6,7-tetrahydro-1H-pyrazolo[4,3-c]pyridine. The reaction mixture was heated to 80° C. and stirred for 16 h. The solvent was then removed under reduced pressure, and the crude product was purified using flash chromatography (30% acetone/$CH_2Cl_2$), affording 0.42 g (96%) of a white solid. MS (electrospray): exact mass calculated for $C_{29}H_{33}F_3N_6O_5S$, 634.22. m/z found, 635.3 [M+H]$^+$. $^1$H-NMR (400 MHz, $CDCl_3$): 8.00 (dd, J=4.8 Hz, 1.5 Hz, 1H), 7.71 and 7.67 (A and B of AA'BB' quartet, $J_{ab}$=8.4 Hz, 4H), 7.22 (dd, J=7.9 Hz, 1.5 Hz, 1H), 6.94 (dd, J=7.9 Hz, 4.8 Hz, 1H), 4.94 (tt, J=12.1 Hz, 4.0 Hz, 1H) 4.57 and 4.55 (A and B of AB quartet, $J_{ab}$=14.5 Hz, 2H), 4.57 (s, 2H), 4.25–4.02 (m, 3H), 3.78–3.61 (m, 2H), 3.16–2.90 (m, 4H), 2.90 (s, 3H), 2.89–2.76 (m, 1H), 2.56–2.43 (m, 3H) 2.23 (t, J=11.2 Hz, 1H), 1.67 (d, J=11.3 Hz, 2H).

Example 24

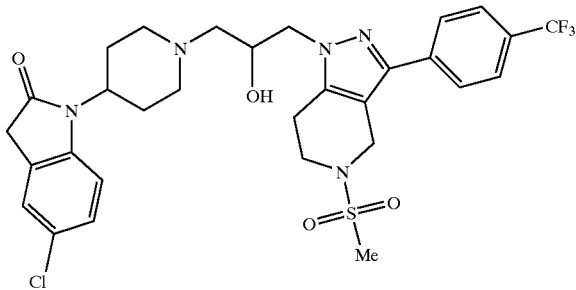

5-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one A. 2-(5-Chloro-2-nitro-phenyl)-malonic acid diethyl ester.

Sodium hydride (2.94 g, 123 mmol) was set stirring in DMSO (100 mL) and heated to 100° C. Diethyl malonate (17.5 mL, 115 mmol) in DMSO (30 mL) was added and after 10 min a clear red solution was obtained. 2,4-Dichloronitrobenzene in DMSO (50 mL) was added. After 1.5 h the mixture was cooled and added to water (1000 mL). The product was extracted with ether. The organics were dried (MgSO$_4$) and evaporated to a clear yellow oil (10 g, 59%). TLC (silica, 20% EtOAc/hexanes): $R_f$=0.36. MS (electrospray): exact mass calculated for $C_{13}H_{14}ClNO_6$, 315.05. m/z found, 338.0 [M+Na]$^+$. $^1$H NMR (400 MHz, $CDCl_3$): 8.05 (d, J=8.7 Hz, 1H), 7.55–7.40 (m, 2H), 5.30 (s, 1H), 4.30 (q, J=7.1 Hz, 4H), 1.31 (t, J=7.1 Hz, 6H).

B. (5-Chloro-2-nitro-phenyl)-acetic acid ethyl ester.

2-(5-Chloro-2-nitro-phenyl)-malonic acid diethyl ester (10.3 g, 32.6 mmol) in DMSO (200 mL) containing LiCl (2.9 g, 68.4 mmol) and water (0.6 mL, 33.3 mmol) was set stirring and heated to 100° C. After 5 h the mixture was cooled to room temperature and added to water (750 mL). The product was extracted with two portions of EtOAc. The organics were combined, washed with water, dried (MgSO$_4$) and evaporated to give 5.9 g (75%) of a clear yellow oil. TLC (silica, 25% EtOAc/hexanes): $R_f$=0.50. $^1$H NMR (400 MHz, $CDCl_3$): 8.21 (d, J=8.8 Hz, 1H), 7.56 (dd, J=8.8, 2.3 Hz, 2H), 7.47 (d, J=2.3 Hz, 1H), 4.30 (q, J=7.2 Hz, 2H), 4.12 (s, 2H), 1.38 (t, J=7.1 Hz, 3H).

C. (2-Amino-5-chloro-phenyl)-acetic acid ethyl ester.

(5-Chloro-2-nitro-phenyl)-acetic acid ethyl ester (5.9 g, 24.2 mmol) in benzene (125 mL) containing PtO$_2$ (500 mg) was placed on a Parr hydrogenator at 40 psi H$_2$. After 18 h the mixture was filtered through celite and evaporated to give a clear brown liquid. The liquid was purified (silica, 25% EtOAc/hexanes) to give 3.3 g (64%) of a clear golden liquid. TLC (silica, 25% EtOAc/hexanes): $R_f$=0.30. MS (electrospray): exact mass calculated for $C_{10}H_{12}ClNO_2$, 213.06. m/z found, 214.1 [M+H]$^+$. $^1$H NMR (400 MHz, $CDCl_3$): 7.20–7.10 (m, 2H), 6.78 (d, J=8.3 Hz, 1H), 4.26 (q, J=7.2, 2H), 1.18 (t, J=7.1 Hz, 3H).

D. 4-(5-Chloro-2-oxo-2,3-dihydro-indol-1-yl)-piperidine-1-carboxylic acid tert-butyl ester.

(2-Amino-5-chloro-phenyl)-acetic acid ethyl ester (3.3 g, 15.4 mmol), 4-oxo-piperidine-1-carboxylic acid tert-butyl ester (4.6 g, 23 mmol) were set stirring in CH$_2$Cl$_2$ (50 mL) and sodium triacetoxyborohydride (4.9 g, 23.1 mmol) was added followed by acetic acid (3 mL). After 5 days saturated NaHCO$_3$ was added and the organics separated. The organics were dried (MgSO$_4$) and evaporated to give 7.5 g of a clear golden oil. The oil was purified (silica, 50% EtOAc/hexanes) to give 3.4 g (63%) of a white solid. TLC (silica, 25% EtOAc/hexanes): $R_f$=0.18. MS (electrospray): exact mass calculated for $C_{18}H_{23}ClN_2O_3$, 350.14. m/z found, 373.1 [M+Na]$^+$. $^1$H NMR (400 MHz, $CDCl_3$): 7.40–7.30 (m, 2H), 7.00 (d, J=8.4 Hz, 1H), 4.55–4.45 (m, 1H), 4.40 (m, 2H), 3.63 (s, 2H), 2.94 (m, 2H), 2.45–2.30 (m, 2H), 1.82 (m, 2H), 1.62 (s, 9H).

E. 5-Chloro-1-piperidin-4-yl-1,3-dihydro-indol-2-one.

4-(5-Chloro-2-oxo-2,3-dihydro-indol-1-yl)-piperidine-1-carboxylic acid tert-butyl ester (3.4 g, 9.7 mmol) was set stirring in 1:1 TFA/CH$_2$Cl$_2$. After 45 min the mixture was evaporated and the golden oil brought up in Et$_2$O. A solid formed and was filtered, washed with Et$_2$O and air dried to give 3.4 g (97%) of a white solid. MS (electrospray): exact mass calculated for $C_{13}H_{15}ClN_2O$, 250.09. m/z found, 251.1 [M+H]$^+$. $^1$H NMR (400 MHz, DMSO-d$_6$): 7.45 (s, 2H), 7.31 (d, J=8.1 Hz, 1H), 4.55–4.45 (m, 1H), 3.68 (s, 2H), 3.50 (d, J=12.3, 2H), 3.14 (m, 2H), 2.70–2.55 (m, 2H), 1.87 (d, J=13.1 Hz, 2H).

F. 5-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one.

5-Chloro-1-piperidin-4-yl-1,3-dihydro-indol-2-one (256 mg, 0.70 mmol) and 5-methanesulfonyl-1-oxiranylmethyl-3-(4-trifluoromethyl-phenyl)-4,5,6,7-tetrahydro-1H-pyrazolo[4,3-c]pyridine (255 mg, 0.64 mmol) were set stirring in EtOH (15 mL) containing Et$_3$N (107 L, 0.77 mmol) at 80° C. After 20 h the mixture was cooled, evaporated, brought up in CH$_2$Cl$_2$ and washed with water. The organics were dried (MgSO$_4$) and evaporated to give a clear golden oil. The oil was purified (silica, 50% acetone/CH$_2$Cl$_2$) to give 225 mg (54%) of a white solid. TLC (silica, 50% acetone/CH$_2$Cl$_2$): R$_f$=0.32. MS (electrospray): exact mass calculated for C$_{30}$H$_{33}$ClF$_3$N$_5$O$_4$S, 651.19. m/z found, 652.2 [M+H]$^+$. $^1$H NMR (400 MHz, CDCl$_3$): 7.82 (d, J=8.1 Hz, 2H), 7.76 (d, J=8.1 Hz, 2H), 7.40–7.25 (m, 2H), 7.04 (d, J=8.1 Hz, 2H), 4.66 (d, J=4.0 Hz, 2H), 4.40–4.10 (m, 4H), 4.05–3.70 (m, 3H), 3.59 (s, 2H), 3.30–3.0 (m, 4H), 2.99 (s, 3H), 2.70–2.40 (m, 5H), 2.28 (m, 2H).

Example 25

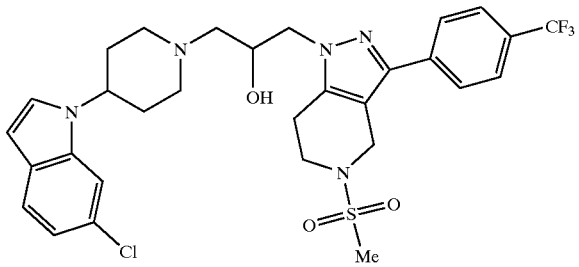

1-[4-(6-Chloro-indol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol.

A. 5-Chloro-2-(2,2-dimethoxy-ethyl)-phenylamine.

To a stirred solution of 10.3 g (60 mmol) of 4-chloro-2-nitrotoluene in dry DMF (120 mL) was added 16.45 g of N,N-dimethylformamide dimethylacetal (138 mmol). The mixture was heated to 140° C. for 18 h after which the solvent was removed under reduced pressure and the residue diluted with 150 mL of MeOH and 15.2 mL of chlorotrimethylsilane (120 mmol). The reaction mixture was then heated to 60° C. overnight. Methanol was then removed under reduced pressure and the residue was taken up in EtOH and transferred to a Parr bottle. 100 mg of 10% Platinum on carbon was added and the reaction mixture was put under 2 atmospheres of hydrogen on a Parr shaker for 8 h. When the reaction was completed the catalyst was removed by filtration and the filtrate was concentrated under reduced pressure. The crude aniline was used without further purification. TLC (silica, 35% EtOAc/hexanes): R$_f$=0.4. MS (electrospray): exact mass calculated for C$_{10}$H$_{14}$ClNO$_2$, 215.07. m/z found, 216.1 [M+H]$^+$.

B. 4-[5-Chloro-2-(2,2-dimethoxy-ethyl)-phenylamino]-piperidine-1-carboxylic acid tert-butyl ester.

To a stirred solution of 2 g of 5-chloro-2-(2,2-dimethoxy-ethyl)-phenylamine, (9.27 mmol) in 50 mL of acetic acid was added 3.7 g of 4-oxo-piperidine-1-carboxylic acid tert-butyl ester (18.5 mmol). The reaction mixture was allowed to stir for 1 h at room temperature before the portion wise addition of 5.9 g of sodium triacetoxyborohydride (27.9 mmol). The reaction mixture was allowed to stir an additional 5 h before removing the solvent under reduced pressure. The crude product was partitioned between CH$_2$Cl$_2$ (250 mL) and water. The aqueous layer was further extracted with CH$_2$Cl$_2$ (2×75 mL). The combined organic layers were then washed with 1 N NaOH (2×50 mL), brine, dried over Na$_2$SO$_4$, and concentrated. Purification by chromatography (silica, 10–25% EtOAc/hexanes) afforded 1.5 g (71%) of desired product. TLC (silica, 35% EtOAc/hexanes): R$_f$=0.49. MS (electrospray): exact mass calculated for C$_{20}$H$_{31}$ClN$_2$O$_4$, 398.20. m/z found, 399.2 [M+H]$^+$. $^1$H NMR (CDCl$_3$, 400 MHz): 6.94 (d, J=7.83 Hz, 1H), 6.61 (dd, J=7.83, 2.02 Hz, 1H), 6.57 (d, J=2.02 Hz, 1H), 4.87 (br s, 1H), 4.40 (t, J=5.31 Hz, 1H), 3.97 (br m, 2H), 3.36 (s, 6H), 3.02 (m, 2H), 2.78 (d, J=5.05 Hz, 2H), 2.00 (m, 2H), 1.47 (s, 9H), 1.37 (m, 2H).

C. 6-Chloro-1-piperidin-4-yl-1H-indole.

To a stirred solution of 1.03 g (2.59 mmol) of 4-[5-chloro-2-(2,2-dimethoxy-ethyl)-phenylamino]-piperidine-1-carboxylic acid tert-butyl ester in 15 mL toluene was added 1.0 g (5.2 mmol) of p-toluenesulfonic acid. The reaction mixture was heated to 60° C. for 20 min, allowed to cool to room temperature and quenched with 100 mL of sat. aqueous NaHCO$_3$ then extracted with EtOAc (3×75 mL). The combined organic layers were washed with brine, dried over Na$_2$SO$_4$, and concentrated to afford 590 mg (98%) of the desired product as a pink oil. MS (electrospray): exact mass calculated for C$_{13}$H$_{15}$ClN$_2$, 234.09. m/z found, 235.1 [M+H]$^+$. $^1$H NMR (CDCl$_3$, 400 MHz, a mixture of amide rotamers): 7.52 (d, J=8.34 Hz, 1H), 7.38 (br s, 1H), 7.21 (d, J=3.28 Hz, 1H), 7.06 (dd, J=8.34, 1.77 Hz, 1H), 6.49 (d, J=3.28 Hz, 1H), 4.24 (m, 1H), 3.30 (m, 2H), 2.85 (dt, J=12.38, 2.53 Hz, 2H), 2.08 (m, 2H), 1.94 (m, 2H).

D. 1-[4-(6-Chloro-indol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol.

To a stirred solution of 86 mg (0.21 mmol) of 5-methanesulfonyl-1-oxiranylmethyl-3-(4-trifluoromethyl-phenyl)-4,5,6,7-tetrahydro-1H-pyrazolo[4,3-c]pyridine in 4 mL of EtOH was added 50 mg (0.39 mmol) of 6-chloro-1-piperidin-4-yl-1H-indole. The solution was heated to 60° C. overnight. The solvent was then removed by rotary evaporation and the crude product was purified by column chromatography (silica, gradient elution from 0–5% 2 N NH$_3$/MeOH in CH$_2$Cl$_2$) to afford 64 mg (48%) of a white solid. MS (electrospray), exact mass calculated for C$_{30}$H$_{33}$ClF$_3$N$_5$O$_3$S: 635.19. m/z found, 636.2 [M+H]$^+$. HPLC (reverse phase conditions 10–90%), t$_R$=4.88 min. $^1$H NMR (CDCl$_3$, 400 MHz): 7.72 and 7.67 (A and B of AB quartet, J=8.80 Hz, 4H), 7.52 (d, J=8.41 Hz, 1H), 7.34 (s, 1H), 7.18 (d, J=3.33 Hz, 1H), 7.07 (dd, J=8.41, 1.76 Hz, 1H), 6.50 (d, J=3.33 Hz, 1H), 4.59 and 4.54 (A and B of AB quartet, J=14.48 Hz, 2H), 4.24 (dd, J=13.69, 2.39 Hz, 1H), 4.21–4.14 (m, 2H), 4.05 (dd, J=13.69, 6.46 Hz, 1H), 3.69 (m, 2H), 3.15 (br d, J=11.54 Hz, 1H), 3.11–2.91 (m, 3H), 2.60–2.48 (m, 3H), 2.28 (dt, J=11.74, 2.15 Hz, 1H), 2.13–1.93 (m, 4H).

Example 26

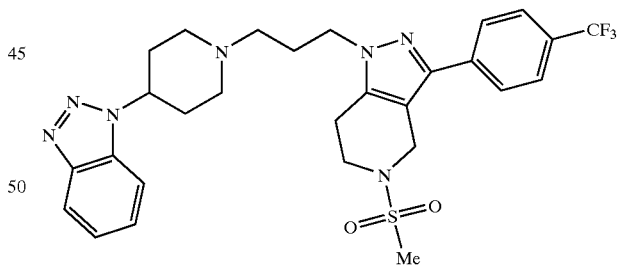

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1H-benzotriazole To a stirred solution of 3-[5-methanesulfonyl-3-(4-trifluoromethyl-phenyl)-4,5,6,7-tetrahydro-pyrazolo[4,3-c]pyridin-1-yl]-propionaldehyde (0.084 g, 0.21 mmol) in CH$_2$Cl$_2$ (0.5 mL) were added 1-piperidin-4-yl-1H-benzotriazole hydrochloride (Maybridge Chemicals, 0.050 g, 0.21 mmol), Et$_3$N (0.1 mL) and glacial AcOH (12 L, 0.21 mmol) in that order and stirred for 20 min. NaBH(OAc)$_3$ (0.058 g, 0.27 mmol) was added and stirred under nitrogen overnight. Saturated NaHCO$_3$ (1 mL) was added and stirred for 30 min. The layers were separated and the aqueous layer was extracted with CH$_2$Cl$_2$ (3 mL). The combined organic extracts were washed with brine (3 mL), dried over Na$_2$SO$_4$, and removed under reduced pressure. MPLC of the crude afforded the desired compound as a white solid (0.098 g, 80%). TLC (silica, 12% MeOH/CH$_2$Cl$_2$): R$_f$=0.44. MS (electrospray): exact mass calculated for C$_{28}$H$_{32}$F$_3$N$_7$O$_2$S, 587.23. m/z found 588.2 [M+H]$^+$. $^1$H NMR (400 MHz, CDCl$_3$): 8.00 (d, J=8.4 Hz, 1H), 7.66 (d, J=8.2 Hz, 2H), 7.59 (d, J=8.2 Hz, 2H), 7.50 (d, J=8.4 Hz, 1H), 7.41 (dt, J=0.9, 7.6 Hz, 1H), 7.30 (dt, J=0.9, 7.6 Hz, 1H), 4.59 (br t, J=11.2 Hz, 1H), 4.50 (s, 2H), 4.10 (t, J=6.7 Hz, 2H), 3.63 (t, J=5.8 Hz, 2H), 3.00 (br d, J=12.0 Hz, 2H), 2.89 (t, J=5.8 Hz, 2H), 2.86 (s, 3H), 2.38–2.27 (m, 4H), 2.17–1.99 (m, 6H).

Example 27

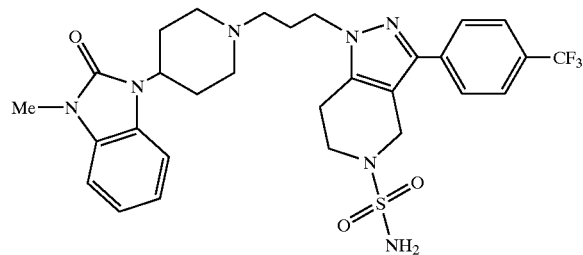

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid amide A. 1-(3-Oxo-propyl)-3-(4-trifluoromethyl-phenyl)-1,4,6,7-tetrahydro-pyrazolo[4,3-c]pyridine-5-carboxylic acid tert-butyl ester.

Dess-Martin periodinane (1.43 g, 3.36 mmol) was added portion wise to a stirred solution of 1-(3-hydroxy-propyl)-3-(4-trifluoromethyl-phenyl)-1,4,6,7-tetrahydropyrazolo[4,3-c]pyridine-5-carboxylic acid tert-butyl ester (1.30 g, 3.05 mmol) in CH$_2$Cl$_2$ (15 mL) at 0° C. under N$_2$. Then the reaction was stirred at 0° C. for 15 min and allowed to warm to room temperature. After stirring at room temperature for 1.5 h the reaction was diluted with Et$_2$O (50 mL) and saturated NaHCO$_3$ (15 mL) was added slowly (caution! gas evolution). Then Na$_2$S$_2$O$_3$.5H$_2$O (5.31 g, 21.4 mmol) was added and stirred for 30 min. The layers were separated and the aqueous layer was extracted with Et$_2$O (2×30 mL). The combined extracts were washed with brine, dried (Na$_2$SO$_4$) and concentrated. MPLC (1–10% MeOH/CH$_2$Cl$_2$) afforded the aldehyde in 79% yield (1.02 g). TLC (silica, 10% MeOH/CH$_2$Cl$_2$): R$_f$=0.67. MS (electrospray) calculated for C$_{12}$H$_{24}$F$_3$N$_3$O$_3$, 424.2 ([M+H]$^+$). m/z found, 424.2. $^1$H NMR (400 MHz, CDCl$_3$): 9.82 (s, 1H), 7.65 (br d, J=8.0 Hz, 2H), 7.54 (br s, 2H), 4.53 (s, 2H), 4.21 (t, J=6.2 Hz, 2H), 3.68 (br s, 2H), 3.04 (t, J=6.2 Hz, 2H), 2.70 (t, J=5.6 Hz, 2H), 1.39 (s, 9H).

B. 1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester.

To a stirred solution of 1-(3-oxo-propyl)-3-(4-trifluoromethyl-phenyl)-1,4,6,7-tetrahydro-pyrazolo[4,3-c]pyridine-5-carboxylic acid tert-butyl ester (0.99 g, 23.6 mmol) in CH$_2$Cl$_2$ (20 mL) were added 1-methyl-3-piperidin-4-yl-1,3-dihydro-benzoimidazol-2-one (0.60 g, 25.9 mmol) and glacial AcOH (0.13 mL, 23.6 mmol) in that order and stirred for 20 min. NaBH(OAc)$_3$ (0.65 g, 30.6 mmol) was added and stirred under nitrogen for 2 h. Saturated NaHCO$_3$ (20 mL) was added and stirred for 30 min, and the layers were separated. The organic extract was washed with brine, dried over Na$_2$SO$_4$, and concentrated under reduced pressure. MPLC of the crude afforded the desired compound as a white solid (1.27 g, 85%). TLC (silica, 7% MeOH/CH$_2$Cl$_2$): R$_f$=0.35. MS (electrospray): exact mass calculated for C$_{34}$H$_{41}$F$_3$N$_6$O$_3$, 638.32. m/z found, 639.3 [M+H]$^+$, 661.2 [M+Na]$^+$. $^1$H NMR (400 MHz, CDCl$_3$): 7.81 (br d, J=8.0 Hz, 2H), 7.68 (br s, 2H), 7.25 (dd, J=1.6, 7.5 Hz, 1H), 7.15–7.07 (m, 2H), 7.02(dd, J=1.6, 7.9 Hz, 1H), 4.70 (br s, 2H), 4.38 (tt, J=4.2, 12.4 Hz, 1H), 4.18 (t, J=6.8 Hz, 2H), 3.82 (s, 2H), 3.45 (s, 3H), 3.07 (d, J=11.6 Hz, 2H), 2.84 (t, J=5.5 Hz, 2H), 2.53–2.42 (m, 2H), 2.44 (t, J=6.7 Hz, 2H), 2.21–2.03 (m, 4H), 1.84 (d, J=12.0 Hz, 2H), 1.52 (s, 9H).

C. 1-Methyl-3-(1-{3-[3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one.

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester (1.19 g, 1.86 mmol) was dissolved in trifluoroacetic acid (5 mL) and CH$_2$Cl$_2$ (5 mL) and allowed to stir at room temperature for 2 h. The reaction mixture was concentrated, diluted with CH$_2$Cl$_2$, and washed with saturated NaHCO$_3$. The organic layer was dried over Na$_2$SO$_4$ and concentrated to afford 1-methyl-3-(1-{3-[3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one (0.955 g, 96%) as a white foam. TLC (silica, 10% MeOH/CH$_2$Cl$_2$): R$_f$=0.19. MS (electrospray) calculated for C$_{29}$H$_{33}$F$_3$N$_6$O, 539.3 ([M+H]$^+$). m/z found, 539.3.

D. 1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid (N-t-butoxy carbonyl)amide.

To a solution of chlorosulfonyl isocyanate (0.018 mL, 0.209 mmol) in CH$_2$Cl$_2$ (0.150 mL) was added 2-methyl-2-propanol (0.020 mL, 0.209 mmol) and the solution was stirred at room temperature for 15 min. This solution was then added dropwise to a solution of 1-methyl-3-(1-{3-[3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one (75 mg, 0.139 mmol) and triethylamine (0.039 mL, 0.279 mmol) in CH$_2$Cl$_2$ (0.4 mL). An additional 0.15 mL of CH$_2$Cl$_2$ was used to transfer all of the material to the reaction mixture. The reaction mixture was allowed to stir overnight. Column chromatography (silica, 2–10% MeOH/CH$_2$Cl$_2$) gave 93 mg (93%) of the title compound. TLC (silica, 5% MeOH/CH$_2$Cl$_2$): R$_f$=0.24. MS (electrospray): calculated for C$_{34}$H$_{42}$F$_3$N$_7$O$_5$S, 718.3 ([M+H]$^+$). m/z found, 718.3.

E. 1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid amide.

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid (N-t-butoxy carbonyl)amide (75 mg, 0.105 mmol) was dissolved in trifluoroacetic acid (0.75 mL) and CH$_2$Cl$_2$ (0.75 mL). The reaction mixture was allowed to stir for 2 h, concentrated, diluted with CH$_2$Cl$_2$ (25 mL) and washed with saturated NaHCO$_3$. The organic layer was dried over Na$_2$SO$_4$, concentrated, and purified by silica gel chromatography (5–10% MeOH/CH$_2$Cl$_2$) to afford 1-{3-[4-(3-methyl-2-oxo-2,3-dihydro-benzoimidazol-1-yl)-piperidin- 1-yl]-propyl}-3-(4-trifluoromethyl-phenyl)-1,4,6,7-tetrahydro-pyrazolo[4,3-c]pyridine-5-sulfonic acid amide (15 mg, 23%). MS (electrospray) calculated for $C_{29}H_{34}F_3N_7O_3S$, 618.2 ([M+H]$^+$). m/z found, 618.2. $^1$H NMR (400 MHz, CDCl$_3$): 7.72 (d, J=8.2 Hz, 2H), 7.63 (d, J=8.2 Hz, 2H), 7.22 (br s, 1H), 7.04–7.11 (m, 2H), 6.95–7.00 (m, 1H), 5.02 (br s, 1H), 4.53 (s, 1H), 4.08–4.36 (m, 3H), 3.68 (br t, J=5.9 Hz, 2H), 3.38 (s, 3H), 2.95–3.01 (m, 2H), 2.41–2.70 (m, 4H), 2.11–2.34 (m, 4H), 1.52–1.94 (m, 6H).

Example 28

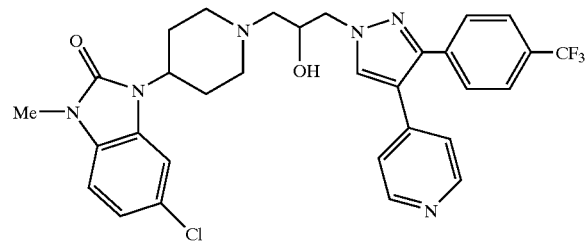

5-Chloro-3-(1-{2-hydroxy-3-[4-pyridin-4-yl-3-(4-trifluoromethyl-phenyl)-pyrazol-1-yl]-propyl}-piperidin-4-yl)-1-methyl-1,3-dihydro-benzoimidazol-2-one A. 4-[1-Oxiranylmethyl-3-(4-trifluoromethyl-phenyl)-1H-pyrazol-4-yl]-pyridine.

To a solution of 4-[3-(4-trifluoromethyl-phenyl)-1H-pyrazol-4-yl]-pyridine (0.5 g, 1.73 mmol) and epichlorohydrin (1.35 mL, 17.3 mmol) in DMF (2 mL) was added cesium carbonate (0.676 g, 2.07 mmol). The reaction mixture was allowed to stir for 24 h, diluted with EtOAc and washed successively with saturated NaHCO$_3$, water, and brine. The organic layer was dried over Na$_2$SO$_4$, concentrated and partially purified by running through a plug of silica gel (5% acetone/CH$_2$Cl$_2$) to afford 4-[1-oxiranylmethyl-3-(4-trifluoromethyl-phenyl)-1H-pyrazol-4-yl]-pyridine (0.198 g, 33%) as an unstable oil. TLC (silica, 20% acetone/CH$_2$Cl$_2$): R$_f$=0.39. MS (electrospray): exact mass calculated for $C_{18}H_{14}F_3N_3O$, 346.1 [M+H]$^+$. m/z found, 346.1.

B. 5-Chloro-3-(1-{2-hydroxy-3-[4-pyridin-4-yl-3-(4-trifluoromethyl-phenyl)-pyrazol-1-yl]-propyl}-piperidin-4-yl)-1-methyl-1,3-dihydro-benzoimidazol-2-one.

To a solution of 4-[1-oxiranylmethyl-3-(4-trifluoromethyl-phenyl)-1H-pyrazol-4-yl]-pyridine (68 mg, 0.197 mmol) and 5-chloro-1-methyl-3-piperidin-4-yl-1,3-dihydro-benzoimidazol-2-one (0.055 g, 0.207 mmol) in EtOH (1 mL) was added triethylamine (0.027 mL, 0.197 mmol). The reaction mixture was heated at 80° C. overnight, concentrated, and purified by column chromatography (silica, 2–10% MeOH/CH$_2$Cl$_2$) to afford the title compound (0.026 g, 22%). MS (electrospray): exact mass calculated for $C_{31}H_{30}ClF_3N_6O_2$, 611.2 [M+H]$^+$. m/z found, 611.2. $^1$H NMR (400 MHz, CDCl$_3$): 8.59 (br s, 2H), 8.20 (s, 1H), 7.67 (d, J=8.2 Hz, 2H), 7.61 (d, J=5.9 Hz, 2H), 7.55 (d, J=8.2 Hz, 2H), 7.35 (br s, 1H), 7.09 (dd, J=8.2, 1.8 Hz, 1H), 6.89 (d, J=8.2 Hz, 1H), 4.55–4.60 (m, 2H), 4.39 (d, J=14.2, 4.1 Hz, 1H), 4.31 (d, J=14.2, 6.1 Hz, 1H), 3.80–3.90 (m, 2H), 3.37 (s, 3H), 3.18–3.33 (m, 2H), 3.02–3.17 (m, 2H), 2.77–2.95 (m, 2H), 1.99 (t, J=12.4 Hz, 2H).

Example 29

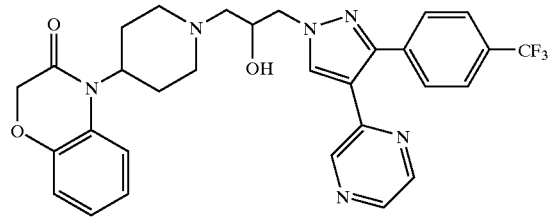

4-(1-{2-Hydroxy-3-[4-pyrazin-2-yl-3-(4-trifluoromethyl-phenyl)-pyrazol-1-yl]-propyl}-piperidin-4-yl)-4H-benzo[1,4]oxazin-3-one A. 4-(2-Hydroxy-phenylamino)-piperidine-1-carboxylic acid tert-butyl ester.

2-Aminophenol (15.0 g, 137 mmol) and 4-oxo-piperidine-1-carboxylic acid tert-butyl ester (27.4 g, 138 mmol) were set stirring in CH$_2$Cl$_2$ (200 mL) at room temperature. Sodium triacetoxyborohydride (40.8 g, 193 mmol) was added in portions over 10 min followed by acetic acid (7.8 mL, 136 mmol). After 18 h saturated NaHCO$_3$ was added, the organics separated, dried (MgSO$_4$) and evaporated to give 36.4 g (91%) of a beige solid. TLC (silica, 50% EtOAc/hexanes): R$_f$=0.56. MS (electrospray): exact mass calculated for $C_{16}H_{24}N_2O_3$, 292.18. m/z found, 315.1 [M+Na]$^+$. $^1$H NMR (400 MHz, CDCl$_3$): 9.20 (s, 1H), 6.80–6.50 (m, 3H), 6.40 (t, J=6.1 Hz, 1H), 4.30 (d, J=8.7 Hz, 1H), 3.88 (d, J=12.6 Hz, 2H), 3.45–3.35 (m, 1H), 3.00–2.75 (br s, 2H), 1.88 (d, J=10.5 Hz, 2H), 1.40 (s, 9H), 1.30–1.20 (m, 2H).

B. 4-(2-Ethoxycarbonylmethoxy-phenylamino)-piperidine-1-carboxylic acid tert-butyl ester.

A mixture of NaH (1.56 g, 65 mmol) in THF (100 mL) was set stirring and cooled to 5° C. 4-(2-Hydroxy-phenylamino)-piperidine-1-carboxylic acid tert-butyl ester (17.5 g, 60 mmol) in THF (100 mL) was added dropwise over 30 min. After 2 h ethyl bromoacetate (7.3 mL, 66 mmol) was added. After stirring at room temperature for 24 h saturated NH$_4$Cl (100 mL) was added and the organics evaporated. The aqueous layer was extracted with EtOAc (2×150 mL). The organics were combined, dried (MgSO$_4$) and evaporated to give 24 g of a deep red liquid. The liquid was purified (silica, 5% acetone/CH$_2$Cl$_2$) to give 21.4 g (94%) of a clear orange liquid. TLC (silica, 5% acetone/CH$_2$Cl$_2$): R$_f$=0.48. MS (electrospray): exact mass calculated for $C_{20}H_{30}N_2O_5$, 378.22. m/z found, 379.2 [M+H]$^+$. $^1$H NMR (400 MHz, DMSO): 7.02 (m, 1H), 6.90–6.70 (m, 3H), 4.74 (s, 2H), 4.37 (q, J=7.1 Hz, 2H), 4.13 (br s, 2H), 3.60–3.50 (m, 1H), 3.08 (m, 2H), 2.16 (m, 2H), 1.60–1.50 (m, 2H), 1.58 (s, 9H), 1.41 (t, J=7.1 Hz, 3H).

C. 4-(2-Carboxymethoxy-phenylamino)-piperidine-1-carboxylic acid tert-butyl ester.

4-(2-Ethoxycarbonylmethoxy-phenylamino)-piperidine-1-carboxylic acid tert-butyl ester (21.4 g, 56.5 mmol) was set stirring in MeOH (150 mL). A solution of NaOH (4.5 g, 112.5 mmol) in water (150 mL) was added. After 3 h the mixture was acidified to pH 4 with 6 N HCl. MeOH was removed under reduced pressure and the aqueous layer extracted with EtOAc (2×150 mL). The organics were combined, dried (MgSO$_4$) and evaporated to give 20 g (100%) of a brown solid. MS (electrospray): exact mass calculated for $C_{18}H_{26}N_2O_5$, 350.18. m/z found, 351.2 [M+H]$^+$.

D. 4-(3-Oxo-2,3-dihydro-benzo[1,4]oxazin-4-yl)-piperidine-1-carboxylic acid tert-butyl ester.

4-(2-Carboxymethoxy-phenylamino)-piperidine-1-carboxylic acid tert-butyl ester (22 g, 63 mmol) was set stirring in CH₂Cl₂ (200 mL). EDC (13 g, 68 mmol) was added in one portion. After 30 min 1 N HCl was added. The organics were seperated, dried (MgSO₄) and evaporated to give 17 g (81%) of a clear brown oil. TLC (silica, 5% acetone/CH₂Cl₂): R$_f$=0.45. MS (electrospray): exact mass calculated for C₁₈H₂₄N₂O₄, 332.17. m/z found, 259.1 [M-BOC+H]⁺. ¹H NMR (400 MHz, CDCl₃): 7.30–7.20 (m, 1H), 7.15–7.10 (m, 3H), 4.61 (s, 2H), 4.60–4.45 (m, 1H), 4.45–4.30 (br s, 2H), 2.88 (t, J=12.5 Hz, 2H), 2.65 (dd, J=12.6, 4.5 Hz, 2H), 1.87 (d, J=12.4 Hz, 2H), 1.60 (s, 9H).

E. 4-Piperidin-4-yl-4H-benzo[1,4]oxazin-3-one.

4-(3-Oxo-2,3-dihydro-benzo[1,4]oxazin-4-yl)-piperidine-1-carboxylic acid tert-butyl ester (17 g, 51 mmol) and 1:1 TFA/CH₂Cl₂ (40 mL) were combined and set stirring. After 45 min the mixture was evaporated to give a clear brown oil. The oil was set stirring and Et₂O was added (300 mL). A solid formed and was filtered, washed with Et₂O and air dried to give 16 g (90%) of a light beige solid. MS (electrospray): exact mass calculated for C₁₃H₁₆N₂O₂, 232.12. m/z found, 233.1 [M+H]⁺. ¹H NMR (400 MHz, CD₃OD): 7.44 (dd, J=6.5, 1.4 Hz, 1H), 7.20–7.7.10 (m, 3H), 4.58 (s, 2H), 4.55–4.45 (m, 1H), 4.65–4.55 (m, 2H), 3.27 (dt, J=13.0, 2.3 Hz, 2H), 3.05 (dd, J=12.3, 4.1 Hz, 2H), 2.15 (d, J=13.8 Hz, 2H).

F. 2-[1-Oxiranylmethyl-3-(4-trifluoromethyl-phenyl)-1H-pyrazol-4-yl]-pyrazine.

To a solution of 2-[3-(4-trifluoromethyl-phenyl)-1H-pyrazol-4-yl]-pyrazine (200 mg, 0.69 mmol) and epichlorohydrin (0.540 mL, 6.9 mmol) in DMF (2 mL) was added cesium carbonate (450 mg, 1.38 mmol). The reaction mixture was allowed to stir for 24 h, diluted with EtOAc, and washed with saturated NaHCO₃, water, and brine. The organic layer was dried over Na₂SO₄, concentrated and purified by column chromatography (silica, 5% acetone/CH₂Cl₂) to afford 2-[1-oxiranylmethyl-3-(4-trifluoromethyl-phenyl)-1H-pyrazol-4-yl]-pyrazine (141 mg, 59%). TLC (silica, 20% acetone/CH₂Cl₂): R$_f$=0.38. MS (electrospray) m/z 347.1 (347.1, calculated for C₁₇H₁₃F₃N₄O, M⁺+H). ¹H NMR (400 MHz, CDCl₃): 8.51 (dd, J=2.8, 1.8 Hz, 1H), 8.45 (d, J=1.5 Hz, 1H), 8.38 (d, J=12.8 Hz, 1H), 8.01 (s, 1H), 7.66 (d, J=8.6 Hz, 1H), 7.62 (d, J=8.6 Hz, 1H), 4.57 (dd, J=14.7, 3.1 Hz, 1H), 4.21 (dd, J=14.7, 6.1 Hz, 1H), 3.44 (m, 1H), 2.91 (t, J=4.5 Hz, 1H), 2.62 (dd, J=4.0, 2.5 Hz, 1H).

G. 4-(1-{2-Hydroxy-3-[4-pyrazin-2-yl-3-(4-trifluoromethyl-phenyl)-pyrazol-1-yl]-propyl}-piperidin-4-yl)-4H-benzo[1,4]oxazin-3-one.

To a solution of 2-[1-oxiranylmethyl-3-(4-trifluoromethyl-phenyl)-1H-pyrazol-4-yl]-pyrazine (76 mg, 0.220 mmol) and 4-piperidin-4-yl-4H-benzo[1,4]oxazin-3-one (61 mg, 0.231 mmol) in EtOH (1.1 mL) was added triethylamine (0.031 mL, 0.220 mmol). The reaction mixture was heated to 80° C. overnight, concentrated, and purified by column chromatography (silica, 5–10% MeOH/CH₂Cl₂) to afford 4-(1-{2-hydroxy-3-[4-pyrazin-2-yl-3-(4-trifluoromethyl-phenyl)-pyrazol-1-yl]-propyl}-piperidin-4-yl)-4H-benzo[1,4]oxazin-3-one (27 mg, 21%). TLC (silica, 5% MeOH/CH₂Cl₂): R$_f$=0.09. MS (electrospray): m/z 579.2 (579.2, calculated for C₃₀H₂₉F₃N₆O₃, M⁺+H). ¹H NMR (400 MHz, CDCl₃): 8.53 (s, 1H), 8.48 (s, 1H), 8.40 (s, 1H), 8.11 (s, 1H), 7.73 (d, J=8.2 Hz, 2H), 7.63 (d, J=8.2 Hz, 2H), 7.16 (d, J=5.4 Hz, 1H), 7.00–7.03 (m, 3H), 4.49 (s, 2H), 4.39 (d, J=10.8 Hz, 1H), 3.13 (d, J=11.9 Hz, 1H), 2.96 (d, J=11.9 Hz, 1H), 2.59–2.80 (m, 2H), 2.40–2.55 (m, 3H), 2.17 (t, J=11.9 Hz, 1H),1.77 (d, J=11.9 Hz, 2H).

Example 30

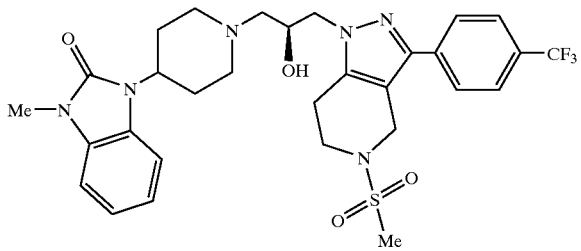

(S)-1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one A. 4-(2-Oxo-2,3-dihydro-benzoimidazol-1-yl)-piperidine-1-carboxylic acid tert-butyl ester.

1-Piperidin-4-yl-1,3-dihydro-benzoimidazol-2-one (7.24 g, 34.1 mmol) and di-tert-butyl dicarbonate (9.12 g, 41.0 mmol) were combined in DMF (80 mL) and the mixture heated to 40° C. under N₂ for 17 h. The mixture was allowed to cool, diluted with EtOAc (800 mL) and washed with saturated NaHCO₃ (150 mL), H₂O (3×150 mL) and brine (150 mL). The combined aqueous washes were extracted with EtOAc (2×150 mL). The combined extracts were dried over Na₂SO₄ and concentrated, to give 4-(2-oxo-2,3-dihydro-benzoimidazol-1-yl)-piperidine-1-carboxylic acid tert-butyl ester (12.36 g, 94%). TLC (silica, 50% EtOAc/hexanes): R$_f$=0.3. MS (electrospray): exact mass calculated for C₁₇H₂₃N₃O₃, 340.16. m/z found, 340.1 [M+Na]⁺. ¹H NMR (CDCl₃, 400 MHz): 10.59 (s, 1H), 7.15–7.11 (m, 2H), 7.08–7.02 (m, 2H), 4.49 (tt, J=8.4, 4.0 Hz, 1H), 4.32 (br s, 2H), 2.89 (br t, J=11.6, 2H), 2.34 (dq, J=12.6, 4.4 Hz, 2H), 1.83 (br d, J=10.5 Hz, 2H) 1.36 (s, 9H).

B. 1-Methyl-3-piperidin-4-yl-1,3-dihydro-benzoimidazol-2-one.

A solution of KHMDS (5.07 g, 25.4 mmol) in THF (40 mL plus a 10 mL rinse) was added via cannula to a solution of 4-(2-oxo-2,3-dihydro-benzoimidazol-1-yl)-piperidine-1-carboxylic acid tert-butyl ester (6.64 g, 20.2 mmol) in THF (20 mL). The mixture was stirred for 25 min then iodomethane (5.2 mL, 84 mmol) was added. The resulting mixture was stirred for 45 min then diluted with EtOAc (700 mL). The EtOAc was washed with H₂O (3×200 mL), saturated NaHCO₃ (150 mL) and brine (150 mL). The combined washes were extracted with EtOAc (2×150 mL). The combined extracts were dried over Na₂SO₄ and concentrated. The crude reaction mixture was purified by column chromatography (silica, 15–60% EtOAc/hexanes) to give the methylated adduct (5.21 g, 78%). The purified material was dissolved in a mixture of CH₂Cl₂ (40 mL) and TFA (35 mL). The mixture was stirred for 4 h then concentrated in vacuo. The residue was dissolved in CH₂Cl₂ (300 mL) and washed with saturated NaHCO₃ (100 mL). The aqueous layer was extracted with 5%MeOH/CH₂Cl₂ (4×150 mL). The combined extracted were dried over Na₂SO₄ and concentrated to yield the title compound (3.85 g, containing inorganic salts) which was suitable for further use. TLC (silica, 5% MeOH/CH₂Cl₂): R$_f$=0.1. MS (electrospray): exact mass calculated for C₁₃H₁₈N₃O, 232.14. m/z found 232.1 [M+H]⁺. ¹H NMR (CDCl₃, 400 Hz): 7.27–7.29 (m, 1H), 7.05–7.12 (m, 2H), 6.99 (dd, J=6.1, 2.1 Hz, 1H), 4.45 (tt, J=12.5, 4.2 Hz, 1H), 3.42 (s, 3H), 3.27 (dd, J=10.2, 2.1 Hz, 2H), 2.81 (dt, J=2.4, 12.4 Hz, 2H), 2.35 (dq, J=12.5, 4.2 Hz, 2H), 2.26 (br s, 1H), 1.83 (dd, J=12.1, 2.1 Hz, 2H).

C. (R)-tert-Butyl-dimethyl-oxiranylmethoxy-silane.

tert-Butyl-chloro-dimethylsilane (12.9 g, 85.5 mmol) followed by Et₃N (19 mL, 136 mmol) was added to a 0° C. solution of (S)-(+)-glycidol (5.0 g, 67 mmol) in CH₂Cl₂ (200 mL). The solution was allowed to warm to 23° C. with stirring over 17 h. The resulting pink solution was diluted with Et₂O (800 mL) and stirred an additional 30 min. The Et₂O layer was washed with saturated aqueous NaHCO₃ (200 mL), H₂O (2×100 mL), brine (100 mL), dried over Na₂SO₄ and concentrated. Purification by column chromatography (silica, 5–10% Et₂O/hexanes) gave (R)-tert-Butyl-dimethyl-oxiranylmethoxy-silane (10.01 g, 79%). TLC (silica, 10% Et₂O/hexanes): $R_f$=0.5. ¹H NMR (CDCl₃, 400 MHz): 3.85 (dd, J=11.9, 3.2 Hz, 1H), 3.66 (dd, J=11.9, 4.8 Hz, 1H), 3.09 (m, 1H), 2.77 (dd, J=5.0, 4.2 Hz, 1H), 2.64 (dd, J=5.2, 2.7 Hz, 1H), 0.90 (s, 9H), 0.08 (s, 3H), 0.07 (s, 3H).

D. (R)-3-[5-Methanesulfonyl-3-(4-trifluoromethyl-phenyl)-4,5,6,7-tetrahydro-pyrazolo[4,3-c]pyridin-1-yl]-propane-1,2-diol.

Cs₂CO₃ (1.88 g, 5.77 mmol) was added to a solution of (R)-tert-Butyl-dimethyl-oxiranylmethoxy-silane (2.72 g, 14.4 mmol) and 5-methanesulfonyl-3-(4-trifluoromethyl-phenyl)-4,5,6,7-tetrahydro-1H-pyrazolo[4,3-c]pyridine (1.70 g, 4.81 mmol) in DMF (13 mL). The mixture was stirred at room temperature for 5 days, then partitioned between EtOAc (400 mL) and saturated NaHCO₃ (100 mL). The EtOAc layer was washed with H₂O (3×75 mL) and brine (100 mL), dried over Na₂SO₄ and concentrated. The residue was dissolved in MeOH (125 mL) and treated with CSA (800 mg). The mixture was stirred for 20 h then concentrated. The residue was re-dissolved in EtOAc (200 mL), washed with saturated NaHCO₃ (100 mL), dried over Na₂SO₄ and concentrated. Purification by column chromatography (silica, 20–60% acetone/CH₂Cl₂) gave the corresponding diol (0.78 g, 40%). TLC (25% acetone/CH₂Cl₂): $R_f$=0.2. MS (electrospray): exact mass calculated for C₁₇H₂₁F₃N₃O₄S, 420.11. m/z found, 420.1 [M+H]⁺. ¹H NMR (CD₃OD/CDCl₃, 400 MHz): 7.74 and 7.67 (A and B of AA'BB', $J_{ab}$=8.3 Hz, 4H), 4.52 (s, 2H), 4.23 (dd, J=13.0, 3.0 Hz, 1H), 4.04–4.11 (m, 2H), 3.64 (t, J=5.9 Hz, 2H), 3.52 and 3.57 (A and B of ABX, $J_{ab}$=11.4, $J_{ax}$=4.8, $J_{bx}$=4.9 Hz, 2H), 2.98 (m, 2H), 2.91 (s, 3H).

E. (R)-5-Methanesulfonyl-1-oxiranylmethyl-3-(4-trifluoromethyl-phenyl)-4,5,6,7-tetrahydro-1H-pyrazolo[4,3-c]pyridine.

PpTs (271 mg, 1.1 mmol) and (R)-3-[5-methanesulfonyl-3-(4-trifluoromethyl-phenyl)-4,5,6,7-tetrahydro-pyrazolo[4,3-c]pyridin-1-yl]-propane-1,2-diol (317 mg, 0.756 mmol) were combined in trimethylorthoacetate (30 mL). The mixture was stirred for 18 h then diluted with EtOAc (125 mL), washed with saturated NaHCO₃ (2×50 mL), brine (50 mL), dried over Na₂SO₄ and concentrated. Purification by chromatography (silica, 100% EtOAc) gave the corresponding orthoacetate (313 mg, 0.678 mmol). The purified orthoacetate was dissolved in CH₂Cl₂ (2.25 mL), cooled to 0° C., and treated with MeOH (25 µL) and AcBr (110 µL, 1.48 mmol). The mixture was allowed to warm over 3 h, then partitioned between EtOAc (50 mL) and saturated NaHCO₃ (20 mL). The EtOAc layer was washed with saturated NaHCO₃ (2×20 mL). The combined washes were extracted with EtOAc (3×20 mL). The combined extracts were dried over Na₂SO₄ and concentrated. The residue was dissolved in EtOH (40 mL) and treated with KOEt (1.0 mL, 40 wt % solution in EtOH). After 1 h the mixture was concentrated to ca. 20 mL and worked up as above. Purification by column chromatography (silica, 100% EtOAc) gave the epoxide (189 mg, 62%). TLC (100% EtOAc): $R_f$=0.35. MS (electrospray): exact mass calculated for C₁₇H₁₉F₃N₃O₃S, 402.10. m/z found, 402.1 M+H]⁺. ¹H NMR (CDCl₃, 400 MHz): 7.72 and 7.67 (A and B of AA'BB', $J_{ab}$=8.3 Hz, 4H), 4.57 and 4.53 (A and B of AB, $J_{ab}$=12.9 Hz, 2H), 4.52 (dd, J=15.2, 2.7 Hz, 1H), 4.12 (dd, J=15.2, 5.4 Hz, 1H), 3.67 (m, 2H), 3.36 (m, 1H), 2.92 (m, 2H), 2.88 (s, 3H), 2.85 (dd, J=4.4, 4.3 Hz, 1H), 2.49 (dd, J=4.6, 2.6 Hz, 1H).

F. (S)-1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one.

A solution of (R)-5-methanesulfonyl-1-oxiranylmethyl-3-(4-trifluoromethyl-phenyl)-4,5,6,7-tetrahydro-1H-pyrazolo[4,3-c]pyridine (134 mg, 0.334 mmol) and 1-methyl-3-piperidin-4-yl-1,3-dihydro-benzoimidazol-2-one (110 mg, 0.476 mmol) in EtOH (0.8 mL) and dichloroethane (0.8 mL) was heated to 80° C. for 18 h. The mixture was then concentrated and the residue purified by column chromatography (silica, 0–50% acetone/CH₂Cl₂) to give the title compound (134 mg, 86%). TLC (20% acetone/CH₂Cl₂) $R_f$=0.3. MS (electrospray): calculated for C₃₀H₃₆F₃N₆O₄S, [M+H]⁺633.24. m/z found, 633.3. ¹H NMR (CDCl₃, 400 MHz): 7.72 and 7.66 (A and B of AA'BB', $J_{ab}$=8.3 Hz, 4H), 7.15 (dd, J=7.0, 1.7 Hz, 1H ), 7.08 (m, 2H), 6.98 (dd, J=6.6, 1.8 Hz, 1H), 4.60 and 4.55(A and B of AB, $J_{ab}$=14.5 Hz, 2H), 4.34 (m, 1H), 4.23 (dd, J=13.8, 2.8 Hz, 1H), 4.15 (m, 1H), 4.23 (dd, J=13.8, 6.6 Hz, 1H), 3.71 (m, 2H), 3.40 (s, 3H), 3.08 (m, 2H), 2.96 (m, 2H), 2.89 (s, 3H), 2.56–2.36 (m, 4H), 2.23 (d, J=11.6 Hz, 1H, 1.81 (m, 2H).

Example 31

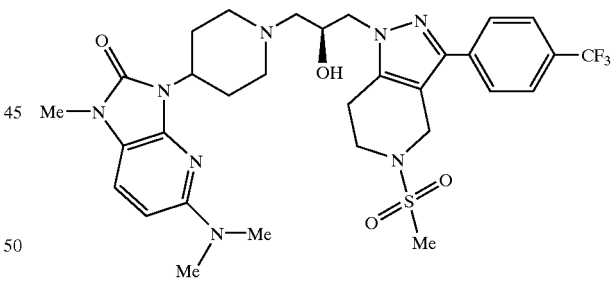

(S)-5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one A. 4-(6-Chloro-3-nitro-pyridin-2-ylamino)-piperidine-1-carboxylic acid tert-butyl ester.

A stirring solution of 20 g (0.10 mol) of 2,6-dichloro-3-nitro-pyridine in DMF (245 mL) was cooled to 0° C. After 5 min, 9.87 g (0.05 mol) of 4-amino-piperidine-1-carboxylic acid tert-butyl ester and 6.8 g (0.05 mol) of K₂CO₃ were added, resulting in a suspension. The mixture was allowed to stir for 5 h at 0° C. The mixture was then partitioned between water (300 mL) and EtOAc (400 mL). The aqueous layer was then extracted with EtOAc (5×400 mL). The organic layer was dried over anhydrous $Na_2SO_4$, and concentrated to give a brown oil. The product was purified using silica gel chromatography (silica, 100% $CH_2Cl_2$, then 10% EtOAc/hexanes) to afford 8.99 g (51%) of the desired product as a bright yellow solid. MS (electrospray): exact mass calculated for $C_{15}H_{21}ClN_4O_4$, 356.13. m/z found, 379.1 [M+Na]$^+$. $^1$H NMR (400 MHz, $CDCl_3$): 8.36 (d, J=8.4 Hz, 1H), 8.27 (d, J=7.3 Hz, 1H), 6.62 (d, J=8.4 Hz, 1H), 4.38–4.26 (m, 1H), 4.14–3.96 (m, 2H), 3.01 (t, J=11.6 Hz, 2H), 2.05 (dd, J=12.4 Hz, 3.03 Hz, 2H), 1.58–1.44 (m, 2H), 1.47 (s, 9H).

B. 4-(6-Dimethylamino-3-nitro-pyridin-2-ylamino)-piperidine-1-carboxylic acid tert-butyl ester.

To a stirring solution of 6 g (0.016 mol) of 4-(6-chloro-3-nitro-pyridin-2-ylamino)-piperidine-1-carboxylic acid tert-butyl ester in $MeOH/CH_2Cl_2$ (84 mL/15 mL) was added 2.2 g (0.05 mol) of dimethylamine in THF (25 mL). The reaction mixture was stirred at room temperature for 16 h, and was then concentrated. The crude product was then dissolved in $CH_2Cl_2$ (400 mL) and washed with saturated $NaHCO_3$ (2×200 mL). The washes were combined and extracted with EtOAc (100 mL). The combined organic layers were dried over $Na_2SO_4$ and concentrated to afford 6.1 g (99%) of the desired product as a bright yellow solid. MS (electrospray): exact mass calculated for $C_{17}H_{27}N_5O_4$, 365.21; m/z found, 388.19 [M+Na]$^+$. $^1$H NMR (400 MHz, $CDCl_3$): 8.74 (d, J=7.07 Hz, 1H), 8.18 (d, J=9.4 Hz, 1H), 5.97 (d, J=7.3 Hz, 1H), 4.28–4.16 (m, 1H), 4.07–3.93 (m, 2H), 3.17 (s, 6H), 3.01 (t, J=11.9 Hz, 2H), 2.05 (dd, J=12.4 Hz and 3.03 Hz, 2H), 1.60–1.50 (m, 2H), 1.47 (s, 9H).

C. 4-(5-Dimethylamino-1-methyl-2-oxo-1,2-dihydro-imidazo[4,5-b]pyridin-3-yl)-piperidine-1-carboxylic acid tert-butyl ester.

A stirring solution of 5.3 g (0.014 mol) of 4-(6-dimethylamino-3-nitro-pyridin-2-ylamino)-piperidine-1-carboxylic acid tert-butyl ester in methanol/EtOAc (73 mL/15 mL) was degassed. 10% Pd/C (1.17 g, 0.5 mmol) was added as a suspension in EtOH (5 mL), followed by ammonium formate (4.5 g, 0.073 mol). The mixture was stirred at room temperature for 3 h. The reaction mixture was then filtered through celite and the filtrate was concentrated, giving a purple oil. The residue was then dissolved in THF (73 mL), and 11.7 g (0.073 mol) of CDI was added, and the reaction was heated to 98° C. and stirred for 16 h. The mixture was then cooled and concentrated. The crude product was then partitioned between EtOAc (800 mL) and $NaHCO_3$ (100 mL), and the organic layer was washed with water (5×100 mL) and NaCl (100 mL). The combined aqueous layers were back-extracted with EtOAc (150 mL). The resulting organic layers were combined and dried over $Na_2SO_4$ and concentrated. The residue (2.4 g) was dissolved in THF (73 mL). To this stirring solution was added KHMDS (3.46 g, 0.017 mol) and iodomethane (10.3 g, 0.072 mol), and the mixture was allowed to stir for 20 min. The solvent was then concentrated, and the crude product was partitioned between EtOAc (600 mL) and $NaHCO_3$ (200 mL). The organic layer was washed with $NaHCO_3$ (150 mL), dried over $Na_2SO_4$, and concentrated. Purification using flash chromatography (silica, 80% EtOAc/hexanes) afforded 2.4 g (67% yield, 3 steps, based upon using 2/3 material at methylation stage) of desired product as a white solid. MS (electrospray): exact mass calculated for $C_{19}H_{29}N_5O_3$, 375.23. m/z found, 276.17 [M+H−100]$^+$. $^1$H NMR: (400 MHz, $CDCl_3$): 7.02 (d, J=8.6 Hz, 1H), 6.15 (d, J=8.6 Hz, 1H), 4.46 (tt, J=12.0 Hz and 4.0 Hz, 1H), 4.38–4.11(m, 2H), 3.33 (s, 3H), 3.01 (s, 6H), 2.95–2.73 (m, 2H), 2.73–2.55 (m, 2H), 1.77–1.61 (m, 2H), 1.47 (s, 9H).

D. 5-Dimethylamino-1-methyl-3-piperidin-4-yl-1,3-dihydro-imidazo[4,5-b]pyridin-2-one.

To a stirring solution of 1.07 g (0.0028 mol) of 4-(5-dimethylamino-1-methyl-2-oxo-1,2-dihydro-imidazo[4,5-b]pyridin-3-yl)-piperidine-1-carboxylic acid tert-butyl ester in $CH_2Cl_2$ (7 mL) was added 7 mL of TFA. After 35 min, the solvent was removed. The residue was partitioned between EtOAc (200 mL) and 1 N NaOH (150 mL). The aqueous layer was extracted with EtOAc (3×100 mL) and the combined organic layers were dried over $Na_2SO_4$ and concentrated to afford 0.74 g (96%) of 5-dimethylamino-1-methyl-3-piperidin-4-yl-1,3-dihydro-imidazo[4,5-b]pyridin-2-one as a white/pink solid. $^1$H NMR (400 MHz, $CDCl_3$): 6.95 (d, J=8.3 Hz, 1H), 6.08 (d, J=8.3 Hz, 1H), 4.35 (tt, J=12.1 Hz, 4.0 Hz, 1H), 3.25 (s, 3H), 3.14 (d, J=12.4 Hz, 2H) 2.97 (s, 6H), 2.66 (td, J=12.9 Hz, 1.3 Hz, 2H), 2.53 (qd, J=12.4 Hz, 4.0 Hz, 2H), 1.69 (d, J=11.9 Hz, 2H).

E. (S)-5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one.

To a stirring solution of 0.24 g (0.0009 mol) of 5-dimethylamino-1-methyl-3-piperidin-4-yl-1,3-dihydro-imidazo[4,5-b]pyridin-2-one in EtOH/Dichloroethane (1.5 mL/1.5 mL) was added 0.23 g (0.0005 mol) of (R)-5-methanesulfonyl-1-oxiranylmethyl-3-(4-trifluoromethyl-phenyl)-4,5,6,7-tetrahydro-1H-pyrazolo[4,3-c]pyridine. The reaction mixture was heated to 80° C. and stirred for 16 h and concentrated. The crude product was then dissolved in $CH_2Cl_2$ (40 mL) and purified using flash chromatography (0–6% $MeOH/CH_2Cl_2$) affording 0.38 g (97%) of the desired product as a white solid. MS (electrospray): exact mass calculated for $C_{31}H_{39}F_3N_8O_4S$, 676.28. m/z found, 677.28 [M+H]$^+$. $^1$H NMR (400 MHz, $CDCl_3$):7.71 and 7.67 (A and B of AA'BB' quartet $J_{ab}$=8.3 Hz, 4H), 7.03 (d, J=8.6 Hz, 1H), 6.16 (d, J=8.6 Hz, 1H), 4.58 and 4.56 (A and B of AB quartet, $J_{ab}$=14.5 Hz, 2H), 4.36 (tt, J=12.1 Hz, 4.04 Hz, 1H), 4.25–4.01 (m, 4H), 3.77–3.60 (m, 2H), 3.33 (s, 3H), 3.16–3.04 (m, 2H), 3.03 (s, 6H), 2.99–2.90 (m, 2H), 2.88 (s, 3H), 2.77 (qd, J=12.1 Hz, 3.54 Hz, 2H), 2.56–2.42 (m, 3H), 2.21 (t, J=11.6 Hz, 1H), 1.75 (d, J=11.6 Hz, 2H).

Example 32

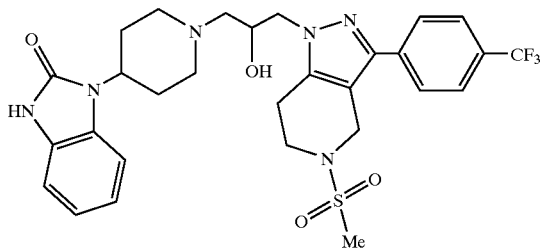

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 33

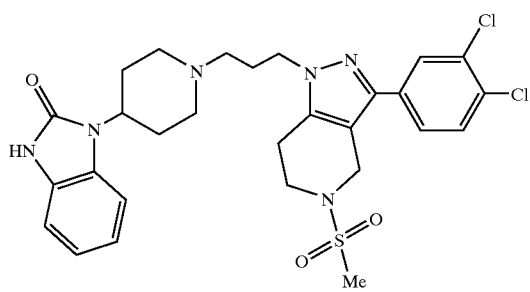

1-(1-{3-[3-(3,4-Dichloro-phenyl)-5-methanesulfonyl-4,5,6,7-tetrahydro-pyrazolo[4,3-c]pyridin-1-yl]-propyl}-piperidin-4-yl)-1,3-dihydro-benzoimidazol-2-one

Example 34

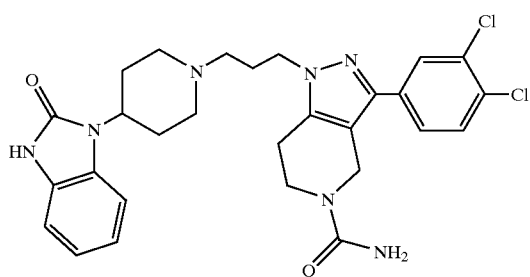

3-(3,4-Dichloro-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid amide

Example 35

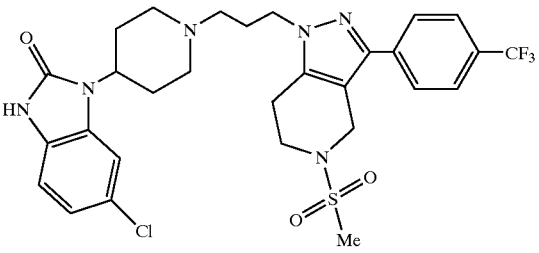

6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 36

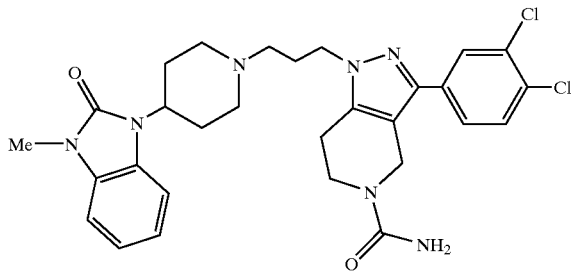

3-(3,4-Dichloro-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide

Example 37

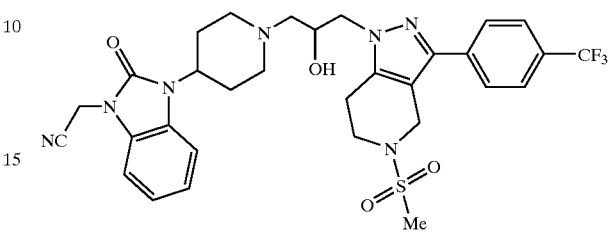

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile

Example 38

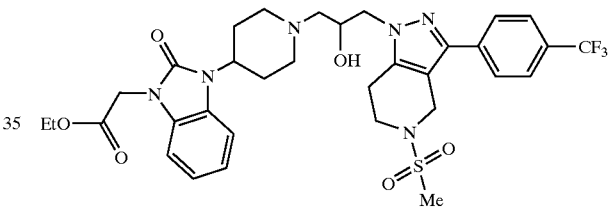

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetic acid ethyl ester

Example 39

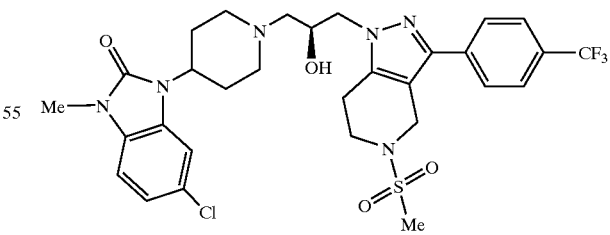

5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one

Example 40

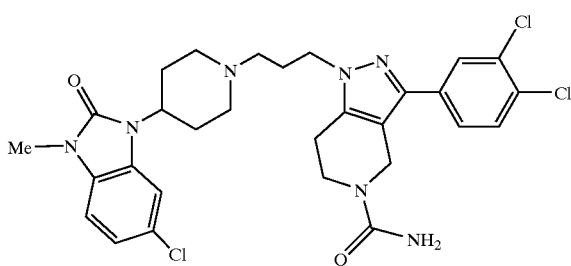

1-{3-[4-(6-Chloro-3-methyl-2-oxo-2,3-dihydro-benzoimidazol-1-yl)-piperidin-1-yl]-propyl}-3-(3,4-dichloro-phenyl)-1,4,6,7-tetrahydro-pyrazolo[4,3-c]pyridine-5-carboxylic acid amide

Example 41

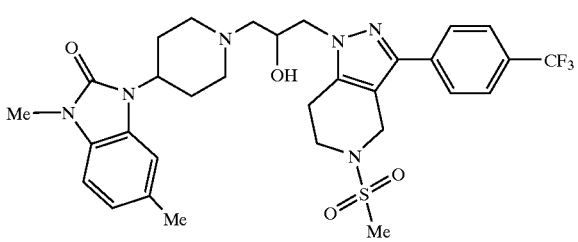

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dimethyl-1,3-dihydro-benzoimidazol-2-one

Example 42

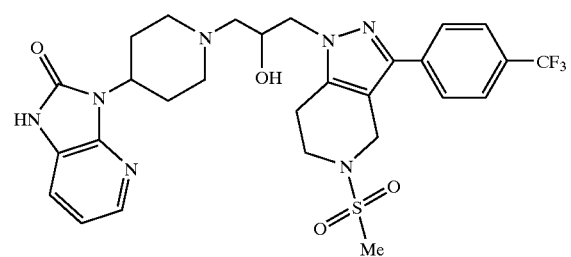

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one

Example 43

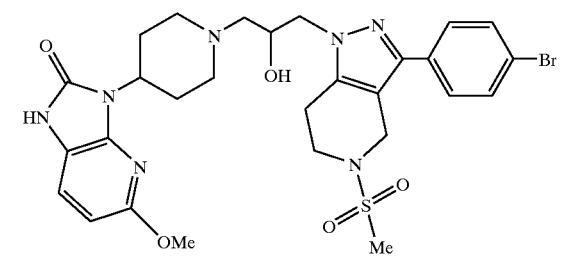

3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-methoxy-1,3-dihydro-imidazo[4,5-b]pyridin-2-one

Example 44

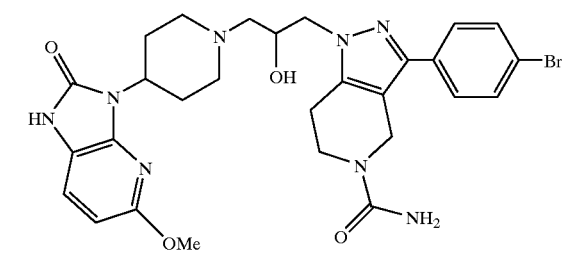

3-(4-Bromo-phenyl)-1-{2-hydroxy-3-[4-(5-methoxy-2-oxo-1,2-dihydro-imidazo[4,5-b]pyridin-3-yl)-piperidin-1-yl]-propyl}-1,4,6,7-tetrahydro-pyrazolo[4,3-c]pyridine-5-carboxylic acid amide

Example 45

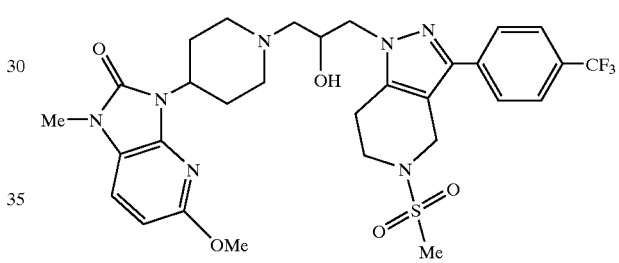

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one

Example 46

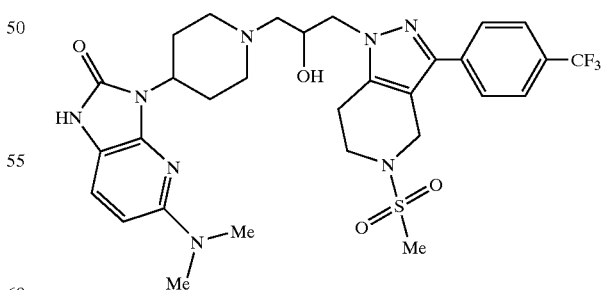

5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one

Example 47

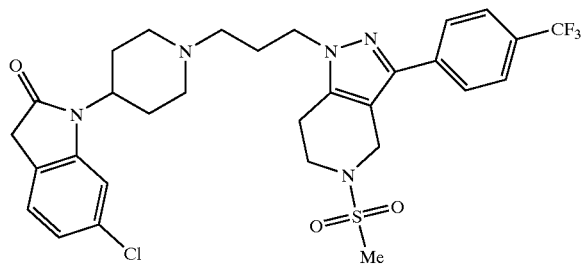

6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one

Example 48

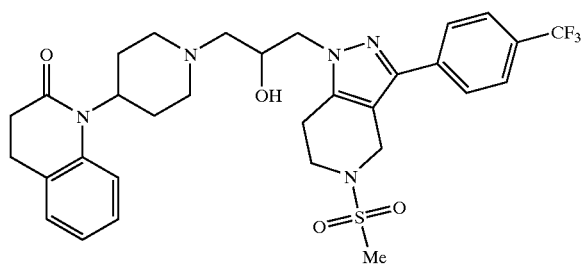

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one

Example 49

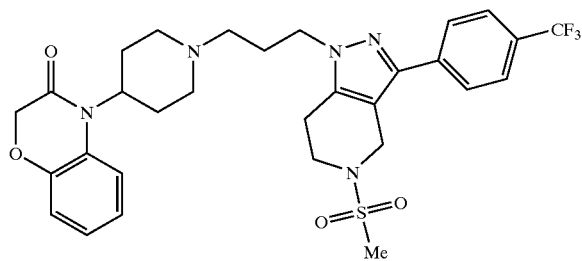

4-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one

Example 50

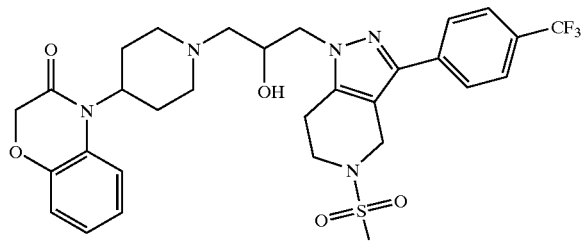

4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one

Example 51

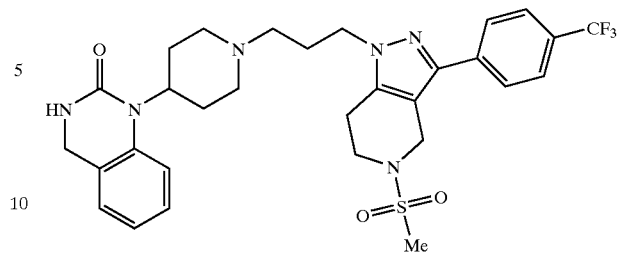

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one

Example 52

Cathepsin S Inhibition Assay.

Recombinant human cathepsin S (CatS) was expressed in the baculovirus system and purified in one step with a thiopropyl-sepharose column. 10-L yielded ~700 mg of CatS and N-terminal sequencing confirmed identity. The assay is run in 100 mM sodium acetate pH 5.0 containing 1 mM DTT and 100 mM NaCl. The substrate for the assay is (Aedens)EKARVLAEAA(Dabcyl)K-amide The $K_m$ for the substrate is around 5 $\mu$M but the presence of substrate inhibition makes kinetic analysis difficult. With 20 $\mu$M substrate the assay rate is linear over the range of 1–8 ng CatS in 100 $\mu$l reaction. Using 2 ng/well of CatS, the production of product is linear and yields ~7-fold signal after 20 min with only 20% loss of substrate. Primary assays are run by quenching the reaction after 20 min with 0.1% SDS and then measuring the fluorescence. For other assays, measurements are taken every min for 20 min. The rate is calculated from the slope of the increase and the percent inhibition is calculated from this (See Tables 1, 2 and 3 below).

TABLE 1

| EXAMPLE | IC$_{50}$ ($\mu$M) |
|---|---|
| 1 | 0.73 |
| 2 | 0.07 |
| 3 | 0.28 |
| 4 | 0.19 |
| 5 | 1.16 |
| 6 | 0.19 |
| 7 | 0.26 |
| 8 | 0.04 |
| 9 | 0.10 |
| 10 | 0.09 |
| 11 | 0.03 |
| 12 | 0.62 |
| 13 | 0.37 |
| 14 | 0.29 |
| 15 | 0.23 |
| 16 | 0.30 |
| 17 | 1.30 |
| 18 | 0.25 |
| 19 | 0.02 |
| 20 | 0.01 |
| 21 | 0.02 |
| 22 | 0.03 |
| 23 | 0.08 |
| 24 | 0.03 |
| 25 | 0.23 |
| 26 | 0.18 |
| 27 | 0.09 |

TABLE 1-continued

| EXAMPLE | IC$_{50}$ ($\mu$M) |
|---|---|
| 28 | 0.89 |
| 29 | 0.78 |
| 30 | 0.04 |
| 31 | 0.07 |

TABLE 2

| EXAMPLE | IC$_{50}$ ($\mu$M) |
|---|---|
| 32 | 0.06 |
| 33 | 0.01 |
| 34 | 0.02 |
| 35 | 0.03 |
| 36 | 0.04 |
| 37 | 0.05 |
| 38 | 0.02 |
| 39 | 0.04 |
| 40 | 0.04 |
| 41 | 0.03 |
| 42 | 0.08 |
| 43 | 0.02 |
| 44 | 0.03 |
| 45 | 0.02 |
| 46 | 0.03 |
| 47 | 0.04 |
| 48 | 0.02 |
| 49 | 0.02 |
| 50 | 0.02 |
| 51 | 0.02 |

Example 101
1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-octahydro-benzoimidazol-2-one Example 102
1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-octahydro-benzoimidazol-2-one Example 103
Acetic acid 1-(1-{3-[5-acetyl-3-(4-bromo-phenyl)-4,5,6,7-tetrahydro-pyrazolo[4,3-c]pyridin-1-yl]-propyl}-piperidin-4-yl)-1H-benzoimidazol-2-yl ester Example 104
Methanesulfonic acid 1-(1-{3-[3-(4-bromo-phenyl)-5-methanesulfonyl-4,5,6,7-tetrahydro-pyrazolo[4,3-c]pyridin-1-yl]-propyl}-piperidin-4-yl)-1H-benzoimidazol-2-yl ester Example 105
1-(1-{3-[5-Acetyl-3-(3,4-dichloro-phenyl)-4,5,6,7-tetrahydro-pyrazolo[4,3-c]pyridin-1-yl]-propyl}-piperidin-4-yl)-5-chloro-1,3-dihydro-indol-2-one Example 106
1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid amide Example 107
1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid methylamide Example 108
Acetic acid 1-(1-{3-[5-acetyl-3-(3,4-dichloro-phenyl)-4,5,6,7-tetrahydro-pyrazolo[4,3-c]pyridin-1-yl]-propyl}-piperidin-4-yl)-1H-benzoimidazol-2-yl ester Example 109
Methanesulfonic acid 1-(1-{3-[3-(3,4-dichloro-phenyl)-5-methanesulfonyl-4,5,6,7-tetrahydro-pyrazolo[4,3-c]pyridin-1-yl]-propyl}-piperidin-4-yl)-1H-benzoimidazol-2-yl ester Example 110
1-[1-{3-[4-(3,5-Dichloro-pyridin-4-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone Example 111
1-[1-{3-[4-(Benzooxazol-2-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone Example 112
1-[1-{3-[4-(Benzooxazol-2-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone Example 113
1-(4-Benzooxazol-2-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol Example 114
1-(4-Benzothiazol-2-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol Example 115
1-{3-[4-(5-Methyl-3-oxo-2,3-dihydro-benzo[1,4]oxazin-4-yl)-piperidin-1-yl]-propyl}-3-(4-trifluoromethyl-phenyl)-1,4,6,7-tetrahydro-pyrazolo[4,3-c]pyridine-5-carboxylic acid amide Example 116
N-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-N-(3-chloro-phenyl)-benzamide Example 117
4-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-methyl-4H-benzo[1,4]oxazin-3-one Example 118
4-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-5-methyl-4H-benzo[1,4]oxazin-3-one Example 119
3-(4-Bromo-phenyl)-1-{3-[4-(5-methyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid amide Example 120
4-(1-{3-[5-Acetyl-3-(4-bromo-phenyl)-4,5,6,7-tetrahydro-pyrazolo[4,3-c]pyridin-1-yl]-propyl}-piperidin-4-yl)-5-methyl-4H-benzo[1,4]oxazin-3-one Example 121
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-methyl-4H-benzo[1,4]oxazin-3-one Example 122
3-(4-Bromo-phenyl)-1-{3-[4-(6-ethanesulfonyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid amide

Example 123
4-(1-{3-[5-Acetyl-3-(4-bromo-phenyl)-4,5,6,7-tetrahydro-pyrazolo[4,3-c]pyridin-1-yl]-propyl}-piperidin-4-yl)-6-ethanesulfonyl-4H-benzo[1,4]oxazin-3-one

Example 124
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-6-ethanesulfonyl-4H-benzo[1,4]oxazin-3-one

Example 125
1-[1-[3-(4-Benzothiazol-2-yl-piperidin-1-yl)-2-hydroxy-propyl]-3-(4-chloro-3-methyl-phenyl)-1,4,6,7-tetrahydro-pyrazolo[4,3-c]pyridin-5-yl]-ethanone

Example 126
1-[1-[3-(4-Benzothiazol-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone

Example 127
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one

Example 128
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one

Example 129
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one

Example 130
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-3,4-dihydro-1H-quinazolin-2-one

Example 131
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl )-6-chloro-3,4-dihydro-1H-quinazolin-2-one

Example 132
1-[3-(4-Bromo-phenyl)-5-methanesulfonyl-4,5,6,7-tetrahydro-pyrazolo[4,3-c]pyridin-1-yl]-3-[4-(6-chloro-2,2-dioxo-3,4-dihydro-2H-2λ$^6$-2,1,3-benzothiadiazin-1-yl)-piperidin-1-yl]-propan-2-ol

Example 133
1-[4-(6-Chloro-2,2-dioxo-2,3-dihydro-2λ$^6$-2,1,3-benzothiadiazol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol

Example 134
1-[1-{3-[4-(6-Chloro-2,2-dioxo-2,3-dihydro-2λ$^6$-2,1,3-benzothiadiazol-1-yl)-piperidin-piperidin-1-yl]-2-hydroxy-propyl}-3-(4-trifluoromethyl-phenyl)-1,4,6,7-tetrahydro-pyrazolo[4,3-c]pyridin-5-yl]-ethanone

Example 135
4-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-4-1,4-benzoxazin-3-one

Example 136
1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one

Example 137
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-3,4-dihydro-1H-quinolin-2-one

Example 138
4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-4H-1,4-benzoxazin-3-one

Example 139
4-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-4H-1,4-benzoxazin-3-one

Example 140
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one

Example 141
1-{2-Hydroxy-3-[4-(2-oxo-3,4-dihydro-2H-quinolin-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester

Example 142
1-{2-Hydroxy-3-[4-(3-oxo-2,3-dihydro-1,4-benzoxazin-4-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester

Example 143
4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-4H-1,4-benzoxazin-3-one

Example 144
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-4H-1,4-benzoxazin-3-one

Example 145
1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3,4-dihydro-1H-quinolin-2-one

Example 146
1-{3-[4-(2-Oxo-3,4-dihydro-2H-quinolin-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester

Example 147
1-{3-[4-(3-Oxo-2,3-dihydro-1,4-benzoxazin-4-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester

Example 148
6-Chloro-4-(1-{3-[5-methanesulfonyl-3-(4-trifluoromethyl-phenyl)-4,5,6,7-tetrahydro-pyrazolo[4,3-c]pyridine-1-yl]-propyl}-piperidin-4-yl)-4H-1,4-benzoxazin-3-one

Example 149
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-6-chloro-4H-1,4-benzoxazin-3-one

Example 150
4-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-4H-1,4-benzoxazin-3-one

Example 151
1-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one

Example 152
4-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-4H-1,4-benzoxazin-3-one

Example 153
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one

Example 154
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-indol-2-one

Example 155
1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one

Example 156
1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-1,3-dihydro-indol-2-one

Example 157
1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-indol-2-one

Example 158
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-indol-2-one

Example 159
1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-1,3-dihydro-indol-2-one

Example 160
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-indol-2-one

Example 161
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-indol-2-one

Example 162
6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one

Example 163
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-chloro-1,3-dihydro-indol-2-one

Example 164
5-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one

Example 165
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-chloro-1,3-dihydro-indol-2-one

Example 166
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-chloro-1,3-dihydro-indol-2-one

Example 167
4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-4H-pyrido[3,2-b]-1,4-oxazin-3-one

Example 168
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dihydro-4,1-benzoxazepin-2-one

Example 169
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,4-dihydro-3,1-benzoxazin-2-one

Example 170
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,4-dihydro-3,1-benzoxazin-2-one

Example 171
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dihydro-4,1-benzoxazepin-2-one

Example 172
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,4-dihydro-3,1-benzoxazin-2-one

Example 173
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,4-dihydro-3,1-benzoxazin-2-one

Example 174
1-(3-(4-Chloro-3-methyl-phenyl)-1-{2-hydroxy-3-[4-(5-nitro-2,3-dihydro-indol-1-yl)-piperidin-1-yl]-propyl}-1,4,6,7-tetrahydro-pyrazolo[4,3-c]pyridin-5-yl)-ethanone

Example 175
1-(3-(4-Chloro-3-methyl-phenyl)-1-{2-hydroxy-3-[4-(6-nitro-2,3-dihydro-indol-1-yl)-piperidin-1-yl]-propyl}-1,4,6,7-tetrahydro-pyrazolo[4,3-c]pyridin-5-yl)-ethanone

Example 176
1-(3-(4-Chloro-3-methyl-phenyl)-1-{2-hydroxy-3-[4-(2-methyl-2,3-dihydro-indol-1-yl)-piperidin-1-yl]-propyl}-1,4,6,7-tetrahydro-pyrazolo[4,3-c]pyridin-5-yl)-ethanone

Example 177
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one

Example 178
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-3,4-dihydro-1H-quinazolin-2-one

Example 179
1(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3,4-dihydro-1H-quinazolin-2-one

Example 180
1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3,4-dihydro-1H-quinazolin-2-one

Example 181
1-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one

Example 182
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1-(3-chloro-phenyl)-3-methyl-urea

Example 183
1-[3-(4-Benzotriazol-1-yl-piperidin-1-yl)-2-hydroxy-propyl]-3-(3,4-dichloro-phenyl)-1,4,6,7-tetrahydro-pyrazolo[4,3-c]pyridine-5-carboxylic acid tert-butyl ester

Example 184
1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid tert-butyl ester

Example 185
5-Chloro-1-(1-{3-[3-(3,4-dichloro-phenyl)-4,5,6,7-tetrahydro-pyrazolo[4,3-c]pyridin-1-yl]-propyl}-piperidin-4-yl)-1,3-dihydro-indol-2-one

Example 186
1-{3-[4-(5-Methyl-3-oxo-2,3-dihydro-benzo[1,4]oxazin-4-yl)-piperidin-1-yl]propyl}-3-(4-trifluoromethyl-phenyl)-1,4,6,7-tetrahydro-pyrazolo[4,3-c]pyridine-5-carboxylic acid tert-butyl ester

Example 187
3-(4-Bromo-phenyl)-1-{3-[4-(5-methyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid tert-butyl ester

Example 188
3-(4-Bromo-phenyl)-1-{3-[4-(6-ethanesulfonyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid tert-butyl ester

Example 187
1-[5-Methanesulfonyl-3-(4-trifluoromethyl-phenyl)-4,5,6,7-tetrahydro-pyrazolo[4,3-c]pyridin-1-yl]-3-[4-(5-trifluoromethyl-benzothiazol-2-yl)-piperidin-1-yl]-propan-2-ol

Example 190
5-Methyl-4-(1-{3-[3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one

Example 191
4-(1-{3-[3-(4-Bromo-phenyl)-4,5,6,7-tetrahydro-pyrazolo[4,3-c]pyridin-1-yl]-propyl}-piperidin-4-yl)-5-methyl-4H-benzo[1,4]oxazin-3-one

Example 192
4-(1-{3-[3-(4-Bromo-phenyl)-4,5,6,7-tetrahydro-pyrazolo[4,3-c]pyridin-1-yl]-propyl}-piperidin-4-yl)-6-ethanesulfonyl-4H-benzo[1,4]oxazin-3-one

Example 193
1-{3-[4-(6-Chloro-indol-1-yl)-piperidin-1-yl]-propyl}-5-methanesulfonyl-3-(4-trifluoromethyl-phenyl)-4,5,6,7-tetrahydro-1H-pyrazolo[4,3-c]pyridine

Example 194
3-(4-Bromo-phenyl)-1-{3-[4-(2-oxo-3,4-dihydro-2H-quinolin-1-yl)-piperidin-1-yl]-propyl}-1,4,6,7-tetrahydro-pyrazolo[4,3-c]pyridine-5-carboxylic acid tert-butyl ester

Example 195
3-(4-Bromo-phenyl)-1-{2-hydroxy-3-[4-(2-oxo-3,4-dihydro-2H-quinolin-1-yl)-piperidin-1-yl]-propyl}-1,4,6,7-tetrahydro-pyrazolo[4,3-c]pyridine-5-carboxylic acid tert-butyl ester

Example 196
3-(4-Bromo-phenyl)-1-{2-hydroxy-3-[4-(3-oxo-2,3-dihydro-1,4-benzoxazin-4-yl)-piperidin-1-yl]-propyl}-1,4,6,7-tetrahydro-pyrazolo[4,3-c]pyridine-5-carboxylic acid tert-butyl ester

Example 197
1-(1-{3-[3-(4-Trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one

Example 198
3-(4-Bromo-phenyl)-1-{3-[4-(3-oxo-2,3-dihydro-1,4-benzoxazin-4-yl)-piperidin-1-yl]-propyl}-1,4,6,7-tetrahydro-pyrazolo[4,3-c]pyridine-5-carboxylic acid tert-butyl ester

Example 199
1-(1-{2-Hydroxy-3-[3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one

Example 200
4-(1-{3-[3-(4-Trifluoromethyl-phenyl)-4,5,6,7-tetrahydro-pyrazolo[4,3-c]pyridin-1-yl]-propyl}-piperidin-4-yl)-4H-1,4-benzoxazin-3-one

Example 201
1-(1-{3-[3-(4-Bromo-phenyl)-4,5,6,7-tetrahydro-pyrazolo[4,3-c]pyridin-1-yl]-propyl}-piperidin-4-yl)-3,4-dihydro-1H-quinolin-2-one

Example 202
4-(1-{3-[3-(4-Bromo-phenyl)-4,5,6,7-tetrahydro-pyrazolo[4,3-c]pyridin-1-yl]-propyl}-piperidin-4-yl)-4H-1,4-benzoxazin-3-one

Example 203
1-(1-{3-[3-(4-Bromo-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one

Example 204
4-(1-{3-[3-(4-Bromo-phenyl)-4,5,6,7-tetrahydro-pyrazolo[4,3-c]pyridin-1-yl]-2-hydroxy-propyl}-piperidin-4-yl)-4H-1,4-benzoxazin-3-one

Example 205
4-(1-{2-Hydroxy-3-[3-(4-trifluoromethyl-phenyl)-4,5,6,7-tetrahydro-pyrazolo[4,3-c]pyridin-1-yl]-propyl}-piperidin-4-yl)-4H-1,4-benzoxazin-3-one

Example 206
1-(3-(3,4-Difluoro-phenyl)-1-{3-[4-(2,3-dihydro-indol-1-yl)-piperidin-1-yl]-2-hydroxy-propyl}-1,4,6,7-tetrahydro-pyrazolo[4,3-c]pyridin-5-yl)-ethanone

Example 207
1-[1-{3-[4-(5-Bromo-2,3-dihydro-indol-1-yl)-piperidin-1-yl]-2-hydroxy-propyl}-3-(4-chloro-3-methyl-phenyl)-1,4,6,7-tetrahydro-pyrazolo[4,3-c]pyridin-5-yl]-ethanone

Example 208
1-(1-{3-[5-Acetyl-3-(3,4-difluoro-phenyl)-4,5,6,7-tetrahydro-pyrazolo[4,3-c]pyridin-1-yl]-2-hydroxy-propyl}-piperidin-4-yl)-1,3-dihydro-indol-2-one

Example 209
1-[1-{3-[4-(5-Bromo-2,3-dihydro-indol-1-yl)-piperidin-1-yl]-2-hydroxy-propyl}-3-(3,4-difluoro-phenyl)-1,4,6,7-tetrahydro-pyrazolo[4,3-c]pyridin-5-yl]-ethanone

Example 210
1-(1-{3-[3-(4-Bromo-phenyl)-4,5,6,7-tetrahydro-pyrazolo[4,3-c]pyridin-1-yl]-2-hydroxy-propyl}-piperidin-4-yl)-3,4-dihydro-1H-quinazolin-2-one

Example 211
1-(1-{3-[3-(4-Trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one

Example 212
1-(1-{3-[3-(4-Bromo-phenyl)-4,5,6,7-tetrahydro-pyrazolo[4,3-c]pyridin-1-yl]-propyl}-piperidin-4-yl)-3,4-dihydro-1H-quinazolin-2-one

Example 213
1-(3-(4-Chloro-phenyl)-1-{3-[4-(3-chloro-phenylamino)-piperidin-1-yl]-2-hydroxy-propyl}-1,4,6,7-tetrahydro-pyrazolo[4,3-c]pyridin-5-yl)-ethanone

Example 214
N-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-N-(3-chloro-phenyl)-acetamide

Example 215
1-(4-Benzoimidazol-1-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol

Example 216
1-(3-(4-Chloro-phenyl)-1-{2-hydroxy-3-[4-(2-methoxy-phenylamino)-piperidin-1-yl]-propyl}-1,4,6,7-tetrahydro-pyrazolo[4,3-c]pyridin-5-yl)-ethanone

Example 217
1-(3-(4-Chloro-phenyl)-1-{3-[4-(2-fluoro-phenylamino)-piperidin-1-yl]-2-hydroxy-propyl}-1,4,6,7-tetrahydro-pyrazolo[4,3-c]pyridin-5-yl)-ethanone

Example 218
1-{3-(4-Chloro-phenyl)-1-[2-hydroxy-3-(4-phenylamino-piperidin-1-yl)-propyl]-1,4,6,7-tetrahydro-pyrazolo[4,3-c]pyridin-5-yl}-ethanone

Example 219
1-(3-(4-Chloro-phenyl)-1-{3-[4-(4-chloro-phenylamino)-piperidin-1-yl]-2-hydroxy-propyl}-1,4,6,7-tetrahydro-pyrazolo[4,3-c]pyridin-5-yl)-ethanone

Example 220
1-[1-{3-[4-(4-Bromo-phenylamino)-piperidin-1-yl]-2-hydroxy-propyl}-3-(4-chloro-phenyl)-1,4,6,7-tetrahydro-pyrazolo[4,3-c]pyridin-5-yl]-ethanone

Example 221
4-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-ylamino)-benzonitrile

Example 222
1-{3-(4-Chloro-phenyl)-1-[2-hydroxy-3-(4-p-tolylamino-piperidin-1-yl)-propyl]-1,4,6,7-tetrahydro-pyrazolo[4,3-c]pyridin-5-yl}-ethanone

Example 223
1-(3-(4-Chloro-phenyl)-1-{2-hydroxy-3-[4-(4-methoxy-phenylamino)-piperidin-1-yl]-propyl}-1,4,6,7-tetrahydro-pyrazolo[4,3-c]pyridin-5-yl)-ethanone

Example 224
1-(3-(4-Chloro-phenyl)-1-{2-hydroxy-3-[4-(3-methoxy-phenylamino)-piperidin-1-yl]-propyl}-1,4,6,7-tetrahydro-pyrazolo[4,3-c]pyridin-5-yl)-ethanone

Example 225
1-(3-(4-Chloro-phenyl)-1-{3-[4-(3,5-dimethoxy-phenylamino)-piperidin-1-yl]-2-hydroxy-propyl}-1,4,6,7-tetrahydro-pyrazolo[4,3-c]pyridin-5-yl)-ethanone

Example 226
1-[1-{3-[4-(5-Chloro-2-methyl-phenylamino)-piperidin-1-yl]-2-hydroxy-propyl}-3-(4-chloro-phenyl)-1,4,6,7-tetrahydro-pyrazolo[4,3-c]pyridin-5-yl]-ethanone

Example 227
1-(3-(4-Chloro-phenyl)-1-{3-[4-(3-chloro-phenylamino)-piperidin-1-yl]-2-hydroxy-propyl}-1,4,6,7-tetrahydro-pyrazolo[4,3-c]pyridin-5-yl)-ethanone

Example 228
[2-(1-{3-[3-(4-Bromo-phenyl)-5-carbamoyl-4,5,6,7-tetrahydro-pyrazolo[4,3-c]pyridin-1-yl]-propyl}-piperidin-4-ylamino)-4-ethanesulfonyl-phenoxy]-acetic acid methyl ester

Example 229
[2-(1-{3-[5-Acetyl-3-(4-bromo-phenyl)-4,5,6,7-tetrahydro-pyrazolo[4,3-c]pyridin-1-yl]-propyl}-piperidin-4-ylamino)-4-ethanesulfonyl-phenoxy]-acetic acid methyl ester

Example 230
[2-(1-{3-[3-(4-Bromo-phenyl)-5-methanesulfonyl-4,5,6,7-tetrahydro-pyrazolo[4,3-c]pyridin-1-yl]-propyl}-piperidin-4-ylamino)-4-ethanesulfonyl-phenoxy]-acetic acid methyl ester

Example 231
3-(4-Bromo-phenyl)-1-{3-[4-(5-ethanesulfonyl-2-methoxycarbonylmethoxy-phenylamino)-piperidin-1-yl]-propyl}-1,4,6,7-tetrahydro-pyrazolo[4,3-c]pyridine-5-carboxylic acid tert-butyl ester

Example 232
[2-(1-{3-[3-(4-Bromo-phenyl)-4,5,6,7-tetrahydro-pyrazolo[4,3-c]pyridin-1-yl]-propyl}-piperidin-4-ylamino)-4-ethanesulfonyl-phenoxy]-acetic acid methyl ester

Example 233
1-{3-(4-Bromo-phenyl)-1-[2-hydroxy-3-(4-o-tolyloxy-piperidin-1-yl)-propyl]-1,4,6,7-tetrahydro-pyrazolo[4,3-c]pyridin-5-yl}-ethanone

Example 234
1-{3-(4-Bromo-phenyl)-1-[2-hydroxy-3-(4-phenoxy-piperidin-1-yl)-propyl]-1,4,6,7-tetrahydro-pyrazolo[4,3-c]pyridin-5-yl}-ethanone

Example 235
1-{3-(4-Bromo-phenyl)-1-[2-hydroxy-3-(4-p-tolyloxy-piperidin-1-yl)-propyl]-1,4,6,7-tetrahydro-pyrazolo[4,3-c]pyridin-5-yl}-ethanone

Example 236
1-(3-(4-Bromo-phenyl)-1-{2-hydroxy-3-[4-(4-methoxy-phenoxy)-piperidin-1-yl]-propyl}-1,4,6,7-tetrahydro-pyrazolo[4,3-c]pyridin-5-yl)-ethanone

Example 237
1-(3-(4-Bromo-phenyl)-1-{3-[4-(4-chloro-phenoxy)-piperidin-1-yl]-2-hydroxy-propyl}-1,4,6,7-tetrahydro-pyrazolo[4,3-c]pyridin-5-yl)-ethanone

Example 238
1-(3-(4-Bromo-phenyl)-1-{3-[4-(3-chloro-phenoxy)-piperidin-1-yl]-2-hydroxy-propyl}-1,4,6,7-tetrahydro-pyrazolo[4,3-c]pyridin-5-yl)-ethanone

Example 239
1-(3-(4-Bromo-phenyl)-1-{3-[4-(3,4-dichloro-phenoxy)-piperidin-1-yl]-2-hydroxy-propyl}-1,4,6,7-tetrahydro-pyrazolo[4,3-c]pyridin-5-yl)-ethanone

Example 240
1-{3-(4-Chloro-3-methyl-phenyl)-1-[2-hydroxy-3-(4-phenoxy-piperidin-1-yl)-propyl]-1,4,6,7-tetrahydro-pyrazolo[4,3-c]pyridin-5-yl}-ethanone

Example 241
1-{3-(4-Chloro-3-methyl-phenyl)-1-[2-hydroxy-3-(4-p-tolyloxy-piperidin-1-yl)-propyl]-1,4,6,7-tetrahydro-pyrazolo[4,3-c]pyridin-5-yl}-ethanone

Example 242
1-(3-(4-Chloro-3-methyl-phenyl)-1-{2-hydroxy-3-[4-(4-methoxy-phenoxy)-piperidin-1-yl]-propyl}-1,4,6,7-tetrahydro-pyrazolo[4,3-c]pyridin-5-yl)-ethanone

Example 243
1-(3-(4-Chloro-3-methyl-phenyl)-1-{3-[4-(4-chloro-phenoxy)-piperidin-1-yl]-2-hydroxy-propyl}-1,4,6,7-tetrahydro-pyrazolo[4,3-c]pyridin-5-yl)-ethanone

Example 244
1-(3-(4-Chloro-3-methyl-phenyl)-1-{3-[4-(3-chloro-phenoxy)-piperidin-1-yl]-2-hydroxy-propyl}-1,4,6,7-tetrahydro-pyrazolo[4,3-c]pyridin-5-yl)-ethanone

Example 245
1-{3-(4-Chloro-3-methyl-phenyl)-1-[2-hydroxy-3-(4-o-tolyloxy-piperidin-1-yl)-propyl]-1,4,6,7-tetrahydro-pyrazolo[4,3-c]pyridin-5-yl}-ethanone

Example 245
1-(3-(4-Chloro-3-methyl-phenyl)-1-{3-[4-(3,4-dichloro-phenoxy)-piperidin-1-yl]-2-hydroxy-propyl}-1,4,6,7-tetrahydro-pyrazolo[4,3-c]pyridin-5-yl)-ethanone

Example 246
2-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yloxy)-benzonitrile

Example 247
2-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yloxy)-benzonitrile

Example 248
1-[3-(4-Bromo-phenyl)-5-methanesulfonyl-4,5,6,7-tetrahydro-pyrazolo[4,3-c]pyridin-1-yl]-3-[4-(4-chloro-phenoxy)-piperidin-1-yl]-propan-2-ol

Example 249
1-[1-{3-[4-(4-Chloro-phenoxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone

Example 250
1-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 251
1-{1-[3-(5-Acetyl-3-phenyl-4,5,6,7-tetrahydro-pyrazolo[4,3-c]pyridin-1-yl)-2-hydroxy-propyl]-piperidin-4-yl}-1,3-dihydro-benzoimidazol-2-one

Example 252
1-(1-{3-[5-Acetyl-3-(4-trifluoromethoxy-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 253
1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 254
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 255
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 256
1-(1-{3-[5-Acetyl-3-(4-chloro-3-nitro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 257
1-(1-{3-[5-Acetyl-3-(4-trifluoromethylsulfanyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 258
1-(1-{3-[5-Acetyl-3-(4-methanesulfonyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 259
1(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 260
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 261
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one

Example 262
1-(1-{3-[5-Acetyl-3-(4-chloro-3-methyl-phenyl)-4,5,6,7-tetrahydro-pyrazolo[4,3-c]pyridin-1-yl]-2-hydroxypropyl}-piperidin-4-yl)-3-isopropyl-1,3-dihydro-benzoimidazol-2-one

Example 263
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-butyl-1,3-dihydro-benzoimidazol-2-one

Example 264
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-benzyl-1,3-dihydro-benzoimidazol-2-one

Example 265
1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-5-fluoro-1,3-dihydro-benzoimidazol-2-one

Example 266
3-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-7-fluoro-2-oxo-2,3-dihydro-1H-benzoimidazole-4-carbonitrile

Example 267
1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-6-fluoro-1,3-dihydro-benzoimidazol-2-one

Example 268
3-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-2-oxo-2,3-dihydro-1H-benzoimidazole-5-carbonitrile

Example 269
1-{2-Hydroxy-3-[4-(2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide

Example 270
1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-benzoimidazol-2-one

Example 271
3-(4-Chloro-3-methyl-phenyl)-1-{2-hydroxy-3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid methylamide

Example 272
3-(4-Chloro-3-methyl-phenyl)-1-{2-hydroxy-3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid ethylamide

Example 273
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one

Example 274
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-methyl-1,3-dihydro-benzoimidazol-2-one

Example 275
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5,6-dichloro-1,3-dihydro-benzoimidazol-2-one

Example 276
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one

Example 277
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-methyl-1,3-dihydro-benzoimidazol-2-one

Example 278
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5,6-dichloro-1,3-dihydro-benzoimidazol-2-one

Example 279
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 280
1-(1-{3-[5-Acetyl-3-(4-chloro-3-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 281
1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-3-(2-morpholin-4-yl-ethyl)-1,3-dihydro-benzoimidazol-2-one

Example 282
1-(1-{3-[5-Acetyl-3-(3-fluoro-4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 283
1-(1-{3-[5-Acetyl-3-(4-bromo-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 284
(R)-1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 285
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-methoxy-1,3-dihydro-benzoimidazol-2-one

Example 286
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-7-chloro-1,3-dihydro-benzoimidazol-2-one

Example 287
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-imidazo[4,5-b]pyridin-2-one

Example 288
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-7-methyl-1,3-dihydro-benzoimidazol-2-one

Example 289
(R)-1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 290
1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 291
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 292
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 293
(S)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 294
(R)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 295
(R)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 296
2-{2-[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-ethyl}-isoindole-1,3-dione

Example 297
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-amino-ethyl)-1,3-dihydro-benzoimidazol-2-one

Example 298
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 299
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one

Example 300
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 301
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one

Example 302
6-Chloro-1-(1-{3-[3-(4-chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-benzoimidazol-2-one

Example 303
1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 304
3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-chloro-1-(2-morpholin-4-yl-ethyl)-1,3-dihydrobenzoimidazol-2-one

Example 305
[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester

Example 306
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2,2,2-trifluoro-ethyl)-1,3-dihydrobenzoimidazol-2-one

Example 307
[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]acetonitrile

Example 308
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-hydroxy-ethyl)-1,3-dihydro-benzoimidazol-2-one

Example 309
1(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one

Example 310
1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 311
1-Ethyl-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 312
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 313
1-(1-{3-[5-Acetyl-3-(4-trifluoromethyl-phenyl)-4,5,6,7-tetrahydro-pyrazolo[4,3-c]pyridin-1-yl]-2-hydroxypropyl}-piperidin-4-yl)-3-(2-hydroxy-ethyl)-1,3-dihydro-benzoimidazol-2-one

Example 314
3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-imidazo[4,5-b]pyridin-2-one

Example 315
[3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetonitrile

Example 316
2-[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetamide

Example 317
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-oxo-tetrahydro-furan-3-yl)-1,3-dihydro-benzoimidazol-2-one

Example 318
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-methoxy-ethyl)-1,3-dihydro-benzoimidazol-2-one

Example 319
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-oxo-butyl)-1,3-dihydro-benzoimidazol-2-one

Example 320
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-diethylamino-ethyl)-1,3-dihydro-benzoimidazol-2-one

Example 321
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-cyclopropylmethyl-1,3-dihydro-benzoimidazol-2-one

Example 322
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-methyl-allyl)-1,3-dihydro-benzoimidazol-2-one

Example 323
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one

Example 324
5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one

Example 325
6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 326
N-[4-(5-Acetyl-1-{2-hydroxy-3-[4-(2-oxo-2,3-dihydro-benzoimidazol-1-yl)-piperidin-1-yl]-propyl}-4,5,6,7-tetrahydro-1H-pyrazolo[4,3-c]pyridin-3-yl)-phenyl]-acetamide

Example 327
[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid

Example 328
1-(1-{3-[5-Acetyl-3-(3-bromo-4-chloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 329
3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one

Example 330
3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one

Example 331
1-(1-{3-[5-(1H-Imidazole-4-carbonyl)-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 332
1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide

Example 333
1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid ethylamide

Example 334
1-(1-{3-[5-(Isoxazole-5-carbonyl)-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 335
1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid (N-t-butoxycarbonyl)amide

Example 336
1-Methyl-3-(1-{3-[5-(5-methyl-isoxazole-3-carbonyl)-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 337
3-(1-{3-[5-Methanesulfonyl-3-(4-trifluoromethyl-phenyl)-4,5,6,7-tetrahydro-pyrazolo[4,3-c]pyridin-1-yl]-propyl}- piperidin-4-yl)-5-methoxy-1-methyl-1,3-dihydro-imidazo[4,5-b]pyridin-2-one

Example 338
3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one

Example 339
5-Dimethylamino-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one

Example 340
3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-1-ethyl-5-methoxy-1,3-dihydro-imidazo[4,5-b]pyridin-2-one

Example 341
1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one

Example 342
1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 343
3-(1-{3-[5-Acetyl-3-(4-bromo-phenyl)-4,5,6,7-tetrahydro-pyrazolo[4,3-c]pyridin-1-yl]-propyl}-piperidin-4-yl)-1-ethyl-5-methoxy-1,3-dihydro-imidazo[4,5-b]pyridin-2-one

Example 344
3-(1-{3-[5-Acetyl-3-(4-bromo-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one

Example 345
1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid benzyl ester

Example 346
5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one

Example 347
1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carbothioic acid methylamide

Example 348
3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid phenylamide

Example 349
1-(1-{3-[5-Benzoyl-3-(4-bromo-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 350
1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3-methyl-1,3-dihydro-benzoimidazol-2-one

Example 351
1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one

Example 352
3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-chloro-1-methyl-1,3-dihydro-benzoimidazol-2-one

Example 353
1-{3-[4-(6-Chloro-3-methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide

Example 354
1-(1-{3-[3-(4-Bromo-phenyl)-5-phenylmethanesulfonyl-4,5,6,7-tetrahydro-pyrazolo[4,3-c]pyridin-1-yl]-propyl}-piperidin-4-yl)-3-methyl-1,3-dihydro-benzoimidazol-2-one

Example 355
1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one

Example 356
3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide

Example 357
3-(1-{3-[5-Acetyl-3-(4-bromo-phenyl)-4,5,6,7-tetrahydro-pyrazolo[4,3-c]pyridin-1-yl]-propyl}-piperidin-4-yl)-5-chloro-1-methyl-1,3-dihydro-benzoimidazol-2-one

Example 358
3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-chloro-1-methyl-1,3-dihydro-benzoimidazol-2-one

Example 359
3-(4-Bromo-phenyl)-1-{3-[4-(6-chloro-3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide

Example 360
3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,5-dimethyl-1,3-dihydro-benzoimidazol-2-one

Example 361
1-(1-{3-[5-Acetyl-3-(4-bromo-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 362
3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-sulfonic acid t-butoxycarbonyl-amide

Example 363
1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-1,3-dihydro-benzoimidazol-2-one

Example 364
1-(1-{3-[5-Acetyl-3-(4-bromo-phenyl)-4,5,6,7-tetrahydro-pyrazolo[4,3-c]pyridin-1-yl]-propyl}-piperidin-4-yl)-1,3-dihydro-benzoimidazol-2-one

Example 365
3-(4-Bromo-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-sulfonic acid t-butoxycarbonyl-amide

Example 366
3-(4-Bromo-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid amide

Example 367
(R)-5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one

Example 368
1-(1-{3-[5-Acetyl-3-(3,4-dichloro-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 369
1-(1-{3-[3-(3,4-Dichloro-phenyl)-5-methanesulfonyl-4,5,6,7-tetrahydro-pyrazolo[4,3-c]pyridin-1-yl]-propyl}-piperidin-4-yl)-3-methyl-1,3-dihydro-benzoimidazol-2-one

Example 370
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-6-methoxy-1,3-dihydro-benzoimidazol-2-one

Example 371
3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-imidazo[4,5-b]pyridin-2-one

Example 372
3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-methoxy-1,3-dihydro-imidazo[4,5-b]pyridin-2-one

Example 373
1-{2-Hydroxy-3-[4-(2-oxo-1,2-dihydro-imidazo[4,5-b]pyridin-3-yl)-piperidin-1-yl]-propyl}-3-(4-trifluoromethyl-phenyl)-1,4,6,7-tetrahydro-pyrazolo[4,3-c]pyridine-5-carboxylic acid amide

Example 374
3-(4-Bromo-phenyl)-1-{2-hydroxy-3-[4-(2-oxo-1,2-dihydro-imidazo[4,5-b]pyridin-3-yl)-piperidin-1-yl]-propyl}-1,4,6,7-tetrahydro-pyrazolo[4,3-c]pyridine-5-carboxylic acid amide

Example 375
[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-imidazo[4,5-b]pyridin-1-yl]-acetonitrile

Example 376
3-(3,4-Dichloro-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid methylamide

Example 377
3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one

Example 378
3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-methoxy-1,3-dihydro-imidazo[4,5-b]pyridin-2-one

Example 379
[3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester

Example 380
[3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester

Example 381
[3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester

Example 382
5-Chloro-3-(1-{3-[3-(3,4-dichloro-phenyl)-5-methanesulfonyl-4,5,6,7-tetrahydro-pyrazolo[4,3-c]pyridin-1-yl]-propyl}-piperidin-4-yl)-1-methyl-1,3-dihydro-benzoimidazol-2-one

Example 383
(R)-1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one

Example 384
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-pyridin-4-ylmethyl-1,3-dihydro-benzoimidazol-2-one

Example 385
(R)-5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one

Example 386
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-chloro-3H-benzooxazol-2-one

Example 387
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-4-methyl-3H-benzooxazol-2-one Example 388
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-2-oxo-2,3-dihydro-benzooxazole-6-carboxylic acid ethyl ester Example 389
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-ethanesulfonyl-3H-benzooxazol-2-one Example 390
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-4-methyl-3H-benzooxazol-2-one Example 391
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzooxazole-6-carboxylic acid ethyl ester Example 392
3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-methoxy-3H-benzooxazol-2-one Example 393
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-ethanesulfonyl-3H-benzooxazol-2-one Example 394
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-methoxy-3H-benzooxazol-2-one Example 395
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3H-benzooxazol-2-one Example 396
3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-chloro-3H-benzooxazol-2-one Example 397
3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3H-oxazolo[4,5-b]pyridin-2-one Example 398
1-[1-[3-(4-Benzooxazol-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone Example 399
1-[1-{2-Hydroxy-3-[4-(6-methyl-benzooxazol-2-yl)-piperidin-1-yl]-propyl}-3-(4-trifluoromethyl-phenyl)-1,4,6,7-tetrahydro-pyrazolo[4,3-c]pyridin-5-yl]-ethanone Example 400
1-[1-{3-[4-(Benzothiazol-2-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone Example 401
1-[1-{2-Hydroxy-3-[4-(5-methyl-benzooxazol-2-yl)-piperidin-1-yl]-propyl}-3-trifluoromethyl-phenyl)-1,4,6,7-tetrahydro-pyrazolo[4,3-c]pyridin-5-yl]-ethanone Example 402
1-(3-(4-Chloro-phenyl)-1-{2-hydroxy-3-[4-(2-methoxy-phenyl)-piperidin-1-yl]-propyl}-1,4,6,7-tetrahydro-pyrazolo[4,3-c]pyridin-5-yl)-ethanone Example 403
3-(4-Chloro-phenyl)-1-{2-hydroxy-3-[4-(2-methoxy-phenyl)-piperidin-1-yl]-propyl}-1,4,6,7-tetrahydro-pyrazolo[4,3-c]pyridine-5-carbaldehyde Example 404
1-[1-[3-(4-Benzo[b]thiophen-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone Example 405
1-[4-(6-Chloro-indol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol

TABLE 3

| EXAMPLE | IC$_{50}$ ($\mu$M) |
| --- | --- |
| 101 | 0.51 |
| 104 | 0.12 |
| 106 | 0.06 |
| 110 | 0.33 |
| 111 | 1.2 |
| 113 | 0.11 |
| 114 | 0.10 |
| 117 | 0.28 |
| 116 | 0.64 |
| 119 | 0.09 |
| 122 | 0.06 |
| 125 | 0.25 |
| 126 | 0.08 |
| 127 | 0.02 |
| 130 | 0.03 |
| 132 | 0.11 |
| 133 | 0.15 |
| 137 | 0.03 |
| 139 | 0.13 |
| 141 | 0.84 |
| 143 | 0.05 |
| 145 | 0.07 |
| 148 | 0.13 |
| 149 | 0.13 |
| 154 | 0.09 |
| 155 | 0.04 |
| 157 | 0.04 |
| 159 | 0.15 |
| 160 | 0.15 |
| 163 | 0.14 |
| 167 | 0.13 |
| 168 | 0.16 |
| 169 | 0.09 |
| 171 | 0.16 |
| 174 | 0.85 |
| 176 | 0.83 |
| 177 | 0.05 |
| 180 | 0.09 |
| 182 | 0.87 |
| 183 | 2.3 |
| 188 | 1.1 |
| 187 | 0.36 |
| 193 | 0.44 |
| 195 | 1.1 |
| 197 | 1.4 |
| 207 | 1.3 |
| 211 | 1.8 |
| 213 | 1.1 |
| 215 | 0.14 |
| 217 | 0.83 |
| 221 | 1.4 |
| 226 | 0.75 |
| 228 | 0.17 |

TABLE 3-continued

| EXAMPLE | IC$_{50}$ ($\mu$M) |
|---|---|
| 233 | 0.34 |
| 236 | 0.71 |
| 239 | 0.34 |
| 244 | 0.65 |
| 246 | 0.30 |
| 249 | 0.69 |
| 252 | 0.13 |
| 253 | 0.14 |
| 256 | 0.64 |
| 257 | 0.26 |
| 258 | 0.23 |
| 259 | 0.12 |
| 260 | 0.48 |
| 261 | 0.35 |
| 264 | 0.34 |
| 266 | 0.66 |
| 267 | 0.28 |
| 268 | 0.30 |
| 269 | 0.12 |
| 270 | 0.04 |
| 272 | 0.33 |
| 273 | 0.09 |
| 275 | 0.12 |
| 277 | 0.06 |
| 280 | 0.23 |
| 281 | 0.33 |
| 284 | 0.26 |
| 285 | 0.13 |
| 286 | 0.21 |
| 289 | 0.20 |
| 290 | 0.15 |
| 293 | 0.16 |
| 294 | 0.28 |
| 296 | 0.34 |
| 300 | 0.14 |
| 301 | 0.18 |
| 304 | 0.14 |
| 305 | 0.11 |
| 306 | 0.09 |
| 307 | 0.09 |
| 308 | 0.13 |
| 313 | 0.23 |
| 314 | 0.14 |
| 315 | 0.08 |
| 316 | 0.28 |
| 320 | 0.39 |
| 321 | 0.08 |
| 325 | 0.09 |
| 327 | 0.52 |
| 329 | 0.08 |
| 330 | 0.06 |
| 331 | 0.06 |
| 333 | 0.24 |
| 334 | 0.08 |
| 335 | 0.39 |
| 336 | 0.16 |
| 337 | 0.10 |
| 339 | 0.20 |
| 340 | 0.09 |
| 342 | 0.38 |
| 345 | 0.55 |
| 346 | 0.07 |
| 347 | 0.48 |
| 348 | 0.19 |
| 354 | 0.93 |
| 359 | 0.04 |
| 365 | 0.11 |
| 366 | 0.05 |
| 367 | 0.03 |
| 371 | 0.08 |
| 374 | 0.08 |
| 375 | 0.05 |
| 379 | 0.07 |
| 383 | 0.18 |
| 384 | 0.17 |
| 385 | 0.04 |
| 386 | 0.37 |
| 387 | 0.34 |
| 388 | 0.32 |
| 392 | 0.27 |
| 395 | 0.39 |
| 396 | 0.31 |
| 397 | 0.12 |
| 398 | 0.19 |
| 399 | 0.51 |
| 400 | 0.55 |
| 401 | 0.32 |

F. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A compound of formula I:

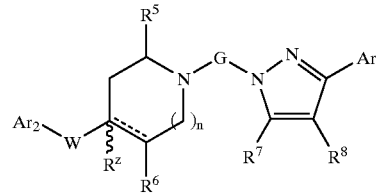

(I)

wherein:

Ar$_2$ is a monocyclic or bicyclic ring system, unsaturated, saturated or aromatic, optionally fused, optionally including between 1 and 5 heteroatom ring moieties independently selected from O, S, N, SO$_2$, and C=O; said Ar$_2$ ring system being optionally substituted with between 1 and 4 substituents, provided that when Ar$_2$ is a bicyclic ring system, then said bicyclic ring system has an attachment ring attached to W at an attachment member of said attachment ring, said attachment member is a heteroatom selected from O, S, and N, or a carbon member, and further provided that when said attachment member is a carbon member, then said attachment ring has either (a) at least two heteroatom ring moieties independently selected from O, S, N, SO$_2$, and C=O, or (b) said attachment ring system has one heteroatom ring moiety selected from O, S, N, SO$_2$, and C=O, and said heteroatom ring moiety is directly attached to said attachment member;

R$^5$ and R$^6$ are independently selected from hydrogen and C$_{1-5}$ alkyl;

R$^7$ and R$^8$ are independently hydrogen, C$_{1-5}$ alkyl, C$_{2-5}$ alkenyl, C$_{1-5}$ alkoxy, C$_{1-5}$ alkylthio, halogen, or a 4–7 membered carbocyclyl or heterocyclyl;

alternatively, R$^7$ and R$^8$ can be taken together to form an optionally substituted 5- to 7-membered carbocyclic or heterocyclic ring, which ring may be unsaturated or aromatic, and may be optionally substituted with between one and three substituents independently selected from halo, cyano, amino, hydroxy, nitro, R$^4$, R$^4$O—, R$^4$S—, R$^4$O(C$_{1-5}$ alkylene)-, R$^4$O (C=O)—, R$^4$(C=O)—, R$^4$(C=S)—, R$^4$(C=O)

O—, $R^4O(C=O)(C=O)$—, $R^4SO_2$, $NHR^{44}SO_2$—, and $NHR^{44}(C=O)$—;

$R^4$ is H, $C_{1-5}$ alkyl, $C_{2-5}$ alkenyl, $C_{1-5}$ heterocyclyl, ($C_{1-5}$ heterocyclyl)$C_{1-6}$ alkylene, phenyl, benzyl, phenethyl, $NH_2$, mono- or di($C_{1-6}$ alkyl)N—, or $R^{42}OR^{43}$—, wherein $R^{42}$ is H, $C_{1-5}$ alkyl, $C_{2-5}$ alkenyl, phenyl, benzyl, phenethyl, $C_{1-5}$ heterocyclyl, or ($C_{1-5}$ heterocyclyl)$C_{1-6}$ alkylene and $R^{43}$ is $C_{1-5}$ alkylene, phenylene, or divalent $C_{1-5}$ heterocyclyl;

$R^{44}$ is any one of the values for $R^4$;

n is 0, 1, or 2;

G is $C_{3-6}$ alkenediyl or straight $C_{3-6}$ alkanediyl, optionally substituted with hydroxy, halogen, $C_{1-5}$ alkoxy, $C_{1-5}$ alkyl, oxo, hydroximino, $CO_2R^k$, $R^kR^lN$, $R^kR^lNCO_2$, (L)-$C_{1-4}$ alkylene-, (L)-$C_{1-5}$ alkoxy, $N_3$, or [(L)-$C_{1-5}$ alkylene]amino;

each of $R^k$ and $R^l$ is independently hydrogen, $C_{1-5}$ alkyl, $C_{3-5}$ alkenyl, phenyl, benzyl, phenethyl, or $C_{1-5}$ heterocyclyl; alternatively $R^k$ and $R^l$, can be taken together to form an optionally substituted 4- to 7-membered heterocyclic ring, which ring may be saturated, unsaturated or aromatic;

L is amino, mono- or di-$C_{1-5}$ alkylamino, pyrrolidinyl, morpholinyl, piperidinyl homopiperidinyl, or piperazinyl, wherein available ring nitrogens may be optionally substituted with $C_{1-5}$ alkyl, benzyl, $C_{2-5}$ acyl, $C_{1-5}$ alkylsulfonyl, or $C_{1-5}$ alkoxycarbonyl;

Ar represents a monocyclic or bicyclic aryl or heteroaryl ring, optionally substituted with between 1 and 3 substituents independently selected from halogen, $C_{1-5}$ alkoxy, $C_{1-5}$ alkyl, $C_{2-5}$ alkenyl, cyano, nitro, $R^{22}R^{23}N$, $R^{24}SO_2$, $R^{24}S$, $R^{24}SO$, $R^{24}OC=O$, $R^{22}R^{23}NC=O$, $C_{1-5}$ haloalkyl, $C_{1-5}$ haloalkoxy, $C_{1-5}$ haloalkylthio, and $C_{1-5}$ alkylthio;

$R^{22}$ is hydrogen, $C_{1-5}$ alkyl, $C_{3-5}$ alkenyl, phenyl, phenethyl, benzyl, or $C_{1-5}$ heterocyclyl, $C_{2-8}$ acyl, aroyl, $R^{38}OC=O$, $R^{25}R^{26}NC=O$, $R^{38}SO$, $R^{38}SO_2$, $R^{38}S$, or $R^{25}R^{26}NSO_2$;

$R^{38}$ is H, $C_{1-5}$ alkyl, $C_{3-5}$ alkenyl, phenyl, benzyl, phenethyl, or $C_{1-5}$ heterocyclyl;

$R^{23}$ is hydrogen, $C_{1-5}$ alkyl, $C_{3-5}$ alkenyl, phenyl, benzyl or $C_{1-5}$ heterocyclyl; alternatively, $R^{22}$ and $R^{23}$ can be taken together to form an optionally substituted 4- to 7-membered heterocyclic ring, which ring may be saturated, unsaturated or aromatic;

$R^{24}$ is $C_{1-5}$ alkyl, $C_{3-5}$ alkenyl, phenyl, benzyl, or $C_{1-5}$ heterocyclyl;

$R^{25}$ and $R^{26}$ independently are hydrogen, $C_{1-5}$ alkyl, $C_{3-5}$ alkenyl, phenyl, benzyl, or $C_{1-5}$ heterocyclyl;

or, alternatively, $R^{25}$ and $R^{26}$ can be taken together to form an optionally substituted 4- to 7-membered heterocyclic ring, which ring may be saturated, unsaturated or aromatic;

W represents O, S, $NR^{27}$, $C=O$, $(C=O)NH$, $NH(C=O)$, $CHR^{28}$, or a covalent bond;

$R^z$ is H or OH and the dashed line is absent; or $R^z$ is absent where the dashed line is an $sp^2$ bond;

$R^{27}$ is hydrogen, $C_{1-5}$ alkyl, $C_{3-5}$ alkenyl, phenyl, naphthyl, benzyl, phenethyl, $C_{1-5}$ heterocyclyl, $C_{2-8}$ acyl, aroyl, $R^{29}OC=O$, $R^{30}R^{31}NC=O$, $R^{29}SO$, $R^{29}S$, $R^{29}SO_2$, or $R^{30}R^{31}NSO_2$;

or, alternatively, $R^{27}$ and part of $Ar_2$ can be taken together to form an optionally substituted 5- or 6-membered heterocyclic ring with optionally 1 to 3 additional heteroatom moieties in the ring selected from O, $NR^9$, $NR^{10}$, N, $SO_2$, $C=O$, and S; which ring may be saturated, unsaturated or aromatic; $R^9$ and $R^{10}$ are independently selected from H, $C_{1-3}$ alkyl, and —$CH_2CO_2(C_{1-4}$ alkyl);

$R^{28}$ is hydrogen, $C_{1-5}$ alkyl, $C_{3-5}$ alkenyl, hydroxy, phenyl, benzyl, $C_{1-5}$ heterocyclyl, $R^{29}O$, $R^{30}R^{31}NC=O$, $R^{29}S$, $R^{29}SO$, $R^{29}SO_2$, or $R^{30}R^{31}NSO_2$;

$R^{29}$ is $C_{1-5}$ alkyl, $C_{3-5}$ alkenyl, phenyl, benzyl, or $C_{1-5}$ heterocyclyl;

$R^{30}$ and $R^{31}$ are independently selected from hydrogen, $C_{1-5}$ alkyl, $C_{3-5}$ alkenyl, phenyl, benzyl, phenethyl, naphthyl, and $C_{1-5}$ heteroaryl;

alternatively, $R^{30}$ and $R^{31}$ can be taken together to form an optionally substituted 4- to 7-membered ring carbocyclic or heterocyclic ring, which ring may be saturated, unsaturated or aromatic;

wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino] $C_{2-5}$ alkylene, [di($C_{1-4}$ alkyl)amino]$C_{2-5}$ alkyl-NH—CO—, and $C_{1-5}$ haloalkoxy;

or a pharmaceutically acceptable salt, amide, or ester thereof; or a stereoisomeric form thereof.

2. A compound of claim 1, wherein $Ar_2$ is selected from 5–7 membered monocyclic rings, and [5,6], [6,6], [6,5], and [5,5] fused bicyclic ring systems, said ring or ring system being carbocyclic or heterocyclic, saturated, unsaturated, or aromatic, optionally substituted with halo, $C_{1-4}$ alkyl, $C_{1-4}$ haloalkyl, $C_{1-4}$ hydroxyalkyl, nitro, hydroxy, amino, mono- or di-($C_{1-6}$ alkyl)amino, $C_{1-4}$ alkoxy, $C_{2-4}$ alkoxycarbonyl, $C_{2-6}$ acyl, $C_{2-6}$ acyloxy, $C_{1-5}$ alkylsulfonyl, $C_{1-5}$ alkoxycarbonyl $C_{1-4}$ alkoxy, cyano, and mono- or di-($C_{1-6}$ alkyl) carbamoyl.

3. A compound of claim 1, wherein $Ar_2$ is selected from 2,5-di($C_{1-6}$ alkyl)aminopyrrolyl and the following 6 formulae:

(a)
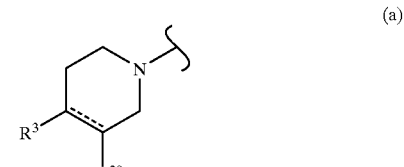

(b)
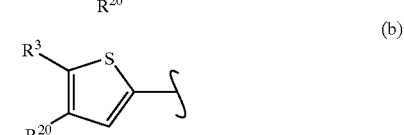

(c)
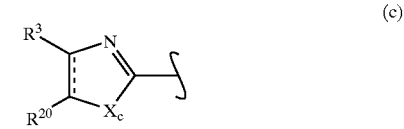

-continued

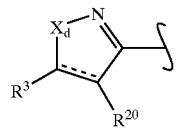
(d)

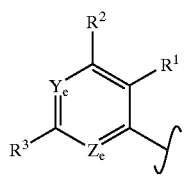
(e)

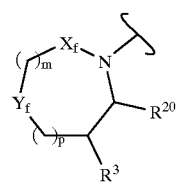
(f)

wherein
each dashed line may be an $sp^2$ bond or absent;
$X_c$ is O, S, or N; and $X_d$ is O or S;
$R^1$ is hydrogen, halogen, $C_{1-5}$ alkoxy, hydroxy, $C_{1-5}$ alkyl, $C_{2-5}$ alkenyl, cyano, nitro, $R^a R^b N$, $C_{2-8}$ acyl, $C_{1-5}$ heterocyclyl, ($C_{1-5}$ heterocyclyl)$C_{1-5}$ alkylene, $R^{11}S$, $R^{11}SO$, $R^{11}SO_2$, $R^c OC=O$, $R^c R^d NC=O$, or $R^c R^d NSO_2$; or $R^1$ can be taken together with $R^{27}$ as provided below;
$R^2$ is hydrogen, halogen, $C_{1-5}$ alkony, hydroxy, $C_{1-5}$ alkyl, $C_{2-5}$ alkenyl, cyano, nitro, $R^e R^f N$, $C_{1-5}$ heterocyclyl, or $C_{2-8}$ acyl;
$R^3$ is hydrogen, halogen, $C_{1-5}$ alkoxy, hydroxy, $C_{1-5}$ alkyl, $C_{2-5}$ alkenyl, cyano, nitro, $R^g R^h N$, $C_{2-8}$ acyl, $C_{1-5}$ heterocyclyl, $R^h OC=O$, $R^g R^h NC=O$, or $R^g R^h NSO_2$;
$R^a$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^i OC=O$, $R^i R^j NC=O$, $R^{12}SO$, $R^{12}SO_2$, $R^{12}S$, and $R^i R^j NSO_2$;
$R^e$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{32}OC=O$, $R^{32}R^{33}NC=O$, $R^{13}SO$, $R^{13}SO_2$, $R^{13}S$, and $R^{32}R^{33}NSO_2$;
$R^m$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{34}OC=O$, $R^{34}R^{35}NC=O$, $R^{15}SO$, $R^{15}SO_2$, $R^{15}S$ and $R^{34}R^{35}NSO_2$;
$R^o$ is selected from hydrogen, $C_{1-5}$ alkyl, $C_{3-5}$ alkenyl, phenyl, benzyl, phenethyl, $C_{1-5}$ heterocyclyl, $C_{2-8}$ acyl, aroyl, $R^{36}OC=O$, $R^{36}R^{37}NC=O$, $R^{19}SO$, $R^{19}SO_2$, $R^{19}S$, and $R^{36}R^{37}NSO_2$;
each of $R^b$, $R^f$, $R^n$, $R^p$, $R^{32}$, $R^{33}$, $R^{34}$, $R^{35}$, $R^{36}$, $R^{37}$, $R^{39}$, and $R^{40}$ is independently selected from hydrogen, $C_{1-5}$ alkyl, $C_{3-5}$ alkenyl, phenyl, benzyl, phenethyl, and $C_{1-5}$ heteroaryl;
alternatively, $R^a$ and $R^b$, $R^e$ and $R^f$, $R^m$ and $R^n$, and $R^o$ and $R^p$, independently, can be taken together to form an optionally substituted 4- to 7-membered heterocyclic ring, which ring may be saturated, unsaturated or aromatic;
each of $R^{11}$, $R^{12}$, $R^{13}$, $R^{14}$, $R^{15}$, $R^{16}$, $R^{19}$, $R^{38}$, and $R^{41}$ is independently $C_{1-5}$ alkyl, $C_{3-5}$ alkenyl, phenyl, benzyl, phenethyl, or $C_{1-5}$ heterocyclyl;
each of $R^c$ and $R^d$, and $R^i$ and $R^j$ are independently are hydrogen, $C_{1-5}$ alkyl, $C_{3-5}$ alkenyl, phenyl, benzyl, phenethyl, or $C_{1-5}$ heteroaryl;
alternatively, $R^c$ and $R^d$, and $R^i$ and $R^j$, independently, can be taken together to form an optionally substituted 4- to 7-membered heterocyclic ring, which ring may be saturated, unsaturated or aromatic;
$R^g$ is hydrogen, $C_{1-5}$ alkyl, $C_{3-5}$ alkenyl, phenyl, benzyl, phenethyl, or $C_{1-5}$ heterocyclyl, $C_{2-8}$ acyl, aroyl, $R^{17}OC=O$, $R^{17}R^{18}NC=O$, $R^{16}S$, $R^{16}SO$, $R^{16}SO_2$, or $R^{17}R^{18}NSO_2$;
$R^h$ is hydrogen, $C_{1-5}$ alkyl, $C_{3-5}$ alkenyl, phenyl, benzyl, phenethyl or $C_{1-5}$ heterocyclyl;
alternatively, $R^g$ and $R^h$ can be taken together to form an optionally substituted 4- to 7-membered heterocyclic ring, which ring may be saturated, unsaturated or aromatic;
$R^{17}$ and $R^{18}$ independently are hydrogen, $C_{1-5}$ alkyl, $C_{3-5}$ alkenyl, phenyl, benzyl, or $C_{1-5}$ heterocyclyl;
alternatively, $R^{17}$ and $R^{18}$ can be taken together to form an optionally substituted 4- to 7-membered heterocyclic ring, which ring may be saturated, unsaturated or aromatic;
$Y_e$ is nitrogen or $R^{20}C$;
$Z_e$ is nitrogen or $R^{21}C$;
$R^{20}$ is hydrogen, halogen, $C_{1-5}$ alkoxy, $C_{1-5}$ alkyl, $C_{2-5}$ alkenyl, cyano, nitro, $R^m R^n N$, $C_{2-8}$ acyl, $R^m OC=O$, $R^{14}S$, $R^{14}SO$, or $R^{14}SO_2$;
$R^{21}$ is hydrogen, halogen, $C_{1-5}$ alkoxy, $C_{1-5}$ alkyl, $C_{2-5}$ alkenyl, cyano, nitro, $R^o R^p N$, $C_{2-8}$ acyl, $R^{16}OC=O$, $R^{11}S$, $R^{11}SO$, or $R^{11}SO_2$;
alternatively, $R^3$ and $R^{20}$ or $R^3$ and $R^{21}$ can be taken together to form an optionally substituted 5- or 6-membered carbocyclic or heterocyclic ring, which ring may be saturated, unsaturated or aromatic; wherein said ring may be optionally substituted with halo, di($C_{1-5}$ alkyl)amino, $C_{2-5}$ acyl, and $C_{1-5}$ alkoxy;
$R^{27}$ is hydrogen, $C_{1-5}$ alkyl, $C_{3-5}$ alkenyl, phenyl, naphthyl, benzyl, phenethyl, $C_{1-5}$ heterocyclyl, $C_{2-8}$ acyl, aroyl, $R^{29}OC=O$, $R^{30}R^{31}NC=O$, $R^{29}SO$, $R^{29}S$, $R^{29}SO_2$, or $R^{30}R^{31}NSO_2$;
or, alternatively, $R^{27}$ and $R^1$ can be taken together to form an optionally substituted 5- or 6-membered heterocyclic ring with optionally 1 to 3 additional heteroatom moieties in the ring selected from O, $NR^9$, $NR^{10}$, N, $SO_2$, $C=O$, and S; which ring may be saturated, unsaturated or aromatic;
$R^9$ and $R^{10}$ are independently selected from H, $C_{1-3}$ alkyl, and —$CH_2CO_2(C_{1-4}$ alkyl);
$X_f$ is $CHR^{1f}$, $=N—$, NH, $C=O$, $SO_2$, $CHSR^{1f}$ wherein, in formula (f), $R^{1f}$ is hydrogen, halogen, $C_{1-5}$ alkoxy, hydroxy, $C_{1-5}$ alkyl, $C_{3-5}$ alkenyl, cyano, nitro, $R^{39}R^{40}N$, $C_{2-8}$ acyl, $C_{1-5}$ heterocyclyl, ($C_{1-5}$ heterocyclyl)$C_{1-5}$ alkylene, $R^{41}S$, $R^{41}SO$, $R^{41}SO_2$, $R^{39}OC=O$, $R^{39}R^{40}NC=O$, $R^{39}R^{40}NSO_2$, $R^{41}SO_3—$ or $R^{39}(C=O)O—$;
$Y_f$ is $CH_2$, $CHR^{2f}$, $=CR^{2f}$, O, or $NR^{2f}$, wherein $R^{2f}$ is H, $C_{1-5}$ alkyl, $C_{3-5}$ alkenyl, $C_{2-8}$ acyl, $C_{1-5}$ heterocyclyl, ($C_{1-5}$ heterocyclyl)-$C_{1-5}$ alkylene, $C_{1-5}$ haloalkyl, $C_{1-5}$ cyanoalkyl, ($C_{1-5}$ alkoxycarbonyl)$C_{1-5}$ alkylene, and (phenylcarbonyl)NH—;
m is 0 or 1;
p is 0 or 1;
wherein each of the above hydrocarbyl or heterocarbyl groups, unless otherwise indicated, and in addition to any specified substituents, is optionally and independently substituted with between 1 and 3 substituents selected from methyl, halomethyl, hydroxymethyl, halo, hydroxy, amino, nitro, cyano, $C_{1-5}$ alkyl, $C_{1-5}$ alkoxy, —COOH, $C_{2-6}$ acyl, [di($C_{1-4}$ alkyl)amino] $C_{2-5}$ alkylene, [di($C_{1-4}$ alkyl)amino]$C_{2-5}$ alkyl-NH—CO—, and $C_{1-5}$ haloalkoxy.

4. A compound of claim 3, wherein $Ar_2$ is selected from formulae (e).

5. A compound of claim 3, wherein $Ar_2$ is selected from formulae (f).

6. A compound of claim 3, wherein $Ar_2$ is selected from formula (a)–(d).

7. A compound of claim 3, wherein $R^1$ is halogen, $C_{1-5}$ alkoxy, hydroxy, $C_{1-5}$ alkyl, cyano, nitro, $R^aR^bN$ or is taken together with $R^{27}$.

8. A compound of claim 7, wherein $R^1$ is taken together with $R^{27}$.

9. A compound of claim 8, wherein $R^1$ and $R^{27}$ taken together are selected from:
 a) —$CH_2NR^9$—(C=O)—
 b) —$OCH_2$(C=O)—
 c) —$CH_2CH_2$(C=O)—
 d) —$CH_2$—O(C=O)—
 e) —$CH_2$S(C=O)—
 f) —O(C=O)—
 g) —$CH_2$(C=O)—
 h) —$NR^9$(C=O)—
 i) —$NR^9(SO_2)$—
 j) —$CH_2NR^9SO_2$—
 k) —$NR^9CH_2$(C=O)— and
 l) —$SCH_2$(C=O)—.

10. A compound of claim 9, wherein $R^1$ and $R^{27}$ taken together are selected from:
 a) —$CH_2$—(C=O)—
 b) —O(C=O)—
 c) —$CH_2CH_2$—
 d) —S(C=O)—
 e) —N=N—
 f) —$NR^9SO_2$—
 g) —N=$CR^9$—
 h) —$NR^9$(C=O)— and
 i) —CH=CH—.

11. A compound of claim 3, wherein $R^2$ is hydrogen, halogen, $C_{1-5}$ alkoxy, $C_{1-5}$ alkyl, cyano, or $R^eR^fN$, where $R^e$ and $R^f$ are H or $C_{1-5}$ alkyl, or are taken together to form a 5–7 membered heterocyclic ring.

12. A compound of claim 3, wherein $R^3$ is hydrogen, halogen, $C_{1-5}$ alkoxy, $C_{1-5}$ alkyl, cyano, nitro, or $R^gR^hN$, where $R^e$ and $R^f$ are H or $C_{1-5}$ alkyl, or are taken together to form a 5–7 membered heterocyclic ring.

13. A compound of claim 1, wherein $R^5$ and $R^6$ are independently selected from hydrogen and $C_{1-3}$ alkyl.

14. A compound of claim 12, wherein one of $R^5$ and $R^6$ is H.

15. A compound of claim 14, wherein $R^5$ and $R^6$ are each H.

16. A compound of claim 1, wherein one of $R^7$ and $R^8$ is H and the other is 5–7 membered carbocyclyl or heterocyclyl.

17. A compound of claim 1, wherein $R^7$ and $R^8$ are taken together to form an optionally substituted 5- to 7-membered carbocyclic or heterocyclic ring.

18. A compound of claim 16, wherein $R^7$ and $R^8$ taken together form a six-membered heterocyclyl.

19. A compound of claim 16, wherein $R^7$ and $R^8$ taken together form pyridinyl, pyrimidinyl, or piperazinyl, optionally N-substituted with —(C=O)$R^4$, —$SO_2R^4$, or —(C=O)$NHR^4$.

20. A compound of claim 3, wherein each of $R^a$, $R^e$, $R^m$, and $R^o$ is independently selected from hydrogen, $C_{1-5}$ alkyl, $C_{2-8}$ acyl, and the respective ROC=O, RRNC=O, RSO, $RSO_2$, and $RRNSO_2$ groups.

21. A compound of claim 19, wherein each of $R^a$, $R^e$, $R^m$, $R^o$, $R^b$, $R^f$, $R^n$, and $R^p$ is independently selected from hydrogen and $C_{1-5}$ alkyl; or, independently, $R^a$ and $R^b$, $R^e$ and $R^f$, $R^m$ and $R^n$, and $R^o$ and $R^p$, taken together, form an optionally substituted 4- to 7-membered carbocyclic or heterocyclic ring.

22. A compound of claim 21, wherein: (1) $R^a$ and $R^b$ taken together are independently morpholinyl, piperidinyl, or pyrrolidinyl; (2) $R^e$ and $R^f$ taken together are morpholinyl, piperidinyl, or pyrrolidinyl; or (3) both (1) and (2) apply.

23. A compound of claim 3, wherein each of $R^c$ and $R^d$, $R^i$ and $R^j$, $R^k$ and $R^l$ is independently hydrogen or $C_{1-5}$ alkyl, alternatively, $R^c$ and $R^d$, $R^i$ and Rj, and $R^k$ and $R^l$, independently, can be taken together to form an optionally substituted 4- to 7-membered heterocyclic ring, which ring may be saturated, unsaturated or aromatic.

24. A compound of claim 23, wherein $R^c$ and $R^d$, $R^i$ and $R^j$, and $R^k$ and $R^l$, independently, are taken together to form an optionally substituted 4- to 7-membered heterocyclic ring, which ring may be saturated, unsaturated or aromatic.

25. A compound of claim 3, wherein each of $R^b$, $R^f$, $R^n$, $R^p$, $R^{32}$, $R^{33}$, $R^{34}$, $R^{35}$, $R^{36}$, $R^{37}$, $R^{39}$, and $R^{40}$ is independently H or $C_{1-5}$ alkyl.

26. A compound of claim 3, wherein each of $R^{11}$, $R^{12}$, $R^{13}$, $R^{14}$, $R^{15}$, $R^{16}$, $R^{19}$, $R^{38}$, and $R^{41}$ is independently H or $C_{1-5}$ alkyl.

27. A compound of claim 3, wherein $R^g$ is $C_{1-5}$ alkyl, $C_{2-8}$ acyl, $R^{17}OC=O$, $R^{17}R^{18}NC=O$, $R^{16}S$, $R^{16}SO$, $R^{16}SO_2$, or $R^{17}R^{18}NSO_2$; and $R^h$ hydrogen or $C_{1-5}$ alkyl; alternatively, $R^g$ and $R^h$ can be taken together to form an optionally substituted 4- to 7-membered heterocyclic ring.

28. A compound of claim 3, wherein $R^{17}$ and $R^{18}$ independently are hydrogen or $C_{1-5}$ alkyl.

29. A compound of claim 1, wherein n is 1.

30. A compound of claim 1, wherein n is 0.

31. A compound of claim 1, wherein G is $C_{3-4}$ alkanediyl, optionally substituted with hydroxy, halogen, (L)-$C_{1-5}$ alkyloxy, or [(L)-$C_{1-5}$ alkylene]amino.

32. A compound of claim 31, wherein G is $C_3$ alkanediyl, optionally substituted with hydroxy, (L)-$C_{1-5}$ alkyloxy, or [(L)-$C_{1-5}$ alkylene]amino.

33. A compound of claim 3, wherein each of $R^{20}$ and $R^{21}$ is independently selected from hydrogen, halogen, $C_{1-5}$ alkoxy, $C_{1-5}$ alkyl, cyano, nitro, and $R^mR^nN$ or $R^oR^pN$, respectively.

34. A compound of claim 33, wherein each of $R^{20}$ and $R^{21}$ is independently selected from hydrogen, halogen, $C_{1-3}$ alkyl, and $R^mR^nN$ or $R^oR^pN$, respectively.

35. A compound of claim 1, wherein Ar represents a monocyclic ring, optionally substituted with 1 to 2 substituents selected from halogen, $C_{1-5}$ alkyl, cyano, azido, nitro, $R^{22}R^{23}N$, halomethyl, and halomethoxy.

36. A compound of claim 35, wherein Ar is a six membered ring substituted with between 1 and 2 substituents independently selected from methyl, halogen, $CF_3$, and $OCF_3$, said substituent or substituents being at the 4-position, or at the 3- and 4-positions, respectively.

37. A compound of claim 1, wherein each of $R^{22}$, $R^{23}$, and $R^{24}$ is hydrogen or $C_{1-5}$ alkyl.

38. A compound of claim 1, wherein $R^{25}$ and $R^{26}$ independently are hydrogen or $C_{1-5}$ alkyl; or, alternatively, $R^{25}$ and $R^{26}$ can be taken together to form an optionally substituted 4- to 7-membered heterocyclic ring.

39. A compound of claim 38, wherein each of $R^{25}$ and $R^{26}$ is independently hydrogen or $C_{1-5}$ alkyl.

40. A compound of claim 1, wherein W is $NR^{27}$.

41. A compound of claim 1, wherein W is $CHR^{28}$, and $R^{28}$ is hydrogen or $C_{1-5}$ alkyl.

42. A compound of claim 1, wherein $R^{29}$ is $C_{1-5}$ alkyl; or $R^{30}$ and $R^{31}$ are independently selected from hydrogen and $C_{1-5}$ alkyl, or $R^{30}$ and $R^{31}$ are taken together to form a 5–6 membered heterocyclyl.

43. A compound of claim 3, wherein $Ar_2$ is formula (e) and $R^1$ halogen, $C_{1-5}$ alkoxy, hydroxy, $C_{1-5}$ alkyl, cyano, nitro, and $R^a R^b N$, or $R^1$ can be taken together with $R^{27}$ as provided below;

$R^2$ is hydrogen, halogen, $C_{1-5}$ alkoxy, $C_{1-5}$ alkyl, or $R^e R^f N$;

$R^3$ is hydrogen, halogen, $C_{1-5}$ alkoxy, hydroxy, $C_{1-5}$ alkyl, cyano, $R^g R^h N$;

$R^5$ and $R^6$ are independently selected from hydrogen and $C_{1-3}$ alkyl;

$R^7$ and $R^8$ independently are taken together to form an optionally substituted 5- to 7-membered carbocyclic or heterocyclic ring, which ring may be saturated, unsaturated or aromatic; each of $R^a$, $R^e$, $R^m$, and $R^o$ is independently selected from hydrogen, $C_{1-5}$ alkyl, $C_{2-8}$ acyl, and the respective $ROC=O$, $RRNC=O$, $RS$, $RSO$, $RSO_2$, and $RRNSO_2$ groups;

each of $R^b$, $R^f$, $R^n$, and $R^p$, is independently selected from hydrogen and $C_{1-5}$ alkyl;

each of $R^{11}$, $R^{12}$, $R^{13}$, $R^{14}$, $R^{15}$, $R^{16}$, $R^{19}$, and $R^{38}$ is independently $C_{1-5}$ alkyl;

each of $R^c$ and $R^d$, $R^i$ and $R^j$, $R^k$ and $R^l$, $R^{32}$ and $R^{33}$, $R^{34}$ and $R^{35}$, $R^{36}$ and $R^{37}$ are independently are hydrogen or $C_{1-5}$ alkyl, or are taken together to form an optionally substituted 4- to 7-membered heterocyclic ring;

$R^g$ is hydrogen, $C_{1-5}$ alkyl, $C_{2-8}$ acyl, $R^{17}OC=O$, $R^{17}R^{18}NC=O$, $R^{16}S$, $R^{16}SO$, $R^{16}SO_2$, or $R^{17}R^{18}NSO_2$;

$R^h$ is hydrogen or $C_{1-5}$ alkyl;

alternatively, $R^g$ and $R^h$ can be taken together to form an optionally substituted 4- to 7-membered heterocyclic ring;

$R^{17}$ and $R^{18}$ independently are hydrogen or $C_{1-5}$ alkyl; n is 0 or 1;

G is $C_{3-4}$ alkenediyl or $C_{3-4}$ alkanediyl, optionally substituted with hydroxy, halogen, $C_{1-5}$ alkyloxy, (L)-$C_{1-5}$ alkoxy, $N_3$, or [(L)-$C_{1-5}$ alkylene]amino;

L is amino, mono- or di-$C_{1-5}$ alkylamino, pyrrolidinyl, morpholinyl, piperidinyl homopiperidinyl, or piperazinyl, wherein available ring nitrogens may be optionally substituted with $C_{1-5}$ alkyl, benzyl, $C_{1-5}$ alkylcarbonyl, or $C_{1-5}$ alkyloxycarbonyl;

$Y_e$ is nitrogen or $R^{20}C$;

$Z_e$ is nitrogen or $R^{21}C$;

$R^{20}$ and $R^{21}$ are independently selected from hydrogen, halogen, $C_{1-5}$ alkoxy, $C_{1-5}$ alkyl, cyano, nitro, and $R^m R^n N$ or $R^o R^p N$, respectively;

alternatively, $R^3$ and $R^{20}$ or $R^3$ and $R^{21}$ can be taken together to form an optionally substituted 5- or 6-membered carbocyclic or heterocyclic ring;

Ar represents a monocyclic or bicyclic aryl or heteroaryl ring, optionally substituted with between 1 and 3 substituents independently selected from halogen, $C_{1-5}$ alkoxy, $C_{1-5}$ alkyl, cyano, azido, nitro, $R^{22}R^{23}N$, $R^{24}SO_2$, $R^{24}OC=O$, $R^{25}R^{26}NC=O$, $CF_3$, $OCF_3$, $CF_3S$, and $C_{1-5}$ alkylthio;

$R^{22}$ is hydrogen, $C_{1-5}$ alkyl, phenyl, benzyl, phenethyl, $C_{1-5}$ heterocyclyl, $C_{2-8}$ acyl, aroyl, $R^{24}OC=O$, $R^{25}R^{26}NC=O$, $R^{24}SO$, $R^{24}SO_2$, or $R^{25}R^{26}NSO_2$;

$R^{23}$ is hydrogen or $C_{1-5}$alkyl;

alternatively, $R^{22}$ and $R^{23}$ can be taken together to form an optionally substituted 4- to 7-membered heterocyclic ring;

$R^{24}$ is hydrogen or $C_{1-5}$ alkyl;

$R^{25}$ and $R^{26}$ are independently hydrogen or $C_{1-5}$ alkyl;

or, alternatively, $R^{25}$ and $R^{26}$ can be taken together to form an optionally substituted 4- to 7-membered heterocyclic;

W is $NR^{27}$ or $CHR^{28}$;

$R^{27}$ is hydrogen, $C_{1-5}$ alkyl, $R^{29}OC=O$, $R^{30}R^{31}NC=O$, $R^{29}SO$, $R^{29}SO_2$, or $R^{30}R^{31}NSO_2$;

or, alternatively, $R^{27}$ and $R^1$ can be taken together to form an optionally substituted 5- or 6-membered heterocyclic ring, which ring may be saturated, unsaturated or aromatic;

$R^{28}$ is hydrogen, hydroxy, $C_{1-5}$ heterocyclyl, phenyl, or $C_{1-5}$ alkyl;

$R^{29}$ is $C_{1-5}$ alkyl; and $R^{30}$ and $R^{31}$ are independently selected from hydrogen, $C_{1-5}$ alkyl; alternatively, $R^{30}$ and $R^{31}$ can be taken together to form an optionally substituted 4- to 7-membered heterocyclic.

44. A compound of claim 42, wherein $R^1$ and $R^{27}$ taken together are selected from:

a) —$CH_2 NR^9$—(C=O)—
b) —$OCH_2(C=O)$—
c) —$CH_2 CH_2(C=O)$—
d) —$CH_2$—$O(C=O)$—
e) —$CH_2 S(C=O)$—
f) —$O(C=O)$—
g) —$CH_2(C=O)$—
h) —$NR^9(C=O)$—
i) —$NR^9(SO_2)$—
j) —$CH_2 NR^9 SO_2$—
k) —$NR^9 CH_2(C=O)$— and
l) —$SCH_2(C=O)$—.

45. A compound of claim 42, wherein $R^1$ taken together with $R_{27}$ are selected from:

a) —$CH_2$—(C=O)—
b) —$O(C=O)$—
c) —$CH_2 CH_2$—
d) —$S(C=O)$—
e) —$N=N$—
f) —$NR^9 SO_2$—
g) —$N=CR^9$—
h) —$NR^9(C=O)$— and
i) —$CH=CH$—.

46. A compound of claim 1, wherein one of $R^5$ and $R^6$ is H, $R^7$ and $R^8$ are taken together to form an optionally substituted 6-membered carbocyclic or heterocyclic ring; and Ar represents a monocyclic ring, optionally substituted with 1 to 2 substituents selected from halogen, $C_{1-5}$ alkyl, cyano, nitro, $R^{22}R^{23}N$, $CF_3$ and $OCF_3$.

47. A compound of claim 46, wherein both $R^5$ and $R^6$ are each H, and Ar is a six membered ring substituted with between 1 and 2 substituents independently selected from halogen, methyl, $CF_3$, and $OCF_3$, said substituent or substituents being at the 4-position, or at the 3- and 4-positions.

48. A compound of claim 47, wherein $R^7$ and $R^8$ taken together form tetrahydropyridinyl, optionally N-substituted with —(C═O)$R^4$, —$SO_2R^4$, or —(C═O)$NHR^4$.

49. A compound of claim 5, wherein $X_f$ is C═O, $SO_2$, or $CHR^{1f}$, and $Y_f$ is O or $NR^{2f}$, where $R^{2f}$ is H, $C_{1-5}$ alkyl, $C_{2-5}$ heterocyclyl, $C_{1-5}$ cyanoalkyl, or $(C_{1-5}$ alkoxycarbonyl$)C_{1-5}$ alkylene.

50. A compound of claim 49, wherein $R^{2f}$ is H, $C_{1-3}$ alkyl, or a $C_{2-5}$ heterocyclyl.

51. A compound of claim 5, wherein $X_f$ is C═O, and $Y_f$ is O, $CHR^{2f}$ or $NR^{2f}$, where $R^{2f}$ is H, $C_{1-5}$ alkyl, $C_{2-5}$ heterocyclyl, $C_{1-5}$ cyanoalkyl, or $(C_{1-5}$ alkoxycarbonyl$)C_{1-5}$ alkylene.

52. A compound of claim 51, wherein $X_f$ is C═O and $Y_f$ is O.

53. A compound of claim 5, wherein m is 0 and p is 0; m is 0 and p is 1; or m is 1 and p is 0.

54. A compound of claim 53, wherein p is 0.

55. A compound of claim 1, wherein $R^z$ is H.

56. A compound of claim 1, wherein $R^z$ is OH.

57. A compound of claim 1, wherein $R^z$ is absent.

58. A compound of claim 3, wherein $R^{20}$ and $R^3$ taken together are a six-membered carbocyclic or heterocyclic ring optionally substituted with between 1 and 3 substituents independently selected from halo, $C_{1-3}$ alkoxy, di($C_{1-3}$ alkyl) amino, and $C_{2-5}$ acyl.

59. A compound of claim 3, wherein each of $R^{20}$ and $R^3$ is H.

60. A compound of claim 1, selected from:

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

1-(1-{3-[3-(3,4-Dichloro-phenyl)-5-methanesulfonyl-4,5,6,7-tetrahydro-pyrazolo[4,3-c]pyridin-1-yl]-propyl}-piperidin-4-yl)-1,3-dihydro-benzoimidazol-2-one;

3-(3,4-Dichloro-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid amide;

6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

3-(3,4-Dichloro-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide;

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile;

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetic acid ethyl ester;

5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one;

1-{3-[4-(6-Chloro-3-methyl-2-oxo-2,3-dihydro-benzoimidazol-1-yl)-piperidin-1-yl]-propyl}-3-(3,4-dichloro-phenyl)-1,4,6,7-tetrahydro-pyrazolo[4,3-c]pyridine-5-carboxylic acid amide;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dimethyl-1,3-dihydro-benzoimidazol-2-one;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one;

3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-methoxy-1,3-dihydro-imidazo[4,5-b]pyridin-2-one;

3-(4-Bromo-phenyl)-1-{2-hydroxy-3-[4-(5-methoxy-2-oxo-1,2-dihydro-imidazo[4,5-b]pyridin-3-yl)-piperidin-1-yl]-propyl}-1,4,6,7-tetrahydro-pyrazolo[4,3-c]pyridine-5-carboxylic acid amide;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one;

5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one;

6-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;

4-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one;

4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one; and 1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one.

61. A compound of claim 1, selected from:

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile; and 4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one.

62. A compound of claim 1, selected from:

2-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-ylamino)-benzonitrile;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3H-benzooxazol-2-one;

1-(3-(4-Chloro-3-methyl-phenyl)-1-{3-[4-(3,4-dichloro-phenoxy)-piperidin-1-yl]-propyl}-1,4,6,7-tetrahydro-pyrazolo[4,3-c]pyridin-5-yl)-ethanone;

1-(3-(4-Chloro-3-methyl-phenyl)-1-{3-[4-(2,3-dihydro-indol-1-yl)-piperidin-1-yl]-2-hydroxy-propyl}-1,4,6,7-tetrahydro-pyrazolo[4,3-c]pyridin-5-yl)-ethanone;

(S)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-(2-morpholin-4-yl-ethyl)-1,3-dihydro-benzoimidazol-2-one;

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

[3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-benzoimidazol-1-yl]-acetonitrile;

5-Chloro-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one;

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;

1-[3-(4-Chloro-3-methyl-phenyl)-1-(3-{4-[3-(4-chloro-phenyl)-[1,2,4]oxadiazol-5-yl]-piperidin-1-yl}-2-hydroxy-propyl)-1,4,6,7-tetrahydro-pyrazolo[4,3-c]pyridin-5-yl]-ethanone;

1-{1-{2-Hydroxy-3-[4-(5-trifluoromethyl-benzothiazol-2-yl)-piperidin-1-yl]-propyl}-3-(4-trifluoromethyl-phenyl)-1,4,6,7-tetrahydro-pyrazolo[4,3-c]pyridin-5-yl]-ethanone;

1-[1-{3-[4-(Benzo[d]isoxazol-3-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(5-Chloro-benzooxazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(Benzothiazol-2-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(3,5-Dichloro-pyridin-4-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(1H-Benzoimidazol-2-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

6-Chloro-4-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one;

6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;

6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one;

1-[4-(6-Chloro-2,2-dioxo-3,4-dihydro-2H-2$\lambda^6$-benzo[1,2,6]thiadiazin-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

4-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-pyrido[3,2-b][1,4]oxazin-3-one;

5-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;

1-[4-(6-Chloro-indol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1H-benzotriazole;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid amide;

5-Chloro-3-(1-{2-hydroxy-3-[4-pyridin-4-yl-3-(4-trifluoromethyl-phenyl)-pyrazol-1-yl]-propyl}-piperidin-4-yl)-1-methyl-1,3-dihydro-benzoimidazol-2-one;

4-(1-{2-Hydroxy-3-[4-pyrazin-2-yl-3-(4-trifluoromethyl-phenyl)-pyrazol-1-yl]-propyl}-piperidin-4-yl)-4H-benzo[1,4]oxazin-3-one;

(S)-1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one; and (S)-5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one.

63. A compound of claim 1, selected from:

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-octahydro-benzoimidazol-2-one;

1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-octahydro-benzoimidazol-2-one;

Acetic acid 1-(1-{3-[5-acetyl-3-(4-bromo-phenyl)-4,5,6,7-tetrahydro-pyrazolo[4,3-c]pyridin-1-yl]-propyl}-piperidin-4-yl)-1H-benzoimidazol-2-yl ester;

Methanesulfonic acid 1-(1-{3-[3-(4-bromo-phenyl)-5-methanesulfonyl-4,5,6,7-tetrahydro-pyrazolo[4,3-c]pyridin-1-yl]-propyl}-piperidin-4-yl)-1H-benzoimidazol-2-yl ester;

1-(1-{3-[5-Acetyl-3-(3,4-dichloro-phenyl)-4,5,6,7-tetrahydro-pyrazolo[4,3-c]pyridin-1-yl]-propyl}-piperidin-4-yl)-5-chloro-1,3-dihydro-indol-2-one;

1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid amide;

1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid methylamide;

Acetic acid 1-(1-{3-[5-acetyl-3-(3,4-dichloro-phenyl)-4,5,6,7-tetrahydro-pyrazolo[4,3-c]pyridin-1-yl]-propyl}-piperidin-4-yl)-1H-benzoimidazol-2-yl ester;

Methanesulfonic acid 1-(1-{3-[3-(3,4-dichloro-phenyl)-5-methanesulfonyl-4,5,6,7-tetrahydro-pyrazolo[4,3-c]pyridin-1-yl]-propyl}-piperidin-4-yl)-1H-benzoimidazol-2-yl ester;

1-[1-{3-[4-(3,5-Dichloro-pyridin-4-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(Benzooxazol-2-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{3-[4-(Benzooxazol-2-ylamino)-piperidin-1-yl]-2-hydroxy-propyl}-3-(4-trifluoromethyl-phenyl)-1,4,6,7-tetrahydro-pyrazolo[4,3-c]pyridin-5-yl]-ethanone; and 1-(4-Benzooxazol-2-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol.

64. A compound of claim 1, selected from:

1-(4-Benzothiazol-2-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol;

1-{3-[4-(5-Methyl-3-oxo-2,3-dihydro-benzo[1,4]oxazin-4-yl)-piperidin-1-yl]-propyl}-3-(4-trifluoromethyl-phenyl)-1,4,6,7-tetrahydro-pyrazolo[4,3-c]pyridine-5-carboxylic acid amide;

N-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-N-(3-chloro-phenyl)-benzamide;

4-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-methyl-4H-benzo[1,4]oxazin-3-one;

4-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-5-methyl-4H-benzo[1,4]oxazin-3-one;

3-(4-Bromo-phenyl)-1-{3-[4-(5-methyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid amide;

4-(1-{3-[5-Acetyl-3-(4-bromo-phenyl)-4,5,6,7-tetrahydro-pyrazolo[4,3-c]pyridin-1-yl]-propyl}-piperidin-4-yl)-5-methyl-4H-benzo[1,4]oxazin-3-one;

4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-methyl-4H-benzo[1,4]oxazin-3-one;

3-(4-Bromo-phenyl)-1-{3-[4-(6-ethanesulfonyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid amide;

4-(1-{3-[5-Acetyl-3-(4-bromo-phenyl)-4,5,6,7-tetrahydro-pyrazolo[4,3-c]pyridin-1-yl]-propyl}-piperidin-4-yl)-6-ethanesulfonyl-4H-benzo[1,4]oxazin-3-one;

4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-6-ethanesulfonyl-4H-benzo[1,4]oxazin-3-one;

1-[1-[3-(4-Benzothiazol-2-yl-piperidin-1-yl)-2-hydroxy-propyl]-3-(4-chloro-3-methyl-phenyl)-1,4,6,7-tetrahydro-pyrazolo[4,3-c]pyridin-5-yl]-ethanone;

1-[1-[3-(4-Benzothiazol-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone;

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-3,4-dihydro-1H-quinolin-2-one;

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-3,4-dihydro-1H-quinazolin-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-6-chloro-3,4-dihydro-1H-quinazolin-2-one;

1-[3-(4-Bromo-phenyl)-5-methanesulfonyl-4,5,6,7-tetrahydro-pyrazolo[4,3-c]pyridin-1-yl]-3-[4-(6-chloro-2,2-dioxo-3,4-dihydro-2H-2$\lambda^6$-2,1,3-benzothiadiazin-1-yl)-piperidin-1-yl]-propan-2-ol;

1-[4-(6-Chloro-2,2-dioxo-2,3-dihydro-2$\lambda^6$-2,1,3-benzothiadiazol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol;

1-[1-{3-[4-(6-Chloro-2,2-dioxo-2,3-dihydro-2$\lambda^6$-2,1,3-benzothiadiazol-1-yl)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

4-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-4-1,4-benzoxazin-3-one;

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-3,4-dihydro-1H-quinolin-2-one;

4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-4H-1,4-benzoxazin-3-one;

4-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-4H-1,4-benzoxazin-3-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one;

1-{2-Hydroxy-3-[4-(2-oxo-3,4-dihydro-2H-quinolin-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester;

1-{2-Hydroxy-3-[4-(3-oxo-2,3-dihydro-1,4-benzoxazin-4-yl)-piperidin-1-yl]-propyl}-3-(4-trifluoromethylphenyl)-1,4,6,7-tetrahydro-pyrazolo[4,3-c]pyridine-5-carboxylic acid tert-butyl ester;
4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-6-chloro-4H-1,4-benzoxazin-3-one; and
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-4H-1,4-benzoxazin-3-one.

65. A compound of claim 1, selected from:
1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3,4-dihydro-1H-quinolin-2-one;
1-{3-[4-(2-Oxo-3,4-dihydro-2H-quinolin-1-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester;
1-{3-[4-(3-Oxo-2,3-dihydro-1,4-benzoxazin-4-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester;
6-Chloro-4-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-4H-1,4-benzoxazin-3-one;
4-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-6-chloro-4H-1,4-benzoxazin-3-one;
4-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-4H-1,4-benzoxazin-3-one;
1-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;
4-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-4H-1,4-benzoxazin-3-one;
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one;
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;
1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-indol-2-one;
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-indol-2-one;
6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;
1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-chloro-1,3-dihydro-indol-2-one;
5-Chloro-1-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-indol-2-one;
1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-chloro-1,3-dihydro-indol-2-one;
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-chloro-1,3-dihydro-indol-2-one;
4-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-4H-pyrido[3,2-b]-1,4-oxazin-3-one;
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dihydro-4,1-benzoxazepin-2-one;
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,4-dihydro-3,1-benzoxazin-2-one;
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,4-dihydro-3,1-benzoxazin-2-one;
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,5-dihydro-4,1-benzoxazepin-2-one;
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,4-dihydro-3,1-benzoxazin-2-one;
1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,4-dihydro-3,1-benzoxazin-2-one;
1-(3-(4-Chloro-3-methyl-phenyl)-1-{2-hydroxy-3-[4-(5-nitro-2,3-dihydro-indol-1-yl)-piperidin-1-yl]-propyl}-1,4,6,7-tetrahydro-pyrazolo[4,3-c]pyridin-5-yl)-ethanone;
1-(3-(4-Chloro-3-methyl-phenyl)-1-{2-hydroxy-3-[4-(6-nitro-2,3-dihydro-indol-1-yl)-piperidin-1-yl]-propyl}-1,4,6,7-tetrahydro-pyrazolo[4,3-c]pyridin-5-yl)-ethanone;
1-(3-(4-Chloro-3-methyl-phenyl)-1-{2-hydroxy-3-[4-(2-methyl-2,3-dihydro-indol-1-yl)-piperidin-1-yl]-propyl}-1,4,6,7-tetrahydro-pyrazolo[4,3-c]pyridin-5-yl)-ethanone;
1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one;

1-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-3,4-dihydro-1H-quinazolin-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3,4-dihydro-1H-quinazolin-2-one;

1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3,4-dihydro-1H-quinazolin-2-one;

1-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1-(3-chloro-phenyl)-3-methyl-urea;

1-[3-(4-Benzotriazol-1-yl-piperidin-1-yl)-2-hydroxy-propyl]-3-(3,4-dichloro-phenyl)-1,4,6,7-tetrahydro-pyrazolo[4,3-c]pyridine-5-carboxylic acid tert-butyl ester;

1-{3-[4-(5-Chloro-2-oxo-2,3-dihydro-indol-1-yl)-piperidin-1-yl]-propyl}-3-(3,4-dichloro-phenyl)-1,4,6,7-tetrahydro-pyrazolo[4,3-c]pyridine-5-carboxylic acid tert-butyl ester;

5-Chloro-1-(1-{3-[3-(3,4-dichloro-phenyl)-4,5,6,7-tetrahydro-pyrazolo[4,3-c]pyridin-1-yl]-propyl}-piperidin-4-yl)-1,3-dihydro-indol-2-one;

1-{3-[4-(5-Methyl-3-oxo-2,3-dihydro-benzo[1,4]oxazin-4-yl)-piperidin-1-yl]-propyl}-3-(4-trifluoromethyl-phenyl)-1,4,6,7-tetrahydro-pyrazolo[4,3-c]pyridine-5-carboxylic acid tert-butyl ester; and 3-(4-Bromo-phenyl)-1-{3-[4-(5-methyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid tert-butyl ester.

66. A compound of claim 1, selected from:

3-(4-Bromo-phenyl)-1-{3-[4-(6-ethanesulfonyl-3-oxo-2,3-dihydro-benzo[1,4]oxazin-4-yl)-piperidin-1-yl]-propyl}-1,4,6,7-tetrahydro-pyrazolo[4,3-c]pyridine-5-carboxylic acid tert-butyl ester;

1-[5-Methanesulfonyl-3-(4-trifluoromethyl-phenyl)-4,5,6,7-tetrahydro-pyrazolo[4,3-c]pyridin-1-yl]-3-[4-(5-trifluoromethyl-benzothiazol-2-yl)-piperidin-1-yl]-propan-2-ol;

5-Methyl-4-(1-{3-[3-(4-trifluoromethyl-phenyl)-4,5,6,7-tetrahydro-pyrazolo[4,3-c]pyridin-1-yl]-propyl}-piperidin-4-yl)-4H-benzo[1,4]oxazin-3-one;

4-(1-{3-[3-(4-Bromo-phenyl)-4,5,6,7-tetrahydro-pyrazolo[4,3-c]pyridin-1-yl]-propyl}-piperidin-4-yl)-5-methyl-4H-benzo[1,4]oxazin-3-one;

4-(1-{3-[3-(4-Bromo-phenyl)-4,5,6,7-tetrahydro-pyrazolo[4,3-c]pyridin-1-yl]-propyl}-piperidin-4-yl)-6-ethanesulfonyl-4H-benzo[1,4]oxazin-3-one;

1-{3-[4-(6-Chloro-indol-1-yl)-piperidin-1-yl]-propyl}-5-methanesulfonyl-3-(4-trifluoromethyl-phenyl)-4,5,6,7-tetrahydro-1H-pyrazolo[4,3-c]pyridine;

3-(4-Bromo-phenyl)-1-{3-[4-(2-oxo-3,4-dihydro-2H-quinolin-1-yl)-piperidin-1-yl]-propyl}-1,4,6,7-tetrahydro-pyrazolo[4,3-c]pyridine-5-carboxylic acid tert-butyl ester;

3-(4-Bromo-phenyl)-1-{2-hydroxy-3-[4-(2-oxo-3,4-dihydro-2H-quinolin-1-yl)-piperidin-1-yl]-propyl}-1,4,6,7-tetrahydro-pyrazolo[4,3-c]pyridine-5-carboxylic acid tert-butyl ester;

3-(4-Bromo-phenyl)-1-{2-hydroxy-3-[4-(3-oxo-2,3-dihydro-1,4-benzoxazin-4-yl)-piperidin-1-yl]-propyl}-1,4,6,7-tetrahydro-pyrazolo[4,3-c]pyridine-5-carboxylic acid tert-butyl ester;

1-(1-{3-[3-(4-Trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;

3-(4-Bromo-phenyl)-1-{3-[4-(3-oxo-2,3-dihydro-1,4-benzoxazin-4-yl)-piperidin-1-yl]-propyl}-1,4,6,7-tetrahydro-pyrazolo[4,3-c]pyridine-5-carboxylic acid tert-butyl ester;

1-(1-{2-Hydroxy-3-[3-(4-trifluoromethyl-phenyl)-4,5,6,7-tetrahydro-pyrazolo[4,3-c]pyridin-1-yl]-propyl}-piperidin-4-yl)-3,4-dihydro-1H-quinolin-2-one;

4-(1-{3-[3-(4-Trifluoromethyl-phenyl)-4,5,6,7-tetrahydro-pyrazolo[4,3-c]pyridin-1-yl]-propyl}-piperidin-4-yl)-4H-1,4-benzoxazin-3-one;

1-(1-{3-[3-(4-Bromo-phenyl)-4,5,6,7-tetrahydro-pyrazolo[4,3-c]pyridin-1-yl]-propyl}-piperidin-4-yl)-3,4-dihydro-1H-quinolin-2-one;

4-(1-{3-[3-(4-Bromo-phenyl)-4,5,6,7-tetrahydro-pyrazolo[4,3-c]pyridin-1-yl]-propyl}-piperidin-4-yl)-4H-1,4-benzoxazin-3-one;

1-(1-{3-[3-(4-Bromo-phenyl)-4,5,6,7-tetrahydro-pyrazolo[4,3-c]pyridin-1-yl]-2-hydroxy-propyl}-piperidin-4-yl)-3,4-dihydro-1H-quinolin-2-one;

4-(1-{3-[3-(4-Bromo-phenyl)-4,5,6,7-tetrahydro-pyrazolo[4,3-c]pyridin-1-yl]-2-hydroxy-propyl}-piperidin-4-yl)-4H-1,4-benzoxazin-3-one;

4-(1-{2-Hydroxy-3-[3-(4-trifluoromethyl-phenyl)-4,5,6,7-tetrahydro-pyrazolo[4,3-c]pyridin-1-yl]-propyl}-piperidin-4-yl)-4H-1,4-benzoxazin-3-one;

1-(3-(3,4-Difluoro-phenyl)-1-{3-[4-(2,3-dihydro-indol-1-yl)-piperidin-1-yl]-2-hydroxy-propyl}-1,4,6,7-tetrahydro-pyrazolo[4,3-c]pyridin-5-yl)-ethanone;

1-[1-{3-[4-(5-Bromo-2,3-dihydro-indol-1-yl)-piperidin-1-yl]-2-hydroxy-propyl}-3-(4-chloro-3-methyl-phenyl)-1,4,6,7-tetrahydro-pyrazolo[4,3-c]pyridin-5-yl]-ethanone;

1-(1-{3-[5-Acetyl-3-(3,4-difluoro-phenyl)-4,5,6,7-tetrahydro-pyrazolo[4,3-c]pyridin-1-yl]-2-hydroxy-propyl}-piperidin-4-yl)-1,3-dihydro-indol-2-one;

1-[1-{3-[4-(5-Bromo-2,3-dihydro-indol-1-yl)-piperidin-1-yl]-2-hydroxy-propyl}-3-(3,4-difluoro-phenyl)-1,4,6,7-tetrahydro-pyrazolo[4,3-c]pyridin-5-yl]-ethanone;

1-(1-{3-[3-(4-Bromo-phenyl)-4,5,6,7-tetrahydro-pyrazolo[4,3-c]pyridin-1-yl]-2-hydroxy-propyl}-piperidin-4-yl)-3,4-dihydro-1H-quinazolin-2-one;

1-(1-{3-[3-(4-Trifluoromethyl-phenyl)-4,5,6,7-tetrahydro-pyrazolo[4,3-c]pyridin-1-yl]-propyl}-piperidin-4-yl)-3,4-dihydro-1H-quinazolin-2-one;

1-(1-{3-[3-(4-Bromo-phenyl)-4,5,6,7-tetrahydro-pyrazolo[4,3-c]pyridin-1-yl]-propyl}-piperidin-4-yl)-3,4-dihydro-1H-quinazolin-2-one;

1-(3-(4-Chloro-phenyl)-1-{3-[4-(3-chloro-phenylamino)-piperidin-1-yl]-2-hydroxy-propyl}-1,4,6,7-tetrahydro-pyrazolo[4,3-c]pyridin-5-yl)-ethanone;

N-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-N-(3-chloro-phenyl)-acetamide;

1-(4-Benzoimidazol-1-yl-piperidin-1-yl)-3-[5-methanesulfonyl-3-(4-trifluoromethyl-phenyl)-4,5,6,7-tetrahydro-pyrazolo[4,3-c]pyridin-1-yl]-propan-2-ol;

1-(3-(4-Chloro-phenyl)-1-{2-hydroxy-3-[4-(2-methoxy-phenylamino)-piperidin-1-yl]-propyl}-1,4,6,7-tetrahydro-pyrazolo[4,3-c]pyridin-5-yl)-ethanone;

1-(3-(4-Chloro-phenyl)-1-{3-[4-(2-fluoro-phenylamino)-piperidin-1-yl]-2-hydroxy-propyl}-1,4,6,7-tetrahydro-pyrazolo[4,3-c]pyridin-5-yl)-ethanone;

1-{3-(4-Chloro-phenyl)-1-[2-hydroxy-3-(4-phenylamino-piperidin-1-yl)-propyl]-1,4,6,7-tetrahydro-pyrazolo[4,3-c]pyridin-5-yl}-ethanone;

1-(3-(4-Chloro-phenyl)-1-{3-[4-(4-chloro-phenylamino)-piperidin-1-yl]-2-hydroxy-propyl}-1,4,6,7-tetrahydro-pyrazolo[4,3-c]pyridin-5-yl)-ethanone;

1-[1-{3-[4-(4-Bromo-phenylamino)-piperidin-1-yl]-2-hydroxy-propyl}-3-(4-chloro-phenyl)-1,4,6,7-tetrahydro-pyrazolo[4,3-c]pyridin-5-yl]-ethanone;

4-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-ylamino)-benzonitrile;

1-{3-(4-Chloro-phenyl)-1-[2-hydroxy-3-(4-p-tolylamino-piperidin-1-yl)-propyl]-1,4,6,7-tetrahydro-pyrazolo[4,3-c]pyridin-5-yl}-ethanone;

1-(3-(4-Chloro-phenyl)-1-{2-hydroxy-3-[4-(4-methoxy-phenylamino)-piperidin-1-yl]-propyl}-1,4,6,7-tetrahydro-pyrazolo[4,3-c]pyridin-5-yl)-ethanone;

1-(3-(4-Chloro-phenyl)-1-{2-hydroxy-3-[4-(3-methoxy-phenylamino)-piperidin-1-yl]-propyl}-1,4,6,7-tetrahydro-pyrazolo[4,3-c]pyridin-5-yl)-ethanone;

1-(3-(4-Chloro-phenyl)-1-{3-[4-(3,5-dimethoxy-phenylamino)-piperidin-1-yl]-2-hydroxy-propyl}-1,4,6,7-tetrahydro-pyrazolo[4,3-c]pyridin-5-yl)-ethanone;

1-[1-{3-[4-(5-Chloro-2-methyl-phenylamino)-piperidin-1-yl]-2-hydroxy-propyl}-3-(4-chloro-phenyl)-1,4,6,7-tetrahydro-pyrazolo[4,3-c]pyridin-5-yl]-ethanone;

1-(3-(4-Chloro-phenyl)-1-{3-[4-(3-chloro-phenylamino)-piperidin-1-yl]-2-hydroxy-propyl}-1,4,6,7-tetrahydro-pyrazolo[4,3-c]pyridin-5-yl)-ethanone;

[2-(1-{3-[3-(4-Bromo-phenyl)-5-carbamoyl-4,5,6,7-tetrahydro-pyrazolo[4,3-c]pyridin-1-yl]-propyl}-piperidin-4-ylamino)-4-ethanesulfonyl-phenoxy]-acetic acid methyl ester;

[2-(1-{3-[5-Acetyl-3-(4-bromo-phenyl)-4,5,6,7-tetrahydro-pyrazolo[4,3-c]pyridin-1-yl]-propyl}-piperidin-4-ylamino)-4-ethanesulfonyl-phenoxy]-acetic acid methyl ester;

[2-(1-{3-[3-(4-Bromo-phenyl)-5-methanesulfonyl-4,5,6,7-tetrahydro-pyrazolo[4,3-c]pyridin-1-yl]-propyl}-piperidin-4-ylamino)-4-ethanesulfonyl-phenoxy]-acetic acid methyl ester; and 3-(4-Bromo-phenyl)-1-{3-[4-(5-ethanesulfonyl-2-methoxycarbonylmethoxy-phenylamino)-piperidin-1-yl]-propyl}-1,4,6,7-tetrahydro-pyrazolo[4,3-c]pyridine-5-carboxylic acid tert-butyl ester.

67. A compound of claim 1, selected from:

2-(1-{3-[3-(4-Bromo-phenyl)-4,5,6,7-tetrahydro-pyrazolo[4,3-c]pyridin-1-yl]-propyl}-piperidin-4-ylamino)-4-ethanesulfonyl-phenoxy]-acetic acid methyl ester;

1-{3-(4-Bromo-phenyl)-1-[2-hydroxy-3-(4-o-tolyloxy-piperidin-1-yl)-propyl]-1,4,6,7-tetrahydro-pyrazolo[4,3-c]pyridin-5-yl}-ethanone;

1-{3-(4-Bromo-phenyl)-1-[2-hydroxy-3-(4-phenoxy-piperidin-1-yl)-propyl]-1,4,6,7-tetrahydro-pyrazolo[4,3-c]pyridin-5-yl}-ethanone;

1-{3-(4-Bromo-phenyl)-1-[2-hydroxy-3-(4-p-tolyloxy-piperidin-1-yl)-propyl]-1,4,6,7-tetrahydro-pyrazolo[4,3-c]pyridin-5-yl}-ethanone;

1-(3-(4-Bromo-phenyl)-1-{2-hydroxy-3-[4-(4-methoxy-phenoxy)-piperidin-1-yl]-propyl}-1,4,6,7-tetrahydro-pyrazolo[4,3-c]pyridin-5-yl)-ethanone;

1-(3-(4-Bromo-phenyl)-1-{3-[4-(4-chloro-phenoxy)-piperidin-1-yl]-2-hydroxy-propyl}-1,4,6,7-tetrahydro-pyrazolo[4,3-c]pyridin-5-yl)-ethanone;

1-(3-(4-Bromo-phenyl)-1-{3-[4-(3-chloro-phenoxy)-piperidin-1-yl]-2-hydroxy-propyl}-1,4,6,7-tetrahydro-pyrazolo[4,3-c]pyridin-5-yl)-ethanone;

1-(3-(4-Bromo-phenyl)-1-{3-[4-(3,4-dichloro-phenoxy)-piperidin-1-yl]-2-hydroxy-propyl}-1,4,6,7-tetrahydro-pyrazolo[4,3-c]pyridin-5-yl)-ethanone;

1-{3-(4-Chloro-3-methyl-phenyl)-1-[2-hydroxy-3-(4-phenoxy-piperidin-1-yl)-propyl]-1,4,6,7-tetrahydro-pyrazolo[4,3-c]pyridin-5-yl}-ethanone;

3-(4-Chloro-3-methyl-phenyl)-1-[2-hydroxy-3-(4-p-tolyloxy-piperidin-1-yl)-propyl]-1,4,6,7-tetrahydro-pyrazolo[4,3-c]pyridin-5-yl}-ethanone;

1-(3-(4-Chloro-3-methyl-phenyl)-1-{2-hydroxy-3-[4-(4-methoxy-phenoxy)-piperidin-1-yl]-propyl}-1,4,6,7-tetrahydro-pyrazolo[4,3-c]pyridin-5-yl)-ethanone;

1-(3-(4-Chloro-3-methyl-phenyl)-1-{3-[4-(4-chloro-phenoxy)-piperidin-1-yl]-2-hydroxy-propyl}-1,4,6,7-tetrahydro-pyrazolo[4,3-c]pyridin-5-yl)-ethanone;

1-(3-(4-Chloro-3-methyl-phenyl)-1-{3-[4-(3-chloro-phenoxy)-piperidin-1-yl]-2-hydroxy-propyl}-1,4,6,7-tetrahydro-pyrazolo[4,3-c]pyridin-5-yl)-ethanone;

1-{3-(4-Chloro-3-methyl-phenyl)-1-[2-hydroxy-3-(4-o-tolyloxy-piperidin-1-yl)-propyl]-1,4,6,7-tetrahydro-pyrazolo[4,3-c]pyridin-5-yl}-ethanone;

1-(3-(4-Chloro-3-methyl-phenyl)-1-{3-[4-(3,4-dichloro-phenoxy)-piperidin-1-yl]-2-hydroxy-propyl}-1,4,6,7-tetrahydro-pyrazolo[4,3-c]pyridin-5-yl)-ethanone;

2-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yloxy)-benzonitrile;

2-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yloxy)-benzonitrile;

1-[3-(4-Bromo-phenyl)-5-methanesulfonyl-4,5,6,7-tetrahydro-pyrazolo[4,3-c]pyridin-1-yl]-3-[4-(4-chloro-phenoxy)-piperidin-1-yl]-propan-2-ol;

1-[1-{3-[4-(4-Chloro-phenoxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-(1-{3-[5-Acetyl-3-(4-chloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-{1-[3-(5-Acetyl-3-phenyl-4,5,6,7-tetrahydro-pyrazolo[4,3-c]pyridin-1-yl)-2-hydroxy-propyl]-piperidin-4-yl}-1,3-dihydro-benzoimidazol-2-one;

1-(1-{3-[5-Acetyl-3-(4-trifluoromethoxy-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-chloro-3-nitro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-trifluoromethylsulfanyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-methanesulfonyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-isopropyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-butyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-benzyl-1,3-dihydro-benzoimidazol-2-one;

1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-5-fluoro-1,3-dihydro-benzoimidazol-2-one;

3-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-7-fluoro-2-oxo-2,3-dihydro-1H-benzoimidazole-4-carbonitrile;

1-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-6-fluoro-1,3-dihydro-benzoimidazol-2-one;

3-(1-{3-[5-Acetyl-3-(4-iodo-phenyl)-4,5,6,7-tetrahydro-pyrazolo[4,3-c]pyridin-1-yl]-2-hydroxy-propyl}-piperidin-4-yl)-2-oxo-2,3-dihydro-1H-benzoimidazole-5-carbonitrile;

1-{2-Hydroxy-3-[4-(2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide;

1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-benzoimidazol-2-one;

3-(4-Chloro-3-methyl-phenyl)-1-{2-hydroxy-3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid methylamide;

3-(4-Chloro-3-methyl-phenyl)-1-{2-hydroxy-3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid ethylamide;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one; and 1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-methyl-1,3-dihydro-benzoimidazol-2-one.

68. A compound of claim 1, selected from:

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5,6-dichloro-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-methyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5,6-dichloro-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

1-(1-{3-[5-Acetyl-3-(4-chloro-3-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[3-(4-Chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-3-(2-morpholin-4-yl-ethyl)-1,3-dihydro-benzoimidazol-2-one;

1-(1-{3-[5-Acetyl-3-(3-fluoro-4-trifluoromethyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

(R)-1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-methoxy-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-7-chloro-1,3-dihydro-benzoimidazol-2-one;

3-(1-{3-[5-Acetyl-3-(4-bromo-phenyl)-4,5,6,7-tetrahydro-pyrazolo[4,3-c]pyridin-1-yl]-2-hydroxypropyl}-piperidin-4-yl)-1,3-dihydro-imidazo[4,5-b]pyridin-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-7-methyl-1,3-dihydro-benzoimidazol-2-one;

(R)-1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

(S)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

(R)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

(R)-1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

2-{2-[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-ethyl}-isoindole-1,3-dione;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-amino-ethyl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-ethyl-1,3-dihydro-benzoimidazol-2-one;

6-Chloro-1-(1-{3-[3-(4-chloro-3-methyl-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-chloro-1-(2-morpholin-4-yl-ethyl)-1,3-dihydrobenzoimidazol-2-one;

[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-aceticacid ethyl ester;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2,2,2-trifluoro-ethyl)-1,3-dihydrobenzoimidazol-2-one;

[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]acetonitrile;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-hydroxy-ethyl)-1,3-dihydro-benzoimidazol-2-one;

1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-6-chloro-1,3-dihydro-benzoimidazol-2-one;

1-(1-{3-[5-Acetyl-3-(3-chloro-4-methyl-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

1-Ethyl-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-3-(2-hydroxy-ethyl)-1,3-dihydro-benzoimidazol-2-one;

3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-1,3-dihydro-imidazo[4,5-b]pyridin-2-one;

[3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetonitrile;

2-[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetamide;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-oxo-tetrahydro-furan-3-yl)-1,3-dihydro-benzoimidazol-2-one; and 1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-methoxy-ethyl)-1,3-dihydro-benzoimidazol-2-one.

69. A compound of claim 1, selected from:

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-oxo-butyl)-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-diethylamino-ethyl)-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-cyclopropylmethyl-1,3-dihydro-benzoimidazol-2-one;

1-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3-(2-methyl-allyl)-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-5-methyl-1,3-dihydro-benzoimidazol-2-one;

5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one;

6-Chloro-1-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

N-[4-(5-Acetyl-1-{2-hydroxy-3-[4-(2-oxo-2,3-dihydro-benzoimidazol-1-yl)-piperidin-1-yl]-propyl}-4,5,6,7-tetrahydro-1H-pyrazolo[4,3-c]pyridin-3-yl)-phenyl]-acetamide;

[3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid;

1-(1-{3-[5-Acetyl-3-(3-bromo-4-chloro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one;

1-(1-{3-[5-(1H-imidazole-4-carbonyl)-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid ethylamide;

1-(1-{3-[5-(isoxazole-5-carbonyl)-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-sulfonic acid (N-t-butoxycarbonyl)amide;

1-Methyl-3-(1-{3-[5-(5-methyl-isoxazole-3-carbonyl)-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one;

3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one;

5-Dimethylamino-3-(1-{3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one;

3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-1-ethyl-5-methoxy-1,3-dihydro-imidazo[4,5-b]pyridin-2-one;

1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-1,3-dihydro-benzoimidazol-2-one;

1-(1-{3-[5-Acetyl-3-(4-nitro-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

3-(1-{3-[5-Acetyl-3-(4-bromo-phenyl)-4,5,6,7-tetrahydro-pyrazolo[4,3-c]pyridin-1-yl]-propyl}-piperidin-4-yl)-1-ethyl-5-methoxy-1,3-dihydro-imidazo[4,5-b]pyridin-2-one;

3-(1-{3-[5-Acetyl-3-(4-bromo-phenyl)-4,5,6,7-tetrahydro-pyrazolo[4,3-c]pyridin-1-yl]-propyl}-piperidin-4-yl)-5-methoxy-1-methyl-1,3-dihydro-imidazo[4,5-b]pyridin-2-one;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid benzyl ester;

5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one;

1-{3-[4-(3-Methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carbothioic acid methylamide;

3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid phenylamide;

1-(1-{3-[5-Benzoyl-3-(4-bromo-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,3-dihydro-benzoimidazol-2-one;

3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-chloro-1-methyl-1,3-dihydro-benzoimidazol-2-one;

1-{3-[4-(6-Chloro-3-methyl-2-oxo-2,3-dihydro-benzoimidazol-1-yl)-piperidin-1-yl]-propyl}-3-(4-trifluoromethyl-phenyl)-1,4,6,7-tetrahydro-pyrazolo[4,3-c]pyridine-5-carboxylic acid amide;

1-(1-{3-[3-(4-Bromo-phenyl)-5-phenylmethanesulfonyl-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[5-Acetyl-3-(3,4-dichloro-phenyl)-4,5,6,7-tetrahydro-pyrazolo[4,3-c]pyridin-1-yl]-2-hydroxy-propyl}-piperidin-4-yl)-3-methyl-1,3-dihydro-benzoimidazol-2-one;

3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide;

3-(1-{3-[5-Acetyl-3-(4-bromo-phenyl)-4,5,6,7-tetrahydro-pyrazolo[4,3-c]pyridin-1-yl]-propyl}-piperidin-4-yl)-5-chloro-1-methyl-1,3-dihydro-benzoimidazol-2-one;

3-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-5-chloro-1-methyl-1,3-dihydro-benzoimidazol-2-one;

3-(4-Bromo-phenyl)-1-{3-[4-(6-chloro-3-methyl-2-oxo-2,3-dihydro-benzoimidazol-1-yl)-piperidin-1-yl]-propyl}-1,4,6,7-tetrahydro-pyrazolo[4,3-c]pyridine-5-carboxylic acid amide;

3-(1-{3-[5-Methanesulfonyl-3-(4-trifluoromethyl-phenyl)-4,5,6,7-tetrahydro-pyrazolo[4,3-c]pyridin-1-yl]-propyl}-piperidin-4-yl)-1,5-dimethyl-1,3-dihydro-benzoimidazol-2-one; and 1-(1-{3-[5-Acetyl-3-(4-bromo-phenyl)-4,5,6,7-tetrahydro-pyrazolo[4,3-c]pyridin-1-yl]-propyl}-piperidin-4-yl)-3-methyl-1,3-dihydro-benzoimidazol-2-one.

70. A compound of claim 1, selected from:

3-(4-Bromo-phenyl)-1-{3-[4-(3-methyl-2-oxo-2,3-dihydro-benzoimidazol-1-yl)-piperidin-1-yl]-propyl}-1,4,6,7-tetrahydro-pyrazolo[4,3-c]pyridine-5-sulfonic acid t-butoxycarbonyl-amide;

1-(1-{3-[3-(4-Bromo-phenyl)-5-methanesulfonyl-4,5,6,7-tetrahydro-pyrazolo[4,3-c]pyridin-1-yl]-propyl}-piperidin-4-yl)-1,3-dihydro-benzoimidazol-2-one;

1-(1-{3-[5-Acetyl-3-(4-bromo-phenyl)-4,5,6,7-tetrahydro-pyrazolo[4,3-c]pyridin-1-yl]-propyl}-piperidin-4-yl)-1,3-dihydro-benzoimidazol-2-one;

3-(4-Bromo-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-sulfonic acid t-butoxycarbonyl-amide;

3-(4-Bromo-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid amide;

(R)-5-Chloro-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-benzoimidazol-2-one;

1-(1-{3-[5-Acetyl-3-(3,4-dichloro-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[3-(3,4-Dichloro-phenyl)-5-methanesulfonyl-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-6-methoxy-1,3-dihydro-benzoimidazol-2-one;

3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-1,3-dihydro-imidazo[4,5-b]pyridin-2-one;

3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-5-methoxy-1,3-dihydro-imidazo[4,5-b]pyridin-2-one;

1-{2-Hydroxy-3-[4-(2-oxo-1,2-dihydro-imidazo[4,5-b]pyridin-3-yl)-piperidin-1-yl]-propyl}-3-(4-trifluoromethyl-phenyl)-1,4,6,7-tetrahydro-pyrazolo[4,3-c]pyridine-5-carboxylic acid amide;

3-(4-Bromo-phenyl)-1-{2-hydroxy-3-[4-(2-oxo-1,2-dihydro-imidazo[4,5-b]pyridin-3-yl)-piperidin-1-yl]-propyl}-1,4,6,7-tetrahydro-pyrazolo[4,3-c]pyridine-5-carboxylic acid amide;

[3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-2-oxo-2,3-dihydro-imidazo[4,5-b]pyridin-1-yl]-acetonitrile;

3-(3,4-Dichloro-phenyl)-1-{3-[4-(2-oxo-2,3-dihydro-benzoimidazol-1-yl)-piperidin-1-yl]-propyl}-1,4,6,7-tetrahydro-pyrazolo[4,3-c]pyridine-5-carboxylic acid methylamide;

3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-1,3-dihydro-imidazo[4,5-b]pyridin-2-one;

3-(1-{3-[5-Acetyl-3-(4-trifluoromethyl-phenyl)-4,5,6,7-tetrahydro-pyrazolo[4,3-c]pyridin-1-yl]-propyl}-piperidin-4-yl)-5-methoxy-1,3-dihydro-imidazo[4,5-b]pyridin-2-one;

[3-(1-{3-[3-(4-Bromo-phenyl)-5-methanesulfonyl-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester;

[3-(1-{3-[5-Acetyl-3-(4-trifluoromethyl-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester;

[3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-2-oxo-2,3-dihydro-benzoimidazol-1-yl]-acetic acid ethyl ester;

5-Chloro-3-(1-{3-[3-(3,4-dichloro-phenyl)-5-methanesulfonyl-4,5,6,7-tetrahydro-pyrazolo[4,3-c]pyridin-1-yl]-propyl}-piperidin-4-yl)-1-methyl-1,3-dihydro-benzoimidazol-2-one;

(R)-1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-methyl-1,3-dihydro-benzoimidazol-2-one;

1-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3-pyridin-4-ylmethyl-1,3-dihydro-benzoimidazol-2-one;

(R)-5-Dimethylamino-3-(1-{2-hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-1-methyl-1,3-dihydro-imidazo[4,5-b]pyridin-2-one;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-5-chloro-3H-benzooxazol-2-one;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-4-methyl-3H-benzooxazol-2-one;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-2-oxo-2,3-dihydro-benzooxazole-6-carboxylic acid ethyl ester;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-ethanesulfonyl-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-4-methyl-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-2-oxo-2,3-dihydro-benzooxazole-6-carboxylic acid ethyl ester;

3-(1-{3-[5-Acetyl-3-(4-bromo-phenyl)-4,5,6,7-tetrahydro-pyrazolo[4,3-c]pyridin-1-yl]-2-hydroxy-propyl}-piperidin-4-yl)-6-methoxy-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-ethanesulfonyl-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-6-methoxy-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-3H-benzooxazol-2-one;

3-(1-{3-[5-Acetyl-3-(4-chloro-3-methyl-phenyl)-4,5,6,7-tetrahydro-pyrazolo[4,3-c]pyridin-1-yl]-2-hydroxy-propyl}-piperidin-4-yl)-5-chloro-3H-benzooxazol-2-one;

3-(1-{2-Hydroxy-3-[5-methanesulfonyl-3-(4-trifluoromethyl-phenyl)-4,5,6,7-tetrahydro-pyrazolo[4,3-c]pyridin-1-yl]-propyl}-piperidin-4-yl)-3H-oxazolo[4,5-b]pyridin-2-one;

1-[1-[3-(4-Benzooxazol-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone;

1-[1-{2-Hydroxy-3-[4-(6-methyl-benzooxazol-2-yl)-piperidin-1-yl]-propyl}-3-(4-trifluoromethyl-phenyl)-1,4,6,7-tetrahydro-pyrazolo[4,3-c]pyridin-5-yl]-ethanone;

1-[1-{3-[4-(Benzothiazol-2-yloxy)-piperidin-1-yl]-2-hydroxy-propyl}-3-(4-trifluoromethyl-phenyl)-1,4,6,7-tetrahydro-pyrazolo[4,3-c]pyridin-5-yl]-ethanone;

1-[1-{2-Hydroxy-3-[4-(5-methyl-benzooxazol-2-yl)-piperidin-1-yl]-propyl}-3-(4-trifluoromethyl-phenyl)-1,4,6,7-tetrahydro-pyrazolo[4,3-c]pyridin-5-yl]-ethanone;

1-(3-(4-Chloro-phenyl)-1-{2-hydroxy-3-[4-(2-methoxy-phenyl)-piperidin-1-yl]-propyl}-1,4,6,7-tetrahydro-pyrazolo[4,3-c]pyridin-5-yl)-ethanone;

3-(4-Chloro-phenyl)-1-{2-hydroxy-3-[4-(2-methoxy-phenyl)-piperidin-1-yl]-propyl}-1,4,6,7-tetrahydro-pyrazolo[4,3-c]pyridine-5-carbaldehyde;

1-[1-[3-(4-Benzo[b]thiophen-2-yl-piperidin-1-yl)-2-hydroxy-propyl]-3-(4-trifluoromethyl-phenyl)-1,4,6,7-tetrahydro-pyrazolo[4,3-c]pyridin-5-yl]-ethanone; and 1-[4-(6-Chloro-indol-1-yl)-piperidin-1-yl]-3-[5-methanesulfonyl-3-(4-trifluoromethyl-phenyl)-4,5,6,7-tetrahydro-pyrazolo[4,3-c]pyridin-1-yl]-propan-2-ol.

71. A pharmaceutical composition, comprising a compound of claim 1, 3, 5, 60, or 61 and a pharmaceutically acceptable carrier.

72. A method for treating a subject with a condition mediated by cathepsin S, said method comprising administering to the subject a therapeutically effective amount of a pharmaceutical composition comprising a compound of claim 1, 3, 5, 60, or 61.

73. A method for inhibiting cathepsin S activity in a subject, said method comprising administering to the subject a therapeutically effective amount of a pharmaceutical composition comprising a compound of claim 1, 3, 60 or 61.

74. A method for treating an autoimmune disease, or inhibiting the progression of an autoimmune disease, in a subject, said method comprising administering to the subject a therapeutically effective amount of a pharmaceutical composition comprising a compound of claim 1, 3, 60, or 61.

75. A method of claim 74, wherein the autoimmune disease is selected from lupus, rheumatoid arthritis, and asthma.

76. A method of claim 74, wherein the autoimmune disease is asthma.

77. A method for treating or inhibiting the progression of tissue transplant rejection in a subject, said method comprising administering to the subject a therapeutically effective amount of a pharmaceutical composition comprising a compound of claim 1, 3, 60, or 61.

78. A method of claim 77, wherein said administration occurs after said subject has undergone a tissue transplant procedure.

79. A method of claim 77, wherein said administration to said subject occurs before or during a tissue transplant procedure.

* * * * *